(12) United States Patent
Burwinkel et al.

(10) Patent No.: US 10,941,451 B2
(45) Date of Patent: Mar. 9, 2021

(54) BIOMARKER PANEL FOR THE DETECTION OF CANCER

(71) Applicant: RUPRECHT-KARLS-UNIVERSITAT HEIDELBERG, Heidelberg (DE)

(72) Inventors: Barbara Burwinkel, Heidelberg (DE); Rongxi Yang, Heidelberg (DE); Andreas Schneeweiss, Nußloch (DE)

(73) Assignee: RUPRECHT-KARLS-UNIVERSITAT HEIDELBERG, Heidelberg (DE)

( * ) Notice: Subject to any disclaimer, the term of this patent is extended or adjusted under 35 U.S.C. 154(b) by 0 days.

(21) Appl. No.: 15/552,421

(22) PCT Filed: Feb. 24, 2016

(86) PCT No.: PCT/EP2016/053813
§ 371 (c)(1),
(2) Date: Aug. 21, 2017

(87) PCT Pub. No.: WO2016/135168
PCT Pub. Date: Sep. 1, 2016

(65) Prior Publication Data
US 2018/0245159 A1 Aug. 30, 2018

(30) Foreign Application Priority Data

Feb. 24, 2015 (EP) .................................... 15156389

(51) Int. Cl.
*C12Q 1/6886* (2018.01)
*C12N 15/11* (2006.01)

(52) U.S. Cl.
CPC ..... *C12Q 1/6886* (2013.01); *C12Q 2600/106* (2013.01); *C12Q 2600/154* (2013.01); *C12Q 2600/158* (2013.01); *C12Q 2600/178* (2013.01)

(58) Field of Classification Search
None
See application file for complete search history.

(56) References Cited

U.S. PATENT DOCUMENTS

| 2013/0130242 A1 | 5/2013 | Sakai et al. | |
| 2015/0197812 A1* | 7/2015 | Burwinkel | C12Q 1/6886 506/9 |

FOREIGN PATENT DOCUMENTS

| CN | 101245386 | 8/2008 |
| JP | 2013-027387 | 2/2013 |
| JP | 2014-036637 | 2/2014 |
| WO | 2003/095679 A1 | 11/2003 |
| WO | 2005/007892 A1 | 1/2005 |
| WO | WO 2005/081867 | 9/2005 |
| WO | WO 2008/102002 | 8/2008 |
| WO | 2009/067655 A2 | 5/2009 |
| WO | WO 2010/056337 | 5/2010 |
| WO | WO 2012/174282 | 12/2012 |
| WO | 2013/190091 A1 | 12/2013 |
| WO | 2014/006160 A1 | 1/2014 |
| WO | 2014/020048 A1 | 2/2014 |

OTHER PUBLICATIONS

Udabage et al. Experimental Cell Research vol. 310:205-217,2005.*
Yang et al. Journal of Clinical Oncology vol. 32(6), Suppl.1, Abstract 26, Jun. 9, 2014.*
Yang, Rongxi et al., "DNA methylation array analyses identified breast cancer-associated HYAL2 methylation in peripheral blood" International Journal of Cancer (2015) vol. 136, pp. 1845-1855.
Maciejczyk, Adam et al., "Elevated nuclear S100P expression is associated with poor survival in early breast cancer patients" Histology and Histopathology (2013) vol. 28, pp. 413-524.
Mohelnikova-Duchonova, Beatrice et al. "The association between the expression of solute carrier transporter and the prognosis of pancreatic cancer" Cancer Chemother Pharmacol (2013) vol. 72, pp. 669-682.
Alvi, Muhammad A. et al. "DNA methylation as an adjunct to histopathology to detect prevalent, inconspicuous dysplasia and early-stage neoplasia in barrett's esophagus" Clinical Cancer Research (2013) vol. 19(4), pp. 378-888.
Koike, Tetsufumi et al. "Hypoxia induces adhesion molecules on cancer cells: A missing link between Warburg effect and induction of selectin-ligand carbohydrates" PNAS (2004) vol. 101(21), pp. 8132-8137.
Mas, Eric et al. "Fucosyltransferase activities in human pancreatic tissue: comparative study between cancer tissues and established tumoral cell lines" Glycobiology (1998) vol. 8(6), pp. 605-613.
Nassar, Farah J. et al. "MiRNA as potential biomarkers of breast cancer in the Lebanese population and in young women: a pilot study" PLOS One (2014) vol. 9(9), p. 107566.
McDermott, Ailbhe M. et al. "Identificaiton and validation of oncologic miRNA biomarkers for luminal a-like breast cancer" PLOS One (2014) vol. 9(1), p. e87032.
Zhao, Xiujuan et al. "MicroRNA-127 is downregulated by tudor-SN protein and contributes to metastasis and proliferation in breast cancer cell line MDA-MB-231" The Anatomical Record (2013) vol. 296, pp. 1842-1849.
Cuk, Katarina et al. "Plasma MicroRNA panel for minimally invasive detection of breast cancer" PLOS One (2013) vol. 3(10), p. e76729.
Cimino, Daniela et al. "miR148b is a major coordinator of breast cancer progression in a relapse-associated microRNA signature by targeting ITGA5, ROCKI, PIK3CA, NRAS, and CSFI" The FASEB Journal (2013) vol. 27 1223-1235.
Sand, Rupninder et al. "Dysregulation of micro RNA expression drives aberrant DNA hypermethylation in basal-like breast cancer" International Journal of Oncology (2014) vol. 44, pp. 563-572.

(Continued)

*Primary Examiner* — Sean McGarry
(74) *Attorney, Agent, or Firm* — McDonnell Boehnen Hulbert & Berghoff LLP

(57) ABSTRACT

The present invention relates to panels of methylation and mi RNA marker as well as their use in the prognosing, diagnosing and/or treatment of cancer, means for detecting said marker, kits comprising said means, and devices for analysing the marker panel.

19 Claims, 65 Drawing Sheets

Figure 25:
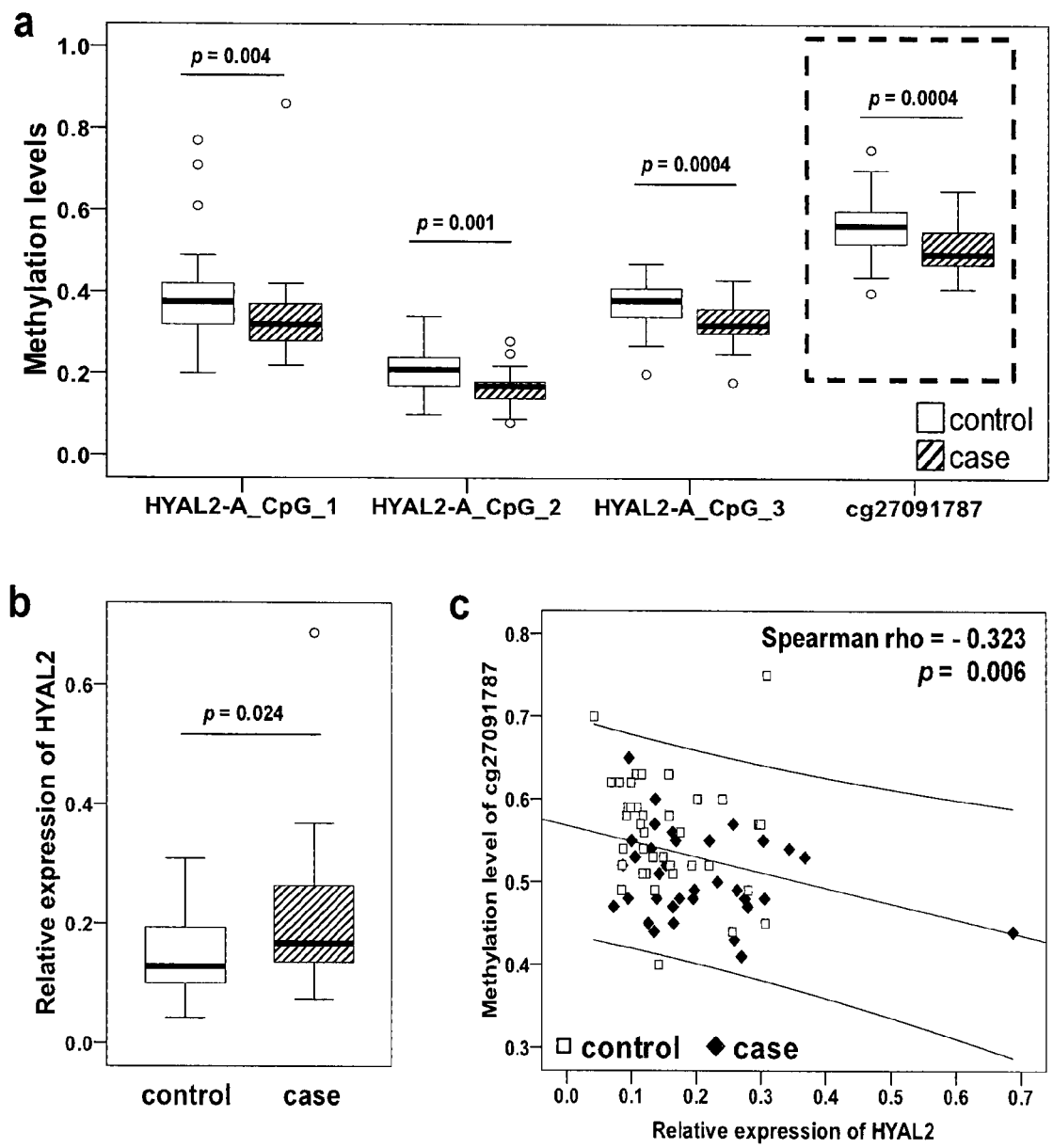

Specification includes a Sequence Listing.

(56) References Cited

OTHER PUBLICATIONS

Kim, Yong-Wan et al. "Differential microRNA expression signatures and cell type-specific association with Taxol resistance in ovarian cancer cells" Drug Design, Development and Therapy (2014) vol. 8(1), pp. 293-314.

Ji, Yi-Fei et al. "S100 family signaling network and related proteins in pancreatic cancer (Review)"International Journal of Molecular Medicine (2014) vol. 33, pp. 769-776.

The International Search Report (ISR) with Written Opinion for PCT/EP2016/05813 dated Jun. 1, 2016, pp. 1-22.

Zhou et al., "Effect of HYAL2 gene silencing on proliferation and invasion in ovary carcinoma SKOV3 cells" J. Fourth Mil. Med. Univ., 30(23):2808-11 (Dec. 2009). English Abstract included.

* cited by examiner

Fig. 1

Blood-based biomarker panel for the early detection of breast cancer

Table 1. Sample description

| Rounds | | First validation round | | Second validation round | | Third validation round | |
|---|---|---|---|---|---|---|---|
| Sample types | | Peripheral blood DNA | | Peripheral blood DNA | | Peripheral blood DNA | |
| Assays | | MassARRAY | | MassARRAY | | MassARRAY | |
| Groups | | Controls | FBC cases | Controls | SBC cases | Controls | SBC cases |
| Sample resources | | Blood donor from Mannheim | Breast cancer centers in Heidelberg and Cologne | Blood donor from Mannheim | University hospital of Heidelberg | University hospital of Heidelberg | University hospital of Heidelberg |
| Target N | | 251 | 270 | 189 | 189 | 151 | 161 |
| Median of age | | 43.0 | 43.0 | 64.0 | 60.0 | 45.0 | 46.0 |
| Rang of age | | 30-67 | 24-78 | 31-69 | 32-87 | 21-77 | 27-61 |
| Assayed N (call rate %) | HYAL2 | 251 (100.0%) | 270 (100.0%) | 189 (100.0%) | 188 (99.5%) | 151 (100.0%) | 161 (100.0%) |
| | DYRK4 | 247 (98.4%) | 268 (99.3%) | 189 (100.0%) | 189 (100.0%) | 150 (99.3%) | 158 (98.1%) |
| | S100P | 251 (100.0%) | 270 (100.0%) | 189 (100.0%) | 189 (100.0%) | 151 (100.0%) | 161 (100.0%) |
| | FUT7 | 251 (100.0%) | 270 (100.0%) | 189 (100.0%) | 189 (100.0%) | 151 (100.0%) | 161 (100.0%) |
| | SLC22A18 | 251 (100.0%) | 270 (100.0%) | 189 (100.0%) | 189 (100.0%) | 151 (100.0%) | 161 (100.0%) |
| | RPTOR | 251 (100.0%) | 270 (100.0%) | 189 (100.0%) | 189 (100.0%) | 151 (100%) | 161 (100.0%) |
| | MGRN1 | 251 (100.0%) | 270 (100.0%) | 189 (100.0%) | 189 (100.0%) | 150 (99.3%) | 158 (98.1%) |
| | RAPSN | 251 (100.0%) | 270 (100.0%) | 189 (100.0%) | 189 (100.0%) | 150 (99.3%) | 161 (100.0%) |
| | miR-127-3p | — | — | — | — | 148 (98.0%) | 153 (95.0%) |
| | miR-148b | — | — | — | — | 148 (98.0%) | 153 (95.0%) |
| | miR-376a | — | — | — | — | 148 (98.0%) | 153 (95.0%) |
| | miR-376c | — | — | — | — | 148 (98.0%) | 153 (95.0%) |
| | miR-409-3p | — | — | — | — | 148 (98.0%) | 153 (95.0%) |
| | miR-652 | — | — | — | — | 148 (98.0%) | 153 (95.0%) |
| | miR-801 | — | — | — | — | 148 (98.0%) | 153 (95.0%) |

Fig. 2

Table 2. Methylation difference of eight genes in the three validation rounds

| CpG sites | First validation round | | | | Second validation round | | | |
|---|---|---|---|---|---|---|---|---|
| | Controls median (IQR) | FBC cases median (IQR) | OR per 10% methylation | p-value * | Controls median (IQR) | Sporadic BC cases median (IQR) | OR per 10% methylation | p-value * |
| HYAL2_CpG_1 | 0.38 (0.33-0.45) | 0.30 (0.26-0.37) | 1.92 (1.57-2.33) | 8.92E-11 | 0.39 (0.32-0.48) | 0.3 (0.26-0.37) | 1.96 (1.56-2.45) | 4.70E-09 |
| HYAL2_CpG_2 | 0.25 (0.20-0.30) | 0.18 (0.14-0.23) | 3.10 (2.32-4.15) | 2.88E-14 | 0.23 (0.18-0.29) | 0.17 (0.13-0.23) | 5.31 (3.49-8.06) | 5.27E-15 |
| HYAL2_CpG_3 | 0.41 (0.36-0.47) | 0.32 (0.28-0.39) | 4.24 (3.14-5.75) | 8.22E-21 | 0.41 (0.36-0.47) | 0.32 (0.28-0.36) | 5.44 (3.69-8.03) | 1.51E-17 |
| HYAL2_CpG_4 | 0.65 (0.59-0.72) | 0.53 (0.48-0.60) | 4.53 (3.42-6.03) | 2.78E-25 | 0.64 (0.58-0.70) | 0.5 (0.46-0.54) | 8.14 (5.37-12.33) | 4.79E-23 |
| DYRK4_CpG_1 | 0.38 (0.19-0.55) | 0.25 (0.15-0.38) | 1.25 (1.15-1.35) | 1.20E-07 | 0.34 (0.23-0.46) | 0.26 (0.19-0.33) | 1.49 (1.28-1.73) | 3.82E-07 |
| DYRK4_CpG_3 | 0.29 (0.16-0.42) | 0.20 (0.12-0.30) | 1.25 (1.14-1.39) | 7.33E-06 | 0.27 (0.18-0.37) | 0.22 (0.17-0.27) | 1.53 (1.27-1.85) | 8.23E-06 |
| S100P_CpG_2,3 | 0.68 (0.64-0.72) | 0.63 (0.59-0.68) | 3.07 (2.31-4.09) | 1.63E-14 | 0.68 (0.64-0.72) | 0.65 (0.61-0.69) | 2.28 (1.59-3.27) | 7.33E-06 |
| S100P_CpG_4 | 0.89 (0.64-0.95) | 0.67 (0.38-0.91) | 1.32 (1.19-1.47) | 1.81E-07 | 0.86 (0.61-0.94) | 0.83 (0.60-0.93) | 1.08 (0.96-1.22) | 0.227 |
| S100P_CpG_7 | 0.58 (0.47-0.72) | 0.41 (0.31-0.54) | 1.61 (1.43-1.82) | 1.53E-14 | 0.49 (0.40-0.67) | 0.43 (0.32-0.61) | 1.34 (1.16-1.56) | 7.99E-05 |
| S100P_CpG_8 | 0.52 (0.45-0.59) | 0.43 (0.37-0.51) | 2.36 (1.93-2.90) | 1.10E-16 | 0.48 (0.42-0.58) | 0.45 (0.38-0.51) | 1.71 (1.37-2.15) | 2.77E-06 |
| S100P_CpG_9 | 0.58 (0.52-0.64) | 0.5 (0.45-0.56) | 2.72 (2.14-3.45) | 1.97E-16 | 0.56 (0.51-0.62) | 0.52 (0.46-0.58) | 2.07 (1.58-2.72) | 1.45E-07 |
| SLC22A18_CpG_3 | 0.21 (0.16-0.26) | 0.18 (0.14-0.21) | 2.70 (1.98-3.67) | 2.67E-10 | 0.19 (0.15-0.24) | 0.16 (0.13-0.18) | 3.78 (2.46-5.81) | 1.20E-09 |
| SLC22A18_CpG_4 | 0.26 (0.21-0.35) | 0.21 (0.17-0.26) | 1.94 (1.57-2.40) | 8.99E-10 | 0.26 (0.21-0.32) | 0.19 (0.16-0.24) | 2.96 (2.15-4.06) | 1.94E-11 |
| SLC22A18_CpG_6 | 0.29 (0.23-0.36) | 0.25 (0.21-0.29) | 2.02 (1.63-2.54) | 1.79E-09 | 0.27 (0.22-0.32) | 0.21 (0.18-0.25) | 3.35 (2.34-4.80) | 4.80E-11 |
| SLC22A18_CpG_8 | 0.65 (0.59-0.70) | 0.60 (0.55-0.65) | 2.22 (1.73-2.85) | 4.99E-10 | 0.62 (0.57-0.67) | 0.58 (0.52-0.61) | 2.61 (1.90-3.60) | 3.44E-09 |

Fig. 2 (continued)

Table 2. Methylation difference of eight genes in the three validation rounds (continued)

| CpG sites | First validation round | | | | Second validation round | | | |
|---|---|---|---|---|---|---|---|---|
| | Controls median (IQR) | FBC cases median (IQR) | OR per 10% methylation | p-value * | Controls median (IQR) | Sporadic BC cases median (IQR) | OR per 10% methylation | p-value * |
| FUT7_CpG_1 | 0.43 (0.25-0.49) | 0.31 (0.23-0.39) | 2.23 (1.87-2.67) | 9.32E-19 | 0.40 (0.30-0.51) | 0.31 (0.26-0.38) | 1.84 (1.52-2.23) | 5.20E-10 |
| FUT7_CpG_2 | 0.28 (0.21-0.32) | 0.20 (0.15-0.25) | 3.14 (2.36-4.17) | 4.08E-15 | 0.21 (0.14-0.28) | 0.16 (0.13-0.20) | 2.04 (1.56-2.67) | 2.26E-07 |
| FUT7_CpG_3 | 0.18 (0.14-0.23) | 0.13 (0.09-0.18) | 3.18 (2.37-4.28) | 2.14E-14 | 0.16 (0.10-0.27) | 0.13 (0.09-0.17) | 1.73 (1.36-2.21) | 9.46E-06 |
| FUT7_CpG_4 | 0.23 (0.19-0.30) | 0.19 (0.13-0.26) | 1.63 (1.34-1.99) | 1.46E-06 | 0.24 (0.18-0.31) | 0.21 (0.16-0.25) | 1.55 (1.23-1.95) | 1.75E-04 |
| cg02679745 | 0.31 (0.25-0.38) | 0.21 (0.15-0.26) | 3.28 (2.59-4.16) | 1.15E-22 | 0.28 (0.20-0.39) | 0.21 (0.16-0.27) | 1.98 (1.60-2.45) | 4.02E-10 |
| FUT7_CpG_7 | 0.13 (0.09-0.18) | 0.08 (0.05-0.12) | 3.87 (2.78-5.39) | 1.85E-15 | 0.12 (0.06-0.19) | 0.09 (0.06-0.13) | 1.46 (1.13-1.88) | 0.004 |
| FUT7_CpG_8 | 0.40 (0.34-0.48) | 0.31 (0.25-0.39) | 1.89 (1.60-2.23) | 3.73E-14 | 0.38 (0.30-0.49) | 0.31 (0.24-0.38) | 1.49 (1.27-1.75) | 6.88E-07 |
| RPTOR_CpG_1 | 0.11 (0.08-0.18) | 0.10 (0.06-0.15) | 1.50 (1.12-2.01) | 0.007 | 0.05 (0.00-0.17) | 0.05 (0.00-0.19) | 1.17 (1.02-1.35) | 0.028 |
| RPTOR_CpG_2 | 0.34 (0.26-0.43) | 0.29 (0.20-0.36) | 1.67 (1.36-2.05) | 1.32E-06 | 0.26 (0.11-0.45) | 0.26 (0.11-0.32) | 1.17 (1.05-1.30) | 0.004 |
| RPTOR_CpG_3 | 0.71 (0.62-0.80) | 0.64 (0.55-0.72) | 1.59 (1.31-1.92) | 1.97E-06 | 0.70 (0.50-0.94) | 0.68 (0.53-0.80) | 1.03 (0.95-1.12) | 0.511 |
| RPTOR_CpG_4 | 0.97 (0.91-1.00) | 0.91 (0.83-0.99) | 2.11 (1.57-2.85) | 7.72E-07 | 0.85 (0.65-1.00) | 0.80 (0.68-0.97) | 1.02 (0.92-1.13) | 0.670 |
| RPTOR_CpG_5 | 0.83 (0.75-0.90) | 0.80 (0.73-0.85) | 1.55 (1.21-2.00) | 6.09E-04 | 0.85 (0.70-0.97) | 0.80 (0.68-0.90) | 1.06 (0.95-1.17) | 0.288 |
| RPTOR_CpG_8 | 0.78 (0.70-0.84) | 0.72 (0.67-0.77) | 2.00 (1.52-2.63) | 8.73E-07 | 0.80 (0.62-0.96) | 0.72 (0.59-0.84) | 1.08 (0.98-1.19) | 0.116 |
| RAPSN_CpG_1 | 0.95 (0.92-0.96) | 0.94 (0.92-0.96) | 1.26 (0.81-1.95) | 0.302 | 0.97 (0.94-0.99) | 0.96 (0.92-0.98) | 1.12 (0.91-1.36) | 0.285 |
| RAPSN_CpG_2 | 0.67 (0.58-0.76) | 0.67 (0.61-0.74) | 1.06 (0.90-1.25) | 0.480 | 0.73 (0.39-0.90) | 0.67 (0.46-0.87) | 1.00 (0.93-1.07) | 0.988 |
| RAPSN_CpG_4 | 0.50 (0.39-0.62) | 0.41 (0.34-0.52) | 1.48 (1.26-1.73) | 1.11E-06 | 0.48 (0.38-0.62) | 0.36 (0.12-0.59) | 1.09 (1.02-1.16) | 0.013 |
| RAPSN_CpG_5 | 0.82 (0.71-0.88) | 0.79 (0.72-0.85) | 1.03 (0.85-1.25) | 0.757 | 0.91 (0.64-0.99) | 0.80 (0.59-0.94) | 1.09 (0.99-1.16) | 0.077 |
| RAPSN_CpG_6 | 0.67 (0.57-0.78) | 0.58 (0.48-0.68) | 1.42 (1.21-1.67) | 1.86E-05 | 0.64 (0.19-0.95) | 0.57 (0.32-0.79) | 1.01 (0.95-1.08) | 0.699 |
| RAPSN_CpG_7 | 0.74 (0.66-0.83) | 0.72 (0.63-0.79) | 1.20 (1.00-1.43) | 0.047 | 0.95 (0.63-1.00) | 0.79 (0.55-0.96) | 1.06 (0.99-1.14) | 0.123 |
| RAPSN_CpG_8 | 0.96 (0.93-0.97) | 0.95 (0.92-0.96) | 1.32 (0.79-2.20) | 0.293 | 0.97 (0.97-0.98) | 0.97 (0.96-0.98) | 0.95 (0.79-1.13) | 0.542 |

Fig. 2 (continued)

Table 2. Methylation difference of eight genes in the three validation rounds (continued)

| CpG sites | First validation round | | | | Second validation round | | | |
|---|---|---|---|---|---|---|---|---|
| | Controls median (IQR) | FBC cases median (IQR) | OR per 10% methylation | p-value * | Controls median (IQR) | Sporadic BC cases median (IQR) | OR per 10% methylation | p-value * |
| MGRN1_CpG_1 | 0.35 (0.23-0.52) | 0.23 (0.10-0.35) | 1.38 (1.22-1.56) | 3.98E-07 | 0.33 (0.02-0.63) | 0.09 (0.00-0.30) | 1.25 (1.15-1.36) | 1.24E-07 |
| MGRN1_CpG_2 | 0.63 (0.53-0.73) | 0.60 (0.56-0.66) | 1.49 (1.19-1.87) | 5.72E-04 | 0.58 (0.42-0.76) | 0.47 (0.38-0.59) | 1.23 (1.11-1.36) | 1.10E-04 |
| MGRN1_CpG_3 | 0.52 (0.32-0.67) | 0.34 (0.22-0.49) | 1.33 (1.19-1.49) | 5.08E-07 | 0.48 (0.07-0.83) | 0.19 (0.04-0.50) | 1.17 (1.10-1.25) | 1.78E-06 |
| MGRN1_CpG_4 | 0.44 (0.31-0.63) | 0.32 (0.22-0.44) | 1.33 (1.19-1.50) | 1.93E-06 | 0.45 (0.06-0.74) | 0.38 (0.04-0.42) | 1.22 (1.14-1.32) | 9.33E-08 |
| MGRN1_CpG_5,6,7,8 | 0.46 (0.33-0.56) | 0.33 (0.24-0.44) | 1.52 (1.30-1.77) | 9.82E-08 | 0.46 (0.10-0.62) | 0.23 (0.09-0.41) | 1.25 (1.15-1.37) | 5.38E-07 |
| MGRN1_CpG_11 | 0.35 (0.22-0.50) | 0.22 (0.10-0.35) | 1.37 (1.21-1.56) | 1.29E-06 | 0.31 (0.01-0.63) | 0.11 (0.00-0.34) | 1.21 (1.12-1.31) | 2.22E-06 |
| MGRN1_CpG_12 | 0.50 (0.35-0.66) | 0.38 (0.27-0.50) | 1.36 (1.21-1.54) | 7.75E-07 | 0.51 (0.09-0.83) | 0.23 (0.07-0.47) | 1.19 (1.11-1.27) | 6.44E-07 |
| MGRN1_CpG_13 | 0.65 (0.53-0.73) | 0.60 (0.56-0.66) | 1.49 (1.19-1.87) | 5.72E-04 | 0.58 (0.42-0.76) | 0.47 (0.38-0.59) | 1.23 (1.11-1.36) | 1.10E-04 |
| MGRN1_CpG_14 | 0.40 (0.33-0.53) | 0.34 (0.24-0.41) | 1.52 (1.28-1.79) | 1.08E-06 | 0.41 (0.02-0.67) | 0.25 (0.00-0.42) | 1.21 (1.12-1.31) | 1.53E-06 |
| MGRN1_CpG_15 | 0.50 (0.34-0.66) | 0.37 (0.26-0.46) | 1.44 (1.26-1.64) | 5.25E-08 | 0.53 (0.12-0.84) | 0.24 (0.05-0.51) | 1.20 (1.12-1.29) | 8.98E-08 |
| MGRN1_CpG_16,17,18 | 0.48 (0.35-0.62) | 0.35 (0.27-0.46) | 1.46 (1.27-1.68) | 2.04E-07 | 0.49 (0.10-0.74) | 0.23 (0.09-0.45) | 1.22 (1.13-1.31) | 2.78E-07 |
| MGRN1_CpG_19,20 | 0.53 (0.40-0.67) | 0.41 (0.33-0.53) | 1.46 (1.26-1.69) | 3.77E-07 | 0.52 (0.20-0.79) | 0.33 (0.18-0.53) | 1.20 (1.11-1.30) | 5.35E-06 |
| MGRN1_CpG_21 | 0.40 (0.33-0.53) | 0.34 (0.24-0.41) | 1.52 (1.28-1.79) | 1.08E-06 | 0.41 (0.02-0.67) | 0.25 (0.00-0.42) | 1.21 (1.12-1.31) | 1.53E-06 |
| MGRN1_CpG_22,23 | 0.49 (0.37-0.59) | 0.37 (0.29-0.47) | 1.52 (1.30-1.77) | 1.05E-07 | 0.46 (0.14-0.71) | 0.26 (0.09-0.45) | 1.23 (1.14-1.34) | 7.12E-07 |
| MGRN1_CpG_26 | 0.48 (0.36-0.61) | 0.38 (0.29-0.48) | 1.35 (1.17-1.55) | 2.45E-05 | 0.44 (0.07-0.74) | 0.26 (0.11-0.49) | 1.16 (1.08-1.25) | 7.97E-05 |
| MGRN1_CpG_27 | 0.51 (0.35-0.65) | 0.38 (0.28-0.50) | 1.37 (1.20-1.55) | 1.94E-06 | 0.47 (0.04-0.79) | 0.19 (0.01-0.49) | 1.16 (1.08-1.23) | 1.09E-05 |
| MGRN1_CpG_28 | 0.49 (0.35-0.58) | 0.36 (0.27-0.46) | 1.41 (1.22-1.63) | 3.65E-06 | 0.44 (0.06-0.74) | 0.21 (0.02-0.44) | 1.20 (1.12-1.29) | 1.25E-06 |
| MGRN1_CpG_29 | 0.56 (0.43-0.69) | 0.46 (0.36-0.57) | 1.38 (1.19-1.56) | 1.03E-05 | 0.52 (0.13-0.84) | 0.33 (0.15-0.57) | 1.14 (1.05-1.22) | 1.68E-04 |
| MGRN1_CpG_31 | 0.48 (0.35-0.61) | 0.40 (0.29-0.50) | 1.33 (1.15-1.53) | 9.66E-05 | 0.43 (0.09-0.76) | 0.26 (0.10-0.49) | 1.16 (1.08-1.25) | 4.73E-05 |
| MGRN1_CpG_32 | 0.39 (0.28-0.51) | 0.30 (0.22-0.39) | 1.32 (1.15-1.53) | 6.18E-05 | 0.39 (0.07-0.70) | 0.17 (0.06-0.38) | 1.20 (1.12-1.30) | 2.04E-06 |
| MGRN1_CpG_34 | 0.48 (0.41-0.60) | 0.43 (0.34-0.53) | 1.24 (1.07-1.44) | 0.003 | 0.51 (0.10-0.76) | 0.34 (0.10-0.56) | 1.11 (1.04-1.19) | 0.003 |

Fig. 2 (continued)

Table 2. Methylation difference of eight genes in the three validation rounds (continued)

| CpG sites | Third validation round | | | |
|---|---|---|---|---|
| | Controls median (IQR) | Sporadic BC cases median (IQR) | OR per 10% methylation | p-value * |
| HYAL2_CpG_1 | 0.27 (0.24-0.31) | 0.25 (0.21-0.28) | 3.01 (1.88-4.85) | 5.13E-06 |
| HYAL2_CpG_2 | 0.19 (0.17-0.23) | 0.16 (0.13-0.20) | 3.04 (1.89-4.88) | 4.48E-06 |
| HYAL2_CpG_3 | 0.32 (0.28-0.36) | 0.28 (0.24-0.32) | 3.50 (2.24-5.48) | 4.13E-08 |
| HYAL2_CpG_4 | 0.52 (0.48-0.55) | 0.47 (0.42-0.51) | 3.28 (2.18-4.94) | 1.19E-08 |
| DYRK4_CpG_1 | 0.32 (0.21-0.40) | 0.22 (0.14-0.33) | 1.20 (1.06-1.36) | 0.003 |
| DYRK4_CpG_3 | 0.25 (0.17-0.33) | 0.19 (0.13-0.28) | 1.26 (1.06-1.51) | 0.010 |
| S100P_CpG_2.3 | 0.71 (0.66-0.73) | 0.67 (0.62-0.72) | 2.86 (1.79-4.55) | 9.93E-06 |
| S100P_CpG_4 | 0.91 (0.83-0.96) | 0.89 (0.82-0.96) | 1.05 (0.92-1.20) | 0.464 |
| S100P_CpG_7 | 0.54 (0.44-0.61) | 0.47 (0.42-0.55) | 1.40 (1.16-1.69) | 5.60E-04 |
| S100P_CpG_8 | 0.54 (0.46-0.60) | 0.47 (0.39-0.56) | 2.00 (1.52-2.64) | 9.85E-07 |
| S100P_CpG_9 | 0.58 (0.54-0.63) | 0.52 (0.46-0.59) | 2.33 (1.69-3.22) | 2.61E-07 |
| SLC22A18_CpG_3 | 0.18 (0.15-0.22) | 0.14 (0.11-0.17) | 4.25 (2.56-7.04) | 1.95E-08 |
| SLC22A18_CpG_4 | 0.22 (0.18-0.28) | 0.17 (0.13-0.23) | 2.60 (1.82-3.70) | 1.16E-07 |
| SLC22A18_CpG_6 | 0.26 (0.21-0.30) | 0.20 (0.16-0.25) | 2.43 (1.70-3.48) | 1.20E-06 |
| SLC22A18_CpG_8 | 0.64 (0.59-0.70) | 0.61 (0.53-0.67) | 1.64 (1.23-2.20) | 8.40E-04 |
| FUT7_CpG_1 | 0.38 (0.30-0.46) | 0.35 (0.25-0.42) | 1.38 (1.13-1.69) | 0.002 |
| FUT7_CpG_2 | 0.23 (0.17-0.30) | 0.21 (0.13-0.27) | 1.35 (1.04-1.76) | 0.025 |
| FUT7_CpG_3 | 0.16 (0.11-0.21) | 0.14 (0.09-0.21) | 1.20 (0.95-1.53) | 0.132 |
| FUT7_CpG_4 | 0.22 (0.16-0.29) | 0.20 (0.15-0.26) | 1.28 (1.01-1.62) | 0.037 |
| cg02679745 | 0.26 (0.20-0.33) | 0.23 (0.16-0.32) | 1.36 (1.08-1.71) | 0.009 |
| FUT7_CpG_7 | 0.12 (0.08-0.18) | 0.09 (0.05-0.14) | 1.61 (1.20-2.16) | 0.001 |
| FUT7_CpG_8 | 0.37 (0.27-0.45) | 0.31 (0.23-0.40) | 1.34 (1.11-1.61) | 0.002 |
| RPTOR_CpG_1 | 0.09 (0.07-0.15) | 0.07 (0.03-0.10) | 3.42 (2.16-5.43) | 1.63E-07 |
| RPTOR_CpG_2 | 0.27 (0.20-0.35) | 0.20 (0.15-0.28) | 2.66 (1.96-3.61) | 2.90E-10 |
| RPTOR_CpG_3 | 0.66 (0.59-0.73) | 0.60 (0.55-0.68) | 1.66 (1.30-2.13) | 5.11E-05 |
| RPTOR_CpG_4 | 0.84 (0.72-0.97) | 0.77 (0.68-0.93) | 1.86 (1.41-2.45) | 1.22E-05 |
| RPTOR_CpG_5 | 0.78 (0.74-0.84) | 0.74 (0.69-0.82) | 1.87 (1.41-2.49) | 1.74E-05 |
| RPTOR_CpG_8 | 0.72 (0.66-0.76) | 0.68 (0.62-0.73) | 2.06 (1.49-2.85) | 1.30E-05 |

Fig. 2 (continued)

Table 2. Methylation difference of eight genes in the three validation rounds (continued)

| CpG sites | Third validation round | | | |
|---|---|---|---|---|
| | Controls median (IQR) | Sporadic BC cases median (IQR) | OR per 10% methylation | p-value * |
| RAPSN_CpG_1 | 0.96 (0.93-0.98) | 0.95 (0.93-0.98) | 1.16 (0.71-1.92) | 0.551 |
| RAPSN_CpG_2 | 0.66 (0.59-0.72) | 0.62 (0.52-0.70) | 1.44 (1.18-1.76) | 4.15E-04 |
| RAPSN_CpG_4 | 0.48 (0.37-0.54) | 0.39 (0.32-0.47) | 1.49 (1.23-1.80) | 5.61E-05 |
| RAPSN_CpG_5 | 0.79 (0.73-0.84) | 0.74 (0.66-0.82) | 1.57 (1.25-1.99) | 1.34E-04 |
| RAPSN_CpG_6 | 0.60 (0.51-0.67) | 0.53 (0.44-0.61) | 1.47 (1.22-1.77) | 4.42E-05 |
| RAPSN_CpG_7 | 0.75 (0.68-0.80) | 0.72 (0.65-0.80) | 1.19 (0.95-1.48) | 0.128 |
| RAPSN_CpG_8 | 0.95 (0.93-0.97) | 0.96 (0.93-0.97) | 0.95 (0.53-1.71) | 0.871 |
| MGRN1_CpG_1 | 0.23 (0.13-0.34) | 0.14 (0.07-0.28) | 1.31 (1.11-1.55) | 0.002 |
| MGRN1_CpG_2 | 0.64 (0.59-0.69) | 0.61 (0.56-0.66) | 1.46 (1.10-1.94) | 0.008 |
| MGRN1_CpG_3 | 0.40 (0.30-0.50) | 0.30 (0.20-0.38) | 1.63 (1.35-1.95) | 1.85E-07 |
| MGRN1_CpG_4 | 0.33 (0.25-0.44) | 0.26 (0.19-0.35) | 1.44 (1.20-1.72) | 6.89E-05 |
| MGRN1_CpG_5.6.7.8 | 0.35 (0.27-0.44) | 0.28 (0.21-0.36) | 1.74 (1.39-2.18) | 1.65E-06 |
| MGRN1_CpG_11 | 0.17 (0.11-0.31) | 0.14 (0.07-0.21) | 1.39 (1.15-1.68) | 6.48E-04 |
| MGRN1_CpG_12 | 0.38 (0.295-0.5) | 0.32 (0.22-0.39) | 1.56 (1.30-1.89) | 2.83E-06 |
| MGRN1_CpG_13 | 0.64 (0.59-0.69) | 0.61 (0.56-0.66) | 1.29 (1.00-1.67) | 0.053 |
| MGRN1_CpG_14 | 0.34 (0.28-0.42) | 0.28 (0.19-0.34) | 1.83 (1.45-2.31) | 4.59E-07 |
| MGRN1_CpG_15 | 0.41 (0.33-0.49) | 0.32 (0.24-0.42) | 1.62 (1.33-1.98) | 1.33E-06 |
| MGRN1_CpG_16.17.18 | 0.37 (0.31-0.47) | 0.31 (0.25-0.38) | 1.61 (1.29-2.01) | 2.11E-05 |
| MGRN1_CpG_19.20 | 0.44 (0.36-0.54) | 0.36 (0.26-0.44) | 1.74 (1.41-2.16) | 2.56E-07 |
| MGRN1_CpG_21 | 0.34 (0.28-0.42) | 0.28 (0.19-0.34) | 1.83 (1.45-2.31) | 4.59E-07 |
| MGRN1_CpG_22.23 | 0.39 (0.31-0.46) | 0.33 (0.25-0.39) | 1.72 (1.37-2.17) | 2.76E-06 |
| MGRN1_CpG_26 | 0.40 (0.32-0.48) | 0.31 (0.25-0.39) | 1.77 (1.43-2.20) | 2.31E-07 |
| MGRN1_CpG_27 | 0.40 (0.30-0.49) | 0.30 (0.20-0.40) | 1.70 (1.40-2.06) | 7.99E-08 |
| MGRN1_CpG_28 | 0.37 (0.29-0.46) | 0.31 (0.22-0.38) | 1.58 (1.28-1.95) | 2.11E-05 |
| MGRN1_CpG_29 | 0.47 (0.40-0.56) | 0.38 (0.32-0.47) | 1.83 (1.47-2.29) | 7.69E-08 |
| MGRN1_CpG_31 | 0.39 (0.33-0.48) | 0.34 (0.27-0.42) | 1.69 (1.35-2.10) | 2.83E-06 |
| MGRN1_CpG_32 | 0.34 (0.26-0.42) | 0.27 (0.17-0.36) | 1.44 (1.20-1.73) | 1.18E-04 |
| MGRN1_CpG_34 | 0.43 (0.35-0.52) | 0.36 (0.29-0.44) | 1.50 (1.25-1.81) | 1.98E-05 |

Fig. 3

Table 3. The discriminatory power of DNA methylation marker sets to distinguish BC cases from healthy controls in samples from other centers (first and second validation rounds)

| Marker sets | First validation round | | Second validation round | | | |
|---|---|---|---|---|---|---|
| | All cases vs. All controls | | All cases vs. All controls | | Stage 0&I vs. All controls | |
| | N (case vs. control) | AUC (95% CI) | N (case vs. control) | AUC (95% CI) | N (case vs. control) | AUC (95% CI) |
| HYAL2 | 267 vs. 250 | 0.85 (0.82-0.89) | 188 vs. 189 | 0.88 (0.85-0.92) | 101 vs. 189 | 0.88 (0.84-0.92) |
| S100P, SLC22A18, DYRK4, FUT7 | 265 vs. 246 | 0.86 (0.83-0.89) | 189 vs. 189 | 0.80 (0.75-0.84) | 101 vs. 189 | 0.78 (0.73-0.83) |
| MGRN1, RPTOR, RAPSN | 267 vs. 250 | 0.80 (0.76-0.84) | 189 vs. 189 | 0.76 (0.71-0.81) | 101 vs. 189 | 0.74 (0.69-0.80) |
| HYAL2, S100P, SLC22A18, DYRK4, FUT7 | 265 vs. 245 | 0.90 (0.88-0.93) | 188 vs. 189 | 0.90 (0.87-0.93) | 101 vs. 189 | 0.90 (0.87-0.94) |
| HYAL2, MGRN1, RPTOR, RAPSN | 267 vs. 249 | 0.90 (0.87-0.92) | 188 vs. 189 | 0.91 (0.88-0.94) | 101 vs. 189 | 0.91 (0.87-0.94) |
| S100P, SLC22A18, DYRK4, FUT7, MGRN1, RPTOR, RAPSN | 265 vs. 245 | 0.91 (0.88-0.93) | 189 vs. 189 | 0.86 (0.83-0.90) | 101 vs. 189 | 0.84 (0.80-0.89) |
| HYAL2, S100P, SLC22A18, DYRK4, FUT7, MGRN1, RPTOR, RAPSN | 265 vs. 244 | 0.94 (0.92-0.96) | 188 vs. 189 | 0.93 (0.91-0.96) | 101 vs. 189 | 0.93 (0.90-0.96) |

Fig. 3 (continued)

Table 3. The discriminatory power of DNA methylation marker sets to distinguish BC cases from healthy controls in samples from other centers (first and second validation rounds)(continued)

| Marker sets | Samples from other centers (1st+2nd validation rounds) | | | | | |
|---|---|---|---|---|---|---|
| | All cases vs. All control | | Age < 50 | | Age >=50 | |
| | N (case vs. control) | AUC (95% CI) | N (case vs. control) | AUC (95% CI) | N (case vs. control) | AUC (95% CI) |
| HYAL2 | 455 vs. 439 | 0.86 (0.84-0.88) | 251 vs. 226 | 0.86 (0.83-0.90) | 204 vs. 213 | 0.86 (0.83-0.90) |
| S100P, SLC22A18, DYRK4, FUT7 | 454 vs. 435 | 0.81 (0.78-0.84) | 251 vs. 223 | 0.88 (0.85-0.91) | 203 vs. 212 | 0.77 (0.73-0.82) |
| MGRN1, RPTOR, RAPSN | 456 vs. 439 | 0.74 (0.71-0.78) | 252 vs. 226 | 0.81 (0.78-0.85) | 204 vs. 213 | 0.74 (0.69-0.79) |
| HYAL2, S100P, SLC22A18, DYRK4, FUT7 | 453 vs. 434 | 0.89 (0.87-0.91) | 250 vs. 222 | 0.92 (0.90-0.95) | 203 vs. 212 | 0.89 (0.85-0.92) |
| HYAL2, MGRN1, RPTOR, RAPSN | 455 vs. 438 | 0.88 (0.86-0.90) | 251 vs. 225 | 0.90 (0.87-0.93) | 204 vs. 213 | 0.89 (0.86-0.93) |
| S100P, SLC22A18, DYRK4, FUT7, MGRN1, RPTOR, RAPSN | 454 vs. 434 | 0.85 (0.82-0.87) | 251 vs. 222 | 0.92 (0.90-0.95) | 203 vs. 212 | 0.84 (0.80-0.87) |
| HYAL2, S100P, SLC22A18, DYRK4, FUT7, MGRN1, RPTOR, RAPSN | 453 vs. 433 | 0.91 (0.89-0.93) | 250 vs. 221 | 0.95 (0.93-0.97) | 203 vs. 212 | 0.92 (0.89-0.94) |

Fig. 4

Table 4. The discriminatory power of DNA methylation marker sets and miRNA marker sets to distinguish BC cases from healthy controls in samples from the third validation round

| Marker sets | All cases vs. All control | | Stage 0&I vs. All controls | | Age < 50 | | Age >=50 | |
|---|---|---|---|---|---|---|---|---|
| | N (case vs. control) | AUC (95% CI) | N (case vs. control) | AUC (95% CI) | N (case vs. control) | AUC (95% CI) | N (case vs. control) | AUC (95% CI) |
| HYAL2 | 161 vs. 149 | 0.72 (0.67-0.78) | 57 vs. 149 | 0.79 (0.72-0.85) | 116 vs. 98 | 0.85 (0.80-0.90) | 45 vs. 51 | 0.73 (0.63-0.83) |
| S100P, SLC22A18, DYRK4, FUT7 | 158 vs. 148 | 0.76 (0.71-0.82) | 55 vs. 148 | 0.84 (0.77-0.90) | 113 vs. 98 | 0.88 (0.84-0.93) | 45 vs. 50 | 0.85 (0.76-0.93) |
| MGRN1, RPTOR, RAPSN | 158 vs. 147 | 0.82 (0.77-0.87) | 56 vs. 147 | 0.89 (0.84-0.94) | 113 vs. 96 | 0.93 (0.89-0.96) | 45 vs. 51 | 0.89 (0.82-0.95) |
| HYAL2, S100P, SLC22A18, DYRK4, FUT7 | 158 vs. 148 | 0.77 (0.72-0.83) | 55 vs. 148 | 0.86 (0.80-0.92) | 113 vs. 98 | 0.90 (0.86-0.94) | 45 vs. 50 | 0.87 (0.80-0.95) |
| HYAL2, MGRN1, RPTOR, RAPSN | 158 vs. 147 | 0.83 (0.78-0.88) | 56 vs. 147 | 0.90 (0.85-0.94) | 113 vs. 96 | 0.94 (0.91-0.97) | 45 vs. 51 | 0.90 (0.84-0.96) |
| S100P, SLC22A18, DYRK4, FUT7, MGRN1, RPTOR, RAPSN | 155 vs. 146 | 0.85 (0.81-0.90) | 54 vs. 146 | 0.94 (0.90-0.97) | 110 vs. 96 | 0.96 (0.94-0.99) | 45 vs. 50 | 1.00 (1.00-1.00) |
| HYAL2, S100P, SLC22A18, DYRK4, FUT7, MGRN1, RPTOR, RAPSN | 155 vs. 146 | 0.86 (0.82-0.90) | 54 vs. 146 | 0.94 (0.91-0.97) | 110 vs. 96 | 0.98 (0.96-1.00) | 45 vs. 50 | 1.00 (1.00-1.00) |
| 7miRNA | 153 vs. 148 | 0.82 (0.77-0.86) | 53 vs. 148 | 0.80 (0.73-0.87) | 109 vs. 98 | 0.90 (0.85-0.94) | 44 vs. 50 | 0.84 (0.76-0.92) |
| HYAL2, 7miRNA | 153 vs. 148 | 0.86 (0.81-0.90) | 53 vs. 148 | 0.86 (0.81-0.92) | 109 vs. 98 | 0.93 (0.90-0.96) | 44 vs. 50 | 0.86 (0.78-0.93) |
| S100P, SLC22A18, DYRK4, FUT7, 7miRNA | 150 vs. 147 | 0.89 (0.86-0.93) | 51 vs. 147 | 0.91 (0.86-0.96) | 106 vs. 98 | 0.96 (0.94-0.98) | 44 vs. 49 | 0.93 (0.87-0.98) |
| MGRN1, RPTOR, RAPSN, 7miRNA | 149 vs. 144 | 0.91 (0.88-0.94) | 52 vs. 144 | 0.95 (0.92-0.98) | 106 vs. 96 | 0.97 (0.95-0.99) | 44 vs. 50 | 0.97 (0.94-1.00) |
| HYAL2, S100P, SLC22A18, DYRK4, FUT7, 7miRNA | 150 vs. 147 | 0.90 (0.86-0.93) | 51 vs. 147 | 0.92 (0.88-0.97) | 106 vs. 98 | 0.97 (0.94-0.99) | 44 vs. 49 | 0.94 (0.89-0.98) |
| HYAL2, MGRN1, RPTOR, RAPSN, 7miRNA | 149 vs. 144 | 0.91 (0.88-0.95) | 52 vs. 144 | 0.96 (0.93-0.99) | 106 vs. 96 | 0.98 (0.96-0.99) | 44 vs. 50 | 1.00 (1.00-1.00) |
| S100P, SLC22A18, DYRK4, FUT7, MGRN1, RPTOR, RAPSN, 7miRNA | 146 vs. 143 | 0.94 (0.91-0.97) | 50 vs. 143 | 1.00 (1.00-1.00) | 103 vs. 96 | 1.00 (1.00-1.00) | 44 vs. 49 | 1.00 (1.00-1.00) |
| HYAL2, S100P, SLC22A18, DYRK4, FUT7, MGRN1, RPTOR,RAPSN, 7miRNA | 146 vs. 143 | 0.94 (0.92-0.97) | 50 vs. 143 | 1.00 (1.00-1.00) | 103 vs. 96 | 1.00 (1.00-1.00) | 44 vs. 49 | 1.00 (1.00-1.00) |

Fig. 5

Table 5. The methylation leveles of the eight genes in sporadic BC patients with different clinical characteristics (cases from second validation round)

| Clinical characteristics (N) | Group (N) | Median of age | Median of methylation levels ||||||
|---|---|---|---|---|---|---|---|---|
| | | | HYAL2_CpG_1 | HYAL2_CpG_2 | HYAL2_CpG_3 | HYAL2_CpG_4 | DYRK4_CpG_1 | DYRK4_CpG_3 |
| Tumour stage (188) | Stage 0&I (101) | 59.23 | 0.30 | 0.17 | 0.33 | 0.50 | 0.25 | 0.23 |
| | Stage II (61) | 57.80 | 0.31 | 0.17 | 0.32 | 0.50 | 0.27 | 0.21 |
| | Stage III (26) | 68.11 | 0.29 | 0.13 | 0.28 | 0.51 | 0.26 | 0.21 |
| | $p$-value (Kruskal Wallis Test) | 0.166 | 0.937 | 0.008 | 0.001 | 0.846 | 0.726 | 0.407 |
| Tumour size (188) | Tis&T1 (119) | 59.23 | 0.30 | 0.17 | 0.33 | 0.50 | 0.26 | 0.22 |
| | T2 (57) | 60.33 | 0.32 | 0.16 | 0.32 | 0.50 | 0.26 | 0.21 |
| | T3 and T4 (12) | 71.04 | 0.26 | 0.12 | 0.27 | 0.52 | 0.24 | 0.22 |
| | $p$-value (Kruskal Wallis Test) | 0.191 | 0.637 | 0.041 | 0.001 | 0.983 | 0.514 | 0.681 |
| Lymph node (LN) involvement (185) | no involved LN (132) | 60.00 | 0.30 | 0.17 | 0.33 | 0.50 | 0.26 | 0.22 |
| | 1-3 involved LN (30) | 55.59 | 0.30 | 0.18 | 0.32 | 0.52 | 0.28 | 0.20 |
| | > 3 involved LN (23) | 67.92 | 0.29 | 0.12 | 0.27 | 0.51 | 0.27 | 0.21 |
| | $p$-value (Kruskal Wallis Test) | 0.265 | 0.875 | 0.003 | 0.004 | 0.661 | 0.946 | 0.139 |
| Grading (187) | Grade 1 (35) | 58.78 | 0.30 | 0.15 | 0.32 | 0.51 | 0.24 | 0.24 |
| | Grade 2 (114) | 61.50 | 0.29 | 0.17 | 0.33 | 0.50 | 0.26 | 0.21 |
| | Grade 3 (38) | 60.42 | 0.32 | 0.16 | 0.32 | 0.50 | 0.26 | 0.21 |
| | $p$-value (Kruskal Wallis Test) | 0.731 | 0.262 | 0.592 | 0.970 | 0.949 | 0.617 | 0.777 |
| ER status (185) | ER negative (23) | 57.72 | 0.34 | 0.16 | 0.32 | 0.50 | 0.26 | 0.22 |
| | ER positive (162) | 60.67 | 0.29 | 0.17 | 0.32 | 0.50 | 0.26 | 0.22 |
| | $p$-value (Mann-Whitney U) | 0.150 | 0.017 | 0.371 | 0.862 | 0.489 | 0.303 | 0.397 |
| PR status (186) | PR negative (38) | 60.97 | 0.33 | 0.16 | 0.32 | 0.51 | 0.25 | 0.21 |
| | PR positive (148) | 59.24 | 0.29 | 0.17 | 0.32 | 0.50 | 0.26 | 0.22 |
| | $p$-value (Mann-Whitney U) | 0.797 | 0.014 | 0.142 | 0.495 | 0.124 | 0.973 | 0.626 |
| Her2 status (185) | Her2 negative (166) | 60.71 | 0.30 | 0.17 | 0.33 | 0.51 | 0.26 | 0.22 |
| | Her2 positive (19) | 51.52 | 0.30 | 0.17 | 0.31 | 0.49 | 0.27 | 0.21 |
| | $p$-value (Mann-Whitney U) | 0.357 | 0.855 | 0.386 | 0.225 | 0.451 | 0.504 | 0.724 |
| Three receptor status (185) | Tripple negative (15) | 59.67 | 0.40 | 0.14 | 0.32 | 0.51 | 0.26 | 0.22 |
| | Others (170) | 59.88 | 0.30 | 0.17 | 0.32 | 0.50 | 0.26 | 0.22 |
| | $p$-value (Mann-Whitney U) | 0.310 | 0.062 | 0.072 | 0.683 | 0.281 | 0.358 | 0.264 |
| Menopause status (180) | premenopause (56) | 47.19 | 0.30 | 0.17 | 0.33 | 0.50 | 0.27 | 0.22 |
| | postmenopause (124) | 67.64 | 0.31 | 0.17 | 0.32 | 0.51 | 0.26 | 0.22 |
| | $p$-value (Mann-Whitney U) | — | 0.678 | 0.627 | 0.558 | 0.157 | 0.756 | 0.294 |
| BC family history (186) | with BC family history (30) | 58.96 | 0.29 | 0.17 | 0.32 | 0.51 | 0.29 | 0.26 |
| | without BC family history (156) | 60.45 | 0.30 | 0.17 | 0.33 | 0.51 | 0.26 | 0.21 |
| | $p$-value (Mann-Whitney U) | 0.296 | 0.533 | 0.243 | 0.211 | 0.476 | 0.202 | 0.055 |

Fig. 5 (continued)

Table 5. The methylation leveles of the eight genes in sporadic BC patients with different clinical characteristics (cases from second validation round) (continued)

| Clinical characteristics (N) | Group (N) | Median of methylation levels ||||| 
|---|---|---|---|---|---|---|
| | | S100P_CpG_2.3 | S100P_CpG_4 | S100P_CpG_7 | S100P_CpG_8 | S100P_CpG_9 |
| Tumour stage (188) | Stage 0&I (101) | 0.65 | 0.83 | 0.40 | 0.44 | 0.52 |
| | Stage II (61) | 0.64 | 0.83 | 0.45 | 0.45 | 0.52 |
| | Stage III (26) | 0.66 | 0.90 | 0.47 | 0.47 | 0.53 |
| | p-value (Kruskal Wallis Test) | 0.427 | 0.746 | 0.290 | 0.843 | 0.679 |
| Tumour size (188) | Tis&T1 (119) | 0.65 | 0.84 | 0.43 | 0.44 | 0.52 |
| | T2 (57) | 0.64 | 0.69 | 0.42 | 0.45 | 0.51 |
| | T3 and T4 (12) | 0.67 | 0.92 | 0.52 | 0.48 | 0.56 |
| | p-value (Kruskal Wallis Test) | 0.223 | 0.298 | 0.306 | 0.570 | 0.230 |
| Lymph node (LN) involvement (185) | no involved LN (132) | 0.65 | 0.82 | 0.41 | 0.44 | 0.52 |
| | 1-3 involved LN (30) | 0.66 | 0.85 | 0.48 | 0.46 | 0.52 |
| | > 3 involved LN (23) | 0.66 | 0.91 | 0.47 | 0.47 | 0.53 |
| | p-value (Kruskal Wallis Test) | 0.572 | 0.549 | 0.205 | 0.355 | 0.429 |
| Grading (187) | Grade 1 (35) | 0.65 | 0.65 | 0.45 | 0.42 | 0.52 |
| | Grade 2 (114) | 0.65 | 0.84 | 0.41 | 0.44 | 0.52 |
| | Grade 3 (38) | 0.66 | 0.86 | 0.51 | 0.47 | 0.53 |
| | p-value (Kruskal Wallis Test) | 0.757 | 0.490 | 0.290 | 0.394 | 0.500 |
| ER status (185) | ER negative (23) | 0.64 | 0.89 | 0.40 | 0.45 | 0.52 |
| | ER positive (162) | 0.65 | 0.83 | 0.43 | 0.45 | 0.52 |
| | p-value (Mann-Whitney U) | 0.376 | 0.195 | 0.988 | 0.606 | 0.725 |
| PR status (186) | PR negative (38) | 0.65 | 0.86 | 0.42 | 0.45 | 0.52 |
| | PR positive (148) | 0.65 | 0.83 | 0.44 | 0.45 | 0.52 |
| | p-value (Mann-Whitney U) | 0.232 | 0.619 | 0.984 | 0.474 | 0.878 |
| Her2 status (185) | Her2 negative (166) | 0.66 | 0.85 | 0.43 | 0.45 | 0.52 |
| | Her2 positive (19) | 0.61 | 0.69 | 0.40 | 0.42 | 0.49 |
| | p-value (Mann-Whitney U) | 0.030 | 0.056 | 0.679 | 0.139 | 0.122 |
| Three receptor status (185) | Tripple negative (15) | 0.66 | 0.91 | 0.48 | 0.46 | 0.52 |
| | Others (170) | 0.65 | 0.83 | 0.43 | 0.44 | 0.52 |
| | p-value (Mann-Whitney U) | 0.801 | 0.172 | 0.697 | 0.749 | 0.774 |
| Menopause status (180) | premenopause (56) | 0.63 | 0.84 | 0.38 | 0.42 | 0.49 |
| | postmenopause (124) | 0.66 | 0.83 | 0.45 | 0.46 | 0.53 |
| | p-value (Mann-Whitney U) | 0.004 | 0.790 | 0.032 | 0.012 | 0.004 |
| BC family history (186) | with BC family history (30) | 0.64 | 0.65 | 0.42 | 0.42 | 0.52 |
| | without BC family history (156) | 0.66 | 0.84 | 0.44 | 0.45 | 0.52 |
| | p-value (Mann-Whitney U) | 0.407 | 0.198 | 0.932 | 0.586 | 0.405 |

Fig. 5 (continued)

Table 5. The methylation leveles of the eight genes in sporadic BC patients with different clinical characteristics (cases from second validation round) (continued)

| Clinical characteristics (N) | Group (N) | Median of methylation levels ||||||
|---|---|---|---|---|---|---|---|
| | | FUT7_CpG_2 | FUT7_CpG_3 | FUT7_CpG_4 | FUT7_CpG_6 | FUT7_CpG_7 | FUT7_CpG_8 |
| Tumour stage (188) | Stage 0&I (101) | 0.17 | 0.13 | 0.22 | 0.22 | 0.09 | 0.34 |
| | Stage II (61) | 0.17 | 0.14 | 0.21 | 0.21 | 0.10 | 0.31 |
| | Stage III (26) | 0.13 | 0.11 | 0.17 | 0.17 | 0.08 | 0.30 |
| | p-value (Kruskal Wallis Test) | 0.033 | 0.135 | 0.169 | 0.003 | 0.226 | 0.790 |
| Tumour size (188) | Tis&T1 (119) | 0.17 | 0.13 | 0.21 | 0.21 | 0.09 | 0.34 |
| | T2 (57) | 0.16 | 0.14 | 0.22 | 0.21 | 0.09 | 0.30 |
| | T3 and T4 (12) | 0.12 | 0.11 | 0.16 | 0.14 | 0.07 | 0.31 |
| | p-value (Kruskal Wallis Test) | 0.220 | 0.720 | 0.448 | 0.010 | 0.180 | 0.296 |
| Lymph node (LN) involvement (185) | no involved LN (132) | 0.17 | 0.13 | 0.22 | 0.21 | 0.09 | 0.31 |
| | 1-3 involved LN (30) | 0.17 | 0.15 | 0.22 | 0.24 | 0.11 | 0.33 |
| | > 3 involved LN (23) | 0.13 | 0.11 | 0.16 | 0.17 | 0.08 | 0.32 |
| | p-value (Kruskal Wallis Test) | 0.044 | 0.207 | 0.080 | 0.017 | 0.194 | 0.957 |
| Grading (187) | Grade 1 (35) | 0.18 | 0.13 | 0.22 | 0.24 | 0.11 | 0.35 |
| | Grade 2 (114) | 0.15 | 0.13 | 0.21 | 0.20 | 0.09 | 0.30 |
| | Grade 3 (38) | 0.18 | 0.14 | 0.20 | 0.22 | 0.10 | 0.33 |
| | p-value (Kruskal Wallis Test) | 0.019 | 0.628 | 0.446 | 0.110 | 0.673 | 0.234 |
| ER status (185) | ER negative (23) | 0.16 | 0.13 | 0.19 | 0.20 | 0.08 | 0.29 |
| | ER positive (162) | 0.17 | 0.13 | 0.21 | 0.21 | 0.09 | 0.33 |
| | p-value (Mann-Whitney U) | 0.653 | 0.691 | 0.378 | 0.478 | 0.107 | 0.607 |
| PR status (186) | PR negative (38) | 0.17 | 0.14 | 0.22 | 0.22 | 0.09 | 0.32 |
| | PR positive (148) | 0.17 | 0.13 | 0.21 | 0.21 | 0.09 | 0.31 |
| | p-value (Mann-Whitney U) | 0.441 | 0.553 | 0.679 | 0.479 | 0.761 | 0.292 |
| Her2 status (185) | Her2 negative (166) | 0.17 | 0.13 | 0.21 | 0.21 | 0.09 | 0.32 |
| | Her2 positive (19) | 0.15 | 0.13 | 0.19 | 0.22 | 0.08 | 0.31 |
| | p-value (Mann-Whitney U) | 0.429 | 0.756 | 0.628 | 0.991 | 0.464 | 0.924 |
| Three receptor status (185) | Tripple negative (15) | 0.17 | 0.11 | 0.19 | 0.20 | 0.08 | 0.29 |
| | Others (170) | 0.17 | 0.13 | 0.21 | 0.21 | 0.09 | 0.33 |
| | p-value (Mann-Whitney U) | 0.397 | 0.254 | 0.327 | 0.371 | 0.036 | 0.323 |
| Menopause status (180) | premenopause (56) | 0.16 | 0.13 | 0.20 | 0.20 | 0.08 | 0.27 |
| | postmenopause (124) | 0.17 | 0.14 | 0.22 | 0.21 | 0.09 | 0.34 |
| | p-value (Mann-Whitney U) | 0.490 | 0.321 | 0.498 | 0.549 | 0.225 | 0.021 |
| BC family history (186) | with BC family history (30) | 0.15 | 0.13 | 0.23 | 0.21 | 0.08 | 0.29 |
| | without BC family history (156) | 0.17 | 0.13 | 0.21 | 0.21 | 0.10 | 0.32 |
| | p-value (Mann-Whitney U) | 0.628 | 0.662 | 0.817 | 0.884 | 0.064 | 0.347 |

Fig. 5 (continued)

Table 5. The methylation leveles of the eight genes in sporadic BC patients with different clinical characteristics (cases from second validation round) (continued)

| Clinical characteristics (N) | Group (N) | Median of methylation levels | | | |
|---|---|---|---|---|---|
| | | SLC22A18_CpG_3 | SLC22A18_CpG_4 | SLC22A18_CpG_6 | SLC22A18_CpG_8 |
| Tumour stage (188) | Stage 0&I (101) | 0.16 | 0.21 | 0.22 | 0.58 |
| | Stage II (61) | 0.16 | 0.19 | 0.22 | 0.57 |
| | Stage III (26) | 0.13 | 0.17 | 0.20 | 0.54 |
| | p-value (Kruskal Wallis Test) | 0.005 | 0.010 | 0.048 | 0.031 |
| Tumour size (188) | Tis&T1 (119) | 0.16 | 0.21 | 0.22 | 0.58 |
| | T2 (57) | 0.16 | 0.19 | 0.21 | 0.59 |
| | T3 and T4 (12) | 0.14 | 0.17 | 0.20 | 0.53 |
| | p-value (Kruskal Wallis Test) | 0.111 | 0.022 | 0.270 | 0.078 |
| Lymph node (LN) involvement (185) | no involved LN (132) | 0.16 | 0.20 | 0.22 | 0.58 |
| | 1-3 involved LN (30) | 0.16 | 0.22 | 0.22 | 0.59 |
| | > 3 involved LN (23) | 0.13 | 0.17 | 0.18 | 0.53 |
| | p-value (Kruskal Wallis Test) | 0.005 | 0.048 | 0.048 | 0.038 |
| Grading (187) | Grade 1 (35) | 0.16 | 0.19 | 0.21 | 0.60 |
| | Grade 2 (114) | 0.16 | 0.19 | 0.21 | 0.57 |
| | Grade 3 (38) | 0.16 | 0.22 | 0.22 | 0.58 |
| | p-value (Kruskal Wallis Test) | 0.292 | 0.152 | 0.533 | 0.158 |
| ER status (185) | ER negative (23) | 0.16 | 0.21 | 0.22 | 0.57 |
| | ER positive (162) | 0.16 | 0.19 | 0.21 | 0.58 |
| | p-value (Mann-Whitney U) | 0.647 | 0.558 | 0.764 | 0.877 |
| PR status (186) | PR negative (38) | 0.15 | 0.21 | 0.22 | 0.57 |
| | PR positive (148) | 0.16 | 0.19 | 0.21 | 0.58 |
| | p-value (Mann-Whitney U) | 0.787 | 0.761 | 0.996 | 0.837 |
| Her2 status (185) | Her2 negative (166) | 0.16 | 0.20 | 0.22 | 0.58 |
| | Her2 positive (19) | 0.15 | 0.19 | 0.19 | 0.57 |
| | p-value (Mann-Whitney U) | 0.606 | 0.700 | 0.188 | 0.809 |
| Three receptor status (185) | Tripple negative (15) | 0.16 | 0.21 | 0.22 | 0.56 |
| | Others (170) | 0.16 | 0.19 | 0.21 | 0.58 |
| | p-value (Mann-Whitney U) | 0.737 | 0.581 | 0.493 | 0.724 |
| Menopause status (180) | premenopause (56) | 0.15 | 0.18 | 0.21 | 0.59 |
| | postmenopause (124) | 0.16 | 0.21 | 0.22 | 0.57 |
| | p-value (Mann-Whitney U) | 0.408 | 0.325 | 0.236 | 0.327 |
| BC family history (186) | with BC family history (30) | 0.16 | 0.21 | 0.22 | 0.58 |
| | without BC family history (156) | 0.16 | 0.19 | 0.22 | 0.58 |
| | p-value (Mann-Whitney U) | 0.403 | 0.391 | 0.748 | 0.342 |

Fig. 5 (continued)

Table 5. The methylation leveles of the eight genes in sporadic BC patients with different clinical characteristics (cases from second validation round) (continued)

| Clinical characteristics (N) | Group (N) | Median of methylation levels ||||||
|---|---|---|---|---|---|---|---|
| | | RPTOR_CpG_1 | RPTOR_CpG_2 | RPTOR_CpG_3 | RPTOR_CpG_4 | RPTOR_CpG_5 | RPTOR_CpG_8 |
| Tumour stage (188) | Stage 0&I (101) | 0.07 | 0.22 | 0.70 | 0.80 | 0.82 | 0.74 |
| | Stage II (61) | 0.02 | 0.18 | 0.67 | 0.75 | 0.75 | 0.72 |
| | Stage III (26) | 0.02 | 0.17 | 0.61 | 0.92 | 0.80 | 0.69 |
| | p-value (Kruskal Wallis Test) | 0.026 | 0.173 | 0.197 | 0.109 | 0.138 | 0.260 |
| Tumour size (188) | Tis&T1 (119) | 0.06 | 0.22 | 0.72 | 0.80 | 0.83 | 0.74 |
| | T2 (57) | 0.02 | 0.19 | 0.62 | 0.76 | 0.74 | 0.69 |
| | T3 and T4 (12) | 0.03 | 0.17 | 0.62 | 0.92 | 0.77 | 0.69 |
| | p-value (Kruskal Wallis Test) | 0.095 | 0.341 | 0.036 | 0.171 | 0.028 | 0.406 |
| Lymph node (LN) involvement (185) | no involved LN (132) | 0.05 | 0.20 | 0.67 | 0.78 | 0.80 | 0.72 |
| | 1-3 involved LN (30) | 0.04 | 0.20 | 0.75 | 0.83 | 0.82 | 0.76 |
| | > 3 involved LN (23) | 0.02 | 0.15 | 0.49 | 0.89 | 0.79 | 0.67 |
| | p-value (Kruskal Wallis Test) | 0.702 | 0.377 | 0.028 | 0.208 | 0.934 | 0.050 |
| Grading (187) | Grade 1 (35) | 0.08 | 0.18 | 0.66 | 0.78 | 0.82 | 0.70 |
| | Grade 2 (114) | 0.04 | 0.20 | 0.68 | 0.78 | 0.81 | 0.72 |
| | Grade 3 (38) | 0.05 | 0.21 | 0.66 | 0.93 | 0.79 | 0.69 |
| | p-value (Kruskal Wallis Test) | 0.231 | 0.798 | 0.666 | 0.052 | 0.812 | 0.919 |
| ER status (185) | ER negative (23) | 0.07 | 0.28 | 0.69 | 0.85 | 0.79 | 0.68 |
| | ER positive (162) | 0.04 | 0.19 | 0.68 | 0.79 | 0.80 | 0.72 |
| | p-value (Mann-Whitney U) | 0.272 | 0.057 | 0.705 | 0.158 | 0.868 | 0.557 |
| PR status (186) | PR negative (38) | 0.08 | 0.25 | 0.65 | 0.81 | 0.81 | 0.68 |
| | PR positive (148) | 0.04 | 0.20 | 0.68 | 0.79 | 0.79 | 0.73 |
| | p-value (Mann-Whitney U) | 0.195 | 0.471 | 0.623 | 0.334 | 0.241 | 0.511 |
| Her2 status (185) | Her2 negative (166) | 0.04 | 0.20 | 0.69 | 0.80 | 0.80 | 0.72 |
| | Her2 positive (19) | 0.08 | 0.22 | 0.63 | 0.84 | 0.79 | 0.68 |
| | p-value (Mann-Whitney U) | 0.294 | 0.305 | 0.632 | 0.633 | 0.885 | 0.561 |
| Three receptor status (185) | Tripple negative (15) | 0.07 | 0.28 | 0.69 | 0.85 | 0.75 | 0.67 |
| | Others (170) | 0.04 | 0.20 | 0.67 | 0.79 | 0.80 | 0.72 |
| | p-value (Mann-Whitney U) | 0.511 | 0.125 | 0.948 | 0.503 | 0.786 | 0.401 |
| Menopause status (180) | premenopause (56) | 0.05 | 0.19 | 0.69 | 0.80 | 0.74 | 0.70 |
| | postmenopause (124) | 0.04 | 0.22 | 0.67 | 0.80 | 0.83 | 0.72 |
| | p-value (Mann-Whitney U) | 0.896 | 0.243 | 0.697 | 0.555 | 0.006 | 0.651 |
| BC family history (186) | with BC family history (30) | 0.05 | 0.20 | 0.73 | 0.85 | 0.77 | 0.73 |
| | without BC family history (156) | 0.05 | 0.20 | 0.66 | 0.79 | 0.81 | 0.71 |
| | p-value (Mann-Whitney U) | 0.373 | 0.442 | 0.113 | 0.166 | 0.224 | 0.973 |

Fig. 5 (continued)

Table 5. The methylation leveles of the eight genes in sporadic BC patients with different clinical characteristics (cases from second validation round) (continued)

| Clinical characteristics (N) | Group (N) | Median of methylation levels ||||||
|---|---|---|---|---|---|---|---|
| | | MGRN1_CpG_1 | MGRN1_CpG_2 | MGRN1_CpG_4 | MGRN1_CpG_5.6.7.8 | MGRN1_CpG_12 | MGRN1_CpG_13 |
| Tumour stage (188) | Stage 0&I (101) | 0.12 | 0.50 | 0.22 | 0.23 | 0.26 | 0.50 |
| | Stage II (61) | 0.09 | 0.48 | 0.14 | 0.19 | 0.24 | 0.48 |
| | Stage III (26) | 0.12 | 0.57 | 0.27 | 0.33 | 0.29 | 0.57 |
| | p-value (Kruskal Wallis Test) | 0.553 | 0.307 | 0.208 | 0.126 | 0.777 | 0.307 |
| Tumour size (188) | Tis&T1 (119) | 0.12 | 0.50 | 0.22 | 0.24 | 0.27 | 0.50 |
| | T2 (57) | 0.07 | 0.50 | 0.14 | 0.23 | 0.23 | 0.50 |
| | T3 and T4 (12) | 0.17 | 0.54 | 0.37 | 0.39 | 0.39 | 0.54 |
| | p-value (Kruskal Wallis Test) | 0.234 | 0.960 | 0.331 | 0.546 | 0.786 | 0.960 |
| Lymph node (LN) involvement (185) | no involved LN (132) | 0.12 | 0.50 | 0.19 | 0.22 | 0.24 | 0.50 |
| | 1-3 involved LN (30) | 0.06 | 0.46 | 0.19 | 0.25 | 0.33 | 0.46 |
| | > 3 involved LN (23) | 0.21 | 0.57 | 0.28 | 0.33 | 0.31 | 0.57 |
| | p-value (Kruskal Wallis Test) | 0.411 | 0.086 | 0.291 | 0.147 | 0.636 | 0.086 |
| Grading (187) | Grade 1 (35) | 0.11 | 0.47 | 0.18 | 0.23 | 0.24 | 0.47 |
| | Grade 2 (114) | 0.12 | 0.50 | 0.21 | 0.23 | 0.27 | 0.50 |
| | Grade 3 (38) | 0.12 | 0.52 | 0.27 | 0.29 | 0.34 | 0.52 |
| | p-value (Kruskal Wallis Test) | 0.826 | 0.609 | 0.587 | 0.500 | 0.877 | 0.609 |
| ER status (185) | ER negative (23) | 0.14 | 0.48 | 0.28 | 0.32 | 0.33 | 0.48 |
| | ER positive (162) | 0.11 | 0.50 | 0.20 | 0.23 | 0.26 | 0.50 |
| | p-value (Mann-Whitney U) | 0.568 | 0.909 | 0.335 | 0.730 | 0.688 | 0.909 |
| PR status (186) | PR negative (38) | 0.14 | 0.50 | 0.27 | 0.31 | 0.34 | 0.50 |
| | PR positive (148) | 0.11 | 0.50 | 0.20 | 0.23 | 0.24 | 0.50 |
| | p-value (Mann-Whitney U) | 0.207 | 0.307 | 0.081 | 0.193 | 0.249 | 0.307 |
| Her2 status (185) | Her2 negative (166) | 0.11 | 0.50 | 0.21 | 0.23 | 0.25 | 0.50 |
| | Her2 positive (19) | 0.12 | 0.52 | 0.22 | 0.26 | 0.27 | 0.52 |
| | p-value (Mann-Whitney U) | 0.620 | 0.496 | 0.991 | 0.729 | 0.998 | 0.496 |
| Three receptor status (185) | Tripple negative (15) | 0.23 | 0.50 | 0.28 | 0.32 | 0.33 | 0.50 |
| | Others (170) | 0.11 | 0.50 | 0.20 | 0.23 | 0.26 | 0.50 |
| | p-value (Mann-Whitney U) | 0.263 | 0.784 | 0.194 | 0.629 | 0.534 | 0.784 |
| Menopause status (180) | premenopause (56) | 0.08 | 0.49 | 0.17 | 0.20 | 0.21 | 0.49 |
| | postmenopause (124) | 0.12 | 0.50 | 0.22 | 0.25 | 0.29 | 0.50 |
| | p-value (Mann-Whitney U) | 0.252 | 0.348 | 0.384 | 0.431 | 0.207 | 0.348 |
| BC family history (186) | with BC family history (30) | 0.13 | 0.50 | 0.23 | 0.22 | 0.24 | 0.50 |
| | without BC family history (156) | 0.11 | 0.50 | 0.20 | 0.25 | 0.27 | 0.50 |
| | p-value (Mann-Whitney U) | 0.415 | 0.818 | 0.535 | 0.818 | 0.427 | 0.818 |

Fig. 5 (continued)

Table 5. The methylation leveles of the eight genes in sporadic BC patients with different clinical characteristics (cases from second validation round) (continued)

| Clinical characteristics (N) | Group (N) | Median of methylation levels | | | | | |
|---|---|---|---|---|---|---|---|
| | | MGRN1_CpG_15 | MGRN1_CpG_16.17.18 | MGRN1_CpG_19.20 | MGRN1_CpG_22.23 | MGRN1_CpG_26 | MGRN1_CpG_27 |
| Tumour stage (188) | Stage 0&I (101) | 0.26 | 0.28 | 0.35 | 0.27 | 0.30 | 0.28 |
| | Stage II (61) | 0.30 | 0.24 | 0.35 | 0.22 | 0.28 | 0.20 |
| | Stage III (26) | 0.42 | 0.32 | 0.41 | 0.30 | 0.39 | 0.36 |
| | p-value (Kruskal Wallis Test) | 0.296 | 0.355 | 0.594 | 0.386 | 0.356 | 0.368 |
| Tumour size (188) | Tis&T1 (119) | 0.27 | 0.29 | 0.35 | 0.27 | 0.30 | 0.28 |
| | T2 (57) | 0.30 | 0.25 | 0.33 | 0.22 | 0.22 | 0.20 |
| | T3 and T4 (12) | 0.39 | 0.38 | 0.46 | 0.33 | 0.46 | 0.45 |
| | p-value (Kruskal Wallis Test) | 0.962 | 0.811 | 0.655 | 0.597 | 0.117 | 0.717 |
| Lymph node (LN) involvement (185) | no involved LN (132) | 0.27 | 0.25 | 0.35 | 0.26 | 0.28 | 0.25 |
| | 1-3 involved LN (30) | 0.29 | 0.26 | 0.36 | 0.29 | 0.32 | 0.32 |
| | > 3 involved LN (23) | 0.45 | 0.33 | 0.41 | 0.30 | 0.40 | 0.38 |
| | p-value (Kruskal Wallis Test) | 0.099 | 0.185 | 0.627 | 0.588 | 0.354 | 0.298 |
| Grading (187) | Grade 1 (35) | 0.28 | 0.28 | 0.35 | 0.24 | 0.27 | 0.21 |
| | Grade 2 (114) | 0.29 | 0.26 | 0.36 | 0.28 | 0.29 | 0.25 |
| | Grade 3 (38) | 0.34 | 0.30 | 0.36 | 0.25 | 0.33 | 0.34 |
| | p-value (Kruskal Wallis Test) | 0.590 | 0.386 | 0.805 | 0.999 | 0.890 | 0.381 |
| ER status (185) | ER negative (23) | 0.30 | 0.33 | 0.37 | 0.31 | 0.33 | 0.35 |
| | ER positive (162) | 0.29 | 0.26 | 0.35 | 0.26 | 0.28 | 0.26 |
| | p-value (Mann-Whitney U) | 0.680 | 0.545 | 0.855 | 0.745 | 0.907 | 0.867 |
| PR status (186) | PR negative (38) | 0.35 | 0.34 | 0.38 | 0.32 | 0.34 | 0.29 |
| | PR positive (148) | 0.29 | 0.26 | 0.34 | 0.26 | 0.28 | 0.22 |
| | p-value (Mann-Whitney U) | 0.166 | 0.232 | 0.345 | 0.183 | 0.292 | 0.387 |
| Her2 status (185) | Her2 negative (166) | 0.30 | 0.28 | 0.35 | 0.27 | 0.28 | 0.25 |
| | Her2 positive (19) | 0.26 | 0.26 | 0.36 | 0.28 | 0.30 | 0.29 |
| | p-value (Mann-Whitney U) | 0.464 | 0.844 | 0.977 | 0.386 | 0.755 | 0.922 |
| Three receptor status (185) | Tripple negative (15) | 0.31 | 0.34 | 0.41 | 0.38 | 0.34 | 0.35 |
| | Others (170) | 0.29 | 0.26 | 0.35 | 0.26 | 0.28 | 0.26 |
| | p-value (Mann-Whitney U) | 0.882 | 0.365 | 0.563 | 0.096 | 0.744 | 0.768 |
| Menopause status (180) | premenopause (56) | 0.18 | 0.19 | 0.29 | 0.23 | 0.22 | 0.17 |
| | postmenopause (124) | 0.33 | 0.29 | 0.38 | 0.29 | 0.32 | 0.29 |
| | p-value (Mann-Whitney U) | 0.023 | 0.082 | 0.187 | 0.251 | 0.090 | 0.141 |
| BC family history (186) | with BC family history (30) | 0.28 | 0.23 | 0.36 | 0.27 | 0.26 | 0.23 |
| | without BC family history (156) | 0.30 | 0.29 | 0.35 | 0.27 | 0.31 | 0.28 |
| | p-value (Mann-Whitney U) | 0.663 | 0.764 | 0.913 | 0.939 | 0.425 | 0.390 |

Fig. 5 (continued)

Table 5. The methylation leveles of the eight genes in sporadic BC patients with different clinical characteristics (cases from second validation round)

| Clinical characteristics (N) | Group (N) | Median of methylation levels | | | | |
|---|---|---|---|---|---|---|
| | | MGRN1_CpG_28 | MGRN1_CpG_29 | MGRN1_CpG_31 | MGRN1_CpG_32 | MGRN1_CpG_34 |
| Tumour stage (188) | Stage 0&I (101) | 0.24 | 0.34 | 0.30 | 0.20 | 0.38 |
| | Stage II (61) | 0.25 | 0.35 | 0.25 | 0.12 | 0.33 |
| | Stage III (26) | 0.37 | 0.45 | 0.36 | 0.37 | 0.43 |
| | p-value (Kruskal Wallis Test) | 0.379 | 0.372 | 0.565 | 0.049 | 0.677 |
| Tumour size (188) | Tis&T1 (119) | 0.24 | 0.36 | 0.30 | 0.20 | 0.36 |
| | T2 (57) | 0.25 | 0.37 | 0.30 | 0.14 | 0.35 |
| | T3 and T4 (12) | 0.42 | 0.49 | 0.44 | 0.36 | 0.44 |
| | p-value (Kruskal Wallis Test) | 0.363 | 0.580 | 0.608 | 0.576 | 0.701 |
| Lymph node (LN) involvement (185) | no involved LN (132) | 0.23 | 0.35 | 0.30 | 0.18 | 0.36 |
| | 1-3 involved LN (30) | 0.28 | 0.37 | 0.27 | 0.21 | 0.27 |
| | > 3 involved LN (23) | 0.38 | 0.45 | 0.37 | 0.38 | 0.44 |
| | p-value (Kruskal Wallis Test) | 0.235 | 0.199 | 0.495 | 0.017 | 0.504 |
| Grading (187) | Grade 1 (35) | 0.23 | 0.37 | 0.29 | 0.20 | 0.33 |
| | Grade 2 (114) | 0.25 | 0.35 | 0.31 | 0.18 | 0.35 |
| | Grade 3 (38) | 0.38 | 0.43 | 0.34 | 0.28 | 0.43 |
| | p-value (Kruskal Wallis Test) | 0.204 | 0.363 | 0.370 | 0.209 | 0.814 |
| ER status (185) | ER negative (23) | 0.38 | 0.42 | 0.36 | 0.27 | 0.42 |
| | ER positive (162) | 0.25 | 0.37 | 0.30 | 0.19 | 0.36 |
| | p-value (Mann-Whitney U) | 0.388 | 0.454 | 0.668 | 0.511 | 0.985 |
| PR status (186) | PR negative (38) | 0.32 | 0.43 | 0.34 | 0.28 | 0.43 |
| | PR positive (148) | 0.25 | 0.37 | 0.30 | 0.18 | 0.35 |
| | p-value (Mann-Whitney U) | 0.247 | 0.200 | 0.315 | 0.106 | 0.452 |
| Her2 status (185) | Her2 negative (166) | 0.25 | 0.37 | 0.30 | 0.19 | 0.36 |
| | Her2 positive (19) | 0.26 | 0.39 | 0.33 | 0.27 | 0.35 |
| | p-value (Mann-Whitney U) | 0.987 | 0.989 | 0.858 | 0.858 | 0.449 |
| Three receptor status (185) | Tripple negative (15) | 0.38 | 0.43 | 0.40 | 0.30 | 0.44 |
| | Others (170) | 0.25 | 0.37 | 0.30 | 0.19 | 0.36 |
| | p-value (Mann-Whitney U) | 0.271 | 0.295 | 0.306 | 0.365 | 0.682 |
| Menopause status (180) | premenopause (56) | 0.18 | 0.27 | 0.25 | 0.16 | 0.32 |
| | postmenopause (124) | 0.28 | 0.40 | 0.32 | 0.20 | 0.40 |
| | p-value (Mann-Whitney U) | 0.283 | 0.054 | 0.138 | 0.169 | 0.314 |
| BC family history (186) | with BC family history (30) | 0.20 | 0.33 | 0.28 | 0.18 | 0.43 |
| | without BC family history (156) | 0.28 | 0.39 | 0.32 | 0.21 | 0.36 |
| | p-value (Mann-Whitney U) | 0.222 | 0.414 | 0.522 | 0.212 | 0.353 |

Fig. 5 (continued)

Table 5. The methylation leveles of the eight genes in sporadic BC patients with different clinical characteristics (cases from second validation round) (continued)

| Clinical characteristics (N) | Group (N) | Median of methylation levels ||||||| 
|---|---|---|---|---|---|---|---|---|
| | | RAPSN_CpG_1 | RAPSN_CpG_2 | RAPSN_CpG_4 | RAPSN_CpG_5 | RAPSN_CpG_6 | RAPSN_CpG_7 | RAPSN_CpG_8 |
| Tumour stage (188) | Stage 0&I (101) | 0.96 | 0.67 | 0.39 | 0.84 | 0.58 | 0.79 | 0.97 |
| | Stage II (61) | 0.95 | 0.71 | 0.36 | 0.78 | 0.64 | 0.79 | 0.98 |
| | Stage III (26) | 0.96 | 0.62 | 0.26 | 0.74 | 0.45 | 0.76 | 0.97 |
| | p-value (Kruskal Wallis Test) | 0.600 | 0.882 | 0.413 | 0.198 | 0.339 | 0.770 | 0.032 |
| Tumour size (188) | Tis&T1 (119) | 0.96 | 0.66 | 0.39 | 0.84 | 0.58 | 0.80 | 0.97 |
| | T2 (57) | 0.96 | 0.67 | 0.36 | 0.79 | 0.54 | 0.78 | 0.97 |
| | T3 and T4 (12) | 0.94 | 0.78 | 0.26 | 0.72 | 0.49 | 0.73 | 0.97 |
| | p-value (Kruskal Wallis Test) | 0.145 | 0.616 | 0.711 | 0.195 | 0.845 | 0.940 | 0.260 |
| Lymph node (LN) involvement (185) | no involved LN (132) | 0.96 | 0.69 | 0.39 | 0.84 | 0.60 | 0.79 | 0.97 |
| | 1-3 involved LN (30) | 0.97 | 0.67 | 0.34 | 0.71 | 0.56 | 0.78 | 0.97 |
| | > 3 involved LN (23) | 0.95 | 0.58 | 0.26 | 0.73 | 0.50 | 0.76 | 0.97 |
| | p-value (Kruskal Wallis Test) | 0.992 | 0.628 | 0.544 | 0.212 | 0.771 | 0.961 | 0.727 |
| Grading (187) | Grade 1 (35) | 0.96 | 0.67 | 0.39 | 0.84 | 0.62 | 0.88 | 0.97 |
| | Grade 2 (114) | 0.96 | 0.74 | 0.36 | 0.80 | 0.57 | 0.77 | 0.97 |
| | Grade 3 (38) | 0.96 | 0.59 | 0.36 | 0.81 | 0.49 | 0.78 | 0.97 |
| | p-value (Kruskal Wallis Test) | 0.904 | 0.160 | 0.970 | 0.678 | 0.625 | 0.652 | 0.330 |
| ER status (185) | ER negative (23) | 0.95 | 0.63 | 0.36 | 0.82 | 0.50 | 0.78 | 0.97 |
| | ER positive (162) | 0.96 | 0.68 | 0.36 | 0.80 | 0.58 | 0.79 | 0.97 |
| | p-value (Mann-Whitney U) | 0.366 | 0.739 | 0.793 | 0.700 | 0.482 | 0.686 | 0.673 |
| PR status (186) | PR negative (38) | 0.94 | 0.60 | 0.36 | 0.85 | 0.60 | 0.80 | 0.97 |
| | PR positive (148) | 0.96 | 0.70 | 0.36 | 0.80 | 0.57 | 0.79 | 0.97 |
| | p-value (Mann-Whitney U) | 0.018 | 0.197 | 0.603 | 0.345 | 0.777 | 0.638 | 0.600 |
| Her2 status (185) | Her2 negative (166) | 0.96 | 0.67 | 0.36 | 0.80 | 0.57 | 0.79 | 0.97 |
| | Her2 positive (19) | 0.94 | 0.75 | 0.44 | 0.80 | 0.53 | 0.70 | 0.97 |
| | p-value (Mann-Whitney U) | 0.078 | 0.443 | 0.222 | 0.736 | 0.957 | 0.116 | 0.097 |
| Three receptor status (185) | Tripple negative (15) | 0.95 | 0.59 | 0.35 | 0.82 | 0.50 | 0.76 | 0.97 |
| | Others (170) | 0.96 | 0.68 | 0.36 | 0.80 | 0.58 | 0.79 | 0.97 |
| | p-value (Mann-Whitney U) | 0.599 | 0.323 | 0.362 | 0.726 | 0.213 | 0.882 | 0.755 |
| Menopause status (180) | premenopause (56) | 0.96 | 0.68 | 0.39 | 0.83 | 0.60 | 0.79 | 0.97 |
| | postmenopause (124) | 0.96 | 0.67 | 0.36 | 0.80 | 0.52 | 0.79 | 0.97 |
| | p-value (Mann-Whitney U) | 0.775 | 0.629 | 0.843 | 0.789 | 0.572 | 0.832 | 0.260 |
| BC family history (186) | with BC family history (30) | 0.96 | 0.71 | 0.38 | 0.76 | 0.62 | 0.72 | 0.97 |
| | without BC family history (156) | 0.96 | 0.67 | 0.36 | 0.82 | 0.57 | 0.81 | 0.97 |
| | p-value (Mann-Whitney U) | 0.809 | 0.721 | 0.657 | 0.372 | 0.749 | 0.305 | 0.586 |

Fig. 6

Table 6. The methylation leveles of the eight genes in sporadic BC patients with different clinical characteristics (cases from the third validation study)

| Clinical characteristics (N) | Group (N) | Median of age | Median of methylation levels | | | | | |
|---|---|---|---|---|---|---|---|---|
| | | | HYAL2_CpG_1 | HYAL2_CpG_2 | HYAL2_CpG_3 | HYAL2_CpG_4 | DYRK4_CpG_1 | DYRK4_CpG_3 |
| Tumour stage (143) | Stage 0&I (57) | 46.22 | 0.24 | 0.16 | 0.27 | 0.45 | 0.20 | 0.18 |
| | Stage II (68) | 46.57 | 0.26 | 0.16 | 0.30 | 0.48 | 0.22 | 0.18 |
| | Stage III&IV (18) | 47.54 | 0.25 | 0.19 | 0.32 | 0.49 | 0.23 | 0.21 |
| | p-value (Kruskal Wallis Test) | 0.271 | 0.026 | 0.141 | 0.062 | 0.365 | 0.647 | 0.582 |
| Tumour size (147) | Tis&T1 (74) | 46.31 | 0.25 | 0.16 | 0.28 | 0.46 | 0.20 | 0.18 |
| | T2 (60) | 47.12 | 0.25 | 0.17 | 0.30 | 0.48 | 0.24 | 0.19 |
| | T3 and T4 (13) | 44.67 | 0.24 | 0.16 | 0.30 | 0.48 | 0.22 | 0.20 |
| | p-value (Kruskal Wallis Test) | 0.446 | 0.416 | 0.728 | 0.312 | 0.543 | 0.424 | 0.888 |
| Lymph node (LN) involvement (139) | no involved LN (96) | 46.54 | 0.24 | 0.16 | 0.27 | 0.45 | 0.22 | 0.18 |
| | 1-3 involved LN (37) | 45.98 | 0.25 | 0.17 | 0.30 | 0.49 | 0.22 | 0.18 |
| | > 3 involved LN (6) | 52.38 | 0.25 | 0.19 | 0.31 | 0.47 | 0.34 | 0.31 |
| | p-value (Kruskal Wallis Test) | 0.171 | 0.180 | 0.717 | 0.158 | 0.364 | 0.492 | 0.127 |
| Grading (187) | Grade 1 (20) | 46.96 | 0.24 | 0.16 | 0.27 | 0.48 | 0.20 | 0.18 |
| | Grade 2 (94) | 46.87 | 0.25 | 0.17 | 0.30 | 0.48 | 0.23 | 0.19 |
| | Grade 3 (33) | 45.27 | 0.24 | 0.16 | 0.30 | 0.45 | 0.25 | 0.19 |
| | p-value (Kruskal Wallis Test) | 0.061 | 0.801 | 0.807 | 0.390 | 0.195 | 0.622 | 0.915 |
| ER status (147) | ER negative (23) | 46.19 | 0.23 | 0.16 | 0.27 | 0.44 | 0.19 | 0.19 |
| | ER positive (125) | 46.71 | 0.25 | 0.16 | 0.29 | 0.48 | 0.24 | 0.18 |
| | p-value (Mann-Whitney U) | 0.184 | 0.377 | 0.540 | 0.220 | 0.042 | 0.656 | 0.815 |
| PR status (148) | PR negative (32) | 45.32 | 0.23 | 0.15 | 0.28 | 0.43 | 0.23 | 0.20 |
| | PR positive (116) | 46.77 | 0.25 | 0.17 | 0.29 | 0.48 | 0.22 | 0.18 |
| | p-value (Mann-Whitney U) | 0.036 | 0.178 | 0.276 | 0.183 | 0.003 | 0.580 | 0.867 |
| Her2 status (148) | Her2 negative (114) | 46.64 | 0.25 | 0.16 | 0.28 | 0.46 | 0.22 | 0.19 |
| | Her2 positive (34) | 46.25 | 0.24 | 0.17 | 0.30 | 0.48 | 0.24 | 0.18 |
| | p-value (Mann-Whitney U) | 0.626 | 0.805 | 0.689 | 0.310 | 0.586 | 0.675 | 0.731 |
| Three receptor status (148) | Tripple negative (17) | 44.76 | 0.25 | 0.16 | 0.25 | 0.41 | 0.17 | 0.18 |
| | Others (131) | 46.72 | 0.25 | 0.16 | 0.29 | 0.48 | 0.23 | 0.19 |
| | p-value (Mann-Whitney U) | 0.052 | 0.486 | 0.332 | 0.082 | 0.010 | 0.308 | 0.658 |
| Menopause status (148) | premenopause (105) | 45.47 | 0.24 | 0.16 | 0.28 | 0.46 | 0.22 | 0.18 |
| | postmenopause (43) | 55.93 | 0.26 | 0.19 | 0.30 | 0.49 | 0.23 | 0.22 |
| | p-value (Mann-Whitney U) | — | 0.043 | 0.004 | 0.093 | 0.012 | 0.274 | 0.145 |

Fig. 6 (continued)

Table 6. The methylation leveles of the eight genes in sporadic BC patients with different clinical characteristics (cases from the third validation study) (continued)

| Clinical characteristics (N) | Group (N) | Median of methylation levels | | | | |
|---|---|---|---|---|---|---|
| | | S100P_CpG_2.3 | S100P_CpG_4 | S100P_CpG_7 | S100P_CpG_8 | S100P_CpG_9 |
| Tumour stage (143) | Stage 0&I (57) | 0.65 | 0.89 | 0.45 | 0.44 | 0.51 |
| | Stage II (68) | 0.69 | 0.90 | 0.48 | 0.50 | 0.54 |
| | Stage III&IV (18) | 0.67 | 0.88 | 0.52 | 0.47 | 0.57 |
| | p-value (Kruskal Wallis Test) | 0.145 | 0.910 | 0.049 | 0.179 | 0.129 |
| Tumour size (147) | Tis&T1 (74) | 0.66 | 0.90 | 0.45 | 0.46 | 0.51 |
| | T2 (60) | 0.67 | 0.87 | 0.48 | 0.46 | 0.53 |
| | T3 and T4 (13) | 0.68 | 0.92 | 0.52 | 0.50 | 0.56 |
| | p-value (Kruskal Wallis Test) | 0.702 | 0.460 | 0.078 | 0.785 | 0.597 |
| Lymph node (LN) involvement (139) | no involved LN (96) | 0.67 | 0.89 | 0.46 | 0.45 | 0.51 |
| | 1-3 involved LN (37) | 0.67 | 0.90 | 0.50 | 0.47 | 0.54 |
| | > 3 involved LN (6) | 0.66 | 0.87 | 0.49 | 0.47 | 0.54 |
| | p-value (Kruskal Wallis Test) | 0.896 | 0.953 | 0.683 | 0.937 | 0.794 |
| Grading (187) | Grade 1 (20) | 0.63 | 0.91 | 0.45 | 0.42 | 0.49 |
| | Grade 2 (94) | 0.68 | 0.88 | 0.48 | 0.48 | 0.54 |
| | Grade 3 (33) | 0.66 | 0.91 | 0.49 | 0.46 | 0.51 |
| | p-value (Kruskal Wallis Test) | 0.234 | 0.807 | 0.676 | 0.368 | 0.294 |
| ER status (147) | ER negative (23) | 0.65 | 0.94 | 0.45 | 0.43 | 0.49 |
| | ER positive (125) | 0.67 | 0.89 | 0.48 | 0.47 | 0.52 |
| | p-value (Mann-Whitney U) | 0.268 | 0.270 | 0.361 | 0.129 | 0.070 |
| PR status (148) | PR negative (32) | 0.66 | 0.92 | 0.47 | 0.44 | 0.51 |
| | PR positive (116) | 0.67 | 0.89 | 0.48 | 0.47 | 0.52 |
| | p-value (Mann-Whitney U) | 0.707 | 0.177 | 0.993 | 0.525 | 0.296 |
| Her2 status (148) | Her2 negative (114) | 0.66 | 0.89 | 0.47 | 0.45 | 0.51 |
| | Her2 positive (34) | 0.69 | 0.90 | 0.50 | 0.51 | 0.55 |
| | p-value (Mann-Whitney U) | 0.169 | 0.534 | 0.549 | 0.118 | 0.188 |
| Three receptor status (148) | Tripple negative (17) | 0.65 | 0.91 | 0.46 | 0.43 | 0.49 |
| | Others (131) | 0.67 | 0.89 | 0.48 | 0.47 | 0.52 |
| | p-value (Mann-Whitney U) | 0.584 | 0.671 | 0.854 | 0.257 | 0.187 |
| Menopause status (148) | premenopause (105) | 0.67 | 0.91 | 0.46 | 0.46 | 0.51 |
| | postmenopause (43) | 0.66 | 0.85 | 0.50 | 0.46 | 0.54 |
| | p-value (Mann-Whitney U) | 0.666 | 0.189 | 0.037 | 0.980 | 0.597 |

Fig. 6 (continued)

Table 6. The methylation leveles of the eight genes in sporadic BC patients with different clinical characteristics (cases from the third validation study) (continued)

| Clinical characteristics (N) | Group (N) | Median of methylation levels | | | | | |
|---|---|---|---|---|---|---|---|
| | | FUT7_CpG_2 | FUT7_CpG_3 | FUT7_CpG_4 | FUT7_CpG_6 | FUT7_CpG_7 | FUT7_CpG_8 |
| Tumour stage (143) | Stage 0&I (57) | 0.19 | 0.15 | 0.20 | 0.24 | 0.09 | 0.30 |
| | Stage II (68) | 0.21 | 0.14 | 0.19 | 0.22 | 0.10 | 0.35 |
| | Stage III&IV (18) | 0.22 | 0.13 | 0.22 | 0.23 | 0.10 | 0.25 |
| | $p$-value (Kruskal Wallis Test) | 0.895 | 0.805 | 0.346 | 0.956 | 0.815 | 0.420 |
| Tumour size (147) | Tis&T1 (74) | 0.21 | 0.15 | 0.19 | 0.24 | 0.09 | 0.30 |
| | T2 (60) | 0.20 | 0.13 | 0.20 | 0.22 | 0.10 | 0.32 |
| | T3 and T4 (13) | 0.22 | 0.17 | 0.22 | 0.20 | 0.11 | 0.31 |
| | $p$-value (Kruskal Wallis Test) | 0.917 | 0.427 | 0.340 | 0.975 | 0.616 | 0.695 |
| Lymph node (LN) involvement (139) | no involved LN (96) | 0.22 | 0.14 | 0.20 | 0.24 | 0.09 | 0.31 |
| | 1-3 involved LN (37) | 0.20 | 0.14 | 0.19 | 0.22 | 0.09 | 0.34 |
| | > 3 involved LN (6) | 0.28 | 0.22 | 0.31 | 0.28 | 0.16 | 0.27 |
| | $p$-value (Kruskal Wallis Test) | 0.173 | 0.076 | 0.239 | 0.325 | 0.107 | 0.976 |
| Grading (187) | Grade 1 (20) | 0.16 | 0.13 | 0.18 | 0.20 | 0.06 | 0.26 |
| | Grade 2 (94) | 0.22 | 0.14 | 0.21 | 0.25 | 0.10 | 0.32 |
| | Grade 3 (33) | 0.18 | 0.14 | 0.18 | 0.20 | 0.10 | 0.31 |
| | $p$-value (Kruskal Wallis Test) | 0.150 | 0.574 | 0.327 | 0.338 | 0.243 | 0.098 |
| ER status (147) | ER negative (23) | 0.20 | 0.12 | 0.17 | 0.19 | 0.10 | 0.32 |
| | ER positive (125) | 0.21 | 0.14 | 0.20 | 0.24 | 0.09 | 0.31 |
| | $p$-value (Mann-Whitney U) | 0.793 | 0.562 | 0.208 | 0.204 | 0.793 | 0.564 |
| PR status (148) | PR negative (32) | 0.23 | 0.16 | 0.19 | 0.23 | 0.11 | 0.33 |
| | PR positive (116) | 0.21 | 0.14 | 0.20 | 0.23 | 0.09 | 0.30 |
| | $p$-value (Mann-Whitney U) | 0.519 | 0.348 | 0.744 | 0.578 | 0.260 | 0.285 |
| Her2 status (148) | Her2 negative (114) | 0.19 | 0.13 | 0.20 | 0.22 | 0.09 | 0.30 |
| | Her2 positive (34) | 0.26 | 0.18 | 0.19 | 0.27 | 0.12 | 0.36 |
| | $p$-value (Mann-Whitney U) | 0.012 | 0.019 | 0.495 | 0.028 | 0.157 | 0.172 |
| Three receptor status (148) | Tripple negative (17) | 0.18 | 0.11 | 0.17 | 0.17 | 0.09 | 0.26 |
| | Others (131) | 0.21 | 0.14 | 0.20 | 0.24 | 0.09 | 0.31 |
| | $p$-value (Mann-Whitney U) | 0.327 | 0.206 | 0.077 | 0.042 | 0.800 | 0.205 |
| Menopause status (148) | premenopause (105) | 0.21 | 0.14 | 0.20 | 0.23 | 0.09 | 0.31 |
| | postmenopause (43) | 0.17 | 0.14 | 0.19 | 0.22 | 0.11 | 0.31 |
| | $p$-value (Mann-Whitney U) | 0.167 | 0.666 | 0.719 | 0.944 | 0.319 | 0.751 |

Fig. 6 (continued)

Table 6. The methylation leveles of the eight genes in sporadic BC patients with different clinical characteristics (cases from the third validation study) (continued)

| Clinical characteristics (N) | Group (N) | Median of methylation levels | | | |
|---|---|---|---|---|---|
| | | SLC22A18_CpG_3 | SLC22A18_CpG_4 | SLC22A18_CpG_6 | SLC22A18_CpG_8 |
| Tumour stage (143) | Stage 0&I (57) | 0.13 | 0.15 | 0.19 | 0.61 |
| | Stage II (68) | 0.15 | 0.18 | 0.22 | 0.63 |
| | Stage III&IV (18) | 0.15 | 0.20 | 0.21 | 0.56 |
| | p-value (Kruskal Wallis Test) | 0.183 | 0.212 | 0.293 | 0.284 |
| Tumour size (147) | Tis&T1 (74) | 0.14 | 0.16 | 0.20 | 0.61 |
| | T2 (60) | 0.15 | 0.18 | 0.22 | 0.63 |
| | T3 and T4 (13) | 0.14 | 0.16 | 0.18 | 0.56 |
| | p-value (Kruskal Wallis Test) | 0.276 | 0.479 | 0.138 | 0.308 |
| Lymph node (LN) involvement (139) | no involved LN (96) | 0.14 | 0.16 | 0.20 | 0.61 |
| | 1-3 involved LN (37) | 0.14 | 0.20 | 0.21 | 0.63 |
| | > 3 involved LN (6) | 0.16 | 0.20 | 0.21 | 0.54 |
| | p-value (Kruskal Wallis Test) | 0.491 | 0.116 | 0.550 | 0.115 |
| Grading (187) | Grade 1 (20) | 0.14 | 0.15 | 0.19 | 0.66 |
| | Grade 2 (94) | 0.14 | 0.18 | 0.21 | 0.61 |
| | Grade 3 (33) | 0.14 | 0.17 | 0.21 | 0.61 |
| | p-value (Kruskal Wallis Test) | 0.904 | 0.683 | 0.848 | 0.199 |
| ER status (147) | ER negative (23) | 0.14 | 0.16 | 0.20 | 0.60 |
| | ER positive (125) | 0.14 | 0.17 | 0.21 | 0.61 |
| | p-value (Mann-Whitney U) | 0.202 | 0.240 | 0.408 | 0.153 |
| PR status (148) | PR negative (32) | 0.14 | 0.17 | 0.20 | 0.60 |
| | PR positive (116) | 0.14 | 0.17 | 0.21 | 0.61 |
| | p-value (Mann-Whitney U) | 0.562 | 0.503 | 0.439 | 0.250 |
| Her2 status (148) | Her2 negative (114) | 0.14 | 0.17 | 0.21 | 0.61 |
| | Her2 positive (34) | 0.15 | 0.20 | 0.23 | 0.62 |
| | p-value (Mann-Whitney U) | 0.907 | 0.521 | 0.430 | 0.830 |
| Three receptor status (148) | Tripple negative (17) | 0.12 | 0.16 | 0.19 | 0.60 |
| | Others (131) | 0.14 | 0.17 | 0.21 | 0.61 |
| | p-value (Mann-Whitney U) | 0.274 | 0.391 | 0.421 | 0.218 |
| Menopause status (148) | premenopause (105) | 0.14 | 0.16 | 0.19 | 0.62 |
| | postmenopause (43) | 0.17 | 0.22 | 0.23 | 0.59 |
| | p-value (Mann-Whitney U) | 0.002 | 0.001 | 0.003 | 0.112 |

Fig. 6 (continued)

Table 6. The methylation leveles of the eight genes in sporadic BC patients with different clinical characteristics (cases from the third validation study) (continued)

| Clinical characteristics (N) | Group (N) | Median of methylation levels ||||||
|---|---|---|---|---|---|---|---|
| | | RPTOR_CpG_1 | RPTOR_CpG_2 | RPTOR_CpG_3 | RPTOR_CpG_4 | RPTOR_CpG_5 | RPTOR_CpG_8 |
| Tumour stage (143) | Stage 0&I (57) | 0.05 | 0.18 | 0.59 | 0.77 | 0.73 | 0.67 |
| | Stage II (68) | 0.07 | 0.19 | 0.62 | 0.81 | 0.72 | 0.67 |
| | Stage III&IV (18) | 0.08 | 0.24 | 0.63 | 0.79 | 0.77 | 0.72 |
| | p-value (Kruskal Wallis Test) | 0.328 | 0.152 | 0.191 | 0.847 | 0.527 | 0.514 |
| Tumour size (147) | Tis&T1 (74) | 0.05 | 0.18 | 0.59 | 0.77 | 0.72 | 0.67 |
| | T2 (60) | 0.08 | 0.21 | 0.62 | 0.77 | 0.73 | 0.69 |
| | T3 and T4 (13) | 0.09 | 0.29 | 0.66 | 0.83 | 0.78 | 0.67 |
| | p-value (Kruskal Wallis Test) | 0.165 | 0.197 | 0.130 | 0.748 | 0.614 | 0.232 |
| Lymph node (LN) involvement (139) | no involved LN (96) | 0.07 | 0.20 | 0.60 | 0.77 | 0.74 | 0.68 |
| | 1-3 involved LN (37) | 0.06 | 0.19 | 0.59 | 0.73 | 0.70 | 0.63 |
| | > 3 involved LN (6) | 0.06 | 0.23 | 0.62 | 0.76 | 0.80 | 0.73 |
| | p-value (Kruskal Wallis Test) | 0.955 | 0.177 | 0.374 | 0.487 | 0.080 | 0.008 |
| Grading (187) | Grade 1 (20) | 0.07 | 0.18 | 0.60 | 0.78 | 0.73 | 0.68 |
| | Grade 2 (94) | 0.07 | 0.20 | 0.60 | 0.77 | 0.74 | 0.68 |
| | Grade 3 (33) | 0.06 | 0.19 | 0.62 | 0.79 | 0.71 | 0.68 |
| | p-value (Kruskal Wallis Test) | 0.669 | 0.426 | 0.456 | 0.868 | 0.719 | 0.987 |
| ER status (147) | ER negative (23) | 0.04 | 0.19 | 0.59 | 0.75 | 0.71 | 0.69 |
| | ER positive (125) | 0.07 | 0.20 | 0.60 | 0.77 | 0.74 | 0.67 |
| | p-value (Mann-Whitney U) | 0.139 | 0.449 | 0.628 | 0.694 | 0.525 | 0.757 |
| PR status (148) | PR negative (32) | 0.06 | 0.19 | 0.61 | 0.79 | 0.72 | 0.69 |
| | PR positive (116) | 0.07 | 0.20 | 0.60 | 0.77 | 0.73 | 0.67 |
| | p-value (Mann-Whitney U) | 0.267 | 0.755 | 0.492 | 0.812 | 0.812 | 0.416 |
| Her2 status (148) | Her2 negative (114) | 0.07 | 0.19 | 0.60 | 0.75 | 0.72 | 0.68 |
| | Her2 positive (34) | 0.09 | 0.23 | 0.64 | 0.86 | 0.78 | 0.68 |
| | p-value (Mann-Whitney U) | 0.463 | 0.065 | 0.090 | 0.002 | 0.036 | 0.862 |
| Three receptor status (148) | Tripple negative (17) | 0.04 | 0.17 | 0.59 | 0.75 | 0.69 | 0.69 |
| | Others (131) | 0.07 | 0.20 | 0.60 | 0.77 | 0.74 | 0.68 |
| | p-value (Mann-Whitney U) | 0.102 | 0.178 | 0.496 | 0.564 | 0.068 | 0.817 |
| Menopause status (148) | premenopause (105) | 0.07 | 0.19 | 0.59 | 0.79 | 0.72 | 0.67 |
| | postmenopause (43) | 0.06 | 0.20 | 0.62 | 0.75 | 0.77 | 0.68 |
| | p-value (Mann-Whitney U) | 0.687 | 0.463 | 0.202 | 0.090 | 0.099 | 0.078 |

Fig. 6 (continued)

Table 6. The methylation leveles of the eight genes in sporadic BC patients with different clinical characteristics (cases from the third validation study) (continued)

| Clinical characteristics (N) | Group (N) | Median of methylation levels ||||||
|---|---|---|---|---|---|---|---|
| | | MGRN1_CpG_1 | MGRN1_CpG_2 | MGRN1_CpG_4 | MGRN1_CpG_5.6.7.8 | MGRN1_CpG_12 | MGRN1_CpG_13 |
| Tumour stage (143) | Stage 0&I (57) | 0.12 | 0.60 | 0.23 | 0.23 | 0.26 | 0.60 |
| | Stage II (68) | 0.14 | 0.62 | 0.27 | 0.29 | 0.35 | 0.62 |
| | Stage III&IV (18) | 0.21 | 0.63 | 0.31 | 0.34 | 0.37 | 0.63 |
| | p-value (Kruskal Wallis Test) | 0.136 | 0.057 | 0.002 | 0.002 | 0.001 | 0.050 |
| Tumour size (147) | Tis&T1 (74) | 0.14 | 0.59 | 0.25 | 0.26 | 0.30 | 0.59 |
| | T2 (60) | 0.12 | 0.61 | 0.26 | 0.28 | 0.32 | 0.61 |
| | T3 and T4 (13) | 0.29 | 0.69 | 0.38 | 0.36 | 0.46 | 0.69 |
| | p-value (Kruskal Wallis Test) | 0.005 | 0.003 | 0.002 | 0.004 | 0.001 | 0.003 |
| Lymph node (LN) involvement (139) | no involved LN (96) | 0.13 | 0.61 | 0.25 | 0.27 | 0.30 | 0.61 |
| | 1-3 involved LN (37) | 0.14 | 0.61 | 0.29 | 0.29 | 0.34 | 0.61 |
| | > 3 involved LN (6) | 0.13 | 0.60 | 0.28 | 0.33 | 0.36 | 0.60 |
| | p-value (Kruskal Wallis Test) | 0.949 | 0.622 | 0.171 | 0.336 | 0.235 | 0.710 |
| Grading (187) | Grade 1 (20) | 0.10 | 0.61 | 0.25 | 0.24 | 0.28 | 0.61 |
| | Grade 2 (94) | 0.14 | 0.61 | 0.26 | 0.29 | 0.33 | 0.61 |
| | Grade 3 (33) | 0.12 | 0.62 | 0.26 | 0.27 | 0.31 | 0.62 |
| | p-value (Kruskal Wallis Test) | 0.296 | 0.815 | 0.209 | 0.255 | 0.350 | 0.907 |
| ER status (147) | ER negative (23) | 0.12 | 0.62 | 0.26 | 0.27 | 0.30 | 0.62 |
| | ER positive (125) | 0.14 | 0.61 | 0.25 | 0.28 | 0.33 | 0.61 |
| | p-value (Mann-Whitney U) | 0.187 | 0.739 | 0.470 | 0.331 | 0.577 | 0.782 |
| PR status (148) | PR negative (32) | 0.12 | 0.62 | 0.25 | 0.28 | 0.31 | 0.63 |
| | PR positive (116) | 0.14 | 0.61 | 0.26 | 0.28 | 0.33 | 0.61 |
| | p-value (Mann-Whitney U) | 0.318 | 0.815 | 0.365 | 0.381 | 0.666 | 0.789 |
| Her2 status (148) | Her2 negative (114) | 0.14 | 0.61 | 0.26 | 0.28 | 0.33 | 0.61 |
| | Her2 positive (34) | 0.14 | 0.61 | 0.25 | 0.29 | 0.32 | 0.61 |
| | p-value (Mann-Whitney U) | 0.306 | 0.950 | 0.535 | 0.612 | 0.909 | 0.669 |
| Three receptor status (148) | Tripple negative (17) | 0.13 | 0.62 | 0.27 | 0.28 | 0.34 | 0.62 |
| | Others (131) | 0.14 | 0.61 | 0.25 | 0.28 | 0.33 | 0.61 |
| | p-value (Mann-Whitney U) | 0.449 | 0.958 | 0.851 | 0.595 | 0.971 | 0.885 |
| Menopause status (148) | premenopause (105) | 0.14 | 0.61 | 0.25 | 0.27 | 0.32 | 0.61 |
| | postmenopause (43) | 0.15 | 0.62 | 0.27 | 0.29 | 0.33 | 0.64 |
| | p-value (Mann-Whitney U) | 0.541 | 0.259 | 0.190 | 0.324 | 0.373 | 0.127 |

Fig. 6 (continued)

Table 6. The methylation leveles of the eight genes in sporadic BC patients with different clinical characteristics (cases from the third validation study) (continued)

| Clinical characteristics (N) | Group (N) | Median of methylation levels | | | | | |
|---|---|---|---|---|---|---|---|
| | | MGRN1_CpG_15 | MGRN1_CpG_16.17.18 | MGRN1_CpG_19.20 | MGRN1_CpG_22.23 | MGRN1_CpG_26 | MGRN1_CpG_27 |
| Tumour stage (143) | Stage 0&I (57) | 0.29 | 0.29 | 0.32 | 0.29 | 0.28 | 0.26 |
| | Stage II (68) | 0.34 | 0.31 | 0.37 | 0.34 | 0.32 | 0.32 |
| | Stage III&IV (18) | 0.39 | 0.36 | 0.42 | 0.39 | 0.36 | 0.38 |
| | p-value (Kruskal Wallis Test) | 0.003 | 0.001 | 0.002 | 0.001 | 0.007 | 0.003 |
| Tumour size (147) | Tis&T1 (74) | 0.31 | 0.29 | 0.34 | 0.31 | 0.31 | 0.29 |
| | T2 (60) | 0.33 | 0.31 | 0.36 | 0.33 | 0.31 | 0.29 |
| | T3 and T4 (13) | 0.43 | 0.41 | 0.47 | 0.44 | 0.40 | 0.43 |
| | p-value (Kruskal Wallis Test) | 0.002 | 0.000 | 0.003 | 0.000 | 0.005 | 0.001 |
| Lymph node (LN) involvement (139) | no involved LN (96) | 0.31 | 0.30 | 0.35 | 0.31 | 0.31 | 0.28 |
| | 1-3 involved LN (37) | 0.34 | 0.33 | 0.38 | 0.34 | 0.33 | 0.31 |
| | > 3 involved LN (6) | 0.38 | 0.36 | 0.38 | 0.34 | 0.33 | 0.33 |
| | p-value (Kruskal Wallis Test) | 0.070 | 0.179 | 0.191 | 0.276 | 0.494 | 0.258 |
| Grading (187) | Grade 1 (20) | 0.31 | 0.29 | 0.33 | 0.31 | 0.31 | 0.25 |
| | Grade 2 (94) | 0.34 | 0.32 | 0.37 | 0.34 | 0.31 | 0.30 |
| | Grade 3 (33) | 0.32 | 0.31 | 0.36 | 0.32 | 0.33 | 0.31 |
| | p-value (Kruskal Wallis Test) | 0.581 | 0.364 | 0.329 | 0.422 | 0.781 | 0.661 |
| ER status (147) | ER negative (23) | 0.32 | 0.31 | 0.36 | 0.32 | 0.31 | 0.31 |
| | ER positive (125) | 0.33 | 0.31 | 0.36 | 0.33 | 0.32 | 0.30 |
| | p-value (Mann-Whitney U) | 0.689 | 0.727 | 0.245 | 0.530 | 0.288 | 0.991 |
| PR status (148) | PR negative (32) | 0.33 | 0.31 | 0.36 | 0.33 | 0.31 | 0.32 |
| | PR positive (116) | 0.32 | 0.31 | 0.36 | 0.33 | 0.32 | 0.30 |
| | p-value (Mann-Whitney U) | 0.795 | 0.708 | 0.200 | 0.600 | 0.246 | 0.960 |
| Her2 status (148) | Her2 negative (114) | 0.33 | 0.31 | 0.36 | 0.33 | 0.31 | 0.29 |
| | Her2 positive (34) | 0.31 | 0.31 | 0.36 | 0.32 | 0.31 | 0.32 |
| | p-value (Mann-Whitney U) | 0.929 | 0.686 | 0.896 | 0.957 | 0.892 | 0.425 |
| Three receptor status (148) | Tripple negative (17) | 0.33 | 0.31 | 0.37 | 0.32 | 0.31 | 0.34 |
| | Others (131) | 0.32 | 0.31 | 0.36 | 0.33 | 0.32 | 0.30 |
| | p-value (Mann-Whitney U) | 0.810 | 0.801 | 0.576 | 0.763 | 0.381 | 0.949 |
| Menopause status (148) | premenopause (105) | 0.32 | 0.30 | 0.36 | 0.32 | 0.31 | 0.30 |
| | postmenopause (43) | 0.34 | 0.33 | 0.36 | 0.33 | 0.33 | 0.32 |
| | p-value (Mann-Whitney U) | 0.563 | 0.202 | 0.423 | 0.483 | 0.279 | 0.206 |

Fig. 6 (continued)

Table 6. The methylation leveles of the eight genes in sporadic BC patients with different clinical characteristics (cases from the third validation study) (continued)

| Clinical characteristics (N) | Group (N) | Median of methylation levels ||||| 
|---|---|---|---|---|---|---|
| | | MGRN1_C pG_28 | MGRN1_C pG_29 | MGRN1_C pG_31 | MGRN1_C pG_32 | MGRN1_C pG_34 |
| Tumour stage (143) | Stage 0&I (57) | 0.26 | 0.35 | 0.29 | 0.24 | 0.33 |
| | Stage II (68) | 0.32 | 0.40 | 0.36 | 0.28 | 0.39 |
| | Stage III&IV (18) | 0.33 | 0.46 | 0.40 | 0.34 | 0.41 |
| | p-value (Kruskal Wallis Test) | 0.006 | 0.001 | 0.008 | 0.007 | 0.005 |
| Tumour size (147) | Tis&T1 (74) | 0.28 | 0.37 | 0.32 | 0.26 | 0.35 |
| | T2 (60) | 0.31 | 0.39 | 0.31 | 0.27 | 0.38 |
| | T3 and T4 (13) | 0.41 | 0.49 | 0.45 | 0.40 | 0.42 |
| | p-value (Kruskal Wallis Test) | 0.007 | 0.001 | 0.004 | 0.004 | 0.123 |
| Lymph node (LN) involvement (139) | no involved LN (96) | 0.28 | 0.37 | 0.30 | 0.27 | 0.35 |
| | 1-3 involved LN (37) | 0.31 | 0.40 | 0.37 | 0.27 | 0.39 |
| | > 3 involved LN (6) | 0.33 | 0.41 | 0.40 | 0.31 | 0.37 |
| | p-value (Kruskal Wallis Test) | 0.466 | 0.374 | 0.097 | 0.489 | 0.122 |
| Grading (187) | Grade 1 (20) | 0.26 | 0.35 | 0.29 | 0.24 | 0.34 |
| | Grade 2 (94) | 0.31 | 0.39 | 0.35 | 0.27 | 0.37 |
| | Grade 3 (33) | 0.29 | 0.38 | 0.29 | 0.28 | 0.35 |
| | p-value (Kruskal Wallis Test) | 0.254 | 0.319 | 0.468 | 0.702 | 0.422 |
| ER status (147) | ER negative (23) | 0.28 | 0.39 | 0.33 | 0.27 | 0.35 |
| | ER positive (125) | 0.31 | 0.38 | 0.34 | 0.27 | 0.37 |
| | p-value (Mann-Whitney U) | 0.537 | 0.835 | 0.933 | 0.976 | 0.254 |
| PR status (148) | PR negative (32) | 0.29 | 0.39 | 0.36 | 0.27 | 0.35 |
| | PR positive (116) | 0.30 | 0.38 | 0.33 | 0.27 | 0.37 |
| | p-value (Mann-Whitney U) | 0.675 | 0.656 | 0.788 | 0.797 | 0.240 |
| Her2 status (148) | Her2 negative (114) | 0.30 | 0.38 | 0.33 | 0.27 | 0.37 |
| | Her2 positive (34) | 0.30 | 0.38 | 0.35 | 0.26 | 0.37 |
| | p-value (Mann-Whitney U) | 0.619 | 0.674 | 0.678 | 0.910 | 0.700 |
| Three receptor status (148) | Tripple negative (17) | 0.31 | 0.40 | 0.33 | 0.28 | 0.36 |
| | Others (131) | 0.30 | 0.38 | 0.34 | 0.27 | 0.37 |
| | p-value (Mann-Whitney U) | 0.825 | 0.990 | 0.858 | 0.884 | 0.777 |
| Menopause status (148) | premenopause (105) | 0.29 | 0.38 | 0.33 | 0.26 | 0.36 |
| | postmenopause (43) | 0.31 | 0.38 | 0.36 | 0.29 | 0.39 |
| | p-value (Mann-Whitney U) | 0.502 | 0.594 | 0.652 | 0.131 | 0.172 |

Fig. 6 (continued)

Table 6. The methylation leveles of the eight genes in sporadic BC patients with different clinical characteristics (cases from the third validation study) (continued)

| Clinical characteristics (N) | Group (N) | Median of methylation levels ||||||| 
| | | RAPSN _CpG_1 | RAPSN _CpG_2 | RAPSN _CpG_4 | RAPSN _CpG_5 | RAPSN _CpG_6 | RAPSN _CpG_7 | RAPSN _CpG_8 |
|---|---|---|---|---|---|---|---|---|
| Tumour stage (143) | Stage 0&I (57) | 0.95 | 0.61 | 0.38 | 0.73 | 0.49 | 0.73 | 0.95 |
| | Stage II (68) | 0.94 | 0.63 | 0.42 | 0.77 | 0.56 | 0.70 | 0.96 |
| | Stage III&IV (18) | 0.95 | 0.63 | 0.41 | 0.75 | 0.56 | 0.74 | 0.96 |
| | p-value (Kruskal Wallis Test) | 0.646 | 0.757 | 0.370 | 0.037 | 0.007 | 0.441 | 0.688 |
| Tumour size (147) | Tis&T1 (74) | 0.94 | 0.61 | 0.38 | 0.73 | 0.51 | 0.73 | 0.96 |
| | T2 (60) | 0.95 | 0.62 | 0.41 | 0.78 | 0.54 | 0.70 | 0.96 |
| | T3 and T4 (13) | 0.97 | 0.64 | 0.53 | 0.71 | 0.65 | 0.73 | 0.96 |
| | p-value (Kruskal Wallis Test) | 0.330 | 0.976 | 0.044 | 0.089 | 0.081 | 0.413 | 0.669 |
| Lymph node (LN) involvement (139) | no involved LN (96) | 0.95 | 0.62 | 0.40 | 0.74 | 0.51 | 0.73 | 0.96 |
| | 1-3 involved LN (37) | 0.94 | 0.62 | 0.39 | 0.76 | 0.55 | 0.69 | 0.96 |
| | > 3 involved LN (6) | 0.97 | 0.59 | 0.41 | 0.75 | 0.59 | 0.77 | 0.98 |
| | p-value (Kruskal Wallis Test) | 0.501 | 0.729 | 0.880 | 0.619 | 0.206 | 0.051 | 0.493 |
| Grading (187) | Grade 1 (20) | 0.97 | 0.61 | 0.41 | 0.73 | 0.52 | 0.75 | 0.95 |
| | Grade 2 (94) | 0.94 | 0.62 | 0.41 | 0.75 | 0.53 | 0.71 | 0.96 |
| | Grade 3 (33) | 0.94 | 0.64 | 0.37 | 0.75 | 0.53 | 0.70 | 0.97 |
| | p-value (Kruskal Wallis Test) | 0.264 | 0.767 | 0.453 | 0.827 | 0.796 | 0.585 | 0.082 |
| ER status (147) | ER negative (23) | 0.94 | 0.64 | 0.35 | 0.73 | 0.47 | 0.71 | 0.96 |
| | ER positive (125) | 0.95 | 0.62 | 0.41 | 0.75 | 0.53 | 0.72 | 0.96 |
| | p-value (Mann-Whitney U) | 0.794 | 0.727 | 0.043 | 0.520 | 0.090 | 0.711 | 0.917 |
| PR status (148) | PR negative (32) | 0.93 | 0.66 | 0.38 | 0.74 | 0.49 | 0.73 | 0.96 |
| | PR positive (116) | 0.95 | 0.62 | 0.41 | 0.75 | 0.53 | 0.71 | 0.96 |
| | p-value (Mann-Whitney U) | 0.137 | 0.773 | 0.217 | 0.818 | 0.389 | 0.510 | 0.891 |
| Her2 status (148) | Her2 negative (114) | 0.95 | 0.62 | 0.39 | 0.75 | 0.53 | 0.72 | 0.96 |
| | Her2 positive (34) | 0.93 | 0.64 | 0.42 | 0.75 | 0.53 | 0.72 | 0.95 |
| | p-value (Mann-Whitney U) | 0.001 | 0.608 | 0.553 | 0.544 | 0.583 | 0.798 | 0.374 |
| Three receptor status (148) | Tripple negative (17) | 0.94 | 0.65 | 0.35 | 0.75 | 0.47 | 0.72 | 0.96 |
| | Others (131) | 0.95 | 0.62 | 0.41 | 0.75 | 0.53 | 0.71 | 0.96 |
| | p-value (Mann-Whitney U) | 0.990 | 0.888 | 0.041 | 0.734 | 0.214 | 0.520 | 0.281 |
| Menopause status (148) | premenopause (105) | 0.94 | 0.62 | 0.38 | 0.75 | 0.53 | 0.71 | 0.96 |
| | postmenopause (43) | 0.95 | 0.62 | 0.43 | 0.75 | 0.54 | 0.74 | 0.96 |
| | p-value (Mann-Whitney U) | 0.540 | 0.788 | 0.016 | 0.891 | 0.418 | 0.234 | 0.633 |

Fig. 6 (continued)

Table 6. The methylation leveles of the eight genes in sporadic BC patients with different clinical characteristics (cases from the third validation study) (continued)

| Clinical characteristics (N) | Group (N) | Median of methylation levels | | | | | | |
|---|---|---|---|---|---|---|---|---|
| | | miR1273p | miR148b | miR376a | miR376c | miR4093p | miR652 | miR801 |
| Tumour stage (143) | Stage 0&I (57) | 32.97 | 31.28 | 35.51 | 33.17 | 32.54 | 29.69 | 30.33 |
| | Stage II (68) | 32.86 | 31.11 | 35.28 | 33.11 | 32.67 | 29.48 | 30.40 |
| | Stage III&IV (18) | 32.92 | 31.23 | 35.07 | 33.17 | 32.74 | 29.71 | 30.17 |
| | p-value (Kruskal Wallis Test) | 0.996 | 0.571 | 0.578 | 0.853 | 0.736 | 0.268 | 0.611 |
| Tumour size (147) | Tis&T1 (74) | 32.88 | 31.26 | 35.34 | 33.07 | 32.57 | 29.66 | 30.32 |
| | T2 (60) | 32.93 | 31.15 | 35.19 | 33.13 | 32.76 | 29.55 | 30.43 |
| | T3 and T4 (13) | 32.99 | 31.23 | 35.34 | 33.50 | 32.74 | 29.64 | 30.18 |
| | p-value (Kruskal Wallis Test) | 0.821 | 0.907 | 0.604 | 0.569 | 0.578 | 0.503 | 0.720 |
| Lymph node (LN) involvement (139) | no involved LN (96) | 32.74 | 31.28 | 35.35 | 33.06 | 32.62 | 29.64 | 30.26 |
| | 1-3 involved LN (37) | 33.13 | 31.16 | 35.34 | 33.24 | 32.86 | 29.56 | 30.46 |
| | > 3 involved LN (6) | 32.37 | 31.05 | 34.67 | 32.71 | 32.31 | 29.09 | 30.36 |
| | p-value (Kruskal Wallis Test) | 0.570 | 0.827 | 0.308 | 0.510 | 0.791 | 0.557 | 0.730 |
| Grading (187) | Grade 1 (20) | 32.84 | 31.43 | 35.54 | 33.37 | 32.30 | 29.62 | 30.75 |
| | Grade 2 (94) | 33.03 | 31.22 | 35.32 | 33.17 | 32.72 | 29.64 | 30.40 |
| | Grade 3 (33) | 32.56 | 31.10 | 35.08 | 32.78 | 32.35 | 29.51 | 30.14 |
| | p-value (Kruskal Wallis Test) | 0.766 | 0.402 | 0.988 | 0.883 | 0.443 | 0.607 | 0.191 |
| ER status (147) | ER negative (23) | 32.65 | 31.36 | 35.07 | 32.98 | 32.33 | 29.80 | 30.25 |
| | ER positive (125) | 32.98 | 31.22 | 35.35 | 33.18 | 32.71 | 29.59 | 30.39 |
| | p-value (Mann-Whitney U) | 0.657 | 0.973 | 0.316 | 0.706 | 0.325 | 0.897 | 0.460 |
| PR status (148) | PR negative (32) | 32.74 | 31.36 | 35.08 | 33.18 | 32.41 | 29.83 | 30.25 |
| | PR positive (116) | 32.97 | 31.22 | 35.34 | 33.17 | 32.69 | 29.57 | 30.39 |
| | p-value (Mann-Whitney U) | 0.955 | 0.732 | 0.536 | 0.990 | 0.788 | 0.496 | 0.313 |
| Her2 status (148) | Her2 negative (114) | 32.96 | 31.23 | 35.32 | 33.19 | 32.70 | 29.60 | 30.29 |
| | Her2 positive (34) | 32.82 | 31.24 | 35.34 | 33.07 | 32.62 | 29.64 | 30.58 |
| | p-value (Mann-Whitney U) | 0.528 | 0.816 | 0.698 | 0.693 | 0.889 | 0.643 | 0.276 |
| Three receptor status (148) | Tripple negative (17) | 32.65 | 31.22 | 34.86 | 33.03 | 31.89 | 29.88 | 30.25 |
| | Others (131) | 32.97 | 31.23 | 35.34 | 33.18 | 32.71 | 29.59 | 30.39 |
| | p-value (Mann-Whitney U) | 0.831 | 0.814 | 0.334 | 0.814 | 0.292 | 0.736 | 0.409 |
| Menopause status (148) | premenopause (105) | 32.81 | 31.32 | 35.32 | 33.19 | 32.56 | 29.72 | 30.45 |
| | postmenopause (43) | 32.99 | 31.10 | 35.36 | 33.16 | 33.03 | 29.52 | 30.14 |
| | p-value (Mann-Whitney U) | 0.776 | 0.063 | 0.792 | 0.711 | 0.205 | 0.331 | 0.024 |

Fig. 7

Table 7. Sample Description of blood-based biomarker panel for the early detection of pancreatic cancer

| Cohort | Sample types | Assays | Groups | Target N | Mean of age (range) | Median of age | Assayed N (call rate %) | | | | | |
|---|---|---|---|---|---|---|---|---|---|---|---|---|
| | | | | | | | HYAL2 | S100P | SLC22A18 | DYRK4 | FUT7 |
| PaCa case and controls | Peripheral blood DNA | MassARRAY | All controls | 191 | 58.7 (21-68) | 61 | 191 (100%) | 191 (100%) | 190 (99.5%) | 191 (100%) | 191 (100%) |
| | | | All PaCa cases | 147 | 62.9 (19-86) | 64 | 147 (100%) | 147 (100%) | 147 (100%) | 147 (100%) | 147 (100%) |
| | | | Male controls | 115 | 59.0 (27-67) | 58 | 115 (100%) | 115 (100%) | 115 (100%) | 115 (100%) | 115 (100%) |
| | | | Male PaCa case | 80 | 62.9 (39-86) | 63.5 | 80 (100%) | 80 (100%) | 80 (100%) | 80 (100%) | 80 (100%) |
| | | | Femal controls | 76 | 60.0 (21-68) | 63 | 76 (100%) | 76 (100%) | 75 (98.7%) | 76 (100%) | 76 (100%) |
| | | | Femal PaCa cas. | 67 | 62.0 (19-79) | 66 | 67 (100%) | 67 (100%) | 67 (100%) | 67 (100%) | 67 (100%) |

Fig.8

Table 8. Methylation differences in genes comparing PaCa cases and controls

| CpG sites | Differences in methylation levels | | | |
|---|---|---|---|---|
| | Controls median (IQR) | PaCa cases median (IQR) | OR (95 % CI) * per -10% methylation | $p$-value * |
| HYAL2_CpG_1 | 0.35 (0.31-0.40) | 0.25 (0.19-0.32) | 2.09 (1.61-2.71) | 2.68E-08 |
| HYAL2_CpG_2 | 0.27 (0.23-0.31) | 0.14 (0.09-0.18) | 7.06 (4.58-10.88) | 8.01E-19 |
| HYAL2_CpG_3 | 0.43 (0.38-0.46) | 0.29 (0.23-0.34) | 7.94 (5.04-12.50) | 3.94E-19 |
| HYAL2_CpG_4 | 0.61 (0.56-0.66) | 0.48 (0.43-0.55) | 4.24 (3.01-5.98) | 1.37E-16 |
| S100P_CpG_2&3 | 0.73 (0.69-0.77) | 0.59 (0.54-0.63) | 14.07 (8.04-24.61) | 1.97E-20 |
| S100P_CpG_4 | 0.74 (0.65-0.90) | 0.62 (0.55-0.82) | 1.55 (1.33-1.82) | 4.90E-08 |
| S100P_CpG_7 | 0.64 (0.54-0.73) | 0.31 (0.21-0.42) | 4.03 (3.01-5.39) | 6.51E-21 |
| S100P_CpG_8 | 0.54 (0.47-0.61) | 0.33 (0.25-0.40) | 3.85 (2.87-5.16) | 2.45E-19 |
| S100P_CpG_9 | 0.62 (0.56-0.68) | 0.43 (0.36-0.50) | 5.02 (3.55-7.09) | 6.61E-20 |
| SLC22A18_CpG_1 | 0.34 (0.26-0.39) | 0.17 (0.13-0.23) | 5.28 (3.60-7.57) | 1.17E-19 |
| SLC22A18_CpG_3 | 0.23 (0.17-0.27) | 0.12 (0.09-0.17) | 8.81 (5.48-14.18) | 3.03E-19 |
| SLC22A18_CpG_4 | 0.30 (0.23-0.38) | 0.13 (0.08-0.20) | 4.23 (3.07-5.83) | 1.03E-18 |
| SLC22A18_CpG_6 | 0.30 (0.25-0.36) | 0.17 (0.11-0.23) | 5.14 (3.59-7.35) | 3.98E-19 |
| SLC22A18_CpG_8 | 0.68 (0.62-0.74) | 0.57 (0.49-0.65) | 2.13 (1.70-2.68) | 7.17E-11 |
| DYRK4_CpG_1 | 0.59 (0.37-0.75) | 0.18 (0.02-0.49) | 1.46 (1.33-1.62) | 3.85E-14 |
| DYRK4_CpG_3 | 0.32 (0.25-0.35) | 0.32 (0.14-0.35) | 1.20 (1.02-1.41) | 0.032 |
| FUT7_CpG_1 | 0.49 (0.36-0.61) | 0.21 (0.15-0.36) | 1.99 (1.70-2.33) | 1.63E-17 |
| FUT7_CpG_2 | 0.42 (0.37-0.47) | 0.27 (0.22-0.33) | 6.95 (4.55-10.61) | 2.77E-19 |
| FUT7_CpG_3 | 0.21 (0.11-0.31) | 0.06 (0.03-0.16) | 2.77 (2.10-3.66) | 6.21E-13 |
| FUT7_CpG_4 | 0.40 (0.33-0.66) | 0.26 (0.21-0.35) | 2.00 (1.66-2.41) | 3.13E-13 |
| FUT7_CpG_6 | 0.31 (0.22-0.39) | 0.14 (0.08-0.22) | 2.36 (1.88-2.98) | 3.12E-13 |
| FUT7_CpG_7 | 0.15 (0.09-0.22) | 0.05 (0.01-0.10) | 3.65 (2.54-5.25) | 2.28E-12 |
| FUT7_CpG_8 | 0.30 (0.20-0.39) | 0.15 (0.10-0.25) | 2.05 (1.65-2.53) | 4.25E-11 |
| All CpG panel | | | | 2.57E-26 |

* logistic regression, adjusted for age and different batches for the measurements

Fig. 8 (continued)

Table 8. Methylation differences in genes comparing PaCa cases and controls (continued)

| CpG sites | Early stage (Stage0&1&2) vs All controls | | | |
|---|---|---|---|---|
| | Controls median (IQR) | PaCa early cases median (IQR) | OR (95 % CI) * per -10% methylation | p-value * |
| HYAL2_CpG_1 | 0.35 (0.31-0.40) | 0.27 (0.20-0.33) | 2.04 (1.46-2.84) | 2.93E-05 |
| HYAL2_CpG_2 | 0.27 (0.23-0.31) | 0.14 (0.08-0.18) | 6.29 (3.88-10.18) | 7.83E-14 |
| HYAL2_CpG_3 | 0.43 (0.38-0.46) | 0.28 (0.23-0.34) | 7.37 (4.41-12.29) | 2.01E-14 |
| HYAL2_CpG_4 | 0.61 (0.56-0.66) | 0.47 (0.42-0.54) | 5.54 (3.54-8.70) | 8.71E-14 |
| S100P_CpG_2&3 | 0.73 (0.69-0.77) | 0.59 (0.54-0.63) | 15.48 (7.84-30.55) | 2.86E-15 |
| S100P_CpG_4 | 0.74 (0.65-0.90) | 0.63 (0.56-0.81) | 1.58 (1.29-1.94) | 1.12E-05 |
| S100P_CpG_7 | 0.64 (0.54-0.73) | 0.31 (0.21-0.47) | 3.77 (2.72-5.23) | 1.50E-15 |
| S100P_CpG_8 | 0.54 (0.47-0.61) | 0.34 (0.26-0.40) | 4.00 (2.80-5.71) | 2.26E-14 |
| S100P_CpG_9 | 0.62 (0.56-0.68) | 0.43 (0.36-0.52) | 5.17 (3.43-7.80) | 4.15E-15 |
| SLC22A18_CpG_1 | 0.34 (0.26-0.39) | 0.18 (0.14-0.23) | 5.48 (3.50-8.56) | 8.53E-14 |
| SLC22A18_CpG_3 | 0.23 (0.17-0.27) | 0.11 (0.08-0.15) | 13.25 (6.89-25.48) | 9.63E-15 |
| SLC22A18_CpG_4 | 0.30 (0.23-0.38) | 0.10 (0.07-0.18) | 5.49 (3.56-8.49) | 1.64E-14 |
| SLC22A18_CpG_6 | 0.30 (0.25-0.36) | 0.14 (0.11-0.22) | 5.47 (3.54-8.47) | 2.28E-14 |
| SLC22A18_CpG_8 | 0.68 (0.62-0.74) | 0.57 (0.48-0.65) | 2.35 (1.76-3.14) | 7.50E-09 |
| DYRK4_CpG_1 | 0.59 (0.37-0.75) | 0.17 (0.02-0.49) | 1.50 (1.33-1.70) | 2.06E-10 |
| DYRK4_CpG_3 | 0.32 (0.25-0.35) | 0.32 (0.12-0.35) | 1.32 (1.05-1.65) | 0.019 |
| FUT7_CpG_1 | 0.49 (0.36-0.61) | 0.21 (0.12-0.31) | 1.94 (1.61-2.34) | 5.49E-12 |
| FUT7_CpG_2 | 0.42 (0.37-0.47) | 0.27 (0.22-0.35) | 6.23 (3.87-10.04) | 5.65E-14 |
| FUT7_CpG_3 | 0.21 (0.11-0.31) | 0.08 (0.04-0.18) | 2.31 (1.69-3.16) | 1.29E-07 |
| FUT7_CpG_4 | 0.40 (0.33-0.66) | 0.27 (0.21-0.36) | 2.01 (1.59-2.55) | 5.86E-09 |
| FUT7_CpG_6 | 0.31 (0.22-0.39) | 0.14 (0.09-0.26) | 2.10 (1.61-2.75) | 4.41E-08 |
| FUT7_CpG_7 | 0.15 (0.09-0.22) | 0.05 (0.01-0.09) | 3.25 (2.14-4.95) | 3.68E-08 |
| FUT7_CpG_8 | 0.30 (0.20-0.39) | 0.15 (0.10-0.26) | 1.92 (1.50-2.46) | 2.74E-07 |
| All CpG panel | | | | 1.66E-18 |

* logistic regression, adjusted for age and different batches for the measurements

Fig. 9

Table 9. Methylation differences in genes comparing PaCa cases and controls stratified by gender

| CpG sites | Male samples | | | |
|---|---|---|---|---|
| | male controls median (IQR) | male PaCa cases median (IQR) | OR (95 % CI) * per -10% methylation | p-value * |
| HYAL2_CpG_1 | 0.36 (0.31-0.41) | 0.25 (0.20-0.32) | 2.43 (1.68-3.53) | 2.60E-06 |
| HYAL2_CpG_2 | 0.28 (0.23-0.31) | 0.14 (0.10-0.18) | 20.70 (8.69-49.27) | 7.56E-12 |
| HYAL2_CpG_3 | 0.43 (0.39-0.47) | 0.28 (0.23-0.34) | 9.60 (5.00-18.43) | 1.10E-11 |
| HYAL2_CpG_4 | 0.63 (0.56-0.68) | 0.47 (0.42-0.54) | 4.95 (3.07-7.98) | 5.35E-11 |
| S100P_CpG_2&3 | 0.74 (0.69-0.77) | 0.59 (0.54-0.63) | 14.72 (6.98-31.04) | 1.59E-12 |
| S100P_CpG_4 | 0.78 (0.67-0.91) | 0.63 (0.56-0.83) | 1.63 (1.32-2.02) | 6.10E-06 |
| S100P_CpG_7 | 0.65 (0.59-0.76) | 0.34 (0.21-0.43) | 5.25 (3.24-8.48) | 1.39E-11 |
| S100P_CpG_8 | 0.56 (0.49-0.63) | 0.35 (0.25-0.42) | 4.27 (2.81-6.47) | 8.94E-12 |
| S100P_CpG_9 | 0.64 (0.58-0.68) | 0.44 (0.36-0.51) | 6.56 (3.85-11.19) | 4.75E-12 |
| SLC22A18_CpG_1 | 0.35 (0.27-0.40) | 0.17 (0.12-0.25) | 4.39 (2.86-6.75) | 1.46E-11 |
| SLC22A18_CpG_3 | 0.23 (0.17-0.27) | 0.12 (0.08-0.17) | 6.08 (3.52-10.52) | 9.95E-11 |
| SLC22A18_CpG_4 | 0.30 (0.23-0.39) | 0.13 (0.09-0.22) | 4.56 (2.94-7.08) | 1.17E-11 |
| SLC22A18_CpG_6 | 0.30 (0.25-0.37) | 0.17 (0.13-0.26) | 4.11 (2.66-6.34) | 1.68E-10 |
| SLC22A18_CpG_8 | 0.68 (0.63-0.76) | 0.61 (0.52-0.67) | 1.87 (1.41-2.47) | 1.21E-05 |
| DYRK4_CpG_1 | 0.62 (0.39-0.75) | 0.24 (0.03-0.56) | 1.38 (1.22-1.57) | 2.77E-07 |
| DYRK4_CpG_3 | 0.32 (0.26-0.35) | 0.31 (0.09-0.35) | 1.21 (0.99-1.49) | 0.068 |
| FUT7_CpG_1 | 0.52 (0.40-0.64) | 0.21 (0.15-0.31) | 2.14 (1.72-2.67) | 8.28E-12 |
| FUT7_CpG_2 | 0.44 (0.39-0.49) | 0.27 (0.22-0.33) | 6.44 (3.73-11.12) | 2.26E-11 |
| FUT7_CpG_3 | 0.22 (0.12-0.33) | 0.07 (0.04-0.13) | 3.15 (2.12-4.70) | 1.58E-08 |
| FUT7_CpG_4 | 0.42 (0.32-0.69) | 0.26 (0.21-0.36) | 2.12 (1.64-2.74) | 1.08E-08 |
| FUT7_CpG_6 | 0.32 (0.25-0.39) | 0.14 (0.08-0.22) | 2.27 (1.70-3.04) | 3.40E-08 |
| FUT7_CpG_7 | 0.17 (0.09-0.22) | 0.05 (0.01-0.10) | 3.32 (2.11-5.20) | 1.91E-07 |
| FUT7_CpG_8 | 0.33 (0.21-0.41) | 0.15 (0.09-0.23) | 2.21 (1.66-2.93) | 5.82E-08 |
| All CpG panel | | | | 3.28E-14 |

* logistic regression, adjusted for age and different batches for the measurements

Fig. 9 (continued)

Table 9. Methylation differences in genes comparing PaCa cases and controls stratified by gender (continued)

| CpG sites | Female samples | | | |
|---|---|---|---|---|
| | female controls median (IQR) | female PaCa cases median | OR (95 % CI) * per -10% methylation | p-value * |
| HYAL2_CpG_1 | 0.35 (0.30-0.38) | 0.25 (0.19-0.33) | 1.76 (1.22-2.54) | 0.002 |
| HYAL2_CpG_2 | 0.25 (0.21-0.30) | 0.14 (0.08-0.18) | 3.44 (2.09-5.66) | 1.00E-06 |
| HYAL2_CpG_3 | 0.41 (0.37-0.44) | 0.30 (0.23-0.34) | 6.88 (3.52-13.46) | 1.73E-08 |
| HYAL2_CpG_4 | 0.60 (0.55-0.64) | 0.48 (0.43-0.55) | 3.41 (2.09-5.58) | 1.02E-06 |
| S100P_CpG_2&3 | 0.72 (0.68-0.75) | 0.60 (0.53-0.63) | 13.61 (5.72-32.39) | 3.55E-09 |
| S100P_CpG_4 | 0.69 (0.63-0.88) | 0.61 (0.55-0.80) | 1.45 (1.14-1.84) | 0.003 |
| S100P_CpG_7 | 0.60 (0.51-0.68) | 0.29 (0.20-0.37) | 3.23 (2.24-4.67) | 4.19E-10 |
| S100P_CpG_8 | 0.51 (0.46-0.58) | 0.31 (0.25-0.39) | 3.39 (2.23-5.15) | 1.14E-08 |
| S100P_CpG_9 | 0.59 (0.54-0.66) | 0.43 (0.35-0.49) | 3.84 (2.43-6.06) | 8.97E-09 |
| SLC22A18_CpG_1 | 0.32 (0.24-0.37) | 0.17 (0.14-0.21) | 8.59 (4.28-17.23) | 1.44E-09 |
| SLC22A18_CpG_3 | 0.22 (0.17-0.26) | 0.11 (0.08-0.15) | 19.70 (7.63-50.83) | 7.22E-10 |
| SLC22A18_CpG_4 | 0.29 (0.22-0.37) | 0.13 (0.06-0.19) | 4.24 (2.58-6.98) | 1.25E-08 |
| SLC22A18_CpG_6 | 0.28 (0.25-0.34) | 0.14 (0.11-0.21) | 8.75 (4.40-17.38) | 6.06E-10 |
| SLC22A18_CpG_8 | 0.65 (0.61-0.71) | 0.55 (0.47-0.63) | 2.76 (1.83-4.16) | 1.32E-06 |
| DYRK4_CpG_1 | 0.56 (0.35-0.73) | 0.16 (0.02-0.37) | 1.62 (1.36-1.92) | 3.33E-08 |
| DYRK4_CpG_3 | 0.32 (0.24-0.35) | 0.32 (0.23-0.35) | 1.20 (0.90-1.59) | 0.215 |
| FUT7_CpG_1 | 0.47 (0.30-0.54) | 0.19 (0.09-0.36) | 1.82 (1.44-2.30) | 5.16E-07 |
| FUT7_CpG_2 | 0.40 (0.35-0.45) | 0.26 (0.22-0.33) | 7.99 (4.03-15.86) | 2.81E-09 |
| FUT7_CpG_3 | 0.17 (0.09-0.25) | 0.06 (0.03-0.17) | 2.37 (1.58-3.53) | 2.61E-05 |
| FUT7_CpG_4 | 0.40 (0.34-0.60) | 0.26 (0.19-0.35) | 1.89 (1.44-2.48) | 4.88E-06 |
| FUT7_CpG_6 | 0.26 (0.18-0.39) | 0.13 (0.08-0.20) | 2.50 (1.71-3.68) | 2.79E-06 |
| FUT7_CpG_7 | 0.13 (0.09-0.22) | 0.05 (0.02-0.09) | 4.17 (2.27-7.68) | 4.28E-06 |
| FUT7_CpG_8 | 0.27 (0.18-0.36) | 0.15 (0.10-0.26) | 1.86 (1.34-2.57) | 1.75E-04 |
| All CpG panel | | | | 7.24E-12 |

* logistic regression, adjusted for age and different batches for the measurements

Fig. 10

Table 10. The discriminatory power of the methylation in genes to distinguish PaCa cases from healthy controls

| CpG sites | Area under curve (AUC), 95% CI | | | |
|---|---|---|---|---|
| | all PaCa cases vs. all controls | stage 0&I&II PaCa cases vs. all controls | Male, PaCa cases vs. controls | Female, PaCa cases vs. controls |
| HYAL2_CpG_1 | 0.77 (0.72-0.83) | 0.76 (0.68-0.83) | 0.79 (0.72-0.86) | 0.75 (0.66-0.83) |
| HYAL2_CpG_2 | 0.90 (0.86-0.94) | 0.90 (0.85-0.95) | 0.94 (0.90-0.97) | 0.86 (0.79-0.92) |
| HYAL2_CpG_3 | 0.90 (0.86-0.94) | 0.90 (0.85-0.94) | 0.92 (0.88-0.96) | 0.87 (0.81-0.94) |
| HYAL2_CpG_4 | 0.86 (0.82-0.90) | 0.87 (0.82-0.93) | 0.89 (0.83-0.94) | 0.83 (0.75-0.90) |
| S100P_CpG_2&3 | 0.93 (0.89-0.96) | 0.92 (0.87-0.96) | 0.93 (0.89-0.97) | 0.92 (0.87-0.97) |
| S100P_CpG_4 | 0.74 (0.68-0.79) | 0.75 (0.67-0.82) | 0.75 (0.68-0.83) | 0.71 (0.63-0.80) |
| S100P_CpG_7 | 0.94 (0.91-0.96) | 0.92 (0.88-0.96) | 0.96 (0.93-0.98) | 0.92 (0.87-0.97) |
| S100P_CpG_8 | 0.90 (0.86-0.94) | 0.88 (0.83-0.94) | 0.91 (0.86-0.96) | 0.89 (0.83-0.96) |
| S100P_CpG_9 | 0.90 (0.86-0.94) | 0.89 (0.84-0.94) | 0.93 (0.88-0.97) | 0.87 (0.80-0.93) |
| SLC22A18_CpG_1 | 0.88 (0.84-0.91) | 0.87 (0.82-0.92) | 0.87 (0.81-0.92) | 0.90 (0.85-0.95) |
| SLC22A18_CpG_3 | 0.87 (0.84-0.91) | 0.89 (0.84-0.93) | 0.85 (0.80-0.91) | 0.91 (0.86-0.96) |
| SLC22A18_CpG_4 | 0.88 (0.84-0.92) | 0.89 (0.84-0.93) | 0.88 (0.83-0.93) | 0.90 (0.85-0.96) |
| SLC22A18_CpG_6 | 0.86 (0.82-0.90) | 0.85 (0.80-0.90) | 0.85 (0.79-0.90) | 0.89 (0.84-0.95) |
| SLC22A18_CpG_8 | 0.77 (0.72-0.82) | 0.77 (0.71-0.84) | 0.76 (0.69-0.83) | 0.80 (0.73-0.88) |
| DYRK4_CpG_1 | 0.79 (0.74-0.84) | 0.79 (0.72-0.85) | 0.78 (0.71-0.85) | 0.82 (0.75-0.89) |
| DYRK4_CpG_3 | 0.67 (0.60-0.73) | 0.67 (0.59-0.75) | 0.69 (0.61-0.77) | 0.63 (0.53-0.72) |
| FUT7_CpG_1 | 0.85 (0.81-0.89) | 0.84 (0.78-0.90) | 0.88 (0.83-0.93) | 0.80 (0.73-0.88) |
| FUT7_CpG_2 | 0.90 (0.87-0.94) | 0.88 (0.83-0.93) | 0.90 (0.86-0.95) | 0.90 (0.85-0.96) |
| FUT7_CpG_3 | 0.81 (0.77-0.86) | 0.77 (0.71-0.84) | 0.84 (0.79-0.90) | 0.77 (0.69-0.85) |
| FUT7_CpG_4 | 0.83 (0.78-0.87) | 0.82 (0.76-0.87) | 0.85 (0.79-0.90) | 0.81 (0.73-0.88) |
| FUT7_CpG_6 | 0.82 (0.77-0.86) | 0.78 (0.72-0.85) | 0.82 (0.76-0.88) | 0.80 (0.72-0.87) |
| FUT7_CpG_7 | 0.83 (0.78-0.87) | 0.80 (0.74-0.87) | 0.83 (0.77-0.89) | 0.81 (0.74-0.88) |
| FUT7_CpG_8 | 0.78 (0.74-0.83) | 0.77 (0.71-0.83) | 0.81 (0.75-0.87) | 0.76 (0.68-0.83) |
| All CpG panel | 0.98 (0.96-0.99) | 0.98 (0.96-0.99) | 0.99 (0.97-1.00) | 0.98 (0.96-1.00) |

Fig. 11

Table 11. The methylation of genes in PaCa patients with different clinical characteristics

| Clinical characteristics (N) | Group (N) | Median of age | Median of methylation levels ||||||||||||
|---|---|---|---|---|---|---|---|---|---|---|---|---|---|
| | | | HYAL2_CpG_1 | HYAL2_CpG_2 | HYAL2_CpG_3 | HYAL2_CpG_4 | DYRK4_CpG_1 | DYRK4_CpG_3 | S100P_pG_2&3 | S100P_C CpG_4 | S100P_CpG_7 | S100P_CpG_8 | S100P_CpG_9 |
| Tumour stage (108) | Stage 0&1&2 (79) | 63.56 | 0.27 | 0.14 | 0.28 | 0.47 | 0.17 | 0.32 | 0.59 | 0.63 | 0.31 | 0.34 | 0.43 |
| | Stage III&IV (29) | 67.55 | 0.25 | 0.14 | 0.30 | 0.48 | 0.18 | 0.29 | 0.59 | 0.61 | 0.34 | 0.35 | 0.45 |
| | p-value* | 0.294 | 0.635 | 0.477 | 0.519 | 0.703 | 0.903 | 0.873 | 0.771 | 0.558 | 0.718 | 0.972 | 0.642 |
| Tumour size (98) | <T3 (10) | 63.67 | 0.27 | 0.14 | 0.31 | 0.49 | 0.25 | 0.30 | 0.61 | 0.77 | 0.32 | 0.37 | 0.44 |
| | T3 & T4 (88) | 64.15 | 0.25 | 0.13 | 0.28 | 0.47 | 0.16 | 0.32 | 0.59 | 0.61 | 0.31 | 0.34 | 0.44 |
| | p-value* | 0.699 | 0.729 | 0.647 | 0.304 | 0.327 | 0.507 | 0.298 | 0.259 | 0.043 | 0.860 | 0.967 | 0.842 |
| Lymph node (LN) | N0 (28) | 63.67 | 0.27 | 0.15 | 0.29 | 0.47 | 0.22 | 0.32 | 0.61 | 0.61 | 0.35 | 0.37 | 0.44 |
| | N1 (71) | 63.92 | 0.24 | 0.13 | 0.28 | 0.47 | 0.16 | 0.33 | 0.58 | 0.63 | 0.30 | 0.31 | 0.42 |
| | p-value* | 0.907 | 0.189 | 0.834 | 0.292 | 0.602 | 0.750 | 0.362 | 0.423 | 0.386 | 0.950 | 0.771 | 0.809 |
| metastasis status | M0 (91) | 63.56 | 0.26 | 0.14 | 0.28 | 0.47 | 0.17 | 0.32 | 0.59 | 0.62 | 0.31 | 0.34 | 0.43 |
| | M1 (20) | 67.84 | 0.25 | 0.15 | 0.31 | 0.49 | 0.29 | 0.31 | 0.60 | 0.62 | 0.34 | 0.35 | 0.46 |
| | p-value* | 0.199 | 0.687 | 0.659 | 0.478 | 0.343 | 0.562 | 0.875 | 0.942 | 0.800 | 0.602 | 0.839 | 0.461 |
| Grading (83) | Grade 1&2 (53) | 64.20 | 0.26 | 0.14 | 0.28 | 0.45 | 0.16 | 0.32 | 0.57 | 0.63 | 0.29 | 0.31 | 0.44 |
| | Grade 3 (30) | 63.41 | 0.21 | 0.14 | 0.29 | 0.49 | 0.17 | 0.33 | 0.59 | 0.61 | 0.33 | 0.35 | 0.42 |
| | p-value* | 0.798 | 0.013 | 0.939 | 0.367 | 0.292 | 0.943 | 0.562 | 0.189 | 0.791 | 0.290 | 0.448 | 0.974 |
| Gender (147) cases | Male (80) | 63.50 | 0.25 | 0.14 | 0.28 | 0.47 | 0.24 | 0.31 | 0.59 | 0.63 | 0.34 | 0.35 | 0.44 |
| | Female (67) | 66.33 | 0.25 | 0.14 | 0.30 | 0.48 | 0.16 | 0.32 | 0.60 | 0.61 | 0.29 | 0.31 | 0.43 |
| | p-value* | 0.605 | 0.853 | 0.933 | 0.784 | 0.301 | 0.134 | 0.239 | 0.907 | 0.491 | 0.234 | 0.425 | 0.713 |

* The p-values are calculated by Mann-Whitney Test

Fig. 11 (continued)

Table 11. The methylation of genes in PaCa patients with different clinical characteristics (continued)

| Clinical characteristics (N) | Group (N) | Median of methylation levels ||||||||||||||
|---|---|---|---|---|---|---|---|---|---|---|---|---|---|---|
| | | SLC22A18_CpG_1 | SLC22A18_CpG_3 | SLC22A18_CpG_4 | SLC22A18_CpG_6 | SLC22A18_CpG_8 | FUT7_CpG_1 | FUT7_CpG_2 | FUT7_CpG_3 | FUT7_CpG_4 | FUT7_CpG_6 | FUT7_CpG_7 | FUT7_CpG_8 |
| Tumour stage (108) | Stage 0&I&2 (79) | 0.18 | 0.12 | 0.13 | 0.16 | 0.57 | 0.22 | 0.27 | 0.08 | 0.27 | 0.14 | 0.05 | 0.15 |
| | Stage III&IV (29) | 0.19 | 0.12 | 0.15 | 0.17 | 0.59 | 0.17 | 0.24 | 0.05 | 0.25 | 0.11 | 0.03 | 0.13 |
| | p-value* | 0.830 | 0.555 | 0.910 | 0.586 | 0.182 | 0.272 | 0.419 | 0.047 | 0.952 | 0.114 | 0.340 | 0.298 |
| Tumour size (98) | <T3 (10) | 0.17 | 0.10 | 0.12 | 0.14 | 0.54 | 0.19 | 0.25 | 0.06 | 0.24 | 0.09 | 0.03 | 0.11 |
| | T3 & T4 (88) | 0.19 | 0.12 | 0.15 | 0.17 | 0.60 | 0.21 | 0.27 | 0.07 | 0.26 | 0.15 | 0.04 | 0.15 |
| | p-value* | 0.468 | 0.264 | 0.288 | 0.092 | 0.068 | 0.253 | 0.191 | 0.601 | 0.235 | 0.008 | 0.336 | 0.130 |
| Lymph node (LN) | N0 (28) | 0.17 | 0.12 | 0.14 | 0.17 | 0.61 | 0.17 | 0.22 | 0.08 | 0.27 | 0.12 | 0.04 | 0.13 |
| | N1 (71) | 0.19 | 0.12 | 0.14 | 0.17 | 0.58 | 0.23 | 0.27 | 0.07 | 0.25 | 0.14 | 0.04 | 0.17 |
| | p-value* | 0.789 | 0.235 | 0.793 | 0.879 | 0.954 | 0.039 | 0.106 | 0.837 | 0.227 | 0.189 | 0.634 | 0.098 |
| metastasis status | M0 (91) | 0.18 | 0.12 | 0.14 | 0.17 | 0.59 | 0.21 | 0.27 | 0.07 | 0.26 | 0.14 | 0.04 | 0.15 |
| | M1 (20) | 0.19 | 0.12 | 0.14 | 0.17 | 0.58 | 0.21 | 0.27 | 0.06 | 0.24 | 0.12 | 0.05 | 0.14 |
| | p-value* | 0.712 | 0.794 | 0.443 | 0.933 | 0.651 | 0.771 | 0.519 | 0.236 | 0.822 | 0.933 | 0.717 | 0.985 |
| Grading (83) | Grade 1&2 (53) | 0.17 | 0.11 | 0.14 | 0.14 | 0.57 | 0.18 | 0.25 | 0.06 | 0.25 | 0.13 | 0.03 | 0.14 |
| | Grade 3 (30) | 0.19 | 0.13 | 0.19 | 0.20 | 0.63 | 0.22 | 0.28 | 0.07 | 0.25 | 0.16 | 0.07 | 0.17 |
| | p-value* | 0.120 | 0.065 | 0.060 | 0.103 | 0.288 | 0.090 | 0.123 | 0.180 | 0.795 | 0.072 | 0.068 | 0.144 |
| Gender (147) cases | Male (80) | 0.17 | 0.13 | 0.13 | 0.17 | 0.61 | 0.21 | 0.27 | 0.07 | 0.26 | 0.14 | 0.05 | 0.15 |
| | Female (67) | 0.17 | 0.11 | 0.13 | 0.14 | 0.55 | 0.24 | 0.26 | 0.06 | 0.26 | 0.13 | 0.05 | 0.15 |
| | p-value* | 0.502 | 0.057 | 0.639 | 0.117 | 0.003 | 0.784 | 0.648 | 0.700 | 0.791 | 0.745 | 0.953 | 0.994 |

* The p-values are calculated by Mann-Whitney Test

Fig. 12

Table 12. Sample Description of blood-based biomarker panel for the early detection of ovarian cancer

| Sample types | Assays | Sample resources | Groups | Target N | mean of age (range) | median of age | Assayed N (call rate %) | | | |
|---|---|---|---|---|---|---|---|---|---|---|
| | | | | | | | HYAL2 | S100P | SLC22A18 | FUT7 |
| DNA from blood pellet | MassARRAY | University hospital of Heidelberg | controls | 148 | 37.9 (21-63) | 38 | 147 (99.3%) | 147 (99.3%) | 147 (99.3%) | 144 (97.3%) |
| | | University hospital of Heidelberg | OvCa cases | 84 | 61.8 (37-80) | 61.5 | 84 (100.0%) | 78 (92.9%) | 84 (100.0%) | 82 (97.6%) |

Fig. 13

Table 13. Methylation differences in genes comparing OvCa cases and controls

| CpG sites | All samples | | |
| --- | --- | --- | --- |
| | controls median (IQR) | OvCa cases median (IQR) | p-value * |
| HYAL2_CpG_1 | 0.33 (0.29-0.37) | 0.25 (0.20-0.32) | 1.57E-08 |
| HYAL2_CpG_2 | 0.21 (0.18-0.24) | 0.15 (0.11-0.20) | 1.57E-09 |
| HYAL2_CpG_3 | 0.37 (0.32-0.40) | 0.32 (0.25-0.36) | 4.08E-07 |
| HYAL2_CpG_4 | 0.53 (0.50-0.58) | 0.47 (0.41-0.54) | 2.51E-07 |
| S100P_CpG_2&3 | 0.66 (0.63-0.69) | 0.63 (0.58-0.67) | 0.008 |
| S100P_CpG_4 | 0.65 (0.60-0.86) | 0.63 (0.57-0.86) | 0.351 |
| S100P_CpG_7 | 0.44 (0.38-0.51) | 0.33 (0.23-0.41) | 3.53E-09 |
| S100P_CpG_8 | 0.43 (0.40-0.49) | 0.39 (0.31-0.46) | 3.92E-04 |
| S100P_CpG_9 | 0.49 (0.44-0.52) | 0.43 (0.37-0.48) | 3.32E-06 |
| SLC22A18_CpG_3 | 0.19 (0.16-0.23) | 0.13 (0.10-0.18) | 4.50E-11 |
| SLC22A18_CpG_4 | 0.25 (0.22-0.30) | 0.16 (0.12-0.25) | 2.74E-10 |
| SLC22A18_CpG_6 | 0.24 (0.22-0.28) | 0.16 (0.12-0.24) | 9.47E-12 |
| SLC22A18_CpG_8 | 0.66 (0.62-0.70) | 0.57 (0.48-0.62) | 3.43E-12 |
| FUT7_CpG_1 | 0.41 (0.34-0.46) | 0.28 (0.20-0.39) | 3.13E-10 |
| FUT7_CpG_2 | 0.21 (0.17-0.25) | 0.14 (0.11-0.19) | 8.80E-09 |
| FUT7_CpG_3 | 0.16 (0.11-0.20) | 0.10 (0.05-0.16) | 8.31E-08 |
| FUT7_CpG_4 | 0.20 (0.16-0.23) | 0.16 (0.11-0.22) | 0.001 |
| FUT7_CpG_6 | 0.28 (0.21-0.34) | 0.14 (0.11-0.24) | 2.79E-10 |
| FUT7_CpG_7 | 0.14 (0.10-0.17) | 0.07 (0.04-0.12) | 2.02E-09 |
| FUT7_CpG_8 | 0.38 (0.31-0.42) | 0.24 (0.15-0.35) | 2.57E-10 |
| All CpG panel | | | 7.42E-16 |

* logistic regression, adjusted for different batches for the measurements

Fig. 14

Table 14. The discriminatory power of the methylation in genes to distinguish OvCa cases from healthy controls

| CpG sites | Area under curve (AUC), 95% CI |
|---|---|
| | All samples |
| HYAL2_CpG_1 | 0.77 (0.70-0.84) |
| HYAL2_CpG_2 | 0.77 (0.70-0.83) |
| HYAL2_CpG_3 | 0.72 (0.65-0.79) |
| HYAL2_CpG_4 | 0.70 (0.63-0.78) |
| S100P_CpG_2&3 | 0.62 (0.54-0.71) |
| S100P_CpG_4 | 0.56 (0.48-0.64) |
| S100P_CpG_7 | 0.77 (0.70-0.84) |
| S100P_CpG_8 | 0.66 (0.58-0.75) |
| S100P_CpG_9 | 0.70 (0.62-0.77) |
| SLC22A18_CpG_3 | 0.79 (0.72-0.85) |
| SLC22A18_CpG_4 | 0.77 (0.70-0.84) |
| SLC22A18_CpG_6 | 0.79 (0.72-0.86) |
| SLC22A18_CpG_8 | 0.82 (0.76-0.88) |
| FUT7_CpG_1 | 0.76 (0.69-0.83) |
| FUT7_CpG_2 | 0.76 (0.69-0.82) |
| FUT7_CpG_3 | 0.73 (0.66-0.80) |
| FUT7_CpG_4 | 0.64 (0.56-0.72) |
| FUT7_CpG_6 | 0.78 (0.71-0.85) |
| FUT7_CpG_7 | 0.77 (0.70-0.84) |
| FUT7_CpG_8 | 0.77 (0.70-0.84) |
| All CpG panel | 0.91 (0.87-0.95) |

Fig. 15

Table 15. The determination of breast cancer related CpG island shore in HYAL2

| CpG sites | Differences in methylation levels | | | | Correlations to HYAL2_CpG_4 | |
|---|---|---|---|---|---|---|
| | Controls median (IQR) | Familial BC cases median (IQR) | OR (95 % CI) * per 10% methylation | p-value* | Spearman rho | p-value |
| HYAL2-C_CpG_1 | 0.66 (0.60-0.71) | 0.63 (0.56-0.67) | 1.66 (1.15-2.41) | 0.007 | 0.393 | < 0.0001 |
| HYAL2-C_CpG_2 | 0.52 (0.47-0.59) | 0.53 (0.46-0.61) | 1.07 (0.81-1.43) | 0.623 | 0.248 | 0.001 |
| HYAL2-C_CpG_3 | 0.63 (0.58-0.66) | 0.59 (0.56-0.64) | 1.39 (0.93-2.08) | 0.113 | 0.357 | < 0.0001 |
| HYAL2-C_CpG_4 | 0.63 (0.58-0.66) | 0.59 (0.56-0.64) | 1.39 (0.93-2.08) | 0.113 | 0.357 | < 0.0001 |
| HYAL2-C_CpG_5 | 0.73 (0.70-0.76) | 0.72 (0.69-0.76) | 1.19 (0.71-2.00) | 0.505 | 0.253 | 0.0005 |
| HYAL2-C_CpG_6 | 0.63 (0.58-0.66) | 0.59 (0.56-0.64) | 1.39 (0.93-2.08) | 0.113 | 0.357 | < 0.0001 |
| HYAL2-C_CpG_7 | 0.40 (0.34-0.45) | 0.39 (0.35-0.44) | 1.26 (0.82-1.95) | 0.291 | 0.287 | < 0.0001 |
| HYAL2-C_CpG_8 | 0.82 (0.76-0.88) | 0.79 (0.71-0.84) | 1.63 (1.15-2.31) | 0.007 | 0.410 | < 0.0001 |
| HYAL2-C_CpG_9.10 | 0.70 (0.51-0.77) | 0.71 (0.57-0.76) | 0.94 (0.79-1.12) | 0.484 | 0.198 | 0.007 |
| HYAL2-C_CpG_11 | 0.74 (0.70-0.77) | 0.70 (0.66-0.75) | 1.88 (1.16-3.03) | 0.010 | 0.463 | < 0.0001 |
| HYAL2-C_CpG_12.13 | 0.90 (0.88-0.92) | 0.89 (0.86-0.91) | 1.21 (0.87-1.69) | 0.258 | 0.270 | 0.0002 |
| HYAL2-C_CpG_14.15 | 0.83 (0.78-0.86) | 0.80 (0.75-0.84) | 1.41 (0.93-2.12) | 0.103 | 0.381 | < 0.0001 |
| HYAL2-C_CpG_16.17 | 0.75 (0.72-0.78) | 0.73 (0.70-0.75) | 2.24 (1.21-4.16) | 0.011 | 0.348 | < 0.0001 |
| HYAL2-B_CpG_1 | 0.66 (0.62-0.69) | 0.61 (0.59-0.65) | 1.77 (1.11-2.84) | 0.017 | 0.534 | < 0.0001 |
| HYAL2-B_CpG_2 | 0.56 (0.49-0.62) | 0.49 (0.43-0.54) | 2.16 (1.51-3.09) | < 0.0001 | 0.621 | < 0.0001 |
| HYAL2-B_CpG_3.4 | 0.63 (0.61-0.66) | 0.59 (0.56-0.63) | 3.50 (1.87-6.56) | < 0.0001 | 0.566 | < 0.0001 |
| HYAL2-B_CpG_5.6 | 0.77 (0.74-0.83) | 0.71 (0.66-0.77) | 3.52 (2.17-5.71) | < 0.0001 | 0.649 | < 0.0001 |
| HYAL2-B_CpG_7 | 0.57 (0.50-0.62) | 0.50 (0.42-0.57) | 2.08 (1.47-2.95) | < 0.0001 | 0.569 | < 0.0001 |
| HYAL2-B_CpG_8 | 0.66 (0.62-0.69) | 0.61 (0.59-0.65) | 1.77 (1.11-2.84) | 0.017 | 0.534 | < 0.0001 |
| HYAL2-B_CpG_9 | 0.36 (0.31-0.41) | 0.30 (0.26-0.37) | 1.88 (1.28-2.76) | 0.001 | 0.482 | < 0.0001 |
| HYAL2-B_CpG_10 | 0.63 (0.59-0.69) | 0.58 (0.52-0.65) | 1.94 (1.35-2.78) | 0.0004 | 0.634 | < 0.0001 |
| HYAL2-B_CpG_11 | 0.53 (0.48-0.59) | 0.47 (0.41-0.52) | 3.05 (1.94-4.78) | < 0.0001 | 0.602 | < 0.0001 |
| HYAL2_CpG_1 | 0.36 (0.31-0.43) | 0.31 (0.26-0.39) | 1.41 (1.08-1.86) | 0.013 | 0.584 | < 0.0001 |
| HYAL2_CpG_2 | 0.24 (0.19-0.28) | 0.16 (0.13-0.21) | 4.40 (2.56-7.57) | < 0.0001 | 0.691 | < 0.0001 |
| HYAL2_CpG_3 | 0.41 (0.36-0.46) | 0.32 (0.28-0.38) | 4.14 (2.51-6.85) | < 0.0001 | 0.774 | < 0.0001 |
| HYAL2_CpG_4 | 0.65 (0.59-0.69) | 0.50 (0.47-0.57) | 8.13 (4.53-14.59) | < 0.0001 | 1.000 | — |

* logistic regression, adjusted for age and different batches for the measurements

Fig 16.

Table 16. The inverse correlation between the methylation and expression of S100P, SLC22A18 and DYRK4 in leucocytes

| CpG sites | Difference in methylation or expression levels | | | Correlations to expression | |
|---|---|---|---|---|---|
| | Controls | Sporadic BC | $p$-value * | Spearman rho | $p$-value |
| S100P_CpG_2&3 | 0.63 (0.58-0.65) | 0.59 (0.56-0.62) | 0.006 | -0.551 | 1.12E-06 |
| S100P_CpG_4 | 0.60 (0.55-0.87) | 0.61 (0.53-0.83) | 0.445 | -0.147 | 0.226 |
| S100P_CpG_7 | 0.36 (0.30-0.40) | 0.29 (0.24-0.33) | 0.001 | -0.501 | 8.55E-06 |
| S100P_CpG_8 | 0.44 (0.38-0.48) | 0.35 (0.32-0.39) | 7.76E-06 | -0.653 | 9.27E-10 |
| S100P_CpG_9 | 0.49 (0.44-0.54) | 0.45 (0.40-0.47) | 0.001 | -0.555 | 5.07E-07 |
| Relative expression of S100P | 1.31 (0.72-2.07) | 3.47 (1.23-20.77) | 0.001 | 1.000 | — |
| SLC22A18_CpG_3 | 0.19 (0.15-0.23) | 0.16 (0.14-0.19) | 0.006 | -0.507 | 5.53E-06 |
| SLC22A18_CpG_4 | 0.26 (0.20-0.31) | 0.21 (0.17-0.24) | 0.006 | -0.536 | 1.21E-06 |
| SLC22A18_CpG_6 | 0.25 (0.20-0.28) | 0.19 (0.17-0.23) | 0.001 | -0.565 | 2.29E-07 |
| SLC22A18_CpG_8 | 0.64 (0.60-0.70) | 0.59 (0.53-0.63) | 0.001 | -0.525 | 2.15E-06 |
| Relative expression of SLC22A18 | 0.69 (0.55-0.87) | 0.76 (0.54-1.23) | 0.311 | 1.000 | — |
| DYRK4_CpG_1 | 0.33 (0.25-0.41) | 0.26 (0.20-0.33) | 0.018 | -0.074 | 0.540 |
| DYRK4_CpG_3 | 0.29 (0.22-0.34) | 0.24 (0.18-0.28) | 0.023 | -0.075 | 0.536 |
| Relative expression of DYRK4 | 0.36 (0.31-0.41) | 0.37 (0.29-0.46) | 0.919 | 1.000 | — |

* Mann-Whitney U test

Fig.17

Table 17. The methylation levels of HYAL2 CpG sites by Illumina 450K

| CpG ID | pvalWald_Group | meanDiff | BUILD | CHR | MAPINFO | LOCATION | ENHANCER |
|---|---|---|---|---|---|---|---|
| cg06721473 | 0.0008 | -0.020 | 36 | 3 | 50330420 | 3'UTR;3'UTR | NA |
| cg08776109 | 0.0006 | -0.022 | 36 | 3 | 50331237 | Body;Body | NA |
| cg00575896 | 0.1133 | -0.007 | 36 | 3 | 50332175 | Body;Body | TRUE |
| cg25630588 | 0.9482 | -0.001 | 36 | 3 | 50332326 | Body;Body | TRUE |
| cg09412061 | 0.9466 | -0.002 | 36 | 3 | 50332470 | Body;Body | NA |
| cg26794477 | 0.8988 | -0.001 | 36 | 3 | 50332596 | Body;Body | NA |
| cg00467652 | 0.3265 | -0.004 | 36 | 3 | 50332648 | Body;Body | NA |
| cg05164052 | 0.2727 | 0.002 | 36 | 3 | 50333326 | 5'UTR;5'UTR | NA |
| cg16563178 | 0.4019 | 0.005 | 36 | 3 | 50333447 | 5'UTR;5'UTR | NA |
| cg10109442 | 0.9007 | 0.000 | 36 | 3 | 50333891 | 5'UTR;1stExon;5'UTR | NA |
| cg04884420 | 0.0674 | 0.003 | 36 | 3 | 50333976 | TSS200;5'UTR | NA |
| cg22280173 | 0.3091 | -0.001 | 36 | 3 | 50333985 | TSS200;5'UTR | NA |
| cg08173110 | 0.5201 | 0.001 | 36 | 3 | 50334009 | TSS200;5'UTR | NA |
| cg23515942 | 0.7374 | 0.001 | 36 | 3 | 50334023 | TSS200;5'UTR | NA |
| cg06211164 | 0.7758 | 0.000 | 36 | 3 | 50334069 | TSS200;5'UTR | NA |
| cg13580654 | 0.6497 | 0.001 | 36 | 3 | 50334101 | TSS200;5'UTR | NA |
| cg07271561 | 0.7449 | -0.003 | 36 | 3 | 50334367 | 5'UTR;TSS1500 | NA |
| cg12976582 | 0.0253 | -0.015 | 36 | 3 | 50334587 | 5'UTR;TSS1500 | NA |
| cg12150256 | 0.4194 | -0.004 | 36 | 3 | 50334853 | 5'UTR;TSS1500 | NA |
| cg13341668 | 0.0938 | -0.008 | 36 | 3 | 50334913 | 5'UTR;TSS1500 | NA |
| cg05118960 | 0.1069 | -0.005 | 36 | 3 | 50334982 | 5'UTR;TSS1500 | NA |
| cg03721058 | 0.0046 | -0.010 | 36 | 3 | 50335045 | 5'UTR;TSS1500 | NA |
| cg00840516 | 0.0074 | -0.014 | 36 | 3 | 50335101 | 5'UTR;1stExon;TSS1500 | NA |
| cg03051392 | 0.0005 | -0.017 | 36 | 3 | 50335180 | 5'UTR;1stExon;TSS1500 | NA |
| cg26460678 | 0.0029 | -0.020 | 36 | 3 | 50335671 | TSS1500 | NA |
| cg27091787 | 0.0044 | -0.028 | 36 | 3 | 50335694 | TSS1500 | NA |
| cg24335984 | 0.0507 | -0.007 | 36 | 3 | 50336558 | TSS1500 | NA |

Fig. 18

Table 18. The methylation levels of S100P CpG sites by Illumina 450K

| CpG ID | pvalWald_Group | meanDiff | BUILD | CHR | MAPINFO | LOCATION | ENHANCER |
|---|---|---|---|---|---|---|---|
| cg02883621 | 0.6312 | -0.003 | 36 | 4 | 6745824 | TSS1500 | NA |
| cg14323984 | 0.7019 | -0.002 | 36 | 4 | 6746104 | TSS1500 | NA |
| cg27027375 | 0.0233 | -0.017 | 36 | 4 | 6746220 | TSS1500 | NA |
| cg14900031 | 0.0010 | -0.021 | 36 | 4 | 6746278 | TSS200 | NA |
| cg14140379 | 0.0011 | -0.029 | 36 | 4 | 6746281 | TSS200 | NA |
| cg25083732 | 0.0534 | -0.027 | 36 | 4 | 6746365 | TSS200 | NA |
| cg07210669 | 0.0117 | -0.028 | 36 | 4 | 6746376 | TSS200 | NA |
| cg26233331 | 0.0002 | -0.040 | 36 | 4 | 6746515 | 1stExon;5'UTR | NA |
| cg22266967 | 0.0014 | -0.033 | 36 | 4 | 6746599 | 1stExon | NA |
| cg02104700 | 0.3792 | -0.003 | 36 | 4 | 6749069 | Body | NA |

Fig. 19

Table 19. The methylation levels of SLC22A18 CpG sites by Illumina 450K

| CpG ID | pvalWald_Group | meanDiff | BUILD | CHR | MAPINFO | LOCATION | ENHANCER |
|---|---|---|---|---|---|---|---|
| cg23335134 | 0.8641 | 0.001 | 36 | 11 | 2866266 | Body | NA |
| cg26874323 | 0.6378 | 0.001 | 36 | 11 | 2866285 | Body | NA |
| cg08222610 | 0.0833 | -0.001 | 36 | 11 | 2866291 | Body | NA |
| cg12240761 | 0.6550 | 0.002 | 36 | 11 | 2869910 | Body | TRUE |
| cg14449910 | 0.1298 | -0.008 | 36 | 11 | 2876265 | Body;TSS1500 | TRUE |
| cg26665035 | 0.0426 | -0.023 | 36 | 11 | 2876339 | Body;TSS1500 | TRUE |
| cg22040301 | 0.2417 | -0.012 | 36 | 11 | 2876374 | Body;TSS1500 | TRUE |
| cg05457684 | 0.0562 | -0.017 | 36 | 11 | 2876384 | Body;TSS1500 | TRUE |
| cg18419977 | 0.8110 | 0.000 | 36 | 11 | 2876628 | Body;TSS1500 | TRUE |
| cg24033661 | 0.4585 | 0.000 | 36 | 11 | 2876631 | Body;TSS1500 | TRUE |
| cg13485320 | 0.6519 | 0.003 | 36 | 11 | 2876704 | Body;TSS1500 | TRUE |
| cg21853021 | 0.9589 | 0.002 | 36 | 11 | 2876722 | Body;TSS1500 | TRUE |
| cg18458509 | 0.0170 | -0.019 | 36 | 11 | 2876765 | Body;TSS1500 | TRUE |
| cg23190089 | 0.0047 | -0.019 | 36 | 11 | 2876785 | Body;TSS1500 | TRUE |
| cg16587707 | 0.0004 | -0.022 | 36 | 11 | 2876841 | Body;TSS1500 | TRUE |
| cg02462487 | 0.0404 | -0.015 | 36 | 11 | 2876926 | Body;TSS1500 | TRUE |
| cg16129800 | 0.0008 | -0.023 | 36 | 11 | 2876990 | Body;TSS1500 | TRUE |
| cg21599100 | 0.0018 | -0.022 | 36 | 11 | 2877013 | Body;TSS1500 | TRUE |
| cg05752118 | 0.0310 | -0.016 | 36 | 11 | 2877140 | Body;TSS1500 | TRUE |
| cg11785933 | 0.0023 | -0.041 | 36 | 11 | 2877193 | Body;TSS1500 | NA |
| cg25427871 | 0.0137 | -0.032 | 36 | 11 | 2877311 | Body;TSS1500 | NA |
| cg22315192 | 0.0044 | -0.016 | 36 | 11 | 2877341 | TSS200;Body | NA |
| cg21019522 | 0.0042 | -0.018 | 36 | 11 | 2877365 | TSS200;Body | NA |
| cg16346422 | 0.0001 | -0.042 | 36 | 11 | 2877395 | TSS200;Body | NA |
| cg16873863 | 0.1148 | -0.009 | 36 | 11 | 2877752 | 5'UTR;5'UTR | NA |
| cg22680591 | 0.5778 | -0.002 | 36 | 11 | 2878627 | 5'UTR;5'UTR;TSS1500 | NA |
| cg15904130 | 0.1653 | 0.003 | 36 | 11 | 2878639 | 5'UTR;5'UTR;TSS1500 | NA |
| cg25073813 | 0.0276 | -0.008 | 36 | 11 | 2878644 | 5'UTR;5'UTR;TSS1500 | NA |
| cg24205453 | 0.4111 | -0.001 | 36 | 11 | 2878910 | 5'UTR;5'UTR;TSS1500 | NA |
| cg18471235 | 0.0055 | 0.011 | 36 | 11 | 2878971 | 5'UTR;5'UTR;TSS1500 | NA |
| cg15739881 | 0.0966 | -0.008 | 36 | 11 | 2879040 | 5'UTR;5'UTR;TSS1500 | NA |
| cg12563184 | 0.2446 | -0.004 | 36 | 11 | 2879067 | 5'UTR;5'UTR;TSS1500 | NA |
| cg04665867 | 0.3414 | -0.003 | 36 | 11 | 2879093 | 5'UTR;5'UTR;TSS1500 | NA |
| cg24041239 | 0.1391 | -0.006 | 36 | 11 | 2879211 | 5'UTR;5'UTR;TSS1500 | NA |
| cg09198782 | 0.3067 | -0.004 | 36 | 11 | 2879338 | 5'UTR;5'UTR;TSS1500 | NA |
| cg07291601 | 0.4683 | -0.002 | 36 | 11 | 2879383 | 5'UTR;5'UTR;TSS1500 | NA |
| cg25548316 | 0.7994 | 0.001 | 36 | 11 | 2879388 | 5'UTR;5'UTR;TSS1500 | NA |

Fig. 19 (continued)

Table 19. The methylation levels of SLC22A18 CpG sites by Illumina 450K (continued)

| CpG ID | pvalWald_Group | meanDiff | BUILD | CHR | MAPINFO | LOCATION | ENHANCER |
|---|---|---|---|---|---|---|---|
| cg10943932 | 0.5082 | 0.000 | 36 | 11 | 2879409 | 5'UTR;5'UTR;TSS1500 | NA |
| cg02081198 | 0.6399 | 0.000 | 36 | 11 | 2879421 | 5'UTR;5'UTR;TSS1500 | NA |
| cg05385260 | 0.0511 | -0.005 | 36 | 11 | 2879428 | 5'UTR;5'UTR;TSS1500 | NA |
| cg16035277 | 0.4744 | 0.005 | 36 | 11 | 2879840 | 5'UTR;5'UTR;TSS1500 | NA |
| cg09781437 | 0.0128 | 0.002 | 36 | 11 | 2879986 | 5'UTR;5'UTR;TSS200 | NA |
| cg02200456 | 0.4292 | -0.001 | 36 | 11 | 2880012 | 5'UTR;5'UTR;TSS200 | NA |
| cg13671930 | 0.6034 | 0.003 | 36 | 11 | 2880014 | 5'UTR;5'UTR;TSS200 | NA |
| cg22132309 | 0.7142 | 0.001 | 36 | 11 | 2880066 | 5'UTR;5'UTR;TSS200 | NA |
| cg16184736 | 0.2003 | -0.001 | 36 | 11 | 2880074 | 5'UTR;5'UTR;TSS200 | NA |
| cg03829241 | 0.4543 | 0.001 | 36 | 11 | 2880080 | 5'UTR;5'UTR;TSS200 | NA |
| cg17992161 | 0.0850 | 0.006 | 36 | 11 | 2880101 | 5'UTR;1stExon;5'UTR;5'UTR | NA |
| cg12733707 | 0.0846 | 0.005 | 36 | 11 | 2880123 | 5'UTR;1stExon;5'UTR;5'UTR | NA |
| cg24139421 | 0.9971 | 0.001 | 36 | 11 | 2880154 | 5'UTR;1stExon;5'UTR;5'UTR | NA |
| cg06211616 | 0.8977 | 0.002 | 36 | 11 | 2880235 | 5'UTR;5'UTR;5'UTR | NA |
| cg24528523 | 0.7157 | 0.000 | 36 | 11 | 2880384 | 5'UTR;5'UTR;5'UTR | NA |
| cg12911952 | 0.0388 | -0.007 | 36 | 11 | 2881099 | 5'UTR;5'UTR;5'UTR | NA |
| cg02719634 | 0.0932 | -0.019 | 36 | 11 | 2881475 | 1stExon;Body;5'UTR;Body | TRUE |
| cg15729154 | 0.0364 | -0.018 | 36 | 11 | 2881602 | 1stExon;Body;5'UTR;Body | TRUE |
| cg07161669 | 0.2605 | 0.000 | 36 | 11 | 2881763 | Body;Body;TSS200 | TRUE |
| cg24724917 | 0.4820 | -0.002 | 36 | 11 | 2882015 | Body;Body;TSS1500 | TRUE |
| cg06495763 | 0.8721 | -0.001 | 36 | 11 | 2882046 | Body;Body;TSS1500 | TRUE |
| cg06048910 | 0.2015 | -0.001 | 36 | 11 | 2882049 | Body;Body;TSS1500 | TRUE |
| cg08472797 | 0.2778 | -0.003 | 36 | 11 | 2882146 | Body;Body;TSS1500 | TRUE |
| cg14101500 | 0.4686 | 0.000 | 36 | 11 | 2882170 | Body;Body;TSS1500 | TRUE |
| cg22833478 | 0.5602 | -0.001 | 36 | 11 | 2882199 | Body;Body;TSS1500 | TRUE |
| cg26137286 | 0.0522 | -0.006 | 36 | 11 | 2882210 | Body;Body;TSS1500 | TRUE |
| cg02390725 | 0.0040 | -0.010 | 36 | 11 | 2882344 | Body;Body;TSS1500 | TRUE |
| cg20716202 | 0.0779 | -0.005 | 36 | 11 | 2882423 | Body;Body;TSS1500 | TRUE |
| cg08999895 | 0.2548 | -0.005 | 36 | 11 | 2882445 | Body;Body;TSS1500 | TRUE |
| cg16530128 | 0.5740 | -0.002 | 36 | 11 | 2882527 | Body;Body;TSS1500 | NA |
| cg08827700 | 0.0045 | -0.008 | 36 | 11 | 2882545 | Body;Body;TSS1500 | NA |
| cg22272492 | 0.0009 | -0.010 | 36 | 11 | 2882572 | Body;Body;TSS1500 | NA |
| cg21991825 | 0.6773 | 0.002 | 36 | 11 | 2882719 | Body;Body;TSS1500 | NA |
| cg23912877 | 0.6175 | 0.000 | 36 | 11 | 2882913 | Body;Body;TSS1500 | NA |
| cg06981073 | 0.5191 | -0.001 | 36 | 11 | 2882920 | Body;Body;TSS1500 | NA |
| cg06669405 | 0.0170 | -0.010 | 36 | 11 | 2882937 | Body;Body;TSS1500 | NA |

Fig. 19 continued

Table 19. The methylation levels of SLC22A18 CpG sites by Illumina 450K (continued)

| CpG ID | pvalWald_Group | meanDiff | BUILD | CHR | MAPINFO | LOCATION | ENHANCER |
|---|---|---|---|---|---|---|---|
| cg09731124 | 0.4994 | -0.004 | 36 | 11 | 2882998 | Body;Body;TSS1500 | NA |
| cg02025860 | 0.4916 | -0.002 | 36 | 11 | 2883177 | Body;Body;TSS1500 | NA |
| cg14168614 | 0.6637 | -0.005 | 36 | 11 | 2883823 | Body;Body | NA |
| cg02660089 | 0.9102 | 0.003 | 36 | 11 | 2886017 | Body;Body | NA |
| cg22858288 | 0.4478 | 0.002 | 36 | 11 | 2886898 | Body;Body | NA |
| cg04726200 | 0.6860 | -0.007 | 36 | 11 | 2887061 | Body;Body | NA |
| cg19497444 | 0.7053 | -0.009 | 36 | 11 | 2887370 | Body;Body | NA |
| cg03336167 | 0.9821 | -0.005 | 36 | 11 | 2887571 | Body;Body | NA |
| cg23698969 | 0.3834 | -0.003 | 36 | 11 | 2887741 | Body;Body | NA |
| cg24409566 | 0.6945 | -0.002 | 36 | 11 | 2890543 | Body;Body | TRUE |
| cg05351334 | 0.6395 | -0.003 | 36 | 11 | 2896968 | Body;Body | NA |
| cg14275836 | 0.7743 | -0.002 | 36 | 11 | 2897889 | Body;Body | NA |
| cg19240938 | 0.2782 | 0.002 | 36 | 11 | 2898612 | Body;Body | NA |
| cg18655584 | 0.9972 | -0.002 | 36 | 11 | 2898669 | Body;Body | NA |
| cg12510502 | 0.5312 | -0.002 | 36 | 11 | 2898752 | Body;Body | NA |
| cg13328151 | 0.2459 | 0.004 | 36 | 11 | 2899615 | Body;Body | NA |
| cg03010425 | 0.9510 | 0.002 | 36 | 11 | 2901347 | Body;Body | NA |
| cg26595893 | 0.8941 | 0.002 | 36 | 11 | 2903050 | 3'UTR;3'UTR | NA |

Fig. 20

Table 20. The methylation levels of DYRK4 CpG sites by Illumina 450K

| CpG ID | pvalWald_Group | meanDiff | BUILD | CHR | MAPINFO | LOCATION | ENHANCER |
|---|---|---|---|---|---|---|---|
| cg24707294 | 0.8090 | -0.003 | 36 | 12 | 4568380 | TSS1500 | NA |
| cg08977032 | 0.5921 | -0.001 | 36 | 12 | 4568578 | TSS1500 | NA |
| cg06270401 | 0.0000 | -0.047 | 36 | 12 | 4569346 | TSS200 | NA |
| cg09581911 | 0.8105 | -0.014 | 36 | 12 | 4569493 | TSS200 | NA |
| cg09418321 | 0.0011 | -0.031 | 36 | 12 | 4569879 | 5'UTR | NA |
| cg01218945 | 0.4078 | 0.001 | 36 | 12 | 4584370 | Body | NA |
| cg24337818 | 0.0539 | -0.002 | 36 | 12 | 4584440 | Body | NA |
| cg00532413 | 0.2381 | 0.000 | 36 | 12 | 4584588 | Body | NA |

Fig. 21

Table 21. The methylation levels of FUT7 CpG sites by Illumina 450K

| CpG ID | pvalWald_Group | meanDiff | BUILD | CHR | MAPINFO | LOCATION | ENHANCER |
|---|---|---|---|---|---|---|---|
| cg02971262 | 0.0031 | -0.011 | 36 | 9 | 139045216 | 5'UTR;Body | NA |
| cg14205519 | 0.5871 | 0.002 | 36 | 9 | 139045571 | 5'UTR;Body | NA |
| cg03630596 | 0.6632 | -0.003 | 36 | 9 | 139045677 | 5'UTR;Body | NA |
| cg13757845 | 0.0082 | -0.023 | 36 | 9 | 139046561 | 5'UTR;1stExon;5'UTR | NA |
| cg09305224 | 0.0001 | -0.030 | 36 | 9 | 139047066 | 5'UTR;1stExon;5'UTR | NA |
| cg02679745 | 0.0000 | -0.036 | 36 | 9 | 139047467 | Body;TSS1500 | NA |

Fig. 22

Table 22. The methylation levels of RAPSN CpG sites by Illumina 450K

| CpG ID | pvalWald_Group | meanDiff | BUILD | CHR | MAPINFO | LOCATION | ENHANCER |
|---|---|---|---|---|---|---|---|
| cg26738160 | 0.6801 | 0.001 | 36 | 11 | 47416086 | 3'UTR;3'UTR | NA |
| cg24812582 | 0.3992 | 0.002 | 36 | 11 | 47419939 | Body;Body | NA |
| cg17614165 | 0.8996 | -0.001 | 36 | 11 | 47425239 | Body;Body | NA |
| cg15270729 | 0.1291 | 0.006 | 36 | 11 | 47425474 | Body;Body | NA |
| cg09163021 | 0.7317 | -0.005 | 36 | 11 | 47427344 | TSS200;TSS200 | NA |
| cg07407499 | 0.0904 | -0.008 | 36 | 11 | 47427367 | TSS200;TSS200 | NA |
| cg14407987 | 0.9251 | -0.002 | 36 | 11 | 47427369 | TSS200;TSS200 | NA |
| cg26454662 | 0.7520 | -0.006 | 36 | 11 | 47427379 | TSS200;TSS200 | NA |
| cg03400491 | 0.2005 | -0.005 | 36 | 11 | 47427463 | TSS200;TSS200 | NA |
| cg19771781 | 0.9445 | -0.001 | 36 | 11 | 47427476 | TSS200;TSS200 | NA |
| cg13047308 | 0.0021 | -0.033 | 36 | 11 | 47427915 | TSS1500;TSS1500 | NA |
| cg27466532 | 0.0000 | -0.045 | 36 | 11 | 47427976 | TSS1500;TSS1500 | NA |
| cg02321133 | 0.9396 | -0.006 | 36 | 11 | 47428365 | TSS1500;TSS1500 | NA |

Fig. 23

Table 23. The methylation levels of RPTOR CpG sites by Illumina 450K

| CpG ID | pvalWald_Group | meanDiff | BUILD | CHR | MAPINFO | LOCATION | ENHANCER |
|---|---|---|---|---|---|---|---|
| cg03140026 | 0.1675 | 0.002 | 36 | 17 | 76131746 | TSS1500;TSS1500 | NA |
| cg14406501 | 0.1416 | -0.015 | 36 | 17 | 76132775 | TSS1500;TSS1500 | NA |
| cg02352203 | 0.2860 | 0.001 | 36 | 17 | 76133032 | TSS200;TSS200 | NA |
| cg13515774 | 0.0979 | 0.000 | 36 | 17 | 76133067 | TSS200;TSS200 | NA |
| cg15600835 | 0.0368 | -0.001 | 36 | 17 | 76133151 | TSS200;TSS200 | NA |
| cg00815931 | 0.1649 | -0.002 | 36 | 17 | 76133168 | TSS200;TSS200 | NA |
| cg03172060 | 0.0707 | -0.007 | 36 | 17 | 76133208 | TSS200;TSS200 | NA |
| cg12045294 | 0.1752 | 0.002 | 36 | 17 | 76133211 | TSS200;TSS200 | NA |
| cg20758492 | 0.4765 | 0.000 | 36 | 17 | 76134834 | Body;Body | NA |
| cg02082642 | 0.8956 | -0.002 | 36 | 17 | 76137204 | Body;Body | NA |
| cg22652378 | 0.0006 | -0.032 | 36 | 17 | 76148437 | Body;Body | TRUE |
| cg25514328 | 0.5802 | 0.004 | 36 | 17 | 76163919 | Body;Body | NA |
| cg11329058 | 0.0369 | 0.012 | 36 | 17 | 76163953 | Body;Body | NA |
| cg18576374 | 0.5514 | -0.001 | 36 | 17 | 76163966 | Body;Body | NA |
| cg06799305 | 0.3461 | 0.000 | 36 | 17 | 76165965 | Body;Body | TRUE |
| cg08129331 | 0.0079 | -0.022 | 36 | 17 | 76175073 | Body;Body | NA |
| cg01561259 | 0.8979 | -0.003 | 36 | 17 | 76175376 | Body;Body | NA |
| cg09929238 | 0.0443 | -0.024 | 36 | 17 | 76175511 | Body;Body | NA |
| cg27210166 | 0.9688 | 0.001 | 36 | 17 | 76189287 | Body;Body | NA |
| cg12088417 | 0.6881 | 0.012 | 36 | 17 | 76189311 | Body;Body | NA |
| cg10162696 | 0.9502 | 0.002 | 36 | 17 | 76191173 | Body;Body | NA |
| cg09133154 | 0.6328 | -0.001 | 36 | 17 | 76191267 | Body;Body | NA |
| cg03520496 | 0.2563 | 0.007 | 36 | 17 | 76191285 | Body;Body | NA |
| cg08732594 | 0.0311 | -0.003 | 36 | 17 | 76196984 | Body;Body | NA |
| cg04687939 | 0.2909 | -0.003 | 36 | 17 | 76197144 | Body;Body | NA |
| cg22280406 | 0.8201 | 0.000 | 36 | 17 | 76197242 | Body;Body | NA |
| cg16027727 | 0.7303 | -0.006 | 36 | 17 | 76200923 | Body;Body | NA |
| cg04951638 | 0.7431 | 0.000 | 36 | 17 | 76208376 | Body;Body | TRUE |
| cg00143364 | 0.2604 | -0.006 | 36 | 17 | 76219939 | Body;Body | TRUE |
| cg20462129 | 0.1050 | -0.002 | 36 | 17 | 76221690 | Body;Body | TRUE |
| cg02462904 | 0.2293 | -0.005 | 36 | 17 | 76221850 | Body;Body | NA |
| cg21925688 | 0.3817 | 0.001 | 36 | 17 | 76221963 | Body;Body | NA |
| cg03637703 | 0.1905 | 0.001 | 36 | 17 | 76232333 | Body;Body | NA |
| cg27551440 | 0.1464 | -0.001 | 36 | 17 | 76232340 | Body;Body | NA |
| cg27313007 | 0.0351 | -0.007 | 36 | 17 | 76232345 | Body;Body | NA |
| cg08811817 | 0.0927 | 0.009 | 36 | 17 | 76237232 | Body;Body | TRUE |
| cg18758433 | 0.0001 | 0.046 | 36 | 17 | 76238196 | Body;Body | TRUE |
| cg26170499 | 0.4804 | 0.000 | 36 | 17 | 76249958 | Body;Body | TRUE |

Fig. 23 (continued)

Table 23. The methylation levels of RPTOR CpG sites by Illumina 450K (continued)

| CpG ID | pvalWald_Group | meanDiff | BUILD | CHR | MAPINFO | LOCATION | ENHANCER |
|---|---|---|---|---|---|---|---|
| cg17442961 | 0.0068 | -0.005 | 36 | 17 | 76250023 | Body;Body | TRUE |
| cg00460639 | 0.3183 | -0.005 | 36 | 17 | 76250229 | Body;Body | TRUE |
| cg01432609 | 0.0032 | -0.026 | 36 | 17 | 76253149 | Body;Body | TRUE |
| cg13303377 | 0.5077 | -0.003 | 36 | 17 | 76254840 | Body;Body | NA |
| cg17944774 | 0.7632 | -0.002 | 36 | 17 | 76258841 | Body;Body | NA |
| cg17051395 | 0.1054 | 0.002 | 36 | 17 | 76258887 | Body;Body | NA |
| cg27454679 | 0.8016 | -0.003 | 36 | 17 | 76259128 | Body;Body | NA |
| cg04681879 | 0.9956 | -0.002 | 36 | 17 | 76259241 | Body;Body | NA |
| cg17434577 | 0.7843 | -0.004 | 36 | 17 | 76259361 | Body;Body | NA |
| cg09592546 | 0.0053 | 0.044 | 36 | 17 | 76267497 | Body;Body | TRUE |
| cg22882460 | 0.4555 | 0.001 | 36 | 17 | 76269243 | Body;Body | NA |
| cg13311292 | 0.2817 | -0.004 | 36 | 17 | 76269258 | Body;Body | NA |
| cg06443231 | 0.6011 | -0.002 | 36 | 17 | 76269860 | Body;Body | NA |
| cg22838354 | 0.7433 | -0.002 | 36 | 17 | 76269879 | Body;Body | NA |
| cg09596252 | 0.2242 | -0.003 | 36 | 17 | 76270088 | Body;Body | NA |
| cg11303920 | 0.5721 | 0.001 | 36 | 17 | 76276168 | Body;Body | NA |
| cg23238734 | 0.3909 | -0.003 | 36 | 17 | 76276202 | Body;Body | NA |
| cg17956530 | 0.7764 | -0.002 | 36 | 17 | 76282294 | Body;Body | NA |
| cg01500570 | 0.0109 | -0.003 | 36 | 17 | 76282362 | Body;Body | NA |
| cg13102028 | 0.2568 | 0.002 | 36 | 17 | 76282603 | Body;Body | NA |
| cg04136113 | 0.9874 | 0.000 | 36 | 17 | 76282617 | Body;Body | NA |
| cg09141931 | 0.9642 | 0.000 | 36 | 17 | 76282804 | Body;Body | TRUE |
| cg06673969 | 0.4171 | -0.009 | 36 | 17 | 76283457 | Body;Body | TRUE |
| cg15116918 | 0.1751 | 0.002 | 36 | 17 | 76284147 | Body;Body | TRUE |
| cg20562478 | 0.6685 | -0.003 | 36 | 17 | 76284834 | Body;Body | TRUE |
| cg20937981 | 0.2068 | 0.004 | 36 | 17 | 76294225 | Body;Body | TRUE |
| cg18780100 | 0.0267 | -0.027 | 36 | 17 | 76297380 | Body;Body | NA |
| cg01498832 | 0.0002 | -0.042 | 36 | 17 | 76297529 | Body;Body | NA |
| cg07786220 | 0.0000 | -0.047 | 36 | 17 | 76297677 | Body;Body | NA |
| cg02240665 | 0.5351 | -0.001 | 36 | 17 | 76297867 | Body;Body | NA |
| cg25985643 | 0.1559 | -0.008 | 36 | 17 | 76298052 | Body;Body | TRUE |
| cg27511181 | 0.0108 | -0.037 | 36 | 17 | 76299819 | Body;Body | TRUE |
| cg11790527 | 0.0069 | -0.022 | 36 | 17 | 76300748 | Body;Body | TRUE |
| cg26733897 | 0.0009 | 0.018 | 36 | 17 | 76309187 | Body;Body | NA |
| cg16918327 | 0.0511 | 0.013 | 36 | 17 | 76309246 | Body;Body | NA |
| cg25673241 | 0.0453 | 0.014 | 36 | 17 | 76309451 | Body;Body | NA |
| cg24667756 | 0.1747 | 0.004 | 36 | 17 | 76313417 | Body;Body | TRUE |
| cg18965980 | 0.5135 | -0.004 | 36 | 17 | 76313643 | Body;Body | TRUE |

Fig. 23 (continued)

Table 23. The methylation levels of RPTOR CpG sites by Illumina 450K (continued)

| CpG ID | pvalWald_Group | meanDiff | BUILD | CHR | MAPINFO | LOCATION | ENHANCER |
|---|---|---|---|---|---|---|---|
| cg25288455 | 0.2248 | 0.009 | 36 | 17 | 76315501 | Body;Body | NA |
| cg06975080 | 0.0168 | 0.012 | 36 | 17 | 76315523 | Body;Body | NA |
| cg10790704 | 0.2922 | 0.000 | 36 | 17 | 76315679 | Body;Body | NA |
| cg18406924 | 0.0116 | 0.018 | 36 | 17 | 76315852 | Body;Body | NA |
| cg19857461 | 0.3144 | 0.002 | 36 | 17 | 76317643 | Body;Body | NA |
| cg18026826 | 0.2440 | 0.001 | 36 | 17 | 76318962 | Body;Body | NA |
| cg26723185 | 0.1380 | 0.001 | 36 | 17 | 76319016 | Body;Body | NA |
| cg03513049 | 0.5379 | 0.003 | 36 | 17 | 76319516 | Body;Body | TRUE |
| cg06872548 | 0.1960 | -0.010 | 36 | 17 | 76331578 | Body;Body | TRUE |
| cg11757444 | 0.0126 | -0.074 | 36 | 17 | 76333768 | Body;Body | NA |
| cg10281768 | 0.0040 | 0.010 | 36 | 17 | 76334821 | Body;Body | NA |
| cg05337636 | 0.2022 | 0.002 | 36 | 17 | 76335132 | Body;Body | NA |
| cg17060157 | 0.0009 | -0.023 | 36 | 17 | 76338722 | Body;Body | NA |
| cg00701918 | 0.3726 | -0.004 | 36 | 17 | 76339590 | Body;Body | NA |
| cg24394819 | 0.6679 | -0.001 | 36 | 17 | 76339644 | Body;Body | NA |
| cg00549398 | 0.9789 | -0.002 | 36 | 17 | 76339796 | Body;Body | TRUE |
| cg16841014 | 0.0766 | -0.019 | 36 | 17 | 76339970 | Body;Body | TRUE |
| cg21143224 | 0.0344 | -0.026 | 36 | 17 | 76340065 | Body;Body | TRUE |
| cg18951390 | 0.7521 | 0.000 | 36 | 17 | 76349863 | Body;Body | TRUE |
| cg11499091 | 0.4517 | 0.006 | 36 | 17 | 76349897 | Body;Body | TRUE |
| cg09516200 | 0.5475 | -0.007 | 36 | 17 | 76349919 | Body;Body | TRUE |
| cg06412669 | 0.5255 | -0.006 | 36 | 17 | 76350145 | Body;Body | TRUE |
| cg16565901 | 0.0031 | -0.022 | 36 | 17 | 76350191 | Body;Body | NA |
| cg20797905 | 0.8335 | 0.009 | 36 | 17 | 76361822 | Body;Body | TRUE |
| cg02675920 | 0.6275 | -0.006 | 36 | 17 | 76362529 | Body;Body | NA |
| cg11222173 | 0.0048 | -0.029 | 36 | 17 | 76362614 | Body;Body | NA |
| cg11153071 | 0.0000 | -0.048 | 36 | 17 | 76362672 | Body;Body | NA |
| cg15096353 | 0.9324 | 0.000 | 36 | 17 | 76362886 | Body;Body | NA |
| cg00523683 | 0.8102 | 0.016 | 36 | 17 | 76363066 | Body;Body | NA |
| cg02185248 | 0.1758 | -0.014 | 36 | 17 | 76363089 | Body;Body | NA |
| cg14343513 | 0.0000 | -0.046 | 36 | 17 | 76367868 | Body;Body | NA |
| cg05098037 | 0.0000 | -0.027 | 36 | 17 | 76367922 | Body;Body | NA |
| cg22386583 | 0.0001 | -0.043 | 36 | 17 | 76368351 | Body;Body | TRUE |
| cg12654199 | 0.0000 | -0.047 | 36 | 17 | 76368421 | Body;Body | TRUE |
| cg15230985 | 0.0024 | -0.014 | 36 | 17 | 76368482 | Body;Body | TRUE |
| cg05651511 | 0.0000 | -0.052 | 36 | 17 | 76368685 | Body;Body | TRUE |
| cg04662369 | 0.0004 | -0.059 | 36 | 17 | 76368913 | Body;Body | TRUE |
| cg14780427 | 0.0171 | -0.031 | 36 | 17 | 76368967 | Body;Body | TRUE |

Fig. 23 (continued)

Table 23. The methylation levels of RPTOR CpG sites by Illumina 450K (continued)

| CpG ID | pvalWald_Group | meanDiff | BUILD | CHR | MAPINFO | LOCATION | ENHANCER |
|---|---|---|---|---|---|---|---|
| cg06153925 | 0.0000 | -0.061 | 36 | 17 | 76369974 | Body;Body | NA |
| cg08454507 | 0.0000 | -0.039 | 36 | 17 | 76370001 | Body;Body | NA |
| cg06418238 | 0.0000 | -0.075 | 36 | 17 | 76370037 | Body;Body | NA |
| cg22878693 | 0.0079 | -0.021 | 36 | 17 | 76370199 | Body;Body | NA |
| cg18469159 | 0.1941 | -0.003 | 36 | 17 | 76370436 | Body;Body | NA |
| cg16115689 | 0.0015 | 0.021 | 36 | 17 | 76378851 | Body;Body | TRUE |
| cg12592365 | 0.0061 | 0.012 | 36 | 17 | 76380543 | Body;Body | TRUE |
| cg15547672 | 0.7579 | -0.002 | 36 | 17 | 76383535 | Body;Body | TRUE |
| cg04566233 | 0.5072 | -0.005 | 36 | 17 | 76385838 | Body;Body | TRUE |
| cg10693767 | 0.4266 | 0.001 | 36 | 17 | 76387719 | Body;Body | NA |
| cg23463786 | 0.2379 | 0.001 | 36 | 17 | 76387740 | Body;Body | NA |
| cg04803424 | 0.2824 | -0.003 | 36 | 17 | 76387797 | Body;Body | NA |
| cg10585621 | 0.7002 | -0.002 | 36 | 17 | 76388048 | Body;Body | NA |
| cg15946337 | 0.6325 | -0.003 | 36 | 17 | 76388093 | Body;Body | NA |
| cg15815120 | 0.4312 | 0.001 | 36 | 17 | 76388256 | Body;Body | NA |
| cg01476242 | 0.2066 | -0.002 | 36 | 17 | 76388625 | Body;Body | NA |
| cg17888563 | 0.2956 | 0.000 | 36 | 17 | 76388653 | Body;Body | NA |
| cg18605975 | 0.6097 | -0.002 | 36 | 17 | 76389318 | Body;Body | NA |
| cg06675781 | 0.4149 | 0.001 | 36 | 17 | 76390230 | Body;Body | NA |
| cg05548508 | 0.3504 | 0.001 | 36 | 17 | 76390392 | Body;Body | NA |
| cg13098428 | 0.1352 | -0.053 | 36 | 17 | 76390409 | Body;Body | NA |
| cg27025953 | 0.6318 | -0.004 | 36 | 17 | 76391155 | Body;Body | NA |
| cg17703078 | 0.8596 | 0.000 | 36 | 17 | 76391181 | Body;Body | NA |
| cg14596352 | 0.5598 | -0.002 | 36 | 17 | 76391776 | Body;Body | NA |
| cg00463485 | 0.1882 | -0.006 | 36 | 17 | 76392152 | Body;Body | NA |
| cg16896879 | 0.8665 | 0.000 | 36 | 17 | 76392689 | Body;Body | NA |
| cg06343673 | 0.5419 | 0.002 | 36 | 17 | 76392827 | Body;Body | NA |
| cg03533386 | 0.8783 | 0.000 | 36 | 17 | 76393148 | Body;Body | TRUE |
| cg01516792 | 0.0487 | -0.012 | 36 | 17 | 76393735 | Body;Body | TRUE |
| cg04162316 | 0.0005 | 0.018 | 36 | 17 | 76400950 | Body;Body | NA |
| cg12028455 | 0.4921 | -0.003 | 36 | 17 | 76403673 | Body;Body | NA |
| cg23542426 | 0.2420 | -0.002 | 36 | 17 | 76404215 | Body;Body | NA |
| cg16980736 | 0.5232 | 0.001 | 36 | 17 | 76404301 | Body;Body | NA |
| cg27460531 | 0.0717 | -0.010 | 36 | 17 | 76406318 | Body;Body | TRUE |
| cg16015295 | 0.0110 | -0.021 | 36 | 17 | 76408074 | Body;Body | TRUE |
| cg13526488 | 0.0051 | -0.025 | 36 | 17 | 76408402 | Body;Body | TRUE |
| cg15616522 | 0.6877 | -0.004 | 36 | 17 | 76408843 | Body;Body | TRUE |
| cg12785535 | 0.6830 | 0.000 | 36 | 17 | 76409987 | Body;Body | NA |

Fig. 23 (continued)

Table 23. The methylation levels of RPTOR CpG sites by Illumina 450K (continued)

| CpG ID | pvalWald_Group | meanDiff | BUILD | CHR | MAPINFO | LOCATION | ENHANCER |
|---|---|---|---|---|---|---|---|
| cg18430553 | 0.9679 | 0.001 | 36 | 17 | 76410136 | Body;Body | NA |
| cg04295549 | 0.9501 | 0.000 | 36 | 17 | 76410264 | Body;Body | NA |
| cg25705936 | 0.6954 | -0.001 | 36 | 17 | 76410459 | Body;Body | NA |
| cg06444734 | 0.3604 | -0.004 | 36 | 17 | 76410674 | Body;Body | NA |
| cg17602102 | 0.5131 | 0.000 | 36 | 17 | 76410754 | Body;Body | NA |
| cg02910299 | 0.0594 | -0.002 | 36 | 17 | 76410761 | Body;Body | NA |
| cg14073057 | 0.1024 | 0.001 | 36 | 17 | 76410958 | Body;Body | NA |
| cg03794617 | 0.0045 | -0.025 | 36 | 17 | 76411594 | Body;Body | NA |
| cg08329754 | 0.0008 | -0.021 | 36 | 17 | 76411610 | Body;Body | NA |
| cg09001356 | 0.0240 | -0.023 | 36 | 17 | 76411656 | Body;Body | NA |
| cg26419477 | 0.6306 | -0.001 | 36 | 17 | 76413754 | Body;Body | NA |
| cg23245933 | 0.0615 | -0.007 | 36 | 17 | 76414205 | Body;Body | NA |
| cg23261154 | 0.5801 | 0.000 | 36 | 17 | 76414316 | Body;Body | NA |
| cg09175325 | 0.0019 | -0.014 | 36 | 17 | 76414794 | Body;Body | TRUE |
| cg14955617 | 0.5025 | 0.001 | 36 | 17 | 76414859 | Body;Body | TRUE |
| cg21550504 | 0.6946 | -0.003 | 36 | 17 | 76414916 | Body;Body | TRUE |
| cg16636468 | 0.6225 | 0.000 | 36 | 17 | 76415169 | Body;Body | TRUE |
| cg25337513 | 0.8629 | 0.000 | 36 | 17 | 76415226 | Body;Body | TRUE |
| cg07126783 | 0.0130 | -0.019 | 36 | 17 | 76415362 | Body;Body | TRUE |
| cg16638092 | 0.0070 | -0.021 | 36 | 17 | 76415369 | Body;Body | TRUE |
| cg08939850 | 0.0289 | -0.024 | 36 | 17 | 76415401 | Body;Body | TRUE |
| cg23715732 | 0.9932 | -0.004 | 36 | 17 | 76416446 | Body;Body | NA |
| cg05113898 | 0.7910 | -0.001 | 36 | 17 | 76416564 | Body;Body | NA |
| cg08219486 | 0.2564 | 0.001 | 36 | 17 | 76416699 | Body;Body | NA |
| cg26633077 | 0.9590 | 0.000 | 36 | 17 | 76417720 | Body;Body | NA |
| cg22984380 | 0.1903 | -0.010 | 36 | 17 | 76417744 | Body;Body | NA |
| cg24155025 | 0.1009 | 0.000 | 36 | 17 | 76417774 | Body;Body | NA |
| cg26332535 | 0.6365 | 0.006 | 36 | 17 | 76417779 | Body;Body | NA |
| cg06919800 | 0.2502 | -0.003 | 36 | 17 | 76417915 | Body;Body | NA |
| cg18607849 | 0.2512 | -0.001 | 36 | 17 | 76418030 | Body;Body | NA |
| cg23210522 | 0.2427 | 0.001 | 36 | 17 | 76418069 | Body;Body | NA |
| cg19287064 | 0.3106 | 0.002 | 36 | 17 | 76418916 | Body;Body | NA |
| cg21876181 | 0.7520 | -0.001 | 36 | 17 | 76419031 | Body;Body | NA |
| cg15826479 | 0.0414 | 0.014 | 36 | 17 | 76421088 | Body;Body | TRUE |
| cg02386420 | 0.3306 | 0.000 | 36 | 17 | 76421465 | Body;Body | TRUE |
| cg18516619 | 0.5753 | 0.003 | 36 | 17 | 76421486 | Body;Body | TRUE |
| cg11637695 | 0.6786 | -0.002 | 36 | 17 | 76422655 | Body;Body | NA |
| cg22644320 | 0.6042 | -0.001 | 36 | 17 | 76422782 | Body;Body | NA |

Fig. 23 (continued)

Table 23. The methylation levels of RPTOR CpG sites by Illumina 450K (continued)

| CpG ID | pvalWald_Group | meanDiff | BUILD | CHR | MAPINFO | LOCATION | ENHANCER |
|---|---|---|---|---|---|---|---|
| cg07530194 | 0.8677 | -0.003 | 36 | 17 | 76423045 | Body;Body | NA |
| cg19122260 | 0.5822 | 0.000 | 36 | 17 | 76423165 | Body;Body | NA |
| cg20502501 | 0.5128 | -0.007 | 36 | 17 | 76423998 | Body;Body | NA |
| cg23248537 | 0.2625 | -0.004 | 36 | 17 | 76424293 | Body;Body | NA |
| cg03443590 | 0.4310 | -0.002 | 36 | 17 | 76424447 | Body;Body | NA |
| cg01464730 | 0.8055 | -0.001 | 36 | 17 | 76424468 | Body;Body | NA |
| cg12100537 | 0.4647 | -0.002 | 36 | 17 | 76426131 | Body;Body | NA |
| cg27101023 | 0.9609 | 0.006 | 36 | 17 | 76426276 | Body;Body | NA |
| cg07475546 | 0.9147 | -0.002 | 36 | 17 | 76426423 | Body;Body | NA |
| cg21005054 | 0.7539 | -0.001 | 36 | 17 | 76426710 | Body;Body | NA |
| cg11824764 | 0.3056 | 0.000 | 36 | 17 | 76427082 | Body;Body | NA |
| cg26263310 | 0.4535 | -0.004 | 36 | 17 | 76428708 | Body;Body | NA |
| cg18173185 | 0.1652 | -0.003 | 36 | 17 | 76429257 | Body;Body | NA |
| cg12434898 | 0.0064 | -0.004 | 36 | 17 | 76432237 | Body;Body | NA |
| cg25899969 | 0.5357 | -0.002 | 36 | 17 | 76432533 | Body;Body | NA |
| cg01911440 | 0.0600 | 0.001 | 36 | 17 | 76432640 | Body;Body | NA |
| cg18648066 | 0.7551 | -0.001 | 36 | 17 | 76433036 | Body;Body | NA |
| cg02284802 | 0.1548 | -0.006 | 36 | 17 | 76433173 | Body;Body | NA |
| cg20500836 | 0.2073 | 0.002 | 36 | 17 | 76433240 | Body;Body | NA |
| cg21507958 | 0.9498 | 0.000 | 36 | 17 | 76433466 | Body;Body | NA |
| cg18091083 | 0.0381 | 0.022 | 36 | 17 | 76433687 | Body;Body | NA |
| cg22888023 | 0.8116 | -0.003 | 36 | 17 | 76434599 | Body;Body | NA |
| cg23019125 | 0.5344 | 0.002 | 36 | 17 | 76434986 | Body;Body | NA |
| cg16826504 | 0.3110 | -0.003 | 36 | 17 | 76435176 | Body;Body | NA |
| cg06756931 | 0.7339 | -0.001 | 36 | 17 | 76435488 | Body;Body | NA |
| cg14202916 | 0.5049 | 0.001 | 36 | 17 | 76435519 | Body;Body | NA |
| cg01767927 | 0.7192 | -0.003 | 36 | 17 | 76435619 | Body;Body | NA |
| cg26360197 | 0.0010 | 0.030 | 36 | 17 | 76436199 | Body;Body | NA |
| cg16541275 | 0.0432 | 0.017 | 36 | 17 | 76436349 | Body;Body | NA |
| cg24844295 | 0.7784 | 0.001 | 36 | 17 | 76436523 | Body;Body | NA |
| cg01518942 | 0.2359 | -0.003 | 36 | 17 | 76437001 | Body;Body | NA |
| cg12284870 | 0.2283 | -0.005 | 36 | 17 | 76437026 | Body;Body | NA |
| cg17481637 | 0.9598 | 0.001 | 36 | 17 | 76437125 | Body;Body | NA |
| cg13945540 | 0.4211 | 0.001 | 36 | 17 | 76437320 | Body;Body | NA |
| cg04102793 | 0.9524 | -0.002 | 36 | 17 | 76437518 | Body;Body | NA |
| cg04515258 | 0.8550 | -0.001 | 36 | 17 | 76440007 | Body;Body | NA |
| cg05815404 | 0.4279 | 0.000 | 36 | 17 | 76440096 | Body;Body | NA |
| cg14271651 | 0.0295 | -0.009 | 36 | 17 | 76440964 | Body;Body | TRUE |

Fig. 23 (continued)

Table 23. The methylation levels of RPTOR CpG sites by Illumina 450K (continued)

| CpG ID | pvalWald_Group | meanDiff | BUILD | CHR | MAPINFO | LOCATION | ENHANCER |
|---|---|---|---|---|---|---|---|
| cg14647957 | 0.3152 | -0.004 | 36 | 17 | 76442838 | Body;Body | NA |
| cg25024459 | 0.7461 | -0.003 | 36 | 17 | 76444221 | Body;Body | NA |
| cg15097361 | 0.0070 | -0.017 | 36 | 17 | 76444296 | Body;Body | NA |
| cg15228441 | 0.9427 | -0.002 | 36 | 17 | 76444525 | Body;Body | TRUE |
| cg04470054 | 0.1395 | -0.003 | 36 | 17 | 76445067 | Body;Body | TRUE |
| cg25512107 | 0.0106 | 0.002 | 36 | 17 | 76445762 | Body;Body | NA |
| cg17323298 | 0.7979 | -0.001 | 36 | 17 | 76445825 | Body;Body | NA |
| cg22809418 | 0.3980 | 0.000 | 36 | 17 | 76445905 | Body;Body | NA |
| cg08905415 | 0.7213 | -0.003 | 36 | 17 | 76446113 | Body;Body | NA |
| cg04494230 | 0.6880 | 0.000 | 36 | 17 | 76446239 | Body;Body | NA |
| cg00516616 | 0.8101 | -0.004 | 36 | 17 | 76446458 | Body;Body | NA |
| cg24832218 | 0.7079 | -0.003 | 36 | 17 | 76447543 | Body;Body | TRUE |
| cg04191427 | 0.7525 | -0.005 | 36 | 17 | 76447854 | Body;Body | NA |
| cg05707492 | 0.3740 | 0.000 | 36 | 17 | 76448079 | Body;Body | TRUE |
| cg05249744 | 0.0233 | -0.027 | 36 | 17 | 76449305 | Body;Body | NA |
| cg23625086 | 0.0284 | 0.002 | 36 | 17 | 76450934 | Body;Body | NA |
| cg15476425 | 0.2539 | 0.001 | 36 | 17 | 76450998 | Body;Body | NA |
| cg22161269 | 0.9634 | -0.002 | 36 | 17 | 76451108 | Body;Body | NA |
| cg01886663 | 0.1208 | -0.014 | 36 | 17 | 76460774 | Body;Body | TRUE |
| cg02878831 | 0.2833 | -0.010 | 36 | 17 | 76462347 | Body;Body | NA |
| cg27129144 | 0.3659 | -0.002 | 36 | 17 | 76463128 | Body;Body | NA |
| cg27394817 | 0.6181 | -0.001 | 36 | 17 | 76463274 | Body;Body | NA |
| cg07434008 | 0.5516 | 0.000 | 36 | 17 | 76463361 | Body;Body | NA |
| cg06617879 | 0.0058 | 0.005 | 36 | 17 | 76464026 | Body;Body | NA |
| cg13979266 | 0.3848 | -0.007 | 36 | 17 | 76464322 | Body;Body | NA |
| cg15358690 | 0.9109 | 0.000 | 36 | 17 | 76464505 | Body;Body | NA |
| cg16116279 | 0.1482 | -0.004 | 36 | 17 | 76464511 | Body;Body | NA |
| cg16721879 | 0.3823 | -0.002 | 36 | 17 | 76464566 | Body;Body | NA |
| cg03119454 | 0.7343 | 0.000 | 36 | 17 | 76465075 | Body;Body | NA |
| cg16886414 | 0.1244 | 0.012 | 36 | 17 | 76465744 | Body;Body | NA |
| cg08314949 | 0.1652 | 0.018 | 36 | 17 | 76465808 | Body;Body | NA |
| cg12078154 | 0.3725 | 0.016 | 36 | 17 | 76465857 | Body;Body | NA |
| cg02251850 | 0.0008 | 0.035 | 36 | 17 | 76466098 | Body;Body | NA |
| cg22091236 | 0.0033 | -0.028 | 36 | 17 | 76468561 | Body;Body | TRUE |
| cg27457201 | 0.0153 | -0.020 | 36 | 17 | 76468827 | Body;Body | NA |
| cg09977718 | 0.0499 | -0.016 | 36 | 17 | 76468868 | Body;Body | NA |
| cg22255288 | 0.0954 | 0.003 | 36 | 17 | 76469013 | Body;Body | NA |
| cg09964933 | 0.6074 | 0.000 | 36 | 17 | 76470841 | Body;Body | NA |

Fig. 23 (continued)

Table 23. The methylation levels of RPTOR CpG sites by Illumina 450K (continued)

| CpG ID | pvalWald_Group | meanDiff | BUILD | CHR | MAPINFO | LOCATION | ENHANCER |
|---|---|---|---|---|---|---|---|
| cg21343406 | 0.3031 | -0.002 | 36 | 17 | 76470926 | Body;Body | NA |
| cg09318637 | 0.8519 | -0.001 | 36 | 17 | 76471009 | Body;Body | NA |
| cg08588357 | 0.0125 | 0.003 | 36 | 17 | 76471270 | Body;Body | NA |
| cg17872658 | 0.0631 | 0.006 | 36 | 17 | 76471456 | Body;Body | NA |
| cg05887890 | 0.2151 | -0.005 | 36 | 17 | 76471606 | Body;Body | NA |
| cg17585356 | 0.7787 | -0.002 | 36 | 17 | 76471716 | Body;Body | NA |
| cg04166962 | 0.5127 | -0.002 | 36 | 17 | 76471833 | Body;Body | NA |
| cg19185574 | 0.8236 | -0.002 | 36 | 17 | 76472226 | Body;Body | NA |
| cg23630758 | 0.2275 | -0.002 | 36 | 17 | 76472307 | Body;Body | NA |
| cg13831388 | 0.4582 | -0.002 | 36 | 17 | 76472454 | Body;Body | NA |
| cg18224819 | 0.8864 | 0.002 | 36 | 17 | 76472571 | Body;Body | NA |
| cg02933375 | 0.8242 | -0.001 | 36 | 17 | 76473423 | Body;Body | NA |
| cg08150315 | 0.5730 | 0.001 | 36 | 17 | 76473562 | Body;Body | NA |
| cg11623293 | 0.2144 | -0.004 | 36 | 17 | 76473655 | Body;Body | NA |
| cg24181389 | 0.9718 | -0.002 | 36 | 17 | 76474340 | Body;Body | NA |
| cg02243479 | 0.6669 | 0.000 | 36 | 17 | 76474554 | Body;Body | NA |
| cg16660971 | 0.8045 | -0.003 | 36 | 17 | 76474624 | Body;Body | NA |
| cg13549638 | 0.0781 | -0.014 | 36 | 17 | 76474671 | Body;Body | NA |
| cg26954228 | 0.5258 | -0.002 | 36 | 17 | 76475078 | Body;Body | NA |
| cg26714263 | 0.3528 | -0.002 | 36 | 17 | 76475106 | Body;Body | NA |
| cg06154633 | 0.7570 | 0.000 | 36 | 17 | 76475200 | Body;Body | NA |
| cg18562896 | 0.3348 | -0.002 | 36 | 17 | 76477462 | Body;Body | NA |
| cg24963810 | 0.7351 | 0.000 | 36 | 17 | 76477488 | Body;Body | NA |
| cg16018154 | 0.3427 | -0.009 | 36 | 17 | 76478165 | Body;Body | NA |
| cg09891288 | 0.9173 | 0.006 | 36 | 17 | 76478269 | Body;Body | NA |
| cg25902229 | 0.7244 | 0.009 | 36 | 17 | 76478683 | Body;Body | NA |
| cg05774614 | 0.0449 | -0.019 | 36 | 17 | 76479134 | Body;Body | NA |
| cg10035831 | 0.2491 | 0.010 | 36 | 17 | 76479682 | Body;Body | NA |
| cg22636722 | 0.4223 | 0.008 | 36 | 17 | 76479858 | Body;Body | TRUE |
| cg00704970 | 0.9120 | 0.003 | 36 | 17 | 76479963 | Body;Body | TRUE |
| cg03502601 | 0.3925 | 0.014 | 36 | 17 | 76479968 | Body;Body | TRUE |
| cg09803959 | 0.0945 | -0.013 | 36 | 17 | 76480109 | Body;Body | TRUE |
| cg24207068 | 0.7115 | -0.004 | 36 | 17 | 76480257 | Body;Body | TRUE |
| cg04658243 | 0.1329 | 0.011 | 36 | 17 | 76480350 | Body;Body | TRUE |
| cg11476241 | 0.8042 | -0.003 | 36 | 17 | 76480830 | Body;Body | TRUE |
| cg24327522 | 0.5242 | -0.004 | 36 | 17 | 76481174 | Body;Body | NA |
| cg10490202 | 0.9245 | -0.001 | 36 | 17 | 76482226 | Body;Body | NA |
| cg17628491 | 0.1611 | -0.072 | 36 | 17 | 76482417 | Body;Body | NA |

Fig. 23 (continued)

Table 23. The methylation levels of RPTOR CpG sites by Illumina 450K (continued)

| CpG ID | pvalWald_Group | meanDiff | BUILD | CHR | MAPINFO | LOCATION | ENHANCER |
|---|---|---|---|---|---|---|---|
| cg21289763 | 0.6645 | -0.004 | 36 | 17 | 76483430 | Body;Body | NA |
| cg17180011 | 0.9825 | 0.000 | 36 | 17 | 76483873 | Body;Body | NA |
| cg15022015 | 0.3763 | 0.001 | 36 | 17 | 76484122 | Body;Body | NA |
| cg05064567 | 0.2731 | -0.006 | 36 | 17 | 76484733 | Body;Body | NA |
| cg04919811 | 0.7690 | 0.000 | 36 | 17 | 76484897 | Body;Body | NA |
| cg16578291 | 0.0447 | 0.003 | 36 | 17 | 76485004 | Body;Body | NA |
| cg19292222 | 0.7272 | -0.006 | 36 | 17 | 76486006 | Body;Body | NA |
| cg23938645 | 0.5029 | -0.001 | 36 | 17 | 76487158 | Body;Body | NA |
| cg06053702 | 0.0003 | -0.010 | 36 | 17 | 76487304 | Body;Body | NA |
| cg10538214 | 0.7647 | -0.003 | 36 | 17 | 76487470 | Body;Body | NA |
| cg16780847 | 0.3163 | -0.004 | 36 | 17 | 76488294 | Body;Body | NA |
| cg10880603 | 0.7098 | -0.002 | 36 | 17 | 76488349 | Body;Body | NA |
| cg11274148 | 0.2864 | -0.001 | 36 | 17 | 76491251 | Body;Body | NA |
| cg01412400 | 0.5867 | 0.001 | 36 | 17 | 76491321 | Body;Body | NA |
| cg12131324 | 0.2116 | -0.005 | 36 | 17 | 76491389 | Body;Body | NA |
| cg19494960 | 0.0803 | -0.002 | 36 | 17 | 76491556 | Body;Body | NA |
| cg00474943 | 0.7289 | -0.001 | 36 | 17 | 76491671 | Body;Body | NA |
| cg24683534 | 0.4077 | -0.005 | 36 | 17 | 76491800 | Body;Body | NA |
| cg04163696 | 0.8307 | 0.000 | 36 | 17 | 76492566 | Body;Body | NA |
| cg16895810 | 0.0604 | -0.003 | 36 | 17 | 76492646 | Body;Body | NA |
| cg09173565 | 0.3509 | 0.000 | 36 | 17 | 76492873 | Body;Body | NA |
| cg22673070 | 0.9268 | -0.004 | 36 | 17 | 76493125 | Body;Body | NA |
| cg16218910 | 0.6600 | -0.002 | 36 | 17 | 76493174 | Body;Body | NA |
| cg19296258 | 0.8778 | -0.001 | 36 | 17 | 76493394 | Body;Body | NA |
| cg05580441 | 0.3368 | 0.000 | 36 | 17 | 76493439 | Body;Body | NA |
| cg08992574 | 0.3860 | -0.002 | 36 | 17 | 76494240 | Body;Body | NA |
| cg02257048 | 0.7990 | 0.000 | 36 | 17 | 76494626 | Body;Body | NA |
| cg07870603 | 0.8592 | 0.001 | 36 | 17 | 76494739 | Body;Body | NA |
| cg01000996 | 0.9733 | -0.002 | 36 | 17 | 76494821 | Body;Body | NA |
| cg00554570 | 0.9380 | -0.001 | 36 | 17 | 76494823 | Body;Body | NA |
| cg06908052 | 0.9305 | -0.001 | 36 | 17 | 76494991 | Body;Body | NA |
| cg10462529 | 0.4569 | -0.001 | 36 | 17 | 76495343 | Body;Body | NA |
| cg06485000 | 0.1252 | -0.005 | 36 | 17 | 76496316 | Body;Body | NA |
| cg10508138 | 0.5197 | -0.003 | 36 | 17 | 76496608 | Body;Body | NA |
| cg02671711 | 0.7700 | 0.000 | 36 | 17 | 76496795 | Body;Body | NA |
| cg19984991 | 0.2472 | 0.002 | 36 | 17 | 76497089 | Body;Body | NA |
| cg00248805 | 0.1761 | 0.002 | 36 | 17 | 76497144 | Body;Body | NA |
| cg19707379 | 0.9561 | 0.000 | 36 | 17 | 76497288 | Body;Body | NA |

Fig. 23 (continued)

Table 23. The methylation levels of RPTOR CpG sites by Illumina 450K (continued)

| CpG ID | pvalWald_Group | meanDiff | BUILD | CHR | MAPINFO | LOCATION | ENHANCER |
|---|---|---|---|---|---|---|---|
| cg14003223 | 0.6147 | 0.000 | 36 | 17 | 76497315 | Body;Body | NA |
| cg14289594 | 0.3493 | -0.003 | 36 | 17 | 76497349 | Body;Body | NA |
| cg16892887 | 0.8649 | 0.003 | 36 | 17 | 76506807 | Body;Body | NA |
| cg04789650 | 0.6675 | -0.003 | 36 | 17 | 76506890 | Body;Body | NA |
| cg21000762 | 0.7766 | -0.001 | 36 | 17 | 76507445 | Body;Body | NA |
| cg14059665 | 0.9123 | -0.002 | 36 | 17 | 76507480 | Body;Body | NA |
| cg15331383 | 0.2774 | -0.004 | 36 | 17 | 76507958 | Body;Body | NA |
| cg01525498 | 0.5356 | -0.003 | 36 | 17 | 76508024 | Body;Body | NA |
| cg07078467 | 0.5535 | 0.002 | 36 | 17 | 76508207 | Body;Body | NA |
| cg15694704 | 0.2755 | -0.009 | 36 | 17 | 76508959 | Body;Body | NA |
| cg06096901 | 0.9803 | 0.000 | 36 | 17 | 76508988 | Body;Body | NA |
| cg21818807 | 0.4883 | 0.000 | 36 | 17 | 76509072 | Body;Body | NA |
| cg09790523 | 0.4747 | -0.003 | 36 | 17 | 76509659 | Body;Body | NA |
| cg09794615 | 0.1099 | 0.010 | 36 | 17 | 76509801 | Body;Body | NA |
| cg05395366 | 0.2359 | 0.005 | 36 | 17 | 76509868 | Body;Body | NA |
| cg17052885 | 0.0947 | -0.005 | 36 | 17 | 76510607 | Body;Body | NA |
| cg21734751 | 0.4560 | 0.000 | 36 | 17 | 76511032 | Body;Body | NA |
| cg12044293 | 0.4862 | -0.001 | 36 | 17 | 76511264 | Body;Body | NA |
| cg17144164 | 0.0500 | -0.002 | 36 | 17 | 76511295 | Body;Body | NA |
| cg24744721 | 0.5349 | -0.001 | 36 | 17 | 76511564 | Body;Body | NA |
| cg06358794 | 0.6246 | 0.001 | 36 | 17 | 76511697 | Body;Body | NA |
| cg26290973 | 0.3413 | 0.001 | 36 | 17 | 76511732 | Body;Body | NA |
| cg02346006 | 0.3890 | -0.001 | 36 | 17 | 76512072 | Body;Body | NA |
| cg21219851 | 0.7685 | -0.001 | 36 | 17 | 76512784 | Body;Body | NA |
| cg07450393 | 0.8688 | 0.000 | 36 | 17 | 76512857 | Body;Body | NA |
| cg16732367 | 0.2475 | 0.001 | 36 | 17 | 76512964 | Body;Body | NA |
| cg09139509 | 0.5410 | 0.001 | 36 | 17 | 76513611 | Body;Body | NA |
| cg06091647 | 0.0260 | 0.005 | 36 | 17 | 76513987 | Body;Body | NA |
| cg05814100 | 0.9118 | -0.003 | 36 | 17 | 76514392 | Body;Body | NA |
| cg25739309 | 0.9893 | -0.007 | 36 | 17 | 76515047 | Body;Body | TRUE |
| cg02638755 | 0.3795 | -0.006 | 36 | 17 | 76516964 | Body;Body | NA |
| cg11188237 | 0.5847 | -0.001 | 36 | 17 | 76516991 | Body;Body | NA |
| cg18802706 | 0.3898 | -0.001 | 36 | 17 | 76517029 | Body;Body | NA |
| cg18612040 | 0.0580 | -0.005 | 36 | 17 | 76519080 | Body;Body | TRUE |
| cg07584637 | 0.1946 | -0.005 | 36 | 17 | 76526172 | Body;Body | NA |
| cg19394169 | 0.2908 | -0.005 | 36 | 17 | 76526269 | Body;Body | NA |
| cg03641032 | 0.6363 | -0.002 | 36 | 17 | 76526363 | Body;Body | NA |
| cg11949518 | 0.3498 | 0.048 | 36 | 17 | 76527360 | Body;Body | NA |

Fig. 23 (continued)

Table 23. The methylation levels of RPTOR CpG sites by Illumina 450K (continued)

| CpG ID | pvalWald_Group | meanDiff | BUILD | CHR | MAPINFO | LOCATION | ENHANCER |
|---|---|---|---|---|---|---|---|
| cg24315876 | 0.3700 | 0.009 | 36 | 17 | 76527706 | Body;Body | NA |
| cg02580745 | 0.1085 | 0.002 | 36 | 17 | 76528696 | Body;Body | NA |
| cg02266055 | 0.7714 | -0.001 | 36 | 17 | 76528924 | Body;Body | NA |
| cg00648660 | 0.7319 | -0.001 | 36 | 17 | 76528951 | Body;Body | NA |
| cg06469955 | 0.3871 | -0.002 | 36 | 17 | 76529741 | Body;Body | NA |
| cg13643509 | 0.4705 | 0.001 | 36 | 17 | 76530250 | Body;Body | TRUE |
| cg19060120 | 0.1430 | -0.007 | 36 | 17 | 76530473 | Body;Body | TRUE |
| cg23736297 | 0.5482 | -0.004 | 36 | 17 | 76530476 | Body;Body | TRUE |
| cg13005428 | 0.0522 | -0.036 | 36 | 17 | 76530973 | Body;Body | TRUE |
| cg16438182 | 0.5382 | 0.000 | 36 | 17 | 76531162 | Body;Body | TRUE |
| cg02033669 | 0.6037 | 0.001 | 36 | 17 | 76531614 | Body;Body | NA |
| cg21238376 | 0.2941 | 0.003 | 36 | 17 | 76534371 | Body;Body | NA |
| cg08999272 | 0.7934 | -0.002 | 36 | 17 | 76536073 | Body;Body | NA |
| cg11782601 | 0.8057 | -0.002 | 36 | 17 | 76536493 | Body;Body | NA |
| cg26729320 | 0.7299 | -0.002 | 36 | 17 | 76536639 | Body;Body | NA |
| cg14600877 | 0.6821 | -0.002 | 36 | 17 | 76536815 | Body;Body | NA |
| cg13597013 | 0.8713 | -0.001 | 36 | 17 | 76537122 | Body;Body | NA |
| cg13762486 | 0.2658 | -0.007 | 36 | 17 | 76537745 | Body;Body | NA |
| cg06420480 | 0.9135 | -0.001 | 36 | 17 | 76537839 | Body;Body | NA |
| cg19443023 | 0.6000 | 0.000 | 36 | 17 | 76537939 | Body;Body | NA |
| cg07081946 | 0.8550 | -0.001 | 36 | 17 | 76538447 | Body;Body | NA |
| cg26469982 | 0.7033 | -0.003 | 36 | 17 | 76538527 | Body;Body | NA |
| cg02254800 | 0.1718 | -0.004 | 36 | 17 | 76538681 | Body;Body | NA |
| cg24343322 | 0.9926 | -0.002 | 36 | 17 | 76539767 | Body;Body | NA |
| cg25057221 | 0.2770 | 0.002 | 36 | 17 | 76539827 | Body;Body | NA |
| cg18425700 | 0.3988 | -0.004 | 36 | 17 | 76539873 | Body;Body | NA |
| cg03052541 | 0.7777 | -0.001 | 36 | 17 | 76540138 | Body;Body | NA |
| cg18815595 | 0.7748 | -0.001 | 36 | 17 | 76540402 | Body;Body | NA |
| cg17779026 | 0.8527 | -0.001 | 36 | 17 | 76540405 | Body;Body | NA |
| cg21831512 | 0.1568 | -0.009 | 36 | 17 | 76540686 | Body;Body | NA |
| cg26932839 | 0.7133 | -0.001 | 36 | 17 | 76540725 | Body;Body | NA |
| cg24180621 | 0.0940 | -0.003 | 36 | 17 | 76540780 | Body;Body | NA |
| cg17831694 | 0.3741 | -0.003 | 36 | 17 | 76544495 | Body;Body | NA |
| cg11762703 | 0.0912 | 0.011 | 36 | 17 | 76544533 | Body;Body | NA |
| cg02403929 | 0.3404 | 0.001 | 36 | 17 | 76544901 | Body;Body | NA |
| cg22486214 | 0.4842 | -0.001 | 36 | 17 | 76545061 | Body;Body | NA |
| cg02047211 | 0.9318 | -0.002 | 36 | 17 | 76547292 | Body;Body | NA |
| cg02864619 | 0.8175 | 0.000 | 36 | 17 | 76548556 | Body;Body | TRUE |

Fig. 23 (continued)

Table 23. The methylation levels of RPTOR CpG sites by Illumina 450K (continued)

| CpG ID | pvalWald_Group | meanDiff | BUILD | CHR | MAPINFO | LOCATION | ENHANCER |
|---|---|---|---|---|---|---|---|
| cg17906851 | 0.2149 | -0.036 | 36 | 17 | 76549665 | Body;Body | NA |
| cg21879029 | 0.7815 | 0.000 | 36 | 17 | 76549770 | Body;Body | NA |
| cg09491897 | 0.2438 | -0.001 | 36 | 17 | 76549864 | Body;Body | NA |
| cg07964113 | 0.1756 | 0.001 | 36 | 17 | 76549884 | Body;Body | NA |
| cg09361653 | 0.9428 | 0.000 | 36 | 17 | 76550887 | Body;Body | NA |
| cg17408291 | 0.7710 | -0.001 | 36 | 17 | 76550967 | Body;Body | NA |
| cg04275040 | 0.2387 | 0.000 | 36 | 17 | 76551223 | Body;Body | NA |
| cg03800447 | 0.4430 | 0.000 | 36 | 17 | 76551344 | Body;Body | NA |
| cg08804421 | 0.4328 | 0.003 | 36 | 17 | 76551392 | Body;Body | NA |
| cg26886231 | 0.4056 | 0.000 | 36 | 17 | 76551484 | Body;Body | NA |
| cg13136721 | 0.5328 | 0.003 | 36 | 17 | 76551778 | Body;Body | NA |
| cg10278297 | 0.3103 | -0.003 | 36 | 17 | 76552433 | Body;Body | NA |
| cg10752731 | 0.3004 | 0.000 | 36 | 17 | 76552729 | 3'UTR;3'UTR | NA |
| cg03890538 | 0.5621 | -0.003 | 36 | 17 | 76552939 | 3'UTR;3'UTR | NA |
| cg18732855 | 0.0473 | 0.001 | 36 | 17 | 76553701 | 3'UTR;3'UTR | NA |
| cg03389944 | 0.4000 | -0.002 | 36 | 17 | 76554181 | 3'UTR;3'UTR | NA |
| cg15432510 | 0.2292 | -0.002 | 36 | 17 | 76554265 | 3'UTR;3'UTR | NA |
| cg09439604 | 0.9534 | -0.002 | 36 | 17 | 76554624 | 3'UTR;3'UTR | NA |
| cg15406978 | 0.4216 | 0.002 | 36 | 17 | 76554688 | 3'UTR;3'UTR | NA |
| cg25290617 | 0.0035 | -0.012 | 36 | 17 | 76554705 | 3'UTR;3'UTR | NA |
| cg23051282 | 0.0132 | -0.002 | 36 | 17 | 76554756 | 3'UTR;3'UTR | NA |

Fig. 24

Table 24. The methylation levels of MGRN1 CpG sites by Illumina 450K

| CpG ID | pvalWald_Group | meanDiff | BUILD | CHR | MAPINFO | LOCATION | ENHANCER |
|---|---|---|---|---|---|---|---|
| cg03819286 | 0.0003 | -0.024 | 36 | 16 | 4613975 | N_Shore | NA |
| cg01678580 | 0.0839 | -0.007 | 36 | 16 | 4614019 | N_Shore | NA |
| cg08058836 | 0.9419 | 0.001 | 36 | 16 | 4614353 | N_Shore | NA |
| cg00369126 | 0.7741 | 0.001 | 36 | 16 | 4614643 | N_Shore | NA |
| cg00203035 | 0.9047 | 0.000 | 36 | 16 | 4614660 | N_Shore | NA |
| cg02283436 | 0.3901 | 0.003 | 36 | 16 | 4614678 | N_Shore | NA |
| cg04367464 | 0.9647 | 0.001 | 36 | 16 | 4614717 | Island | NA |
| cg01482556 | 0.5192 | 0.001 | 36 | 16 | 4614719 | Island | NA |
| cg00588858 | 0.2908 | -0.001 | 36 | 16 | 4615007 | Island | NA |
| cg10442572 | 0.4991 | 0.001 | 36 | 16 | 4615385 | Island | NA |
| cg16118148 | 0.7137 | 0.001 | 36 | 16 | 4615388 | Island | NA |
| cg08142943 | 0.8882 | 0.001 | 36 | 16 | 4615652 | S_Shore | NA |
| cg08147187 | 0.9335 | -0.001 | 36 | 16 | 4619397 | S_Shelf | NA |
| cg00693240 | 0.6552 | 0.000 | 36 | 16 | 4624508 |  | NA |
| cg02404489 | 0.9706 | 0.000 | 36 | 16 | 4624597 |  | NA |
| cg08524372 | 0.8553 | -0.002 | 36 | 16 | 4624732 |  | NA |
| cg05459609 | 0.0097 | -0.004 | 36 | 16 | 4629951 |  | TRUE |
| cg07741192 | 0.8363 | 0.000 | 36 | 16 | 4630014 |  | TRUE |
| cg02968175 | 0.4863 | -0.001 | 36 | 16 | 4630021 |  | TRUE |
| cg03336832 | 0.9156 | -0.002 | 36 | 16 | 4636109 | N_Shelf | NA |
| cg03427191 | 0.0004 | 0.024 | 36 | 16 | 4637113 | N_Shore | NA |
| cg23233631 | 0.1891 | -0.004 | 36 | 16 | 4638221 | Island | NA |
| cg09440989 | 0.0021 | -0.007 | 36 | 16 | 4639882 | S_Shore | NA |
| cg04071866 | 0.0023 | -0.020 | 36 | 16 | 4640738 | N_Shore | NA |
| cg00639215 | 0.1100 | 0.001 | 36 | 16 | 4642770 | Island | NA |
| cg05782454 | 0.2161 | -0.005 | 36 | 16 | 4642835 | Island | NA |
| cg26700932 | 0.2518 | -0.004 | 36 | 16 | 4643004 | S_Shore | NA |
| cg05287064 | 0.4451 | -0.003 | 36 | 16 | 4645946 | S_Shelf | NA |
| cg02647929 | 0.0001 | -0.029 | 36 | 16 | 4654081 |  | NA |
| cg06323332 | 0.0000 | -0.032 | 36 | 16 | 4654230 |  | NA |
| cg27193519 | 0.0001 | -0.042 | 36 | 16 | 4654444 |  | NA |
| cg01922891 | 0.0000 | -0.031 | 36 | 16 | 4654648 |  | NA |
| cg04962621 | 0.0001 | -0.034 | 36 | 16 | 4654734 |  | NA |
| cg01156249 | 0.0244 | -0.018 | 36 | 16 | 4654795 |  | NA |
| cg07635227 | 0.0124 | -0.014 | 36 | 16 | 4654816 |  | NA |
| cg09250423 | 0.2256 | 0.002 | 36 | 16 | 4657753 |  | NA |
| cg03420907 | 0.4692 | 0.001 | 36 | 16 | 4657773 |  | NA |
| cg08760128 | 0.3017 | -0.001 | 36 | 16 | 4663508 |  | NA |

Fig. 24 (continued)

Table 24. The methylation levels of MGRN1 CpG sites by Illumina 450K (continued)

| CpG ID | pvalWald_Group | meanDiff | BUILD | CHR | MAPINFO | LOCATION | ENHANCER |
|---|---|---|---|---|---|---|---|
| cg27004760 | 0.7278 | -0.002 | 36 | 16 | 4663623 |  | NA |
| cg03693714 | 0.1679 | -0.004 | 36 | 16 | 4663817 |  | NA |
| cg05383524 | 0.7179 | -0.001 | 36 | 16 | 4666971 | N_Shelf | NA |
| cg04087057 | 0.7062 | -0.003 | 36 | 16 | 4668188 | N_Shelf | NA |
| cg27436118 | 0.0002 | -0.031 | 36 | 16 | 4669906 | N_Shore | NA |
| cg08782022 | 0.0048 | -0.048 | 36 | 16 | 4670137 | N_Shore | TRUE |
| cg01662869 | 0.0000 | -0.045 | 36 | 16 | 4670411 | Island | TRUE |
| cg00736299 | 0.0000 | -0.043 | 36 | 16 | 4670466 | Island | TRUE |
| cg02074956 | 0.0000 | -0.032 | 36 | 16 | 4670658 | N_Shore | TRUE |
| cg10505257 | 0.0003 | -0.030 | 36 | 16 | 4671640 | Island | NA |
| cg07812289 | 0.6799 | 0.000 | 36 | 16 | 4671719 | Island | NA |
| cg05901634 | 0.3634 | 0.003 | 36 | 16 | 4671822 | Island | NA |
| cg00504410 | 0.0025 | -0.014 | 36 | 16 | 4672263 | Island | NA |
| cg03963853 | 0.1509 | -0.002 | 36 | 16 | 4672370 | Island | NA |
| cg07248377 | 0.0109 | -0.015 | 36 | 16 | 4672407 | Island | NA |
| cg10908196 | 0.0021 | -0.018 | 36 | 16 | 4672912 | Island | NA |
| cg01861603 | 0.8633 | -0.002 | 36 | 16 | 4672974 | Island | NA |
| cg16520815 | 0.0002 | -0.030 | 36 | 16 | 4673182 | Island | NA |
| cg09306188 | 0.0000 | -0.057 | 36 | 16 | 4673254 | S_Shore | NA |
| cg04208175 | 0.8742 | -0.002 | 36 | 16 | 4674630 | S_Shore | NA |
| cg04083430 | 0.0087 | -0.035 | 36 | 16 | 4676064 | S_Shelf | NA |
| cg16778018 | 0.0922 | -0.006 | 36 | 16 | 4676226 | S_Shelf | NA |
| cg26627888 | 0.1955 | 0.002 | 36 | 16 | 4676420 | S_Shelf | NA |
| cg16576106 | 0.8006 | 0.000 | 36 | 16 | 4676779 | S_Shelf | NA |
| cg02072002 | 0.8181 | 0.000 | 36 | 16 | 4676796 | S_Shelf | NA |
| cg16420089 | 0.6085 | -0.002 | 36 | 16 | 4676870 | S_Shelf | NA |
| cg02352612 | 0.1408 | -0.005 | 36 | 16 | 4677994 |  | NA |
| cg00033551 | 0.0179 | -0.012 | 36 | 16 | 4678569 |  | NA |
| cg03157150 | 0.8802 | -0.002 | 36 | 16 | 4678681 |  | NA |
| cg09005651 | 0.0003 | -0.013 | 36 | 16 | 4680695 | N_Shelf | NA |
| cg10090769 | 0.0093 | -0.013 | 36 | 16 | 4680792 | N_Shelf | NA |

SEQUENCE LISTING

<160> NUMBER OF SEQ ID NOS: 67

<210> SEQ ID NO 1
<211> LENGTH: 21
<212> TYPE: RNA
<213> ORGANISM: Homo sapiens

<400> SEQUENCE: 1
aauggcgcca cuaggguugu g                                              21

<210> SEQ ID NO 2
<211> LENGTH: 25
<212> TYPE: RNA
<213> ORGANISM: Homo sapiens

<400> SEQUENCE: 2
caacccuagg agagggugcc auuca                                          25

<210> SEQ ID NO 3
<211> LENGTH: 24
<212> TYPE: RNA
<213> ORGANISM: Homo sapiens

<400> SEQUENCE: 3
gauugcucug cgugcggaau cgac                                           24

<210> SEQ ID NO 4
<211> LENGTH: 21
<212> TYPE: RNA
<213> ORGANISM: Homo sapiens

<400> SEQUENCE: 4
aacauagagg aaauuccacg u                                              21

<210> SEQ ID NO 5
<211> LENGTH: 21
<212> TYPE: RNA
<213> ORGANISM: Homo sapiens

<400> SEQUENCE: 5
gguggauauu ccuucuaugu u                                              21

<210> SEQ ID NO 6
<211> LENGTH: 21
<212> TYPE: RNA
<213> ORGANISM: Homo sapiens

<400> SEQUENCE: 6
aucauagagg aaaauccacg u                                              21

<210> SEQ ID NO 7
<211> LENGTH: 22
<212> TYPE: RNA
<213> ORGANISM: Homo sapiens

```
<400> SEQUENCE: 7
guagauucuc cuucuaugag ua                                              22

<210> SEQ ID NO 8
<211> LENGTH: 22
<212> TYPE: RNA
<213> ORGANISM: Homo sapiens

<400> SEQUENCE: 8
ucggauccgu cugagcuugg cu                                              22

<210> SEQ ID NO 9
<211> LENGTH: 22
<212> TYPE: RNA
<213> ORGANISM: Homo sapiens

<400> SEQUENCE: 9
cugaagcuca gagggcucug au                                              22

<210> SEQ ID NO 10
<211> LENGTH: 22
<212> TYPE: RNA
<213> ORGANISM: Homo sapiens

<400> SEQUENCE: 10
gaauguugcu cggugaaccc cu                                              22

<210> SEQ ID NO 11
<211> LENGTH: 23
<212> TYPE: RNA
<213> ORGANISM: Homo sapiens

<400> SEQUENCE: 11
agguuacccg agcaacuuug cau                                             23

<210> SEQ ID NO 12
<211> LENGTH: 22
<212> TYPE: RNA
<213> ORGANISM: Homo sapiens

<400> SEQUENCE: 12
ucagugcauc acagaacuuu gu                                              22

<210> SEQ ID NO 13
<211> LENGTH: 22
<212> TYPE: RNA
<213> ORGANISM: Homo sapiens

<400> SEQUENCE: 13
aaguucuguu auacacucag gc                                              22

<210> SEQ ID NO 14
<211> LENGTH: 2005
<212> TYPE: DNA
<213> ORGANISM: Homo sapiens

<400> SEQUENCE: 14
tttcctctca gggggcagca ggaagtgagg agaaagggct gggatgggag gcgggagcgg      60
atgggaggga atgggggttta tcaagtcctc ggcgagctgc ccaacgggca gcagctggcg    120
caagtagcct agctgagag gctcacccca ggaaggaggg aggccaccga cctactgggc     180
cgacggactc ccacacagtt cctgagctgg tgccaggcag gtgacacctc ctgcagcccc    240
```

| | |
|---|---|
| cagcatgcgg gcaggcccag gccccaccgt tacattggcc ctggtgctgg cggtgtcatg | 300 |
| ggccatggag ctcaagccca cagcaccacc catcttcact ggccggccct ttgtggtagc | 360 |
| gtgggacgtg cccacacagg actgtggccc acgcctcaag gtgccactgg acctgaatgc | 420 |
| ctttgatgtg caggcctcac ctaatgaggg ttttgtgaac cagaatatta ccatcttcta | 480 |
| ccgcgaccgt ctaggcctgt atccacgctt cgattctgcc ggaaggtctg tgcatggtgg | 540 |
| tgtgccacag aatgtcagcc tttgggcaca ccggaagatg ctgcagaaac gtgtggagca | 600 |
| ctacattcgg acacaggagt ctgcggggct ggcggtcatc gactgggagg actggcgacc | 660 |
| tgtgtgggtg cgcaactggc aggacaaaga tgtgtatcgc cggttatcac gccagctagt | 720 |
| ggccagtcgt caccctgact ggcctccaga ccgcatagtc aaacaggcac aatatgagtt | 780 |
| tgagttcgca gcacagcagt tcatgctgga gacactgcgt tatgtcaagg cagtgcggcc | 840 |
| ccggcacctc tggggcttct acctcttttcc tgactgctac aatcatgatt atgtgcagaa | 900 |
| ctgggagagc tacacaggcc gctgccctga tgttgaggtg gcccgcaatg accagctggc | 960 |
| ctggctgtgg gctgagagca cggccctctt cccgtctgtc tacctggacg agacacttgc | 1020 |
| ttcctcccgc catggccgca actttgtgag cttccgtgtt caggaggccc ttcgtgtggc | 1080 |
| tcgcacccac catgccaacc atgcactccc agtctacgtt tcacacgac ccacctacag | 1140 |
| ccgcaggctc acggggctta gtgagatgga cctcatctct accattggcg agagtgcggc | 1200 |
| cctgggcgca gctggtgtca tcctctgggg tgacgcgggg tacaccacaa gcacggagac | 1260 |
| ctgccagtac ctcaaagatt acctgacacg gctgctggtc ccctacgtgg tcaatgtgtc | 1320 |
| ctgggccacc caatattgca gccgggccca gtgccatggc catgggcgct gtgtgcgccg | 1380 |
| caacccccagt gccagtacct tcctgcatct cagcaccaac agtttccgcc tagtgcctgg | 1440 |
| ccatgcacct ggtgaacccc agctgcgacc tgtgggggag ctcagttggg ccgacattga | 1500 |
| ccacctgcag acacacttcc gctgccagtg ctacttgggc tggagtggtg agcaatgcca | 1560 |
| gtgggaccat aggcaggcag ctggaggtgc cagcgaggcc tgggctgggt cccacctcac | 1620 |
| cagtctgctg gctctggcag ccctggcctt tacctggacc ttgtaggggt ctcctgccta | 1680 |
| gctgcctagc aagctggcct ctaccacaag ggctctctta ggcatgtagg accctgcagg | 1740 |
| gggtggacaa actggagtct ggagtgggca gagcccccag gaagcccagg agggcatcca | 1800 |
| taccagctcg cacccccctg ttctaagggg gaggggaagt ccctgggagg ccccttctct | 1860 |
| ccctgccaga ggggaaggag ggtacagctg ggctggggag gacctgaccc tactcccttg | 1920 |
| ccctagatag tttattatta ttattatttt ggggtctctt ttgtaaatta aacataaaac | 1980 |
| aattgcttct ctgcttggat tttgt | 2005 |

<210> SEQ ID NO 15
<211> LENGTH: 2413
<212> TYPE: DNA
<213> ORGANISM: Homo sapiens

<400> SEQUENCE: 15

| | |
|---|---|
| tttcctctca gggggcagca ggaagtgagg agaaagggct gggatgggag gcgggagcgg | 60 |
| atgggaggga atgggggttta tcaagtcctc ggcgagctgc ccaacgggca gcagctggcg | 120 |
| caagtagcct agctggagag gctcaccccca ggaaggaggg aggccaccga cctactgggc | 180 |
| cgacggactc ccacacaggg ctggcggcgc cgcggagctg ggaggactga accaccggcc | 240 |
| tcgggctgca ggggaaacat ttcaggctga ctggcgctcg tggctgagac tcccatagaa | 300 |
| agcccggctc agaggggcat tagggtccta aatgggcggc cacgtccctc tgcagaggac | 360 |

```
ctggggctct tcgagcccga aacgaggcac cggcaccgag aaaggtggac cacaccttcc    420
cgccccgtcc gcaagtccaa tcccgggccc acctccgcac tggagtctta aagggccagc    480
gtgcctgggg gcggagccag cagaggcgct gagccgggcc gcgcctgggc gaacggccgg    540
agcgggctgg gctgggcccg ggatggcggt ggccctggcg ccgtcccgg tggcgccccg     600
cgcgagttcc tgagctggtg ccaggcaggt gacacctcct gcagccccca gcatgcgggc    660
aggcccaggc cccaccgtta cattggccct ggtgctggcg gtgtcatggg ccatggagct    720
caagcccaca gcaccaccca tcttcactgg ccggccctt tgtggtagcgt gggacgtgcc    780
cacacaggac tgtggcccac gcctcaaggt gccactggac ctgaatgcct ttgatgtgca    840
ggcctcacct aatgagggtt ttgtgaacca gaatattacc atcttctacc gcgaccgtct    900
aggcctgtat ccacgcttcg attctgccgg aaggtctgtg catggtggtg tgccacagaa    960
tgtcagcctt tgggcacacc ggaagatgct gcagaaacgt gtggagcact acattcggac   1020
acaggagtct gcggggctgg cggtcatcga ctgggaggac tggcgacctg tgtgggtgcg   1080
caactggcag gacaaagatg tgtatcgccg gttatcacgc cagctagtgg ccagtcgtca   1140
ccctgactgg cctccagacc gcatagtcaa acaggcacaa tatgagtttg agttcgcagc   1200
acagcagttc atgctggaga cactgcgtta tgtcaaggca gtgcggcccc ggcacctctg   1260
gggcttctac ctctttcctg actgctacaa tcatgattat gtgcagaact gggagagcta   1320
cacaggccgc tgccctgatg ttgaggtggc ccgcaatgac cagctggcct ggctgtgggc   1380
tgagagcacg gccctcttcc cgtctgtcta cctggacgag acacttgctt cctcccgcca   1440
tggccgcaac tttgtgagct ccgtgttca ggaggcccctt cgtgtggctc gcacccacca   1500
tgccaaccat gcactcccag tctacgtctt cacacgaccc acctacagcc gcaggctcac   1560
ggggcttagt gagatggacc tcatctctac cattggcgag agtgcggccc tgggcgcagc   1620
tggtgtcatc ctctggggtg acgcggggta caccacaagc acggagacct gccagtacct   1680
caaagattac ctgacacggc tgctggtccc ctacgtggtc aatgtgtcct gggccaccca   1740
atattgcagc cgggcccagt gccatggcca tgggcgctgt gtgcgccgca accccagtgc   1800
cagtaccttc ctgcatctca gcaccaacag tttccgccta gtgcctggcc atgcacctgg   1860
tgaaccccag ctgcgacctg tgggggagct cagttgggcc gacattgacc acctgcagac   1920
acacttccgc tgccagtgct acttgggctg gagtggtgag caatgccagt gggaccatag   1980
gcaggcagct ggaggtgcca gcgaggcctg ggctgggtcc cacctcacca gtctgctggc   2040
tctggcagcc ctggccttta cctggacctt gtaggggtct cctgcctagc tgcctagcaa   2100
gctggcctct accacaaggg ctctcttagg catgtaggac cctgcagggg gtggacaaac   2160
tggagtctgg agtgggcaga gccccaggaa agcccaggag ggcatccata ccagctcgca   2220
cccccctgtt ctaagggggga ggggaagtcc ctgggaggcc ccttctctcc ctgccagagg   2280
ggaaggaggg tacagctggg ctggggagga cctgacccta ctcccttgcc ctagatagtt   2340
tattattatt attattttgg ggtctctttt gtaaattaaa cataaaacaa ttgcttctct   2400
gcttggattt tgt                                                     2413
```

<210> SEQ ID NO 16
<211> LENGTH: 473
<212> TYPE: PRT
<213> ORGANISM: Homo sapiens

```
<400> SEQUENCE: 16

Met Arg Ala Gly Pro Gly Pro Thr Val Thr Leu Ala Leu Val Leu Ala
1               5                   10                  15

Val Ser Trp Ala Met Glu Leu Lys Pro Thr Ala Pro Pro Ile Phe Thr
            20                  25                  30

Gly Arg Pro Phe Val Val Ala Trp Asp Val Pro Thr Gln Asp Cys Gly
        35                  40                  45

Pro Arg Leu Lys Val Pro Leu Asp Leu Asn Ala Phe Asp Val Gln Ala
    50                  55                  60

Ser Pro Asn Glu Gly Phe Val Asn Gln Asn Ile Thr Ile Phe Tyr Arg
65                  70                  75                  80

Asp Arg Leu Gly Leu Tyr Pro Arg Phe Asp Ser Ala Gly Arg Ser Val
                85                  90                  95

His Gly Gly Val Pro Gln Asn Val Ser Leu Trp Ala His Arg Lys Met
            100                 105                 110

Leu Gln Lys Arg Val Glu His Tyr Ile Arg Thr Gln Glu Ser Ala Gly
        115                 120                 125

Leu Ala Val Ile Asp Trp Glu Asp Trp Arg Pro Val Trp Val Arg Asn
    130                 135                 140

Trp Gln Asp Lys Asp Val Tyr Arg Arg Leu Ser Arg Gln Leu Val Ala
145                 150                 155                 160

Ser Arg His Pro Asp Trp Pro Pro Asp Arg Ile Val Lys Gln Ala Gln
                165                 170                 175

Tyr Glu Phe Glu Phe Ala Ala Gln Gln Phe Met Leu Glu Thr Leu Arg
            180                 185                 190

Tyr Val Lys Ala Val Arg Pro Arg His Leu Trp Gly Phe Tyr Leu Phe
        195                 200                 205

Pro Asp Cys Tyr Asn His Asp Tyr Val Gln Asn Trp Glu Ser Tyr Thr
    210                 215                 220

Gly Arg Cys Pro Asp Val Glu Val Ala Arg Asn Asp Gln Leu Ala Trp
225                 230                 235                 240

Leu Trp Ala Glu Ser Thr Ala Leu Phe Pro Ser Val Tyr Leu Asp Glu
                245                 250                 255

Thr Leu Ala Ser Ser Arg His Gly Arg Asn Phe Val Ser Phe Arg Val
            260                 265                 270

Gln Glu Ala Leu Arg Val Ala Arg Thr His His Ala Asn His Ala Leu
        275                 280                 285

Pro Val Tyr Val Phe Thr Arg Pro Thr Tyr Ser Arg Arg Leu Thr Gly
    290                 295                 300

Leu Ser Glu Met Asp Leu Ile Ser Thr Ile Gly Glu Ser Ala Ala Leu
305                 310                 315                 320

Gly Ala Ala Gly Val Ile Leu Trp Gly Asp Ala Gly Tyr Thr Thr Ser
                325                 330                 335

Thr Glu Thr Cys Gln Tyr Leu Lys Asp Tyr Leu Thr Arg Leu Leu Val
            340                 345                 350

Pro Tyr Val Val Asn Val Ser Trp Ala Thr Gln Tyr Cys Ser Arg Ala
        355                 360                 365

Gln Cys His Gly His Gly Arg Cys Val Arg Arg Asn Pro Ser Ala Ser
    370                 375                 380

Thr Phe Leu His Leu Ser Thr Asn Ser Phe Arg Leu Val Pro Gly His
385                 390                 395                 400

Ala Pro Gly Glu Pro Gln Leu Arg Pro Val Gly Glu Leu Ser Trp Ala
                405                 410                 415
```

```
Asp Ile Asp His Leu Gln Thr His Phe Arg Cys Gln Cys Tyr Leu Gly
            420                 425                 430

Trp Ser Gly Glu Gln Cys Gln Trp Asp His Arg Gln Ala Ala Gly Gly
        435                 440                 445

Ala Ser Glu Ala Trp Ala Gly Ser His Leu Thr Ser Leu Leu Ala Leu
450                 455                 460

Ala Ala Leu Ala Phe Thr Trp Thr Leu
465                 470

<210> SEQ ID NO 17
<211> LENGTH: 473
<212> TYPE: PRT
<213> ORGANISM: Homo sapiens

<400> SEQUENCE: 17

Met Arg Ala Gly Pro Gly Pro Thr Val Thr Leu Ala Leu Val Leu Ala
1               5                   10                  15

Val Ser Trp Ala Met Glu Leu Lys Pro Thr Ala Pro Pro Ile Phe Thr
            20                  25                  30

Gly Arg Pro Phe Val Val Ala Trp Asp Val Pro Thr Gln Asp Cys Gly
        35                  40                  45

Pro Arg Leu Lys Val Pro Leu Asp Leu Asn Ala Phe Asp Val Gln Ala
    50                  55                  60

Ser Pro Asn Glu Gly Phe Val Asn Gln Asn Ile Thr Ile Phe Tyr Arg
65                  70                  75                  80

Asp Arg Leu Gly Leu Tyr Pro Arg Phe Asp Ser Ala Gly Arg Ser Val
                85                  90                  95

His Gly Gly Val Pro Gln Asn Val Ser Leu Trp Ala His Arg Lys Met
            100                 105                 110

Leu Gln Lys Arg Val Glu His Tyr Ile Arg Thr Gln Glu Ser Ala Gly
        115                 120                 125

Leu Ala Val Ile Asp Trp Glu Asp Trp Arg Pro Val Trp Val Arg Asn
    130                 135                 140

Trp Gln Asp Lys Asp Val Tyr Arg Arg Leu Ser Arg Gln Leu Val Ala
145                 150                 155                 160

Ser Arg His Pro Asp Trp Pro Pro Asp Arg Ile Val Lys Gln Ala Gln
                165                 170                 175

Tyr Glu Phe Glu Phe Ala Ala Gln Gln Phe Met Leu Glu Thr Leu Arg
            180                 185                 190

Tyr Val Lys Ala Val Arg Pro Arg His Leu Trp Gly Phe Tyr Leu Phe
        195                 200                 205

Pro Asp Cys Tyr Asn His Asp Tyr Val Gln Asn Trp Glu Ser Tyr Thr
    210                 215                 220

Gly Arg Cys Pro Asp Val Glu Val Ala Arg Asn Asp Gln Leu Ala Trp
225                 230                 235                 240

Leu Trp Ala Glu Ser Thr Ala Leu Phe Pro Ser Val Tyr Leu Asp Glu
                245                 250                 255

Thr Leu Ala Ser Ser Arg His Gly Arg Asn Phe Val Ser Phe Arg Val
            260                 265                 270

Gln Glu Ala Leu Arg Val Ala Arg Thr His His Ala Asn His Ala Leu
        275                 280                 285

Pro Val Tyr Val Phe Thr Arg Pro Thr Tyr Ser Arg Arg Leu Thr Gly
    290                 295                 300

Leu Ser Glu Met Asp Leu Ile Ser Thr Ile Gly Glu Ser Ala Ala Leu
305                 310                 315                 320
```

Gly Ala Ala Gly Val Ile Leu Trp Gly Asp Ala Gly Tyr Thr Thr Ser
                325                 330                 335

Thr Glu Thr Cys Gln Tyr Leu Lys Asp Tyr Leu Thr Arg Leu Leu Val
            340                 345                 350

Pro Tyr Val Val Asn Val Ser Trp Ala Thr Gln Tyr Cys Ser Arg Ala
        355                 360                 365

Gln Cys His Gly His Gly Arg Cys Val Arg Arg Asn Pro Ser Ala Ser
    370                 375                 380

Thr Phe Leu His Leu Ser Thr Asn Ser Phe Arg Leu Val Pro Gly His
385                 390                 395                 400

Ala Pro Gly Glu Pro Gln Leu Arg Pro Val Gly Glu Leu Ser Trp Ala
                405                 410                 415

Asp Ile Asp His Leu Gln Thr His Phe Arg Cys Gln Cys Tyr Leu Gly
            420                 425                 430

Trp Ser Gly Glu Gln Cys Gln Trp Asp His Arg Gln Ala Ala Gly Gly
        435                 440                 445

Ala Ser Glu Ala Trp Ala Gly Ser His Leu Thr Ser Leu Leu Ala Leu
    450                 455                 460

Ala Ala Leu Ala Phe Thr Trp Thr Leu
465                 470

<210> SEQ ID NO 18
<211> LENGTH: 3868
<212> TYPE: DNA
<213> ORGANISM: Homo sapiens

<400> SEQUENCE: 18
gtgggggctc gaggcgcctc cgcggccgtg gacgagcgtc cgtgcggcct ggtccgggcc      60
atgtccgcgt gaggaccccg ccgctgtcgc cgctcccgtt ccggccctgg cccctctgcc     120
cggcagcgcc gcgcaccatg gctccattc tcagccgccg catcgcgggg gtggaggaca     180
tcgacatcca ggcgaactcg gcctatcgct accctccgaa gtccggaaac tactttgctt     240
cgcacttttt catgggagga gagaaattcg acaccccca ccctgaaggt tacctctttg     300
gagagaacat ggatctgaac ttcctgggca gccgccggt ccagtttccc tacgtcactc     360
ctgcccccca cgagcccgtg aagacgctgc ggagcctggt gaacatccgc aaagactccc     420
tgcggctggt gaggtacaaa gacgatgccg acagccccac cgaggacggc gacaagcccc     480
gggtgctcta cagcctggag ttcaccttcg acgccgatgc ccgcgtggcc atcaccatct     540
actgccaggc atcggaggag ttcctgaacg gcagggcagt atacagcccc aagagcccct     600
cgctacagtc cgagaccgtc cactacaaga gaggggtgag ccagcagttc tccctgccct     660
ccttcaagat tgacttctcg gaatggaagg atgacgagct gaactttgac ctggaccggg     720
gcgtgtttcc agtagtcatc caggctgtgg tggacgaagg agatgtggtg gaagtgactg     780
gccacgccca cgtgctcttg gctgcctttg aaaagcacat ggacggcagc ttctctgtga     840
agccttttaaa gcagaagcaa attgtggacc gggtcagcta cctcctgcag agatctatg     900
gcattgagaa caagaacaac caggagacca gccctcggc cgacgagaac agcgacaaca     960
gcaacgagtg tgtggtgtgc ctgtccgacc tgcgggacac gctgatcctg ccctgccgcc    1020
acctgtgcct ctgtacctcc tgcgccgaca cgctgcgcta ccaggccaac aactgcccca    1080
tctgccggct gctttccgg gcctcctgc agatccgggc ggtgcggaag aagccaggag    1140
ccctgtcccc cgtgtcctt cagcccgtcc tggcccagag cctggagcat gatgagcact    1200
ctaactctga cagcgtccca cctggctacg agcccatctc gctgctcgag gcgctcaacg    1260

```
gcctccgggc tgtctccccg gccatcccct cggcccctct ttatgaagaa atcacctatt    1320
caggcatctc ggacggcctg tcccaggcca gctgtcccct cgcggctatc gaccacatcc    1380
tggacagcag ccgccagaag ggcaggccgc agagcaaggc ccccgacagc accctacggt    1440
ccccgtcttc ccccatccac gaagaggatg aggagaagct ctccgaggac gtggacgccc    1500
ctcccccact gggtggcgca gagctggccc tgcgggaaag cagctcccct gagagtttca    1560
taacagaaga ggttgatgag tcgtcgtcac cacagcaagg gacccgagca gcttccattg    1620
agaatgtcct gcaggacagc agccccgagc actgtggccg aggcccacct gctgacatct    1680
acctgccagg acggcccacc tccatggaga cggcccacgg cctcgccacc accagcccca    1740
cctggcctcc acttggtggc cccagccccg atcccagcgc cgccgagctg accccactct    1800
gagagcctgg ccgagctggc agcatggagc cctcggctcc ccagactttg ccgaggggct    1860
gctccggacc ccgttgtgag ccggcctcct gtctgcatgc cccctgtggc caccaggctc    1920
cgaggggccg tggtgactct tgatcaaaga gcacagtgaa ctgtcccttc tgagtctccc    1980
ttttctacag ttgatatatt tgtaactggt acaagatgaa ggacacagc tttccatccc    2040
tagttcagag cccccgttcc ccagggtcct gtgggctgag cggctggggc tggggctgcc    2100
cacgtgtggc ctccgctggc tctgcctgct cctgcaacag tgcggtccct gcccggagaa    2160
ctcaggaggc ctgcagaaga gaactgattg gtggtcgaag caccatcttc acagatgttc    2220
aggggcagtg gggggctcca ggcacggtca atgaaggaaa cagtgcctgt ccacccaccc    2280
tgcgtgtcac tgtggcggcc tggctgtcgc tgcttttttgt cctctgccgt gtttgcgcgg    2340
cctcagtgcc ctccctggtg cgtctgcgct ggggccctca gtgctcgggg ccttggggtg    2400
catgggtgcc gccctgggca gctagagtgt ctcagcccgg tgctgggcct ggccgagggg    2460
cggaggcaca gctgcttcca gcagccagca ttcagtggcc ttgtcaccaa gctccacacc    2520
tcctcctggt gctggctttg gtgacatcac aaggcccctc caggtgcagg ggcttctgtt    2580
tggcaggccc ctgccaggga ggacctggtg gcctcctcat tctcttttgc cattggaatg    2640
tccccttgca gttctcttct ctttttttttt tttttgaga tggagtttca ctcttgctgc    2700
ccaggctgga gtgcagtggc tcaatctcgg gtcactgcaa cctccgcctc ccgggttcaa    2760
gtgatcgtcc tgccttaggc tcctgagtag ctggggatta caggtgccta ccagcatgct    2820
cggctaattt ttttgtattt ttagtagaga agggatttca ccatgttggc cgggctggtc    2880
tcaaactcct aaggtcatcc acctgcctcg gcctcccaga gtgctgagat tacaggcgtg    2940
agcctccgcg cccggccccc ttgcagttct ctctgatttg gtttgttctg tctcaggctt    3000
ctgtggcagg actggcccag ggaggaggaa gccagcagca cacctgggga atgggtccc    3060
ggccgggagg cttggcctct gggcgacctc gtcctgtttt ttttgtttgt ttgtttgttt    3120
ttttaaaggt aaacctcctg ggccgcagat ggcaaaggga gtgcctgggc ctggtgaccc    3180
agggctggat ccaccccgtgc ggagccctgg gccaggcagg tgtctgctgc tcacctggct    3240
ctggagggct gccctgcagc tgggcctggg gacaggtcgg ctgtggggca gctcagtacc    3300
ctccctgagg ctcacggtgg ctccgagcat gaggtccgcc tcctgggcga gacccagcag    3360
tggacagcat ggtcctcaca cccagctccc tgcacaccca ggccagccac ccctcccgct    3420
cgtgcacagg cacgcagatg cgctcacacg tacacacaca caaatgcacg cccacttgca    3480
catgctcacg cacatgttca cacatgcaca ctcacgctca cacatgctgt cacgcataca    3540
cacacgcaca tactcctgca catgttccca tgcatgtgtg tgcactcgga ccgagcatct    3600
cccacgcacc tctaccccac cccaagcacc tctctccccc catgcacctc tccccaacaa    3660
```

| | |
|---|---|
| cacacacagc cccctgcacc gcccgccccc cgccccacc aaggcccag cctctggcca | 3720 |
| tcagtcctgg tgccagagct ttgcgtgaag ttcgggccgc agagtgggcc gctgggactc | 3780 |
| ccatgtgctg ccgtctgatg tgctcagatg ggctcatcgt tggttcgttt ttactgtata | 3840 |
| tttatagtaa taaaatcatg cagcaata | 3868 |

<210> SEQ ID NO 19
<211> LENGTH: 6471
<212> TYPE: DNA
<213> ORGANISM: Homo sapiens

<400> SEQUENCE: 19

| | |
|---|---|
| gtgggggctc gaggcgcctc cgcggccgtg gacgagcgtc cgtgcggcct ggtccgggcc | 60 |
| atgtccgcgt gaggacccct ccgctgtcgc cgctcccgtt ccggccctgg cccctctgcc | 120 |
| cggcagcgcc gcgcaccatg ggctccattc tcagccgccg catcgcgggg gtggaggaca | 180 |
| tcgacatcca ggcgaactcg gcctatcgct accctccgaa gtccggaaac tactttgctt | 240 |
| cgcactttt catgggagga gagaaattcg acaccccca ccctgaaggt tacctctttg | 300 |
| gagagaacat ggatctgaac ttcctgggca gccgcccggt ccagtttccc tacgtcactc | 360 |
| ctgccccca cgagccgtg aagacgctgc ggagcctggt gaacatccgc aaagactccc | 420 |
| tgcggctggt gaggtacaaa gacgatgccg acagccccac cgaggacggc gacaagcccc | 480 |
| gggtgctcta cagcctggag ttcaccttcg acgccgatgc ccgcgtggcc atcaccatct | 540 |
| actgccaggc atcggaggag ttcctgaacg gcagggcagt atacagcccc aagagcccct | 600 |
| cgctacagtc cgagaccgtc cactacaaga gaggggtgag ccagcagttc tccctgccct | 660 |
| ccttcaagat tgacttctcg gaatggaagg atgacgagct gaactttgac ctggaccggg | 720 |
| gcgtgtttcc agtagtcatc caggctgtgg tggacgaagg agatgtggtg gaagtgactg | 780 |
| gccacgccca cgtgctcttg gctgccttg aaaagcacat ggacggcagc ttctctgtga | 840 |
| agcctttaaa gcagaagcaa attgtggacc gggtcagcta cctcctgcag agatctatg | 900 |
| gcattgagaa caagaacaac caggagacca agccctcgga cgacgagaac agcgacaaca | 960 |
| gcaacgagtg tgtggtgtgc ctgtccgacc tgcgggacac gctgatcctg ccctgccgcc | 1020 |
| acctgtgcct ctgtacctcc tgccgccgaca cgctgcgcta ccaggccaac aactgcccca | 1080 |
| tctgccggct gcctttccgg gccctcctgc agatccgggc ggtgcggaag aagccaggag | 1140 |
| ccctgtcccc cgtgtccttc agccccgtcc tggcccagag cctggagcat gatgagcact | 1200 |
| cttgtccctt taaaaaatca agccgcacc ccgcctccct ggccagcaag aaacctaaaa | 1260 |
| gggaaacaaa ctctgacagc gtcccacctg gctacgagcc catctcgctg ctcgaggcgc | 1320 |
| tcaacgccct ccgggctgtc tccccggcca tccctcggc ccctctttat gaagaaatca | 1380 |
| cctattcagg catctcggac ggcctgtccc aggccagctg tcccctcgcg gctatcgacc | 1440 |
| acatcctgga cagcagccgc cagaagggca ggccgcagag caaggccccc gacagcaccc | 1500 |
| tacggtcccc gtcttccccc atccacgaag aggatgagga gaagctctcc gaggacgtgg | 1560 |
| acgcccctcc cccactgggt ggcgcagagc tggccctgcg ggaaagcagc tcccctgaga | 1620 |
| gtttcataac agaagaggtt gatgagtcgt cgtcaccaca gcaagggacc cgagcagctt | 1680 |
| ccattgagaa tgtcctgcag acagcagcc ccgagcactg tggccgaggc ccacctgctg | 1740 |
| acatctacct gccagccctg gggcccgact cctgctctgt tggtatagac gagtaagccg | 1800 |
| gtacgtgacc tccagacgc gcttcggggg ctctgacgcg cgtccttgga gagaggagcc | 1860 |
| ctccccctgct ctctggcggg ggttccttct ggttttttggg tcttcgtccg catccgcatc | 1920 |

```
ttcccagggg ccctggattc cgaatccaga gctctccagt ggctgctgca ccttcccca    1980
gaaagtggcc tcctgggggg tcctgacttt cggggccaga ggtctctcca tctggactag    2040
gcggccggtc aggctcttct tccagccttg aggggccctg aacagtccc agcccaggca     2100
gggagacaga cacagcccag gtgcgccaga gccactgtcc actgcgggag gcaggagctt    2160
gagggatgag ggcagcaccg tggagggaac cccagggaga catgggtga gcgtcccaag     2220
gggagaggcc tgggcctggc cttgttccgg atggtccac catgagttcg catcggtcct     2280
gcagcagaca cgttaggacg ctcagcaggt ccactcccgt gttccggtcg tggctttaac    2340
aattcatggg gaaagaatgc gccccgattg ggagagcccc tggatcacgt cttcccaagc    2400
tcagtccctg tctcttggag ggagtccgtc ctcgagggc cctctggtgc caggggaga     2460
gtatcttgcg tcctgtcctg agggcgtccg ctcacacagc cacctgctcc cccgctccct    2520
ccttcccttg tcagcatggc caccgtgggc ctggcatcac catgggcctg gcacacagtc    2580
cctcgtgggc tgcctttgtg ccatgagccc actgctgccg actcacctgt ccctcccagt    2640
actggaacct tctggaacac cagcactaaa agataggagg ccctgtgagg ttggcatccc    2700
ccatccccc caagaggcgc cctctaccag ggtggcccag gtgagtgttt tacagaaggc     2760
ggctctgtcc aggcagtggt tcgcacctat aagcccggta ctttgggaga ccgaggggat    2820
agatcacttg agcccaggaa ttcaagatca gtgtagaaaa catagacccc ctctctatga    2880
aaaataaaaa attggcttgg gcgtggtagc ttgtgcctgt ggtcccagct actcaggggt    2940
gctgaggtgg gaggattgcc ggagctgggg aggtcaaggc ccactccagc ctgagacgct    3000
gtctcaataa aaaaaaatac acacacaccc acccacccac tccagcctga ccctgtct     3060
caagaaaaaa aaatacaca cacacacaca cacacacaca cacacggggg agagagagaa     3120
ggcagctcca ggagtgccac caaaatgtag gcagacggat tggggaccct ctgccttccc    3180
agagggtctt ggcacacaag ctgcgtgcag ctctggtctg ccgaggccca tgcagcctgc    3240
tgggaggtgc ctggccgggg gtgcaggctc taagaggccc tttcccttg ggtgacttg     3300
agccgggtca gggagaactt cgcttctttt gactgcgctc tgcattccca tgaacctctg    3360
tcttcttgag cccagcgagt ccctctgttg accctgtcc tgagccatta taccctaga     3420
ttgaaacagt cagcaccttt cagacggccc cggcctgcgc atcggtggaa ggtgccgtgc    3480
gaatgtcacg attcaggtca agcttccgga gctggggagt gcaggtgtga tctagaacag    3540
ggctcacagc ctcggaaacc tgctctcgcc gcggcccccg aagaaaatag acgcccttca    3600
ccggagagtg gggcctgggc cgtgtctgct gggagccatg tgtcagggct ggtggctggg    3660
tgtcaggcag ccctgaggcc atgctggccc cgtcccaggc tctgcaccag caccattgcc    3720
caagccccag ggacgccaga cccatctggg gacagcgccc ggcggcgtcg tgcaggccac    3780
agtctgggca ttggggctct gtgggaggct cctctctttg ccttgcagta gccatccggg    3840
ggctactctg agcacgggct tgttctcacc cagggccgct ccccaccct gcaccctggg     3900
ttgaccgagt ccaccctaa cccagccgta agaaccttgg caggacagtg gctggccaca    3960
tcccaggaaa ccggaaccag ggcaagggca ggaggcccag agggcatcca ccgcggtgcc    4020
gtgtcgcgct ctgactcggg gctgcagatc tgctgtgggt gtccgggat ctgggatcgt     4080
ctgtcccaag agggacacag cgtatttggc acagttaggg agtccccggg cccttggtgt    4140
gctcacatct gagtgaatgc tgttgtggcc acaggcggcg ggagtggggg tgctggatgg    4200
cccagccccct ctgggctcc agatcggtag gagcgggtgg cgtggcacca ggcatccgag    4260
tgtgaccctc ctccctctgc tcccacctgc aggacggccc acctccatgg agacggccca    4320
```

```
cggcctcgcc accaccagcc ccacctggcc tccacttggt ggccccagcc ccgatcccag    4380
cgccgccgag ctgaccccac tctgagagcc tggccgagct ggcagcatgg agccctcggc    4440
tccccagact ttgccgaggg gctgctccgg accccgttgt gagccggcct cctgtctgca    4500
tgccccctgt ggccaccagg ctccgagggg ccgtggtgac tcttgatcaa agagcacagt    4560
gaactgtccc ttctgagtct ccctttctca cagttgatat atttgtaact ggtacaagat    4620
gaaggacagc agctttccat ccctagttca gagccccgt tccccagggt cctgtgggct    4680
gagcggctgg ggctggggct gcccacgtgt ggcctccgct ggctctgcct gctcctgcaa    4740
cagtgcggtc cctgcccgga gaactcagga ggcctgcaga agagaactga ttggtggtcg    4800
aagcaccatc ttcacagatg ttcaggggca gtgggggggct ccaggcacgg tcaatgaagg    4860
aaacagtgcc tgtccaccca ccctgcgtgt cactgtggcg gcctggctgt cgctgctttt    4920
tgtcctctgc cgtgtttgcg cggcctcagt gccctcctg gtgcgtctgc gctggggccc    4980
tcagtgctcg ggccttggg gtgcatgggt gccgccctgg gcagctagag tgtctcagcc    5040
cggtgctggg cctggccgag gggcggaggc acagctgctt ccagcagcca gcattcagtg    5100
gccttgtcac caagctccac acctcctcct ggtgctggct ttggtgacat cacaaggccc    5160
ctccaggtgc aggggcttct gtttggcagg cccctgccag ggaggacctg gtggcctcct    5220
cattctcttt tgccattgga atgtcccctt gcagttctct tctcttttt ttttttttg     5280 agatggagtt tcactcttgc tgcccaggct ggagtgcagt ggctcaatct cgggtcactg    5340
caacctccgc ctcccgggtt caagtgatcg tcctgcctta ggctcctgag tagctgggga    5400
ttacaggtgc ctaccagcat gctcggctaa tttttttgta tttttagtag agaagggatt    5460
tcaccatgtt ggccgggctg gtctcaaact cctaaggtca tccacctgcc tcggcctccc    5520
agagtgctga gattacaggc gtgagcctcc gcgcccggcc ccttgcagt tctctctgat    5580 ttggtttgtt ctgtctcagg cttctgtggc aggactggcc cagggaggag gaagccagca    5640
gcacacctgg ggaatggggt cccggccggg aggcttggcc tctgggcgac ctcgtcctgt    5700
tttttttgtt tgtttgtttg ttttttaaa ggtaaacctc ctgggccgca gatggcaaag    5760
ggagtgcctg ggcctggtga cccagggctg gatccacccc tgcggagccc tgggccaggc    5820
aggtgtctgc tgctcacctg gctctggagg gctgccctgc agctgggcct ggggacaggt    5880
cggctgtggg gcagctcagt accctccctg aggctcacgg tggctccgag catgaggtcc    5940
gcctcctggg cgagacccag cagtggacag catggtcctc acacccagct ccctgcacac    6000
ccaggccagc caccctccc gctcgtgcac aggcacgcag atgcgctcac acgtacacac    6060
acacaaatgc acgcccactt gcacatgctc acgcacatgt tcacacatgc acactcacgc    6120
tcacacatgc tgtcacgcat acacacacgc acatactcct gcacatgttc ccatgcatgt    6180
gtgtgcactc ggaccgagca tctcccacgc acctctaccc cacccaagc acctctctcc     6240 ccccatgcac ctctccccaa caacacacac agccccctgc accgcccgcc cccgccccc     6300 accaaggccc cagcctctgg ccatcagtcc tggtgccaga gctttgcgtg aagttcgggc    6360
cgcagagtgg cccgctggga ctcccatgtg ctgccgtctg atgtgctcag atgggctcat    6420
cgttggttcg tttttactgt atatttatag taataaaatc atgcagcaat a             6471

<210> SEQ ID NO 20
<211> LENGTH: 6405
<212> TYPE: DNA
<213> ORGANISM: Homo sapiens
```

<400> SEQUENCE: 20

```
gtggggctc gaggcgcctc cgcggccgtg gacgagcgtc cgtgcggcct ggtccgggcc      60
atgtccgcgt gaggaccccg ccgctgtcgc cgctcccgtt ccggccctgg cccctctgcc     120
cggcagcgcc gcgcaccatg ggctccattc tcagccgccg catcgcgggg gtggaggaca     180
tcgacatcca ggcgaactcg gcctatcgct accctccgaa gtccggaaac tactttgctt     240
cgcactttt catgggagga gagaaattcg acaccccca ccctgaaggt tacctctttg     300
gagagaacat ggatctgaac ttcctgggca gccgcccggt ccagtttccc tacgtcactc     360
ctgccccca cgagcccgtg aagacgctgc ggagcctggt gaacatccgc aaagactccc     420
tgcggctggt gaggtacaaa gacgatgccg acagccccac cgaggacggc gacaagcccc     480
gggtgctcta cagcctggag ttcaccttcg acgccgatgc ccgcgtggcc atcaccatct     540
actgccaggc atcggaggag ttcctgaacg gcagggcagt atacagcccc aagagcccct     600
cgctacagtc cgagaccgtc cactacaaga gaggggtgag ccagcagttc tccctgccct     660
ccttcaagat tgacttctcg gaatggaagg atgacgagct gaactttgac ctggaccggg     720
gcgtgttcc agtagtcatc caggctgtgg tggacgaagg agatgtggtg gaagtgactg     780
gccacgccca cgtgctcttg gctgcctttg aaaagcacat ggacggcagc ttctctgtga     840
agcctttaaa gcagaagcaa attgtggacc gggtcagcta cctcctgcag gagatctatg     900
gcattgagaa caagaacaac caggagacca agccctcgga cgacgagaac agcgacaaca     960
gcaacgagtg tgtggtgtgc ctgtccgacc tgcgggacac gctgatcctg ccctgccgcc    1020
acctgtgcct ctgtacctcc tgcgccgaca cgctgcgcta ccaggccaac aactgcccca    1080
tctgccggct gccttccgg gccctcctgc agatccgggc ggtgcggaag aagccaggag    1140
ccctgtcccc cgtgtccttc agcccgtcc tggcccagag cctggagcat gatgagcact    1200
ctaactctga cagcgtccca cctggctacg agcccatctc gctgctcgag gcgctcaacg    1260
gcctccgggc tgtctccccg gccatcccct cggcccctct ttatgaagaa atcacctatt    1320
caggcatctc ggacggcctg tcccaggcca gctgtcccct cgcggctatc gaccacatcc    1380
tggacagcag ccgccagaag ggcaggccgc agagcaaggc ccccgacagc accctacggt    1440
ccccgtcttc ccccatccac gaagaggatg aggagaagct ctccgaggac gtggacgccc    1500
ctccccact gggtggcgca gagctggccc tgcgggaaag cagctcccct gagagtttca    1560
taacagaaga ggttgatgag tcgtcgtcac cacagcaagg gacccgagca gcttccattg    1620
agaatgtcct gcaggacagc agccccgagc actgtggccg aggccacct gctgacatct    1680
acctgccagc cctggggccc gactcctgct ctgttggtat agacgagtaa gccggtacgt    1740
gacctcccag acgcgcttcg ggggctctga cgcgcgtcct tggagagagg agccctcccc    1800
tgctctctgg cgggggttcc ttctggtttt tgggtcttcg tccgcatccg catcttccca    1860
ggggccctgg attccgaatc cagagctctc cagtggctgc tgcaccttcc cccagaaagt    1920
ggcctcctgg ggggtcctga cttcgggc cagaggtctc tccatctgga ctaggcggcc    1980
ggtcaggctc ttcttccagc cttgaggggc cctggaacag tcccagccca ggcagggaga    2040
cagacacagc ccaggtgcgc cagagccact gtccactgcg ggaggcagga gcttgaggga    2100
tgagggcagc accgtggagg gaaccccagg gagacatggg gtgagcgtcc caaggggaga    2160
ggcctgggc tggccttgtt ccggatggtc ccaccatgag ttcgcatcgg tcctgcagca    2220
gacacgttag gacgctcagc aggtccactc ccgtgttccg gtcgtggctt taacaattca    2280
tggggaaaga atgcgccccg attgggagag ccctggatc acgtcttccc aagctcagtc    2340
```

-continued

```
cctgtctctt ggagggagtc cgtcctcgag gggccctctg gtgcccaggg gagagtatct    2400
tgcgtcctgt cctgagggcg tccgctcaca cagccacctg ctccccgct ccctccttcc     2460 cttgtcagca tggccaccgt gggcctggca tcaccatggg cctggcacac agtccctcgt    2520
gggctgcctt tgtgccatga gcccactgct gccgactcac ctgtccctcc cagtactgga    2580
accttctgga acaccagcac taaaagatag gaggccctgt gaggttggca tcccccatcc    2640 ccccaagag cgccctcta ccagggtggc ccaggtgagt gttttacaga aggcggctct      2700
gtccaggcag tggttcgcac ctataagccc ggtactttgg gagaccgagg ggatagatca    2760
cttgagccca ggaattcaag atcagtgtag aaaacataga cccctctct atgaaaata     2820 aaaaattggc ttgggcgtgg tagcttgtgc ctgtggtccc agctactcag gggtgctgag    2880
gtgggaggat tgccggagct ggggaggtca aggcccactc cagcctgaga cgctgtctca    2940
ataaaaaaaa atacacacac ccccacccac ccactccagc ctgagaccct gtctcaagaa    3000 aaaaaaata cacacacaca cacacacaca cacacacg ggggagagag agaaggcagc     3060
tccaggagtg ccaccaaaat gtaggcagac ggattgggga ccctctgcct tcccagaggg    3120
tcttggcaca caagctgcgt gcagctctgg tctgccgagg cccatgcagc ctgctgggag    3180
gtgcctggcc gggggtgcag gctctaagag gccctttccc cttgggtgga cttgagccgg    3240
gtcagggaga acttcgcttc ttttgactgc gctctgcatt cccatgaacc tctgtcttct    3300
tgagcccagc gagtccctct gttgacccct gtcctgagcc attataccccc tagattgaaa    3360 cagtcagcac ctttcagacg gccccggcct gcgcatcggt ggaaggtgcc gtgcgaatgt    3420
cacgattcag gtcaagcttc cggagctggg gagtgcaggt gtgatctaga acagggctca    3480
cagcctcgga aacctgctct cgccgcggcc cccgaagaaa atagacgccc ttcaccggag    3540 agtgggggcct gggccgtgtc tgctgggagc catgtgtcag gctggtggc tgggtgtcag    3600 gcagccctga ggccatgctg gccccgtccc aggctctgca ccagcaccat gcccaagcc    3660 ccagggacgc cagacccatc tggggacagc gcccggcggc gtcgtgcagg ccacagtctg    3720
ggcattgggg ctctgtggga ggctcctctc tttgccttgc agtagccatc cgggggctac    3780
tctgagcacg gccttgttct cacccagggc cgctccccac ccctgcaccc tgggttgacc    3840
gagttccacc ctaacccagc cgtaagaacc ttggcaggac agtggctggc cacatcccag    3900
gaaaccggaa ccagggcaag ggcaggaggc ccagagggca tccaccgcgg tgccgtgtcg    3960
cgctctgact cggggctgca gatctgctgt gggtgtccgg ggatctggga tcgtctgtcc    4020
caagagggac acagcgtatt tggcacagtt agggagtccc cgggcccttg gtgtgctcac    4080
atctgagtga atgctgttgt ggccacaggc ggcgggagtg ggggtgctgg atggcccagc    4140
ccctctgggg ctccagatcg gtaggagcgg gtggcgtggc accaggcatc cgagtgtgac    4200
cctcctccct ctgctcccac ctgcaggacg gcccacctcc atggagacgg cccacggcct    4260
cgccaccacc agccccacct ggcctccact tggtggcccc agcccgatc ccagcgccgc     4320 cgagctgacc ccactctgag agcctggccg agctggcagc atggagccct cggctcccca    4380
gactttgccg aggggctgct ccggaccccg ttgtgagccg gcctcctgtc tgcatgcccc    4440
ctgtggccac caggctccga ggggccgtgg tgactcttga tcaaagagca cagtgaactg    4500
tcccttctga gtctccctt tctacagttg atatatttgt aactggtaca agatgaagga    4560
cagcagcttt ccatccctag ttcagagccc ccgttcccca gggtcctgtg ggctgagcgg    4620
ctggggctgg ggctgcccac gtgtggcctc cgctggctct gcctgctcct gcaacagtgc    4680
```

| | |
|---|---|
| ggtccctgcc cggagaactc aggaggcctg cagaagagaa ctgattggtg gtcgaagcac | 4740 |
| catcttcaca gatgttcagg ggcagtgggg ggctccaggc acggtcaatg aaggaaacag | 4800 |
| tgcctgtcca cccaccctgc gtgtcactgt ggcggcctgg ctgtcgctgc tttttgtcct | 4860 |
| ctgccgtgtt tgcgcggcct cagtgccctc cctggtgcgt ctgcgctggg ccctcagtg | 4920 |
| ctcggggcct tggggtgcat gggtgccgcc ctgggcagct agagtgtctc agcccggtgc | 4980 |
| tgggcctggc cgaggggcgg aggcacagct gcttccagca gccagcattc agtggccttg | 5040 |
| tcaccaagct ccacacctcc tcctggtgct ggctttggtg acatcacaag gcccctccag | 5100 |
| gtgcagggg ttctgtttgg caggcccctg ccagggagga cctggtggcc tcctcattct | 5160 |
| cttttgccat tggaatgtcc ccttgcagtt ctcttctctt tttttttttt tttgagatgg | 5220 |
| agtttcactc ttgctgccca ggctggagtg cagtggctca atctcgggtc actgcaacct | 5280 |
| ccgcctcccg ggttcaagtg atcgtcctgc cttaggctcc tgagtagctg gggattacag | 5340 |
| gtgcctacca gcatgctcgg ctaattttt tgtatttta gtagagaagg gatttcacca | 5400 |
| tgttggccgg gctggtctca aactcctaag gtcatccacc tgcctcggcc tcccagagtg | 5460 |
| ctgagattac aggcgtgagc ctccgcgccc ggcccccttg cagttctctc tgatttggtt | 5520 |
| tgttctgtct caggcttctg tggcaggact ggcccaggga ggaggaagcc agcagcacac | 5580 |
| ctggggaatg gggtcccggc cgggaggctt ggcctctggg cgacctcgtc ctgttttttt | 5640 |
| tgtttgtttg tttgtttttt taaaggtaaa cctcctgggc cgcagatggc aaagggagtg | 5700 |
| cctgggcctg gtgacccagg gctggatcca cccctgcgga gccctgggcc aggcaggtgt | 5760 |
| ctgctgctca cctggctctg gagggctgcc ctgcagctgg gctggggac aggtcggctg | 5820 |
| tggggcagct cagtacccctc cctgaggctc acggtggctc cgagcatgag gtccgcctcc | 5880 |
| tgggcgagac ccagcagtgg acagcatggt cctcacaccc agctccctgc acccccaggc | 5940 |
| cagccacccc tcccgctcgt gcacaggcac gcagatgcgc tcacacgtac acacacacaa | 6000 |
| atgcacgccc acttgcacat gctcacgcac atgttcacac atgcacactc acgctcacac | 6060 |
| atgctgtcac gcatacacac acgcacatac tcctgcacat gttcccatgc atgtgtgtgc | 6120 |
| actcggaccg agcatctccc acgcacctct accccacccc aagcacctct ctcccccat | 6180 |
| gcacctctcc ccaacaacac acacagcccc ctgcaccgcc cgcccccgc ccccaccaag | 6240 |
| gccccagcct ctggccatca gtcctggtgc cagagctttg cgtgaagttc gggccgcaga | 6300 |
| gtggcccgct gggactccca tgtgctgccg tctgatgtgc tcagatgggc tcatcgttgg | 6360 |
| ttcgttttta ctgtatattt atagtaataa aatcatgcag caata | 6405 |

<210> SEQ ID NO 21
<211> LENGTH: 3934
<212> TYPE: DNA
<213> ORGANISM: Homo sapiens

<400> SEQUENCE: 21

| | |
|---|---|
| gtgggggctc gaggcgcctc cgcggccgtg gacgagcgtc cgtgcggcct ggtccgggcc | 60 |
| atgtccgcgt gaggacccccg ccgctgtcgc cgctcccgtt ccggccctgg cccctctgcc | 120 |
| cggcagcgcc gcgcaccatg ggctccattc tcagccgccg catcgcgggg gtggaggaca | 180 |
| tcgacatcca ggcgaactcg gcctatcgct accctccgaa gtccggaaac tactttgctt | 240 |
| cgcactttt catgggagga gagaaattcg acaccccccca ccctgaaggt tacctctttg | 300 |
| gagagaacat ggatctgaac ttcctgggca gccgcccggc ccagtttccc tacgtcactc | 360 |
| ctgccccca cgagcccgtg aagacgctgc ggagcctggt gaacatccgc aaagactccc | 420 |

```
tgcggctggt gaggtacaaa gacgatgccg acagccccac cgaggacggc gacaagcccc    480
gggtgctcta cagcctggag ttcaccttcg acgccgatgc ccgcgtggcc atcaccatct    540
actgccaggc atcggaggag ttcctgaacg gcagggcagt atacagcccc aagagcccct    600
cgctacagtc cgagaccgtc cactacaaga gaggggtgag ccagcagttc tccctgccct    660
ccttcaagat tgacttctcg gaatggaagg atgacgagct gaactttgac ctggaccggg    720
gcgtgttccc agtagtcatc caggctgtgg tggacgaagg agatgtggtg gaagtgactg    780
gccacgccca cgtgctcttg gctgcctttg aaaagcacat ggacggcagc ttctctgtga    840
agcctttaaa gcagaagcaa attgtggacc gggtcagcta cctcctgcag gagatctatg    900
gcattgagaa caagaacaac caggagacca agccctcgga cgacgagaac agcgacaaca    960
gcaacgagtg tgtggtgtgc ctgtccgacc tgcgggacac gctgatcctg ccctgccgcc   1020
acctgtgcct ctgtacctcc tgcgccgaca cgctgcgcta ccaggccaac aactgcccca   1080
tctgccggct gccttttccgg gccctcctgc agatccgggc ggtgcggaag aagccaggag   1140
ccctgtcccc cgtgtccttc agcccccgtcc tggcccagag cctggagcat gatgagcact   1200
cttgtccctt taaaaaatca aagccgcacc ccgcctccct ggccagcaag aaacctaaaa   1260
gggaaacaaa ctctgacagc gtcccaccctg gctacgagcc catctcgctg ctcgaggcgc   1320
tcaacggcct ccgggctgtc tccccggcca tcccctcggc ccctctttat gaagaaatca   1380
cctattcagg catctcggac ggcctgtccc aggccagctg tccccctcgcg ctatcgacc   1440 acatcctgga cagcagccgc cagaagggca ggccgcagag caaggccccc gacagcaccc   1500
tacggtcccc gtcttccccc atccacgaag aggatgagga gaagctctcc gaggacgtgg   1560
acgcccctcc cccactgggt ggcgcagagc tggccctgcg ggaaagcagc tcccctgaga   1620
gtttcataac agaagaggtt gatgagtcgt cgtcaccaca gcaagggacc cgagcagctt   1680
ccattgagaa tgtcctgcag gacagcagcc ccgagcactg tggccgaggc ccacctgctg   1740
acatctacct gccaggacgg cccacctcca tggagacggc ccacggcctc gccaccacca   1800
gccccacctg gcctccactt ggtggcccca gccccgatcc cagcgccgcc gagctgaccc   1860
cactctgaga gcctggccga gctggcagca tggagccctc ggctccccag actttgccga   1920
ggggctgctc cggaccccgt tgtgagccgg cctcctgtct gcatgccccc tgtggccacc   1980
aggctccgag gggccgtggt gactcttgat caaagagcac agtgaactgt ccttctgag   2040 tctccctttt ctacagttga tatatttgta actggtacaa gatgaaggac agcagctttc   2100
catccctagt tcagagcccc cgttcccag ggtcctgtgg gctgagcggc tgggctggg   2160 gctgccacg tgtggcctcc gctggctctg cctgctcctg caacagtgcg gtccctgccc   2220
ggagaactca ggaggcctgc agaagagaac tgattggtgg tcgaagcacc atcttcacag   2280
atgttcaggg gcagtggggg gctccaggca cggtcaatga aggaaacagt gcctgtccac   2340
ccaccctgcg tgtcactgtg gcggcctggc tgtcgctgct ttttgtcctc tgccgtgttt   2400
gcgcggcctc agtgccctcc ctggtgcgtc tgcgctgggg ccctcagtgc tcggggcctt   2460
ggggtgcatg ggtgccgccc tgggcagcta gagtgtctca gcccggtgct gggcctggcc   2520
gaggggcgga ggcacagctg cttccagcag ccagcattca gtggccttgt caccaagctc   2580
cacacctcct cctggtgctg gctttggtga catcacaagg cccctccagg tgcaggggct   2640
tctgtttggc aggcccctgc cagggaggac ctggtggcct cctcattctc ttttgccatt   2700
ggaatgtccc cttgcagttc tcttctcttt tttttttttt ttgagatgga gtttcactct   2760
tgctgcccag gctggagtgc agtggctcaa tctcgggtca ctgcaacctc cgcctccgg   2820
```

-continued

```
gttcaagtga tcgtcctgcc ttaggctcct gagtagctgg ggattacagg tgcctaccag    2880
catgctcggc taattttttt gtattttag tagagaaggg atttcaccat gttggccggg     2940
ctggtctcaa actcctaagg tcatccacct gcctcggcct cccagagtgc tgagattaca    3000
ggcgtgagcc tccgcgcccg gccccttgc agttctctct gatttggttt gttctgtctc     3060
aggcttctgt ggcaggactg gcccagggag gaggaagcca gcagcacacc tggggaatgg    3120
ggtcccggcc gggaggcttg gcctctgggc gacctcgtcc tgtttttttt gtttgtttgt    3180 ttgtttttt aaaggtaaac ctcctgggcc gcagatggca aagggagtgc ctgggcctgg     3240
tgacccaggg ctggatccac ccctgcgag ccctgggcca ggcaggtgtc tgctgctcac     3300
ctggctctgg agggctgccc tgcagctggg cctggggaca ggtcggctgt ggggcagctc    3360
agtaccctcc ctgaggctca cggtggctcc gagcatgagg tccgcctcct gggcgagacc    3420
cagcagtgga cagcatggtc ctcacaccca gctccctgca cccaggcc agccaccct      3480 cccgctcgtg cacaggcacg cagatgcgct cacacgtaca cacacacaaa tgcacgccca    3540
cttgcacatg ctcacgcaca tgttcacaca tgcacactca cgctcacaca tgctgtcacg    3600
catacacaca cgcacatact cctgcacatg ttcccatgca tgtgtgtgca ctcggaccga    3660
gcatctccca cgcacctcta ccccaccca agcacctctc tccccccatg cacctctccc     3720
caacaacaca cacagccccc tgcaccgccc gcccccgcc cccaccaagg ccccagcctc     3780
tggccatcag tcctggtgcc agagcttttgc gtgaagttcg ggccgcagag tggcccgctg    3840
ggactcccat gtgctgccgt ctgatgtgct cagatgggct catcgttggt tcgttttac      3900 tgtatattta tagtaataaa atcatgcagc aata                                 3934
```

<210> SEQ ID NO 22
<211> LENGTH: 554
<212> TYPE: PRT
<213> ORGANISM: Homo sapiens

<400> SEQUENCE: 22

```
Met Gly Ser Ile Leu Ser Arg Arg Ile Ala Gly Val Glu Asp Ile Asp
1               5                   10                  15

Ile Gln Ala Asn Ser Ala Tyr Arg Tyr Pro Pro Lys Ser Gly Asn Tyr
            20                  25                  30

Phe Ala Ser His Phe Phe Met Gly Gly Glu Lys Phe Asp Thr Pro His
        35                  40                  45

Pro Glu Gly Tyr Leu Phe Gly Glu Asn Met Asp Leu Asn Phe Leu Gly
    50                  55                  60

Ser Arg Pro Val Gln Phe Pro Tyr Val Thr Pro Ala Pro His Glu Pro
65                  70                  75                  80

Val Lys Thr Leu Arg Ser Leu Val Asn Ile Arg Lys Asp Ser Leu Arg
                85                  90                  95

Leu Val Arg Tyr Lys Asp Asp Ala Asp Ser Pro Thr Glu Asp Gly Asp
            100                 105                 110

Lys Pro Arg Val Leu Tyr Ser Leu Glu Phe Thr Phe Asp Ala Asp Ala
        115                 120                 125

Arg Val Ala Ile Thr Ile Tyr Cys Gln Ala Ser Glu Glu Phe Leu Asn
    130                 135                 140

Gly Arg Ala Val Tyr Ser Pro Lys Ser Pro Ser Leu Gln Ser Glu Thr
145                 150                 155                 160

Val His Tyr Lys Arg Gly Val Ser Gln Gln Phe Ser Leu Pro Ser Phe
                165                 170                 175
```

Lys Ile Asp Phe Ser Glu Trp Lys Asp Asp Glu Leu Asn Phe Asp Leu
            180                 185                 190

Asp Arg Gly Val Phe Pro Val Val Ile Gln Ala Val Val Asp Glu Gly
        195                 200                 205

Asp Val Val Glu Val Thr Gly His Ala His Val Leu Leu Ala Ala Phe
    210                 215                 220

Glu Lys His Met Asp Gly Ser Phe Ser Val Lys Pro Leu Lys Gln Lys
225                 230                 235                 240

Gln Ile Val Asp Arg Val Ser Tyr Leu Leu Gln Glu Ile Tyr Gly Ile
                245                 250                 255

Glu Asn Lys Asn Asn Gln Glu Thr Lys Pro Ser Asp Asp Glu Asn Ser
            260                 265                 270

Asp Asn Ser Asn Glu Cys Val Val Cys Leu Ser Asp Leu Arg Asp Thr
        275                 280                 285

Leu Ile Leu Pro Cys Arg His Leu Cys Leu Cys Thr Ser Cys Ala Asp
    290                 295                 300

Thr Leu Arg Tyr Gln Ala Asn Asn Cys Pro Ile Cys Arg Leu Pro Phe
305                 310                 315                 320

Arg Ala Leu Leu Gln Ile Arg Ala Val Arg Lys Lys Pro Gly Ala Leu
                325                 330                 335

Ser Pro Val Ser Phe Ser Pro Val Leu Ala Gln Ser Leu Glu His Asp
            340                 345                 350

Glu His Ser Asn Ser Asp Ser Val Pro Pro Gly Tyr Glu Pro Ile Ser
        355                 360                 365

Leu Leu Glu Ala Leu Asn Gly Leu Arg Ala Val Ser Pro Ala Ile Pro
    370                 375                 380

Ser Ala Pro Leu Tyr Glu Ile Thr Tyr Ser Gly Ile Ser Asp Gly
385                 390                 395                 400

Leu Ser Gln Ala Ser Cys Pro Leu Ala Ala Ile Asp His Ile Leu Asp
                405                 410                 415

Ser Ser Arg Gln Lys Gly Arg Pro Gln Ser Lys Ala Pro Asp Ser Thr
            420                 425                 430

Leu Arg Ser Pro Ser Ser Pro Ile His Glu Glu Asp Glu Glu Lys Leu
        435                 440                 445

Ser Glu Asp Val Asp Ala Pro Pro Leu Gly Gly Ala Glu Leu Ala
    450                 455                 460

Leu Arg Glu Ser Ser Ser Pro Glu Ser Phe Ile Thr Glu Glu Val Asp
465                 470                 475                 480

Glu Ser Ser Ser Pro Gln Gln Gly Thr Arg Ala Ala Ser Ile Glu Asn
                485                 490                 495

Val Leu Gln Asp Ser Ser Pro Glu His Cys Gly Arg Gly Pro Pro Ala
            500                 505                 510

Asp Ile Tyr Leu Pro Gly Arg Pro Thr Ser Met Glu Thr Ala His Gly
        515                 520                 525

Leu Ala Thr Thr Ser Pro Thr Trp Pro Pro Leu Gly Gly Pro Ser Pro
    530                 535                 540

Asp Pro Ser Ala Ala Glu Leu Thr Pro Leu
545                 550

<210> SEQ ID NO 23
<211> LENGTH: 552
<212> TYPE: PRT
<213> ORGANISM: Homo sapiens

```
<400> SEQUENCE: 23

Met Gly Ser Ile Leu Ser Arg Arg Ile Ala Gly Val Glu Asp Ile Asp
1               5                   10                  15

Ile Gln Ala Asn Ser Ala Tyr Arg Tyr Pro Pro Lys Ser Gly Asn Tyr
            20                  25                  30

Phe Ala Ser His Phe Phe Met Gly Glu Lys Phe Asp Thr Pro His
        35                  40                  45

Pro Glu Gly Tyr Leu Phe Gly Glu Asn Met Asp Leu Asn Phe Leu Gly
    50                  55                  60

Ser Arg Pro Val Gln Phe Pro Tyr Val Thr Pro Ala Pro His Glu Pro
65                  70                  75                  80

Val Lys Thr Leu Arg Ser Leu Val Asn Ile Arg Lys Asp Ser Leu Arg
                85                  90                  95

Leu Val Arg Tyr Lys Asp Asp Ala Asp Ser Pro Thr Glu Asp Gly Asp
            100                 105                 110

Lys Pro Arg Val Leu Tyr Ser Leu Glu Phe Thr Phe Asp Ala Asp Ala
            115                 120                 125

Arg Val Ala Ile Thr Ile Tyr Cys Gln Ala Ser Glu Glu Phe Leu Asn
        130                 135                 140

Gly Arg Ala Val Tyr Ser Pro Lys Ser Pro Ser Leu Gln Ser Glu Thr
145                 150                 155                 160

Val His Tyr Lys Arg Gly Val Ser Gln Gln Phe Ser Leu Pro Ser Phe
                165                 170                 175

Lys Ile Asp Phe Ser Glu Trp Lys Asp Asp Glu Leu Asn Phe Asp Leu
            180                 185                 190

Asp Arg Gly Val Phe Pro Val Val Ile Gln Ala Val Asp Glu Gly
        195                 200                 205

Asp Val Val Glu Val Thr Gly His Ala His Val Leu Leu Ala Ala Phe
    210                 215                 220

Glu Lys His Met Asp Gly Ser Phe Ser Val Lys Pro Leu Lys Gln Lys
225                 230                 235                 240

Gln Ile Val Asp Arg Val Ser Tyr Leu Leu Gln Glu Ile Tyr Gly Ile
                245                 250                 255

Glu Asn Lys Asn Asn Gln Glu Thr Lys Pro Ser Asp Asp Glu Asn Ser
            260                 265                 270

Asp Asn Ser Asn Glu Cys Val Val Cys Leu Ser Asp Leu Arg Asp Thr
        275                 280                 285

Leu Ile Leu Pro Cys Arg His Leu Cys Leu Cys Thr Ser Cys Ala Asp
    290                 295                 300

Thr Leu Arg Tyr Gln Ala Asn Asn Cys Pro Ile Cys Arg Leu Pro Phe
305                 310                 315                 320

Arg Ala Leu Leu Gln Ile Arg Ala Val Arg Lys Lys Pro Gly Ala Leu
                325                 330                 335

Ser Pro Val Ser Phe Ser Pro Val Leu Ala Gln Ser Leu Glu His Asp
            340                 345                 350

Glu His Ser Cys Pro Phe Lys Lys Ser Lys Pro His Pro Ala Ser Leu
        355                 360                 365

Ala Ser Lys Lys Pro Lys Arg Glu Thr Asn Ser Asp Ser Val Pro Pro
    370                 375                 380

Gly Tyr Glu Pro Ile Ser Leu Leu Ala Leu Asn Gly Leu Arg Ala
385                 390                 395                 400

Val Ser Pro Ala Ile Pro Ser Ala Pro Leu Tyr Glu Glu Ile Thr Tyr
                405                 410                 415
```

```
Ser Gly Ile Ser Asp Gly Leu Ser Gln Ala Ser Cys Pro Leu Ala Ala
            420                 425                 430

Ile Asp His Ile Leu Asp Ser Ser Arg Gln Lys Gly Arg Pro Gln Ser
            435                 440                 445

Lys Ala Pro Asp Ser Thr Leu Arg Ser Pro Ser Ser Pro Ile His Glu
450                 455                 460

Glu Asp Glu Glu Lys Leu Ser Glu Asp Val Asp Ala Pro Pro Pro Leu
465                 470                 475                 480

Gly Gly Ala Glu Leu Ala Leu Arg Glu Ser Ser Pro Glu Ser Phe
                485                 490                 495

Ile Thr Glu Glu Val Asp Glu Ser Ser Pro Gln Gln Gly Thr Arg
            500                 505                 510

Ala Ala Ser Ile Glu Asn Val Leu Gln Asp Ser Ser Pro Glu His Cys
            515                 520                 525

Gly Arg Gly Pro Pro Ala Asp Ile Tyr Leu Pro Ala Leu Gly Pro Asp
            530                 535                 540

Ser Cys Ser Val Gly Ile Asp Glu
545                 550

<210> SEQ ID NO 24
<211> LENGTH: 530
<212> TYPE: PRT
<213> ORGANISM: Homo sapiens

<400> SEQUENCE: 24

Met Gly Ser Ile Leu Ser Arg Arg Ile Ala Gly Val Glu Asp Ile Asp
1               5                   10                  15

Ile Gln Ala Asn Ser Ala Tyr Arg Tyr Pro Pro Lys Ser Gly Asn Tyr
            20                  25                  30

Phe Ala Ser His Phe Phe Met Gly Gly Glu Lys Phe Asp Thr Pro His
            35                  40                  45

Pro Glu Gly Tyr Leu Phe Gly Glu Asn Met Asp Leu Asn Phe Leu Gly
        50                  55                  60

Ser Arg Pro Val Gln Phe Pro Tyr Val Thr Pro Ala Pro His Glu Pro
65                  70                  75                  80

Val Lys Thr Leu Arg Ser Leu Val Asn Ile Arg Lys Asp Ser Leu Arg
                85                  90                  95

Leu Val Arg Tyr Lys Asp Asp Ala Asp Ser Pro Thr Glu Asp Gly Asp
            100                 105                 110

Lys Pro Arg Val Leu Tyr Ser Leu Glu Phe Thr Phe Asp Ala Asp Ala
            115                 120                 125

Arg Val Ala Ile Thr Ile Tyr Cys Gln Ala Ser Glu Glu Phe Leu Asn
        130                 135                 140

Gly Arg Ala Val Tyr Ser Pro Lys Ser Pro Ser Leu Gln Ser Glu Thr
145                 150                 155                 160

Val His Tyr Lys Arg Gly Val Ser Gln Gln Phe Ser Leu Pro Ser Phe
                165                 170                 175

Lys Ile Asp Phe Ser Glu Trp Lys Asp Asp Glu Leu Asn Phe Asp Leu
            180                 185                 190

Asp Arg Gly Val Phe Pro Val Val Ile Gln Ala Val Asp Glu Gly
            195                 200                 205

Asp Val Val Glu Val Thr Gly His Ala His Val Leu Leu Ala Ala Phe
        210                 215                 220

Glu Lys His Met Asp Gly Ser Phe Ser Val Lys Pro Leu Lys Gln Lys
225                 230                 235                 240
```

-continued

Gln Ile Val Asp Arg Val Ser Tyr Leu Leu Gln Glu Ile Tyr Gly Ile
                245                 250                 255

Glu Asn Lys Asn Asn Gln Glu Thr Lys Pro Ser Asp Asp Glu Asn Ser
            260                 265                 270

Asp Asn Ser Asn Glu Cys Val Val Cys Leu Ser Asp Leu Arg Asp Thr
        275                 280                 285

Leu Ile Leu Pro Cys Arg His Leu Cys Leu Cys Thr Ser Cys Ala Asp
    290                 295                 300

Thr Leu Arg Tyr Gln Ala Asn Asn Cys Pro Ile Cys Arg Leu Pro Phe
305                 310                 315                 320

Arg Ala Leu Leu Gln Ile Arg Ala Val Arg Lys Lys Pro Gly Ala Leu
                325                 330                 335

Ser Pro Val Ser Phe Ser Pro Val Leu Ala Gln Ser Leu Glu His Asp
            340                 345                 350

Glu His Ser Asn Ser Asp Ser Val Pro Pro Gly Tyr Glu Pro Ile Ser
        355                 360                 365

Leu Leu Glu Ala Leu Asn Gly Leu Arg Ala Val Ser Pro Ala Ile Pro
    370                 375                 380

Ser Ala Pro Leu Tyr Glu Glu Ile Thr Tyr Ser Gly Ile Ser Asp Gly
385                 390                 395                 400

Leu Ser Gln Ala Ser Cys Pro Leu Ala Ala Ile Asp His Ile Leu Asp
                405                 410                 415

Ser Ser Arg Gln Lys Gly Arg Pro Gln Ser Lys Ala Pro Asp Ser Thr
            420                 425                 430

Leu Arg Ser Pro Ser Ser Pro Ile His Glu Glu Asp Glu Leu Lys Leu
        435                 440                 445

Ser Glu Asp Val Asp Ala Pro Pro Leu Gly Gly Ala Glu Leu Ala
    450                 455                 460

Leu Arg Glu Ser Ser Ser Pro Glu Ser Phe Ile Thr Glu Glu Val Asp
465                 470                 475                 480

Glu Ser Ser Ser Pro Gln Gln Gly Thr Arg Ala Ala Ser Ile Glu Asn
                485                 490                 495

Val Leu Gln Asp Ser Ser Pro His Cys Gly Arg Gly Pro Pro Ala
            500                 505                 510

Asp Ile Tyr Leu Pro Ala Leu Gly Pro Asp Ser Cys Ser Val Gly Ile
        515                 520                 525

Asp Glu
    530

<210> SEQ ID NO 25
<211> LENGTH: 576
<212> TYPE: PRT
<213> ORGANISM: Homo sapiens

<400> SEQUENCE: 25

Met Gly Ser Ile Leu Ser Arg Arg Ile Ala Gly Val Glu Asp Ile Asp
1               5                   10                  15

Ile Gln Ala Asn Ser Ala Tyr Arg Tyr Pro Pro Lys Ser Gly Asn Tyr
            20                  25                  30

Phe Ala Ser His Phe Phe Met Gly Gly Glu Lys Phe Asp Thr Pro His
        35                  40                  45

Pro Glu Gly Tyr Leu Phe Gly Glu Asn Met Asp Leu Asn Phe Leu Gly
    50                  55                  60

Ser Arg Pro Val Gln Phe Pro Tyr Val Thr Pro Ala Pro His Glu Pro
65                  70                  75                  80

```
Val Lys Thr Leu Arg Ser Leu Val Asn Ile Arg Lys Asp Ser Leu Arg
             85                  90                  95

Leu Val Arg Tyr Lys Asp Asp Ala Asp Ser Pro Thr Glu Asp Gly Asp
            100                 105                 110

Lys Pro Arg Val Leu Tyr Ser Leu Glu Phe Thr Phe Asp Ala Asp Ala
            115                 120                 125

Arg Val Ala Ile Thr Ile Tyr Cys Gln Ala Ser Glu Glu Phe Leu Asn
            130                 135                 140

Gly Arg Ala Val Tyr Ser Pro Lys Ser Pro Ser Leu Gln Ser Glu Thr
145                 150                 155                 160

Val His Tyr Lys Arg Gly Val Ser Gln Gln Phe Ser Leu Pro Ser Phe
                165                 170                 175

Lys Ile Asp Phe Ser Glu Trp Lys Asp Asp Glu Leu Asn Phe Asp Leu
                180                 185                 190

Asp Arg Gly Val Phe Pro Val Ile Gln Ala Val Val Asp Glu Gly
            195                 200                 205

Asp Val Val Glu Val Thr Gly His Ala His Val Leu Leu Ala Ala Phe
            210                 215                 220

Glu Lys His Met Asp Gly Ser Phe Ser Val Lys Pro Leu Lys Gln Lys
225                 230                 235                 240

Gln Ile Val Asp Arg Val Ser Tyr Leu Leu Gln Glu Ile Tyr Gly Ile
                245                 250                 255

Glu Asn Lys Asn Asn Gln Glu Thr Lys Pro Ser Asp Asp Glu Asn Ser
                260                 265                 270

Asp Asn Ser Asn Glu Cys Val Val Cys Leu Ser Asp Leu Arg Asp Thr
            275                 280                 285

Leu Ile Leu Pro Cys Arg His Leu Cys Leu Cys Thr Ser Cys Ala Asp
            290                 295                 300

Thr Leu Arg Tyr Gln Ala Asn Asn Cys Pro Ile Cys Arg Leu Pro Phe
305                 310                 315                 320

Arg Ala Leu Leu Gln Ile Arg Ala Val Arg Lys Lys Pro Gly Ala Leu
                325                 330                 335

Ser Pro Val Ser Phe Ser Pro Val Leu Ala Gln Ser Leu Glu His Asp
                340                 345                 350

Glu His Ser Cys Pro Phe Lys Lys Ser Lys Pro His Pro Ala Ser Leu
            355                 360                 365

Ala Ser Lys Lys Pro Lys Arg Glu Thr Asn Ser Asp Ser Val Pro Pro
370                 375                 380

Gly Tyr Glu Pro Ile Ser Leu Leu Glu Ala Leu Asn Gly Leu Arg Ala
385                 390                 395                 400

Val Ser Pro Ala Ile Pro Ser Ala Pro Leu Tyr Glu Glu Ile Thr Tyr
                405                 410                 415

Ser Gly Ile Ser Asp Gly Leu Ser Gln Ala Ser Cys Pro Leu Ala Ala
                420                 425                 430

Ile Asp His Ile Leu Asp Ser Ser Arg Gln Lys Gly Arg Pro Gln Ser
            435                 440                 445

Lys Ala Pro Asp Ser Thr Leu Arg Ser Pro Ser Pro Ile His Glu
450                 455                 460

Glu Asp Glu Glu Lys Leu Ser Glu Asp Val Asp Ala Pro Pro Leu
465                 470                 475                 480

Gly Gly Ala Glu Leu Ala Leu Arg Glu Ser Ser Pro Glu Ser Phe
                485                 490                 495
```

```
Ile Thr Glu Glu Val Asp Glu Ser Ser Pro Gln Gln Gly Thr Arg
            500                 505                 510

Ala Ala Ser Ile Glu Asn Val Leu Gln Asp Ser Pro Glu His Cys
        515                 520                 525

Gly Arg Gly Pro Pro Ala Asp Ile Tyr Leu Pro Gly Arg Pro Thr Ser
    530                 535                 540

Met Glu Thr Ala His Gly Leu Ala Thr Thr Ser Pro Thr Trp Pro Pro
545                 550                 555                 560

Leu Gly Gly Pro Ser Pro Asp Pro Ser Ala Ala Glu Leu Thr Pro Leu
                565                 570                 575
```

<210> SEQ ID NO 26
<211> LENGTH: 6382
<212> TYPE: DNA
<213> ORGANISM: Homo sapiens

<400> SEQUENCE: 26

| | | | | | |
|---|---|---|---|---|---|
| cggtgcattc | tgggtcctgg | caatatggcg | tcctccttga | tgggctgatg | agatgagttt | 60 |
| cactgtagct | ccaaaccaga | gggcaaagct | cccatgaccc | aataagccca | cattgtccct | 120 |
| ttcctccgtg | gttccgtgtc | gcccgttcct | caggactcgt | tctcaggcag | agagagcct | 180 |
| cggggctgaa | ggccaggacc | agccaggccg | cgcggacctg | aggttgagga | accgggtgca | 240 |
| ggcgagcacg | atgggccggt | cgtggctctg | gttgcagcag | ctcagacgag | tgcgggaccc | 300 |
| gcagggctga | gagtggctgg | aggagaccca | gggcccttg | aacccgatcc | cttggccgga | 360 |
| gacctcagcc | cagtcggccc | agtgggcgaa | ccggcaccaa | gagcggcctg | cctgtcttcg | 420 |
| gaactgctga | ggcggtggag | gccgagagca | gggtcatcgt | gaggcctgaa | gtctcttacg | 480 |
| cttttggcag | ctcccctcgc | agcccctctg | gaaacgtaca | gcctcaggag | cagccagtgg | 540 |
| cttgggacct | ggggtggtgt | gtgtctgcgg | agcttcttgg | gctgccccat | tcctagcgg | 600 |
| ccccacctc | cccacttccc | gctcagagtt | agagataagg | atctcagact | tttgcctgag | 660 |
| taagggtctc | cgcactcttt | atccatttgg | ttttcgattt | cccgtttttg | tttcttattt | 720 |
| caccaattct | ggtacacgct | agttttaag | gctggaggtt | ctcgagcgct | tgctgccaag | 780 |
| gactccccca | cccctcccc | cactgatgga | gtccgaaatg | ctgcaatcgc | tcttctggg | 840 |
| cctgggggag | gaagatgagg | ctgatcttac | agactggaac | ctacctttgg | cttttatgaa | 900 |
| aaagaggcac | tgtgagaaaa | ttgaaggctc | caaatcctta | gctcagagct | ggaggatgaa | 960 |
| ggatcggatg | aagacagtca | gtgttgcctt | agttttgtgc | ctgaatgttg | gtgtggaccc | 1020 |
| tcccgatgtg | gtgaagacca | cgccctgtgc | acgcttggaa | tgctggatcg | atcctctgtc | 1080 |
| gatgggtcct | cagaaagctc | tggaaaccat | cggtgcaaat | ttacagaagc | agtacgagaa | 1140 |
| ctggcagcca | agggcccggt | acaagcagag | ccttgaccca | actgtggatg | aagtcaagaa | 1200 |
| gctctgcacg | tccttacgtc | gcaacgccaa | ggaggagcga | gtcctctttc | actacaatgg | 1260 |
| ccacggggtg | ccccggccca | cagtcaacgg | ggaggtctgg | gtcttcaaca | agaactacac | 1320 |
| gcagtacatc | cctctgtcca | tatatgacct | gcagacgtgg | atgggcagcc | cgtcgatctt | 1380 |
| cgtctacgac | tgctccaatg | ctggcttgat | cgtcaagtcc | ttcaagcagt | tcgcactaca | 1440 |
| gcgggagcag | gagctggagg | tagctgcaat | caacccaaat | caccctcttg | ctcagatgcc | 1500 |
| tttgcctccg | tcgatgaaaa | actgcatcca | gctggcagcc | tgcgaggcca | ccgagctgct | 1560 |
| gcccatgatc | cccgacctcc | cggctgacct | attcacctcc | tgcctcacca | cccccatcaa | 1620 |
| gatcgccctg | cgctggtttt | gcatgcagaa | atgtgtcagt | ctggtgcctg | gcgtcacact | 1680 |

```
ggatttgata gaaaagatcc ctggccgcct gaacgacagg aggacgcccc tgggtgaact      1740
gaactggatc ttcacagcca tcacagacac catcgcgtgg aacgtgctcc cccgggatct      1800
cttccaaaag ctcttcagac aggacttgct ggtggctagt ctgtttcgaa attttttatt      1860
ggcggaaagg attatgaggt cgtataactg cactcccgtc agcagcccgc gtctgccgcc      1920
cacgtacatg cacgccatgt ggcaagcctg ggacctggct gttgacatct gtctgtctca      1980
gctgccgacg atcatcgagg aaggcactgc gtttcggcac agcccgttct cgccgagca      2040 gctgaccgca ttccaggtgt ggctcaccat gggcgtggag aaccgaaacc cacccgaaca      2100
gctgcccatc gtcctgcagg tgctgttaag ccaagtgcac cggctgagag cattggactt      2160
gcttggaaga ttttttggacc tgggtccctg ggcagtgagc ctggccttgt ctgtcggcat      2220
cttcccctac gtgctgaagc tgctccagag ctcggcccga gagctgcggc cacttctcgt      2280
tttcatctgg gccaagatcc tcgcagtgga cagcgagctg gtggtggctc tgagtcatct      2340
tgtggttcag tatgaaagca atttctgcac cgtggccctg cagttcatag aagaggaaaa      2400
gaactacgcc ttgccttctc cagcaaccac agagggaggg agtttgaccc cagtgcgaga      2460
cagcccgtgc accccagac ttcgttctgt gagctcctat ggaaacatcc gtgctgtcgc       2520
cacagccagg agcctcaaca aatctttgca gaacctgagt ttgacagagg aatctggtgg      2580
cgcggtggcg ttctcccccg gaaacctcag caccagcagc agcgccagca gcaccctggg      2640
cagccccgag aatgaggagc atatcctgtc cttcgagacc atcgacaaga tgcgccgcgc      2700
cagctcctac tcctcccctca actccctcat cggagtttcc tttaacagtg tttacactca      2760
gatttggaga gtcctgctgc acctggctgc tgaccccctat ccagaggtct cggacgtggc      2820
catgaaagta ctcaacagca tcgcctacaa ggccaccgtg aacgcccggc cgcagcgcgt      2880
cctggacacc tcctccctca cgcagtcggc ccccgccagc cccaccaaca agggcgtgca      2940
catccaccag gcggggggct cccctccggc gtccagcacc agcagctcca gcctgaccaa      3000
cgatgtggcc aagcagccgg tcagccgaga cttgccttct ggccggccgg gcaccacagg      3060
ccccgctggg gcgcagtaca cccctcactc ccaccagttc ccccggacac ggaagatgtt      3120
cgacaagggc ccagagcaga ctgcggacga cgcggacgat gctgctggac acaaaagttt      3180
catctccgcc acggtgcaga cggggttctg cgactggagc gcccgctatt ttgcccagcc      3240
cgtcatgaag atcccagaag agcacgacct ggagagtcag atccgcaagg agcgggagtg      3300
gcggttcctg cgaaacagcc gtgtcaggag gcaggcccag caagtcattc agaagggcat      3360
tacgagattg gacgaccaaa tatttctgaa caggaacccc ggcgtccccct ctgtggtgaa      3420 attccacccc ttcacgccgt gcatcgccgt agccgacaag gacagcatct gcttttggga      3480
ctgggagaaa gggagaagc tggattattt ccacaatggg aaccctcggt acacgagggt       3540
cactgccatg gagtatctga acggccagga ctgctcgctt ctgctgacgg ccacagacga      3600
tggtgccatc agggtctgga gaatttttgc tgatttggaa aagaacccag agatggtgac      3660
cgcgtggcag gggctctcgg acatgctgcc aacgacgcga ggagctggga tggtggtgga      3720
ctgggagcag agaccggcc tcctcatgag ctcaggagac gtgcggatcg tccggatctg      3780
ggacacagac cgtgagatga aggtgcagga catccctacg ggcgcagaca gctgtgtgac      3840
gagtctgtcc tgtgattccc accgctcact catcgtggct ggcctcggtg acggctccat      3900
ccgcgtctac gacagaagga tggcactcag cgaatgccgc gtcatgacgt accgggagca      3960
cacagcctgg gtggtgaagg cctccctgca gaagcgtccc gacggccaca tcgtgagtgt      4020
gagcgtcaat ggagatgtgc gcatctttga tcccccggatg cctgagtcgg taaatgtgct      4080
```

```
tcagatcgtg aaggggctga cggccctgga catccacccc caggcggacc tgatcgcatg    4140
tggctccgtc aatcagttca ccgccatcta acagcagc ggagagctca tcaacaacat    4200
caagtactac gacggcttca tgggccagcg ggtcggcgcc atcagctgcc tggccttcca    4260
cccgcactgg cctcacctgg ccgtgggaag caacgactac tacatctccg tgtactcggt    4320
ggagaagcgt gtcagatagc ggcgtgaccc gggcccacca ggccacggcc gcctgctgta    4380
catagtgaag ctgtcactcg ccggggcacg gggcgtcggc tgctgcggcc ccgcagtgtg    4440
aacgttggct gctgccttag ctgctgatga cggcaggagg gccctgctac tcgcttttgt    4500
ctgtcttcgc tgtcgtgtct ggaatgtcag ggaaggggag ggctcgggtt gacggtggct    4560
tcccactgag caccagcatc caggtgcacc cccgcggcca cggcgcctct gtccctctcc    4620
tgttctgtgt ttctctgaga cgctgaaagg ggaaacacct cactttattt ccatgtaatc    4680
agagcattag ctgcagaaaa accccccgac agagccctgg cggagaggca ggcgctgggg    4740
ctcctacggg tccctggggc agctgtcccc atcaggccaa gagcgagcga gaggcgctgc    4800
cccagccagg cccaccacct ctcacagtca gtgcacgcaa gcagggacat ttcctagcca    4860
gctgggggac actggaaatt cgggaaacca agagagagga agaaggagac gcccctccaa    4920
ctggcgggtg tgaaggaagc cgcccagggg tccgggctgt ccttggccgc tggcagcatc    4980
actgagcagg aagcgcacag cccacccctcc ccgcacctcc aggtctctgg actccagttt    5040
tggcccctct cacacagagc tgtcagcagg ggccgctgtg gcggtgcaca ggggaggcag    5100
gtccttggcg aggtagcccc tgccttaatc cacggggctc ctttccctcc gaagggctgc    5160
tcttccccac aggcgcgggg acagcagccc gacctgtggt ctccatgcct gtgccctcac    5220
acaggtgtag cacacgcatg tgcagatggc accacggccg gcacctgggg gcacacacat    5280
gcaggcggcg tggtctccct gctctgtccc cacacgttcc tcacatacag gcaagaggca    5340
ctgccgggtc ccggacggct ccgggtgaca ccagccccgt ctccagcctt gagccgccca    5400
tgctgatgcg acctcggctg acagctgggc ctgtggtgca gacaggagct gtgtggacag    5460
tcccgcccag gagggggccgc agggcgtgta tgagcagttt tgcaaacaga acacaaccac    5520
aatgatggta ttttgaaaag tgttctttcc gtgttcgtcg ggaatcagga ttattgagag    5580
gtgaaggagc caggtggctt cattctggcg gtgagaggcc cacgaccacg ggagtgagag    5640
ctggtgtggc gaggcccggc tctcctgcgg tgtggctggt ggcctgccgt ggccaagagc    5700
atcttctggg tggatggaac cctgcctggt cacatttggc cagagacaca cctggccctc    5760 aggggggctga gctggagact gagctggggc tggccgggac gtgacaaggc aggacagagg    5820
cggcccctcc gctgctcctt tttggaatgc gagctcccac cagaagaagg ttccggcacg    5880
aatcccatcc ccacgtctgg gccgagaaag cagcccgggt ccggaaggtg tagagagtcc    5940
cggcctcact cagctcacag ggcgtgccag gcggcaacac cagaatcttc cagaagccca    6000
gctccacccg cacacgcagc ttcccatcca gtccttcaac tcaattctta cccaacacgc    6060
gtttctgttt gttttgagac aaaatcacca cctgtcaaaa ggcaggtggc tccagagggg    6120
tcaagacccc cccccgcccc cgctccaccc tggagcccac cccatgggc accgcgtgcc    6180 gcctgcacgt gggctgtctt cacaggtctg atgtgaaaat tcaatcacga cgttaaccgg    6240
ctcgagagag cgccggccta gaggctcatt atctatttat tttaccaaac gcgaattgag    6300
acggactttg acaaaacacg aaatggtaat gtgaagctaa gagcagagag tgaccaacag    6360
taaacaacac gcgcagactc cg    6382
```

```
<210> SEQ ID NO 27
<211> LENGTH: 6856
<212> TYPE: DNA
<213> ORGANISM: Homo sapiens

<400> SEQUENCE: 27
cggtgcattc tgggtcctgg caatatggcg tcctccttga tgggctgatg agatgagttt      60
cactgtagct ccaaaccaga gggcaaagct cccatgaccc aataagccca cattgtccct     120
ttcctccgtg gttccgtgtc gcccgttttct caggactcgt tctcaggcag gagagagcct    180
cggggctgaa ggccaggacc agccaggccg cgcggacctg aggttgagga accgggtgca     240
ggcgagcacg atgggccggt cgtggctctg gttgcagcag ctcagacgag tgcgggaccc     300
gcagggctga gagtggctgg aggagaccca gggccctttg aacccgatcc cttggccgga     360
gacctcagcc cagtcggccc agtgggcgaa ccggcaccaa gagcggcctg cctgtcttcg     420
gaactgctga ggcggtggag gccgagagca gggtcatcgt gaggcctgaa gtctcttacg     480
cttttggcag ctcccctcgc agcccctctg gaaacgtaca gcctcaggag cagccagtgg     540
cttgggacct ggggtggtgt gtgtctgcgg agcttcttgg gctgccccat tcctagcgg      600 cccccacctc cccacttccc gctcagagtt agagataagg atctcagact tttgcctgag     660
taagggtctc cgcactcttt atccatttgg ttttcgattt cccgtttttg tttcttattt     720
caccaattct ggtacacgct agtttttaag gctggaggtt ctcgagcgct tgctgccaag     780 gactcccca ccccctcccc cactgatgga gtccgaaatg ctgcaatcgc ctcttctggg      840
cctgggggag gaagatgagg ctgatcttac agactggaac ctacctttgg cttttatgaa     900
aaagaggcac tgtgagaaaa ttgaaggctc caaatcctta gctcagagct ggaggatgaa     960
ggatcggatg aagacagtca gtgttgcctt agttttgtgc ctgaatgttg gtgtggaccc    1020
tcccgatgtg gtgaagacca cgccctgtgc acgcttggaa tgctggatcg atcctctgtc    1080
gatgggtcct cagaaagctc tggaaaccat cggtgcaaat ttacagaagc agtacgagaa    1140
ctggcagcca agggcccggt acaagcagag ccttgaccca actgtggatg aagtcaagaa    1200
gctctgcacg tccttacgtc gcaacgccaa ggaggagcga gtcctctttc actacaatgg    1260
ccacggggtg ccccggccca cagtcaacgg ggaggtctgg gtcttcaaca agaactacac    1320
gcagtacatc cctctgtcca tatatgacct gcagacgtgg atgggcagcc cgtcgatctt    1380
cgtctacgac tgctccaatg ctggcttgat cgtcaagtcc ttcaagcagt tcgcactaca    1440
gcgggagcag gagctggagg tagctgcaat caacccaaat caccctcttg ctcagatgcc    1500
tttgcctccg tcgatgaaaa actgcatcca gctggcagcc tgcgaggcca ccgagctgct    1560
gcccatgatc cccgacctcc cggctgacct attcacctcc tgcctcacca ccccatcaa    1620 gatcgccctg cgctggtttt gcatgcagaa atgtgtcagt ctggtgcctg gcgtcacact    1680
ggatttgata gaaaagatcc ctggccgcct gaacgacagg aggacgcccc tgggtgaact    1740
gaactggatc ttcacagcca tcacagacac catcgcgtgg aacgtgctcc cccgggatct    1800
cttccaaaag ctcttcagac aggacttgct ggtggctagt ctgtttcgaa atttttatt     1860 ggcggaaagg attatgaggt cgtataactg cactcccgtc agcagcccgc gtctgccgcc    1920
cacgtacatg cacgccatgt ggcaagcctg ggacctggct gttgacatct gtctgtctca    1980
gctgccgacg atcatcgagg aaggcactgc gtttcggcac agcccgttct tcgccgagca    2040
gctgaccgca ttccaggtgt ggctcaccat gggcgtggaa aaccgaaacc cacccgaaca    2100
gctgcccatc gtcctgcagg tgctgttaag ccaagtgcac cggctgagag cattggactt    2160
```

```
gcttggaaga ttttggacc tgggtccctg gcagtgagc ctggccttgt ctgtcggcat    2220
cttcccctac gtgctgaagc tgctccagag ctcggcccga gagctgcggc cacttctcgt    2280
tttcatctgg gccaagatcc tcgcagtgga cagctcgtgc aagcggacc tcgtgaagga    2340 caacggccac aagtacttcc tgtcggtcct ggcggacccc tacatgccag ctgaacaccg    2400
gaccatgacg gctttcattc tcgccgtgat cgtcaacagc tatcacacgg ggcaggaagc    2460
ctgccttcag ggaaacctca ttgccatctg cctggagcag ctcaacgacc cgcacccctt    2520
gctgcgccag tgggtggcca tctgcctcgg caggatctgg cagaacttcg actcggcgag    2580
gtggtgcggc gtgagggaca cgctcatga aagctctac agcctcctct ccgaccccat    2640
tcccgaggtc cgctgcgcag cggtcttcgc ccttggcacg ttcgtgggca actctgcaga    2700
gaggacggac cactccacca ccatcgacca aacgtggcc atgatgctgg cccagctggt    2760
cagcgacggg agccccatgg tccggaagga gctggtggtg gctctgagtc atcttgtggt    2820
tcagtatgaa agcaatttct gcaccgtggc cctgcagttc atagaagagg aaaagaacta    2880
cgccttgcct tctccagcaa ccacagaggg agggagtttg accccagtgc gagacagccc    2940
gtgcaccccc agacttcgtt ctgtgagctc ctatggaaac atccgtgctg tcgccacagc    3000
caggagcctc aacaaatctt tgcagaacct gagtttgaca gaggaatctg gtggcgcggt    3060
ggcgttctcc cccggaaacc tcagcaccag cagcagcgcc agcagcaccc tgggcagccc    3120
cgagaatgag gagcatatcc tgtccttcga gaccatcgac aagatgcgcc gcgccagctc    3180
ctactcctcc ctcaactccc tcatcggagt ttcctttaac agtgtttaca ctcagatttg    3240
gagagtcctg ctgcacctgg ctgctgaccc ctatccagag gtctcggacg tggccatgaa    3300
agtactcaac agcatcgcct acaaggccac cgtgaacgcc cggccgcagc gcgtcctgga    3360
cacctcctcc ctcacgcagt cggccccgc cagccccacc aacaagggcg tgcacatcca    3420
ccaggcgggg ggctcccctc cggcgtccag caccagcagc tccagcctga ccaacgatgt    3480
ggccaagcag ccggtcagcc gagacttgcc ttctggccgg ccgggcacca caggccccgc    3540
tggggcgcag tacacccctc actcccacca gttcccccgg acacggaaga tgttcgacaa    3600
gggcccagag cagactgcgg acgacgcgga cgatgctgct ggacacaaaa gtttcatctc    3660
cgccacggtg cagacggggt tctgcgactg gagcgcccgc tattttgccc agcccgtcat    3720
gaagatccca aagagcacg acctggagag tcagatccgc aaggagcggg agtggcggtt    3780
cctgcgaaac agccgtgtca ggaggcaggc ccagcaagtc attcagaagg cattacgag    3840 attggacgac caaatatttc tgaacaggaa ccccggcgtc ccctctgtgg tgaaattcca    3900 cccccttcacg ccgtgcatcg ccgtagccga caaggacagc atctgctttt gggactggga    3960
gaaaggggaa aagctggatt atttccacaa tgggaaccct cggtacacga gggtcactgc    4020
catggagtat ctgaacggcc aggactgctc gcttctgctg acggccacag acgatggtgc    4080
catcagggtc tggaagaatt ttgctgattt ggaaaagaac ccagagatgg tgaccgcgtg    4140
gcaggggctc tcggacatgc tgccaacgac gcgaggagct gggatggtgg tggactggga    4200
gcaggagacc ggcctcctca tgagctcagg agacgtgcgg atcgtccgga tctgggacac    4260
agaccgtgag atgaaggtgc aggacatccc tacgggcgca gacagctgtg tgacgagtct    4320
gtcctgtgat tcccaccgct cactcatcgt ggctggcctc ggtgacggct ccatccgcgt    4380
ctacgacaga aggatggcac tcagcgaatg ccgcgtcatg acgtaccggg agcacacagc    4440
ctgggtggtg aaggcctccc tgcagaagcg tcccgacggc cacatcgtga gtgtgagcgt    4500
caatggagat gtgcgcatct ttgatccccg gatgcctgag tcggtaaatg tgcttcagat    4560
```

```
cgtgaagggg ctgacggccc tggacatcca cccccaggcg gacctgatcg catgtggctc    4620
cgtcaatcag ttcaccgcca tctacaacag cagcggagag ctcatcaaca acatcaagta    4680
ctacgacggc ttcatgggcc agcgggtcgg cgccatcagc tgcctggcct tccacccgca    4740
ctggcctcac ctggccgtgg gaagcaacga ctactacatc tccgtgtact cggtggagaa    4800
gcgtgtcaga tagcggcgtg acccgggccc accaggccac ggccgcctgc tgtacatagt    4860
gaagctgtca ctcgccgggg cacggggcgt cggctgctgc ggccccgcag tgtgaacgtt    4920
ggctgctgcc ttagctgctg atgacggcag gagggccctg ctactcgctt ttgtctgtct    4980
tcgctgtcgt gtctggaatg tcagggaagg ggagggctcg ggttgacggt ggcttcccac    5040
tgagcaccag catccaggtg caccccgcg gccacggcgc ctctgtccct tcctgttct     5100 gtgtttctct gagacgctga aaggggaaac acctcacttt atttccatgt aatcagagca    5160
ttagctgcag aaaaacccccc cgacagagcc ctggcggaga ggcaggcgct ggggctccta    5220
cgggtccctg gggcagctgt ccccatcagg ccaagagcga gcgagaggcg ctgccccagc    5280
caggcccacc acctctcaca gtcagtgcac gcaagcaggg acatttccta gccagctggg    5340
ggacactgga aattcgggaa accaagagag aggaagaagg agacgcccct ccaactggcg    5400
ggtgtgaagg aagccgccca ggggtccggg ctgtccttgg ccgctggcag catcactgag    5460
caggaagcgc acagcccacc ctccccgcac ctccaggtct ctggactcca gttttgccc     5520 ctctcacaca gagctgtcag caggggccgc tgtggcggtg cacaggggag gcaggtcctt    5580
ggcgaggtag cccctgcctt aatccacggg gctcctttcc ctccgaaggg ctgctcttcc    5640
ccacaggcgc ggggacagca gcccgacctg tggtctccat gcctgtgccc tcacacaggt    5700
gtagcacacg catgtgcaga tggcaccacg gccggcacct gggggcacac acatgcaggc    5760
ggcgtggtct ccctgctctg tccccacacg ttcctcacat acaggcaaga ggcactgccg    5820
ggtcccggac ggctccgggt gacaccagcc ccgtctccag ccttgagccg cccatgctga    5880
tgcgacctcg gctgacagct gggcctgtgg tgcagacagg agctgtgtgg acagtcccgc    5940
ccaggagggg ccgcagggcg tgtatgagca gttttgcaaa cagaacacaa ccacaatgat    6000
ggtattttga aaagtgttct ttccgtgttc gtcgggaatc aggattattg agaggtgaag    6060
gagccaggtg gcttcattct ggcggtgaga ggcccacgac cacgggagtg agagctggtg    6120
tggcgaggcc cggctctcct gcggtgtggc tggtggcctg ccgtggccaa gagcatcttc    6180
tgggtggatg gaaccctgcc tggtcacatt tggccagaga cacacctggc cctcaggggg    6240
ctgagctgga gactgagctg gggctggccg ggacgtgaca aggcaggaca gaggcggccc    6300
ctccgctgct ccttttttgga atgcgagctc ccaccagaag aaggttccgg cacgaatccc    6360
atccccacgt ctgggccgag aaagcagccc gggtccggaa ggtgtagaga gtcccggcct    6420
cactcagctc acagggcgtg ccaggcggca acaccagaat cttccagaag cccagctcca    6480
cccgcacacg cagcttccca tccagtcctt caactcaatt cttacccaac acgcgtttct    6540
gtttgttttg agacaaaatc accacctgtc aaaaggcagg tggctccaga ggggtcaaga    6600 ccccccccccg ccccgctcc accctggagc ccacccccat gggcaccgcg tgccgcctgc    6660
acgtgggctg tcttcacagg tctgatgtga aaattcaatc acgacgttaa ccggctcgag    6720
agagcgccgg cctagaggct cattatctat ttattttacc aaacgcgaat tgagacggac    6780
tttgacaaaa cacgaaatgg taatgtgaag ctaagagcag agagtgacca acagtaaaca    6840
acacgcgcag actccg                                                   6856
```

```
<210> SEQ ID NO 28
<211> LENGTH: 1177
<212> TYPE: PRT
<213> ORGANISM: Homo sapiens

<400> SEQUENCE: 28

Met Glu Ser Glu Met Leu Gln Ser Pro Leu Leu Gly Leu Gly Glu Glu
1               5                   10                  15

Asp Glu Ala Asp Leu Thr Asp Trp Asn Leu Pro Leu Ala Phe Met Lys
            20                  25                  30

Lys Arg His Cys Glu Lys Ile Glu Gly Ser Lys Ser Leu Ala Gln Ser
        35                  40                  45

Trp Arg Met Lys Asp Arg Met Lys Thr Val Ser Val Ala Leu Val Leu
    50                  55                  60

Cys Leu Asn Val Gly Val Asp Pro Pro Asp Val Val Lys Thr Thr Pro
65                  70                  75                  80

Cys Ala Arg Leu Glu Cys Trp Ile Asp Pro Leu Ser Met Gly Pro Gln
                85                  90                  95

Lys Ala Leu Glu Thr Ile Gly Ala Asn Leu Gln Lys Gln Tyr Glu Asn
            100                 105                 110

Trp Gln Pro Arg Ala Arg Tyr Lys Gln Ser Leu Asp Pro Thr Val Asp
        115                 120                 125

Glu Val Lys Lys Leu Cys Thr Ser Leu Arg Arg Asn Ala Lys Glu Glu
130                 135                 140

Arg Val Leu Phe His Tyr Asn Gly His Gly Val Pro Arg Pro Thr Val
145                 150                 155                 160

Asn Gly Glu Val Trp Val Phe Asn Lys Asn Tyr Thr Gln Tyr Ile Pro
                165                 170                 175

Leu Ser Ile Tyr Asp Leu Gln Thr Trp Met Gly Ser Pro Ser Ile Phe
            180                 185                 190

Val Tyr Asp Cys Ser Asn Ala Gly Leu Ile Val Lys Ser Phe Lys Gln
        195                 200                 205

Phe Ala Leu Gln Arg Glu Gln Glu Leu Glu Val Ala Ala Ile Asn Pro
    210                 215                 220

Asn His Pro Leu Ala Gln Met Pro Leu Pro Pro Ser Met Lys Asn Cys
225                 230                 235                 240

Ile Gln Leu Ala Ala Cys Glu Ala Thr Glu Leu Leu Pro Met Ile Pro
                245                 250                 255

Asp Leu Pro Ala Asp Leu Phe Thr Ser Cys Leu Thr Thr Pro Ile Lys
            260                 265                 270

Ile Ala Leu Arg Trp Phe Cys Met Gln Lys Cys Val Ser Leu Val Pro
        275                 280                 285

Gly Val Thr Leu Asp Leu Ile Glu Lys Ile Pro Gly Arg Leu Asn Asp
    290                 295                 300

Arg Arg Thr Pro Leu Gly Glu Leu Asn Trp Ile Phe Thr Ala Ile Thr
305                 310                 315                 320

Asp Thr Ile Ala Trp Asn Val Leu Pro Arg Asp Leu Phe Gln Lys Leu
                325                 330                 335

Phe Arg Gln Asp Leu Leu Val Ala Ser Leu Phe Arg Asn Phe Leu Leu
            340                 345                 350

Ala Glu Arg Ile Met Arg Ser Tyr Asn Cys Thr Pro Val Ser Ser Pro
        355                 360                 365

Arg Leu Pro Pro Thr Tyr Met His Ala Met Trp Gln Ala Trp Asp Leu
    370                 375                 380
```

```
Ala Val Asp Ile Cys Leu Ser Gln Leu Pro Thr Ile Ile Glu Glu Gly
385                 390                 395                 400

Thr Ala Phe Arg His Ser Pro Phe Phe Ala Glu Gln Leu Thr Ala Phe
            405                 410                 415

Gln Val Trp Leu Thr Met Gly Val Glu Asn Arg Asn Pro Pro Glu Gln
        420                 425                 430

Leu Pro Ile Val Leu Gln Val Leu Leu Ser Gln Val His Arg Leu Arg
                435                 440                 445

Ala Leu Asp Leu Leu Gly Arg Phe Leu Asp Leu Gly Pro Trp Ala Val
    450                 455                 460

Ser Leu Ala Leu Ser Val Gly Ile Phe Pro Tyr Val Leu Lys Leu Leu
465                 470                 475                 480

Gln Ser Ser Ala Arg Glu Leu Arg Pro Leu Leu Val Phe Ile Trp Ala
            485                 490                 495

Lys Ile Leu Ala Val Asp Ser Glu Leu Val Val Ala Leu Ser His Leu
        500                 505                 510

Val Val Gln Tyr Glu Ser Asn Phe Cys Thr Val Ala Leu Gln Phe Ile
        515                 520                 525

Glu Glu Glu Lys Asn Tyr Ala Leu Pro Ser Pro Ala Thr Thr Glu Gly
    530                 535                 540

Gly Ser Leu Thr Pro Val Arg Asp Ser Pro Cys Thr Pro Arg Leu Arg
545                 550                 555                 560

Ser Val Ser Ser Tyr Gly Asn Ile Arg Ala Val Ala Thr Ala Arg Ser
            565                 570                 575

Leu Asn Lys Ser Leu Gln Asn Leu Ser Leu Thr Glu Glu Ser Gly Gly
        580                 585                 590

Ala Val Ala Phe Ser Pro Gly Asn Leu Ser Thr Ser Ser Ser Ala Ser
    595                 600                 605

Ser Thr Leu Gly Ser Pro Glu Asn Glu Glu His Ile Leu Ser Phe Glu
610                 615                 620

Thr Ile Asp Lys Met Arg Arg Ala Ser Ser Tyr Ser Ser Leu Asn Ser
625                 630                 635                 640

Leu Ile Gly Val Ser Phe Asn Ser Val Tyr Thr Gln Ile Trp Arg Val
            645                 650                 655

Leu Leu His Leu Ala Ala Asp Pro Tyr Pro Glu Val Ser Asp Val Ala
        660                 665                 670

Met Lys Val Leu Asn Ser Ile Ala Tyr Lys Ala Thr Val Asn Ala Arg
        675                 680                 685

Pro Gln Arg Val Leu Asp Thr Ser Ser Leu Thr Gln Ser Ala Pro Ala
    690                 695                 700

Ser Pro Thr Asn Lys Gly Val His Ile His Gln Ala Gly Gly Ser Pro
705                 710                 715                 720

Pro Ala Ser Ser Thr Ser Ser Ser Leu Thr Asn Asp Val Ala Lys
            725                 730                 735

Gln Pro Val Ser Arg Asp Leu Pro Ser Gly Arg Pro Gly Thr Thr Gly
            740                 745                 750

Pro Ala Gly Ala Gln Tyr Thr Pro His Ser His Gln Phe Pro Arg Thr
            755                 760                 765

Arg Lys Met Phe Asp Lys Gly Pro Glu Gln Thr Ala Asp Asp Ala Asp
        770                 775                 780

Asp Ala Ala Gly His Lys Ser Phe Ile Ser Ala Thr Val Gln Thr Gly
785                 790                 795                 800

Phe Cys Asp Trp Ser Ala Arg Tyr Phe Ala Gln Pro Val Met Lys Ile
```

```
                805                 810                 815
Pro Glu Glu His Asp Leu Glu Ser Gln Ile Arg Lys Glu Arg Glu Trp
            820                 825                 830

Arg Phe Leu Arg Asn Ser Arg Val Arg Arg Gln Ala Gln Gln Val Ile
            835                 840                 845

Gln Lys Gly Ile Thr Arg Leu Asp Asp Gln Ile Phe Leu Asn Arg Asn
    850                 855                 860

Pro Gly Val Pro Ser Val Val Lys Phe His Pro Phe Thr Pro Cys Ile
865                 870                 875                 880

Ala Val Ala Asp Lys Asp Ser Ile Cys Phe Trp Asp Trp Lys Gly
                885                 890                 895

Glu Lys Leu Asp Tyr Phe His Asn Gly Asn Pro Arg Tyr Thr Arg Val
            900                 905                 910

Thr Ala Met Glu Tyr Leu Asn Gly Gln Asp Cys Ser Leu Leu Leu Thr
            915                 920                 925

Ala Thr Asp Asp Gly Ala Ile Arg Val Trp Lys Asn Phe Ala Asp Leu
    930                 935                 940

Glu Lys Asn Pro Glu Met Val Thr Ala Trp Gln Gly Leu Ser Asp Met
945                 950                 955                 960

Leu Pro Thr Thr Arg Gly Ala Gly Met Val Val Asp Trp Glu Gln Glu
                965                 970                 975

Thr Gly Leu Leu Met Ser Ser Gly Asp Val Arg Ile Val Arg Ile Trp
            980                 985                 990

Asp Thr Asp Arg Glu Met Lys Val Gln Asp Ile Pro Thr Gly Ala Asp
            995                 1000                 1005

Ser Cys Val Thr Ser Leu Ser Cys Asp Ser His Arg Ser Leu Ile
    1010                1015                1020

Val Ala Gly Leu Gly Asp Gly Ser Ile Arg Val Tyr Asp Arg Arg
    1025                1030                1035

Met Ala Leu Ser Glu Cys Arg Val Met Thr Tyr Arg Glu His Thr
    1040                1045                1050

Ala Trp Val Val Lys Ala Ser Leu Gln Lys Arg Pro Asp Gly His
    1055                1060                1065

Ile Val Ser Val Ser Val Asn Gly Asp Val Arg Ile Phe Asp Pro
    1070                1075                1080

Arg Met Pro Glu Ser Val Asn Val Leu Gln Ile Val Lys Gly Leu
    1085                1090                1095

Thr Ala Leu Asp Ile His Pro Gln Ala Asp Leu Ile Ala Cys Gly
    1100                1105                1110

Ser Val Asn Gln Phe Thr Ala Ile Tyr Asn Ser Ser Gly Glu Leu
    1115                1120                1125

Ile Asn Asn Ile Lys Tyr Tyr Asp Gly Phe Met Gly Gln Arg Val
    1130                1135                1140

Gly Ala Ile Ser Cys Leu Ala Phe His Pro His Trp Pro His Leu
    1145                1150                1155

Ala Val Gly Ser Asn Asp Tyr Tyr Ile Ser Val Tyr Ser Val Glu
    1160                1165                1170

Lys Arg Val Arg
    1175

<210> SEQ ID NO 29
<211> LENGTH: 1335
<212> TYPE: PRT
<213> ORGANISM: Homo sapiens
```

```
<400> SEQUENCE: 29

Met Glu Ser Glu Met Leu Gln Ser Pro Leu Leu Gly Leu Gly Glu Glu
1               5                   10                  15

Asp Glu Ala Asp Leu Thr Asp Trp Asn Leu Pro Leu Ala Phe Met Lys
            20                  25                  30

Lys Arg His Cys Glu Lys Ile Glu Gly Ser Lys Ser Leu Ala Gln Ser
        35                  40                  45

Trp Arg Met Lys Asp Arg Met Lys Thr Val Ser Val Ala Leu Val Leu
    50                  55                  60

Cys Leu Asn Val Gly Val Asp Pro Pro Asp Val Val Lys Thr Thr Pro
65                  70                  75                  80

Cys Ala Arg Leu Glu Cys Trp Ile Asp Pro Leu Ser Met Gly Pro Gln
                85                  90                  95

Lys Ala Leu Glu Thr Ile Gly Ala Asn Leu Gln Lys Gln Tyr Glu Asn
            100                 105                 110

Trp Gln Pro Arg Ala Arg Tyr Lys Gln Ser Leu Asp Pro Thr Val Asp
        115                 120                 125

Glu Val Lys Lys Leu Cys Thr Ser Leu Arg Arg Asn Ala Lys Glu Glu
130                 135                 140

Arg Val Leu Phe His Tyr Asn Gly His Gly Val Pro Arg Pro Thr Val
145                 150                 155                 160

Asn Gly Glu Val Trp Val Phe Asn Lys Asn Tyr Thr Gln Tyr Ile Pro
                165                 170                 175

Leu Ser Ile Tyr Asp Leu Gln Thr Trp Met Gly Ser Pro Ser Ile Phe
            180                 185                 190

Val Tyr Asp Cys Ser Asn Ala Gly Leu Ile Val Lys Ser Phe Lys Gln
        195                 200                 205

Phe Ala Leu Gln Arg Glu Gln Glu Leu Glu Val Ala Ala Ile Asn Pro
210                 215                 220

Asn His Pro Leu Ala Gln Met Pro Leu Pro Pro Ser Met Lys Asn Cys
225                 230                 235                 240

Ile Gln Leu Ala Ala Cys Glu Ala Thr Glu Leu Leu Pro Met Ile Pro
                245                 250                 255

Asp Leu Pro Ala Asp Leu Phe Thr Ser Cys Leu Thr Thr Pro Ile Lys
            260                 265                 270

Ile Ala Leu Arg Trp Phe Cys Met Gln Lys Cys Val Ser Leu Val Pro
        275                 280                 285

Gly Val Thr Leu Asp Leu Ile Glu Lys Ile Pro Gly Arg Leu Asn Asp
290                 295                 300

Arg Arg Thr Pro Leu Gly Glu Leu Asn Trp Ile Phe Thr Ala Ile Thr
305                 310                 315                 320

Asp Thr Ile Ala Trp Asn Val Leu Pro Arg Asp Leu Phe Gln Lys Leu
                325                 330                 335

Phe Arg Gln Asp Leu Leu Val Ala Ser Leu Phe Arg Asn Phe Leu Leu
            340                 345                 350

Ala Glu Arg Ile Met Arg Ser Tyr Asn Cys Thr Pro Val Ser Ser Pro
        355                 360                 365

Arg Leu Pro Pro Thr Tyr Met His Ala Met Trp Gln Ala Trp Asp Leu
370                 375                 380

Ala Val Asp Ile Cys Leu Ser Gln Leu Pro Thr Ile Ile Glu Glu Gly
385                 390                 395                 400

Thr Ala Phe Arg His Ser Pro Phe Phe Ala Glu Gln Leu Thr Ala Phe
```

-continued

```
                405                 410                 415
Gln Val Trp Leu Thr Met Gly Val Glu Asn Arg Asn Pro Pro Glu Gln
            420                 425                 430
Leu Pro Ile Val Leu Gln Val Leu Ser Gln Val His Arg Leu Arg
        435                 440                 445
Ala Leu Asp Leu Leu Gly Arg Phe Leu Asp Leu Gly Pro Trp Ala Val
    450                 455                 460
Ser Leu Ala Leu Ser Val Gly Ile Phe Pro Tyr Val Leu Lys Leu Leu
465                 470                 475                 480
Gln Ser Ser Ala Arg Glu Leu Arg Pro Leu Leu Val Phe Ile Trp Ala
                485                 490                 495
Lys Ile Leu Ala Val Asp Ser Ser Cys Gln Ala Asp Leu Val Lys Asp
            500                 505                 510
Asn Gly His Lys Tyr Phe Leu Ser Val Leu Ala Asp Pro Tyr Met Pro
        515                 520                 525
Ala Glu His Arg Thr Met Thr Ala Phe Ile Leu Ala Val Ile Val Asn
    530                 535                 540
Ser Tyr His Thr Gly Gln Glu Ala Cys Leu Gln Gly Asn Leu Ile Ala
545                 550                 555                 560
Ile Cys Leu Glu Gln Leu Asn Asp Pro His Pro Leu Leu Arg Gln Trp
                565                 570                 575
Val Ala Ile Cys Leu Gly Arg Ile Trp Gln Asn Phe Asp Ser Ala Arg
            580                 585                 590
Trp Cys Gly Val Arg Asp Ser Ala His Glu Lys Leu Tyr Ser Leu Leu
        595                 600                 605
Ser Asp Pro Ile Pro Glu Val Arg Cys Ala Ala Val Phe Ala Leu Gly
    610                 615                 620
Thr Phe Val Gly Asn Ser Ala Glu Arg Thr Asp His Ser Thr Thr Ile
625                 630                 635                 640
Asp His Asn Val Ala Met Met Leu Ala Gln Leu Val Ser Asp Gly Ser
                645                 650                 655
Pro Met Val Arg Lys Glu Leu Val Val Ala Leu Ser His Leu Val Val
            660                 665                 670
Gln Tyr Glu Ser Asn Phe Cys Thr Val Ala Leu Gln Phe Ile Glu Glu
        675                 680                 685
Glu Lys Asn Tyr Ala Leu Pro Ser Pro Ala Thr Thr Glu Gly Gly Ser
    690                 695                 700
Leu Thr Pro Val Arg Asp Ser Pro Cys Thr Pro Arg Leu Arg Ser Val
705                 710                 715                 720
Ser Ser Tyr Gly Asn Ile Arg Ala Val Ala Thr Ala Arg Ser Leu Asn
                725                 730                 735
Lys Ser Leu Gln Asn Leu Ser Leu Thr Glu Ser Gly Gly Ala Val
            740                 745                 750
Ala Phe Ser Pro Gly Asn Leu Ser Thr Ser Ser Ala Ser Ser Thr
        755                 760                 765
Leu Gly Ser Pro Glu Asn Glu Glu His Ile Leu Ser Phe Glu Thr Ile
    770                 775                 780
Asp Lys Met Arg Arg Ala Ser Ser Tyr Ser Ser Leu Asn Ser Leu Ile
785                 790                 795                 800
Gly Val Ser Phe Asn Ser Val Tyr Thr Gln Ile Trp Arg Val Leu Leu
                805                 810                 815
His Leu Ala Ala Asp Pro Tyr Pro Glu Val Ser Asp Val Ala Met Lys
            820                 825                 830
```

```
Val Leu Asn Ser Ile Ala Tyr Lys Ala Thr Val Asn Ala Arg Pro Gln
        835                 840                 845

Arg Val Leu Asp Thr Ser Ser Leu Thr Gln Ser Ala Pro Ala Ser Pro
    850                 855                 860

Thr Asn Lys Gly Val His Ile His Gln Ala Gly Gly Ser Pro Pro Ala
865                 870                 875                 880

Ser Ser Thr Ser Ser Ser Leu Thr Asn Asp Val Ala Lys Gln Pro
                885                 890                 895

Val Ser Arg Asp Leu Pro Ser Gly Arg Pro Gly Thr Thr Gly Pro Ala
        900                 905                 910

Gly Ala Gln Tyr Thr Pro His Ser His Gln Phe Pro Arg Thr Arg Lys
        915                 920                 925

Met Phe Asp Lys Gly Pro Glu Gln Thr Ala Asp Ala Asp Ala
    930                 935                 940

Ala Gly His Lys Ser Phe Ile Ser Ala Thr Val Gln Thr Gly Phe Cys
945                 950                 955                 960

Asp Trp Ser Ala Arg Tyr Phe Ala Gln Pro Val Met Lys Ile Pro Glu
                965                 970                 975

Glu His Asp Leu Glu Ser Gln Ile Arg Lys Glu Arg Glu Trp Arg Phe
            980                 985                 990

Leu Arg Asn Ser Arg Val Arg Arg  Gln Ala Gln Gln Val  Ile Gln Lys
        995                 1000                1005

Gly Ile  Thr Arg Leu Asp Asp  Gln Ile Phe Leu Asn  Arg Asn Pro
    1010            1015                1020

Gly Val  Pro Ser Val Val Lys  Phe His Pro Phe Thr  Pro Cys Ile
    1025            1030                1035

Ala Val  Ala Asp Lys Asp Ser  Ile Cys Phe Trp Asp  Trp Glu Lys
    1040            1045                1050

Gly Glu  Lys Leu Asp Tyr Phe  His Asn Gly Asn Pro  Arg Tyr Thr
    1055            1060                1065

Arg Val  Thr Ala Met Glu Tyr  Leu Asn Gly Gln Asp  Cys Ser Leu
    1070            1075                1080

Leu Leu  Thr Ala Thr Asp Asp  Gly Ala Ile Arg Val  Trp Lys Asn
    1085            1090                1095

Phe Ala  Asp Leu Glu Lys Asn  Pro Glu Met Val Thr  Ala Trp Gln
    1100            1105                1110

Gly Leu  Ser Asp Met Leu Pro  Thr Thr Arg Gly Ala  Gly Met Val
    1115            1120                1125

Val Asp  Trp Glu Gln Glu Thr  Gly Leu Leu Met Ser  Ser Gly Asp
    1130            1135                1140

Val Arg  Ile Val Arg Ile Trp  Asp Thr Asp Arg Glu  Met Lys Val
    1145            1150                1155

Gln Asp  Ile Pro Thr Gly Ala  Asp Ser Cys Val Thr  Ser Leu Ser
    1160            1165                1170

Cys Asp  Ser His Arg Ser Leu  Ile Val Ala Gly Leu  Gly Asp Gly
    1175            1180                1185

Ser Ile  Arg Val Tyr Asp Arg  Arg Met Ala Leu Ser  Glu Cys Arg
    1190            1195                1200

Val Met  Thr Tyr Arg Glu His  Thr Ala Trp Val Val  Lys Ala Ser
    1205            1210                1215

Leu Gln  Lys Arg Pro Asp Gly  His Ile Val Ser Val  Ser Val Asn
    1220            1225                1230
```

```
Gly Asp Val Arg Ile Phe Asp Pro Arg Met Pro Glu Ser Val Asn
    1235                1240                1245

Val Leu Gln Ile Val Lys Gly Leu Thr Ala Leu Asp Ile His Pro
    1250                1255                1260

Gln Ala Asp Leu Ile Ala Cys Gly Ser Val Asn Gln Phe Thr Ala
    1265                1270                1275

Ile Tyr Asn Ser Ser Gly Glu Leu Ile Asn Asn Ile Lys Tyr Tyr
    1280                1285                1290

Asp Gly Phe Met Gly Gln Arg Val Gly Ala Ile Ser Cys Leu Ala
    1295                1300                1305

Phe His Pro His Trp Pro His Leu Ala Val Gly Ser Asn Asp Tyr
    1310                1315                1320

Tyr Ile Ser Val Tyr Ser Val Glu Lys Arg Val Arg
    1325                1330                1335

<210> SEQ ID NO 30
<211> LENGTH: 1555
<212> TYPE: DNA
<213> ORGANISM: Homo sapiens

<400> SEQUENCE: 30
```

| | | |
|---|---|---|
| atcccggaag gaccggtgtc taggtcaccc tggagcgctc accccaccgg cacccgtgcc | 60 |
| caagcccgcc cctgcaaagg caggcaaggc caggcgggtg ctgcctggga cccagtgact | 120 |
| cagcacccct gcccggatca actggacttt gcccctgc tccgccagcc tcctgcttgg | 180 |
| atctctcctg ggtctccctg ctgcgcctgt ccaggatgca gggagctcgg gctcccaggg | 240 |
| accagggccg gtcccccggc aggatgagcg ctctaggccg gtcctcggtc atcttgctta | 300 |
| cctacgtgct ggccgccaca gaacttacct gcctcttcat gcagttctcc atcgtgccat | 360 |
| acctgtctcg gaaactgggc ctggattcca ttgccttcgg ctacctgcaa accaccttcg | 420 |
| gggtgctgca gctgctgggc gggccggtat ttggcaggtt cgcagaccag cgcggggcgc | 480 |
| gggcggcgct cacgctctcc ttcctggctg ccttggcgct ctacctgctc ctggcggccg | 540 |
| cctccagccc ggccctgccc ggggtctacc tgctcttcgc ctcgcgcctg cccggagcgc | 600 |
| tcatgcacac gctgccagcc gcccagatgg tcatcacgga cctgtcggca cccgaggagc | 660 |
| ggcccgcggc cctgggccgg ctgggcctct gcttcggcgt cggagtcatc ctcggctccc | 720 |
| tgctgggcgg gaccctggtc tccgcgtacg ggattcagtg cccggccatc ctggctgccc | 780 |
| tggccaccct cctgggagct gtcctcagct tcacctgcat cccgccagc accaagggg | 840 |
| ccaaaactga cgcccaggct ccactgccag gcggcccccg ggccagtgtg ttcgacctga | 900 |
| aggccatcgc ctccctgctg cggctgccag acgtcccgag gatcttcctg gtgaaggtgg | 960 |
| cctccaactg ccccacaggg ctcttcatgg tcatgttctc catcatctcc atggacttct | 1020 |
| tccagctgga ggccgcccaa gctggctacc tcatgtcctt cttcgggctc ctccagatgg | 1080 |
| tgacccaggg cctggtcatc gggcagctga gcagccactt ctcggaggag gtgctgctcc | 1140 |
| gggccagcgt gctggtcttc atcgtggtgg gcctggccat ggcctggatg tccagcgtct | 1200 |
| tccacttctg cctcctggtg cccggcctgg tgttcagcct ctgcaccctc aacgtggtca | 1260 |
| ccgacagcat gctgatcaag gctgtctcca cctcggacac agggaccatg ctgggcctct | 1320 |
| gcgcctctgt acaaccactg ctccgaactc tgggaccac ggtcggcggc ctcctgtacc | 1380 |
| gcagctttgg cgtccccgtc ttcggccacg tgcaggttgc tatcaatacc cttgtcctcc | 1440 |
| tggtcctctg gaggaaacct atgccccaga ggaaggacaa agtccggtga ccgctgccca | 1500 |

```
gacacagact ggcaataaac tcctactaaa tccctccgaa aaaaaaaaaa aaaaa        1555
```

<210> SEQ ID NO 31
<211> LENGTH: 1563
<212> TYPE: DNA
<213> ORGANISM: Homo sapiens

<400> SEQUENCE: 31

```
gacaaaaaaa aaggtctctc cgatttcctc tgctcaacca gttccctggc tacctgaggc      60
cctgcttcac ctggaggaag acagtggcaa ggccaggcgg gtgctgcctg ggacccagtg     120
actcagcacc cctgcccgga tcaactggac ttttgccccc tgctccgcca gcctcctgct     180
tggatctctc ctgggtctcc ctgctgcgcc tgtccaggat gcaggagct cgggctccca      240
gggaccaggg ccgtcccccc ggcaggatga gcgctctagg ccgtcctcg gtcatcttgc      300
ttacctacgt gctggccgcc acagaactta cctgcctctt catgcagttc tccatcgtgc     360
catacctgtc tcggaaactg ggcctggatt ccattgcctt cggctacctg caaaccacct     420
tcggggtgct gcagctgctg ggcgggccgg tatttggcag gttcgcagac cagcgcgggg     480
cgcgggcggc gctcacgctc tccttcctgg ctgccttggc gctctacctg ctcctggcgg     540
ccgcctccag cccggccctg ccggggtct acctgctctt cgcctcgcgc ctgcccggag      600
cgctcatgca cacgctgcca gccgcccaga tggtcatcac ggacctgtcg gcacccgagg     660
agcggccccgc ggccctgggc cggctgggcc tctgcttcgg cgtcggagtc atcctcggct     720
ccctgctggg cgggaccctg gtctccgcgt acgggattca gtgcccggcc atcctggctg     780
ccctggccac cctcctggga gctgtcctca gcttcacctg catccccgcc agcaccaaag     840
gggccaaaac tgacgcccag gctccactgc caggcggccc ccgggccagt gtgttcgacc     900
tgaaggccat cgcctcccctg ctgcggctgc cagacgtccc gaggatcttc ctggtgaagg     960
tggcctccaa ctgccccaca gggctcttca tggtcatgtt ctccatcatc tccatggact    1020
tcttccagct ggaggccgcc caagctggct acctcatgtc cttcttcggg ctcctccaga    1080
tggtgaccca gggcctggtc atcgggcagc tgagcagcca cttctcggag gaggtgctgc    1140
tccgggccag cgtgctggtc ttcatcgtgg tgggcctggc catggcctgg atgtccagcg    1200
tcttccactt ctgcctcctg gtgcccggcc tggtgttcag cctctgcacc ctcaacgtgg    1260
tcaccgacag catgctgatc aaggctgtct ccacctcgga cacagggacc atgctgggcc    1320
tctgcgcctc tgtacaacca ctgctccgaa ctctgggacc cacggtcggc ggcctcctgt    1380
accgcagctt ggcgtccccc gtcttcggcc acgtgcaggt tgctatcaat accccttgtcc    1440
tcctggtcct ctggaggaaa cctatgcccc agaggaagga caaagtccgg tgaccgctgc    1500
ccagacacag actggcaata aactcctact aaatccctcc gaaaaaaaaa aaaaaaaaa     1560
aaa                                                                  1563
```

<210> SEQ ID NO 32
<211> LENGTH: 424
<212> TYPE: PRT
<213> ORGANISM: Homo sapiens

<400> SEQUENCE: 32

```
Met Gln Gly Ala Arg Ala Pro Arg Asp Gln Gly Arg Ser Pro Gly Arg
1               5                   10                  15

Met Ser Ala Leu Gly Arg Ser Ser Val Ile Leu Leu Thr Tyr Val Leu
            20                  25                  30

Ala Ala Thr Glu Leu Thr Cys Leu Phe Met Gln Phe Ser Ile Val Pro
```

```
                35                  40                  45
Tyr Leu Ser Arg Lys Leu Gly Leu Asp Ser Ile Ala Phe Gly Tyr Leu
 50                  55                  60

Gln Thr Thr Phe Gly Val Leu Gln Leu Leu Gly Pro Val Phe Gly
 65                  70                  75                  80

Arg Phe Ala Asp Gln Arg Gly Ala Arg Ala Leu Thr Leu Ser Phe
                 85                  90                  95

Leu Ala Ala Leu Ala Leu Tyr Leu Leu Ala Ala Ser Ser Pro
                100                 105                 110

Ala Leu Pro Gly Val Tyr Leu Leu Phe Ala Ser Arg Leu Pro Gly Ala
                115                 120                 125

Leu Met His Thr Leu Pro Ala Ala Gln Met Val Ile Thr Asp Leu Ser
130                 135                 140

Ala Pro Glu Glu Arg Pro Ala Ala Leu Gly Arg Leu Gly Leu Cys Phe
145                 150                 155                 160

Gly Val Gly Val Ile Leu Gly Ser Leu Leu Gly Gly Thr Leu Val Ser
                165                 170                 175

Ala Tyr Gly Ile Gln Cys Pro Ala Ile Leu Ala Ala Leu Ala Thr Leu
                180                 185                 190

Leu Gly Ala Val Leu Ser Phe Thr Cys Ile Pro Ala Ser Thr Lys Gly
                195                 200                 205

Ala Lys Thr Asp Ala Gln Ala Pro Leu Pro Gly Gly Pro Arg Ala Ser
210                 215                 220

Val Phe Asp Leu Lys Ala Ile Ala Ser Leu Leu Arg Leu Pro Asp Val
225                 230                 235                 240

Pro Arg Ile Phe Leu Val Lys Val Ala Ser Asn Cys Pro Thr Gly Leu
                245                 250                 255

Phe Met Val Met Phe Ser Ile Ile Ser Met Asp Phe Gln Leu Glu
                260                 265                 270

Ala Ala Gln Ala Gly Tyr Leu Met Ser Phe Phe Gly Leu Leu Gln Met
                275                 280                 285

Val Thr Gln Gly Leu Val Ile Gly Gln Leu Ser Ser His Phe Ser Glu
290                 295                 300

Glu Val Leu Leu Arg Ala Ser Val Leu Val Phe Ile Val Val Gly Leu
305                 310                 315                 320

Ala Met Ala Trp Met Ser Ser Val Phe His Phe Cys Leu Leu Val Pro
                325                 330                 335

Gly Leu Val Phe Ser Leu Cys Thr Leu Asn Val Val Thr Asp Ser Met
                340                 345                 350

Leu Ile Lys Ala Val Ser Thr Ser Asp Thr Gly Thr Met Leu Gly Leu
                355                 360                 365

Cys Ala Ser Val Gln Pro Leu Leu Arg Thr Leu Gly Pro Thr Val Gly
                370                 375                 380

Gly Leu Leu Tyr Arg Ser Phe Gly Val Pro Val Phe Gly His Val Gln
385                 390                 395                 400

Val Ala Ile Asn Thr Leu Val Leu Leu Val Leu Trp Arg Lys Pro Met
                405                 410                 415

Pro Gln Arg Lys Asp Lys Val Arg
                420

<210> SEQ ID NO 33
<211> LENGTH: 855
<212> TYPE: PRT
<213> ORGANISM: Homo sapiens
```

<400> SEQUENCE: 33

```
Gln Ser Ser Ala Arg Glu Leu Arg Pro Leu Leu Val Phe Ile Trp Ala
1               5                   10                  15

Lys Ile Leu Ala Val Asp Ser Ser Cys Gln Ala Asp Leu Val Lys Asp
            20                  25                  30

Asn Gly His Lys Tyr Phe Leu Ser Val Leu Ala Asp Pro Tyr Met Pro
        35                  40                  45

Ala Glu His Arg Thr Met Thr Ala Phe Ile Leu Ala Val Ile Val Asn
    50                  55                  60

Ser Tyr His Thr Gly Gln Glu Ala Cys Leu Gln Gly Asn Leu Ile Ala
65                  70                  75                  80

Ile Cys Leu Glu Gln Leu Asn Asp Pro His Pro Leu Leu Arg Gln Trp
                85                  90                  95

Val Ala Ile Cys Leu Gly Arg Ile Trp Gln Asn Phe Asp Ser Ala Arg
            100                 105                 110

Trp Cys Gly Val Arg Asp Ser Ala His Glu Lys Leu Tyr Ser Leu Leu
        115                 120                 125

Ser Asp Pro Ile Pro Glu Val Arg Cys Ala Ala Val Phe Ala Leu Gly
    130                 135                 140

Thr Phe Val Gly Asn Ser Ala Glu Arg Thr Asp His Ser Thr Thr Ile
145                 150                 155                 160

Asp His Asn Val Ala Met Met Leu Ala Gln Leu Val Ser Asp Gly Ser
                165                 170                 175

Pro Met Val Arg Lys Glu Leu Val Val Ala Leu Ser His Leu Val Val
            180                 185                 190

Gln Tyr Glu Ser Asn Phe Cys Thr Val Ala Leu Gln Phe Ile Glu Glu
        195                 200                 205

Glu Lys Asn Tyr Ala Leu Pro Ser Pro Ala Thr Thr Glu Gly Gly Ser
    210                 215                 220

Leu Thr Pro Val Arg Asp Ser Pro Cys Thr Pro Arg Leu Arg Ser Val
225                 230                 235                 240

Ser Ser Tyr Gly Asn Ile Arg Ala Val Ala Thr Ala Arg Ser Leu Asn
                245                 250                 255

Lys Ser Leu Gln Asn Leu Ser Leu Thr Glu Glu Ser Gly Gly Ala Val
            260                 265                 270

Ala Phe Ser Pro Gly Asn Leu Ser Thr Ser Ser Ala Ser Ser Thr
        275                 280                 285

Leu Gly Ser Pro Glu Asn Glu Glu His Ile Leu Ser Phe Glu Thr Ile
    290                 295                 300

Asp Lys Met Arg Arg Ala Ser Ser Tyr Ser Ser Leu Asn Ser Leu Ile
305                 310                 315                 320

Gly Val Ser Phe Asn Ser Val Tyr Thr Gln Ile Trp Arg Val Leu Leu
                325                 330                 335

His Leu Ala Ala Asp Pro Tyr Pro Glu Val Ser Asp Val Ala Met Lys
            340                 345                 350

Val Leu Asn Ser Ile Ala Tyr Lys Ala Thr Val Asn Ala Arg Pro Gln
        355                 360                 365

Arg Val Leu Asp Thr Ser Ser Leu Thr Gln Ser Pro Ala Ser Pro
    370                 375                 380

Thr Asn Lys Gly Val His Ile His Gln Ala Gly Gly Ser Pro Pro Ala
385                 390                 395                 400

Ser Ser Thr Ser Ser Ser Ser Leu Thr Asn Asp Val Ala Lys Gln Pro
```

-continued

```
            405                 410                 415
Val Ser Arg Asp Leu Pro Ser Gly Arg Pro Gly Thr Thr Gly Pro Ala
            420                 425                 430

Gly Ala Gln Tyr Thr Pro His Ser His Gln Phe Pro Arg Thr Arg Lys
            435                 440                 445

Met Phe Asp Lys Gly Pro Glu Gln Thr Ala Asp Ala Asp Asp Ala
    450                 455                 460

Ala Gly His Lys Ser Phe Ile Ser Ala Thr Val Gln Thr Gly Phe Cys
465                 470                 475                 480

Asp Trp Ser Ala Arg Tyr Phe Ala Gln Pro Val Met Lys Ile Pro Glu
            485                 490                 495

Glu His Asp Leu Glu Ser Gln Ile Arg Lys Glu Arg Glu Trp Arg Phe
            500                 505                 510

Leu Arg Asn Ser Arg Val Arg Arg Gln Ala Gln Val Ile Gln Lys
            515                 520                 525

Gly Ile Thr Arg Leu Asp Asp Gln Ile Phe Leu Asn Arg Asn Pro Gly
            530                 535                 540

Val Pro Ser Val Val Lys Phe His Pro Phe Thr Pro Cys Ile Ala Val
545                 550                 555                 560

Ala Asp Lys Asp Ser Ile Cys Phe Trp Asp Trp Glu Lys Gly Glu Lys
                565                 570                 575

Leu Asp Tyr Phe His Asn Gly Asn Pro Arg Tyr Thr Arg Val Thr Ala
            580                 585                 590

Met Glu Tyr Leu Asn Gly Gln Asp Cys Ser Leu Leu Leu Thr Ala Thr
            595                 600                 605

Asp Asp Gly Ala Ile Arg Val Trp Lys Asn Phe Ala Asp Leu Glu Lys
            610                 615                 620

Asn Pro Glu Met Val Thr Ala Trp Gln Gly Leu Ser Asp Met Leu Pro
625                 630                 635                 640

Thr Thr Arg Gly Ala Gly Met Val Val Asp Trp Glu Gln Glu Thr Gly
                645                 650                 655

Leu Leu Met Ser Ser Gly Asp Val Arg Ile Val Arg Ile Trp Asp Thr
            660                 665                 670

Asp Arg Glu Met Lys Val Gln Asp Ile Pro Thr Gly Ala Asp Ser Cys
            675                 680                 685

Val Thr Ser Leu Ser Cys Asp Ser His Arg Ser Leu Ile Val Ala Gly
            690                 695                 700

Leu Gly Asp Gly Ser Ile Arg Val Tyr Asp Arg Arg Met Ala Leu Ser
705                 710                 715                 720

Glu Cys Arg Val Met Thr Tyr Arg Glu His Thr Ala Trp Val Val Lys
                725                 730                 735

Ala Ser Leu Gln Lys Arg Pro Asp Gly His Ile Val Ser Val Ser Val
            740                 745                 750

Asn Gly Asp Val Arg Ile Phe Asp Pro Arg Met Pro Glu Ser Val Asn
            755                 760                 765

Val Leu Gln Ile Val Lys Gly Leu Thr Ala Leu Asp Ile His Pro Gln
            770                 775                 780

Ala Asp Leu Ile Ala Cys Gly Ser Val Asn Gln Phe Thr Ala Ile Tyr
785                 790                 795                 800

Asn Ser Ser Gly Glu Leu Ile Asn Asn Ile Lys Tyr Tyr Asp Gly Phe
                805                 810                 815

Met Gly Gln Arg Val Gly Ala Ile Ser Cys Leu Ala Phe His Pro His
            820                 825                 830
```

Trp Pro His Leu Ala Val Gly Ser Asn Asp Tyr Tyr Ile Ser Val Tyr
    835                 840                 845

Ser Val Glu Lys Arg Val Arg
    850                 855

<210> SEQ ID NO 34
<211> LENGTH: 2428
<212> TYPE: DNA
<213> ORGANISM: Homo sapiens

<400> SEQUENCE: 34

| | | | | | |
|---|---|---|---|---|---|
| ctgggcccag | cctatagtca | gcggtgtcta | tgggcatgga | tctggacggg | gaaaaggaca | 60 |
| aagcagcctc | catccacagt | tcattccggg | accaggccct | tgcaggcacg | cgctgggctc | 120 |
| ctgtgggaag | acactaaggg | ccccaggaca | gacctcctct | ccgggcatct | gggttcctag | 180 |
| atggcagagg | tggcagagtg | gggtgggatg | gcccaattgg | gagctttagc | ttccggcaaa | 240 |
| gagctgagca | cagtacatct | tcaatgtgta | agattctcct | gggagaccag | ggcccagctg | 300 |
| gtggtgagct | gggggaagtg | ggtgatactg | ccgtgggagg | agccacctgg | ccctctgggg | 360 |
| aagtgcactc | gctgtctgca | gcgcccaggc | ctgggtagct | gggtggggc | tggggggcca | 420 |
| tctgtgctca | gggtgcctgc | acctgggcct | tctctgccct | gggccaagcc | tgcccgagcc | 480 |
| tctctgtcct | ctgcctgccc | agctggacat | tctctgggcct | ctctggagac | cagtggggtg | 540 |
| ggctgtgggg | gcgtcatatt | gccctggctt | ggcatccctc | ttgtggctgt | accctccca | 600 |
| gcagccccag | gactagcaag | tccccgagat | ggggtgggg | acagtggttg | atgccaaagg | 660 |
| ttgtggggc | aggggcgggg | caggagcagg | aaggtcccct | gagttccctc | accttgggca | 720 |
| gagataaaag | gagcacagtt | ccaggcgggg | ctgagctagg | gcgtagctgt | gatttcaggg | 780 |
| gcacctctgg | cggctgccgt | gatttgagaa | tctcgggtct | cttggctgac | tgatcctggg | 840 |
| agactgtgga | tgaataatgc | tgggcacggc | cccacccgga | ggctgcgagg | cttgggggtc | 900 |
| ctggccgggg | tggctctgct | cgctgccctc | tggctcctgt | ggctgctggg | gtcagcccct | 960 |
| cggggtaccc | cggcacccca | gcccacgatc | accatccttg | tctggcactg | gcccttcact | 1020 |
| gaccagcccc | cagagctgcc | cagcgacacc | tgcacccgct | acggcatcgc | ccgctgccac | 1080 |
| ctgagtgcca | accgaagcct | gctggccagc | gccgacgccg | tggtcttcca | ccaccgcgag | 1140 |
| ctgcagaccc | ggcggtccca | cctgccctg | gcccagcggc | cgcgagggca | gcctgggtg | 1200 |
| tgggcctcca | tggagtctcc | tagccacacc | cacggcctca | gccacctccg | aggcatcttc | 1260 |
| aactgggtgc | tgagctaccg | gcgcgactcg | gacatctttg | tgccctatgg | ccgcctggag | 1320 |
| ccccactggg | ggccctcgcc | accgctgcca | gccaagagca | gggtggccgc | ctgggtggtc | 1380 |
| agcaacttcc | aggagcggca | gctgcgtgcc | aggctgtacc | ggcagctggc | gcctcatctg | 1440 |
| cgggtggatg | tctttggccg | tgccaatgga | cggccactgt | gcgccagctg | cctggtgccc | 1500 |
| accgtggccc | agtaccgctt | ctacctgtcc | tttgagaact | ctcagcaccg | cgactacatt | 1560 |
| acggagaaat | tctggcgcaa | cgcactggtg | gctggcactg | tgccagtggt | gctggggccc | 1620 |
| ccacgggcca | cctatgaggc | cttcgtgccg | gctgacgcct | tcgtgcatgt | ggatgacttt | 1680 |
| ggctcagccc | gagagctggc | ggcttttcctc | actggcatga | atgagagccg | ataccaacgc | 1740 |
| ttcctttgcct | ggcgtgacag | gctccgcgtg | cgactgttca | ccgactggcg | ggaacgtttc | 1800 |
| tgtgccatct | gtaccgcta | cccacaccta | ccccgcagcc | aagtctatga | ggaccttgag | 1860 |
| ggttggtttc | aggcctgaga | tccgctggcc | ggggaggtg | ggtgtgggtg | gaagggctgg | 1920 |

-continued

```
gtgtcgaaat caaaccacca ggcatccggc ccttaccggc aagcagcggg ctaacgggag    1980
gctgggcaca gaggtcagga agcagggggtg gggggtgcag gtgggcactg gagcatgcag    2040
aggaggtgag agtgggaggg aggtaacggg tgcctgctgc ggcagacggg aggggaaagg    2100
ctgccgagga ccctccccac cctgaacaaa tcttgggtgg gtgaaggcct ggctggaaga    2160
gggtgaaagg cagggcccct ggggctgggg ggcaccccag cctgaagttt gtggggcca     2220 aacctgggac cccgagcttc ctcggtagca gaggccctgt ggtccccgag acacaggcac    2280
gggtccctgc cacgtccata gttctgaggt ccctgtgtgt aggctggggc ggggcccagg    2340
agaccacggg gagcaaacca gcttgttctg ggctcaggga gggagggcgg tggacaataa    2400
acatctgagc agtgaaaaaa aaaaaaaa                                       2428
```

<210> SEQ ID NO 35
<211> LENGTH: 342
<212> TYPE: PRT
<213> ORGANISM: Homo sapiens

<400> SEQUENCE: 35

```
Met Asn Asn Ala Gly His Gly Pro Thr Arg Arg Leu Arg Gly Leu Gly
1               5                   10                  15

Val Leu Ala Gly Val Ala Leu Leu Ala Leu Trp Leu Leu Trp Leu
            20                  25                  30

Leu Gly Ser Ala Pro Arg Gly Thr Pro Ala Pro Gln Pro Thr Ile Thr
        35                  40                  45

Ile Leu Val Trp His Trp Pro Phe Thr Asp Gln Pro Pro Glu Leu Pro
    50                  55                  60

Ser Asp Thr Cys Thr Arg Tyr Gly Ile Ala Arg Cys His Leu Ser Ala
65                  70                  75                  80

Asn Arg Ser Leu Leu Ala Ser Ala Asp Ala Val Val Phe His His Arg
                85                  90                  95

Glu Leu Gln Thr Arg Arg Ser His Leu Pro Leu Ala Gln Arg Pro Arg
            100                 105                 110

Gly Gln Pro Trp Val Trp Ala Ser Met Glu Ser Pro Ser His Thr His
        115                 120                 125

Gly Leu Ser His Leu Arg Gly Ile Phe Asn Trp Val Leu Ser Tyr Arg
    130                 135                 140

Arg Asp Ser Asp Ile Phe Val Pro Tyr Gly Arg Leu Glu Pro His Trp
145                 150                 155                 160

Gly Pro Ser Pro Pro Leu Pro Ala Lys Ser Arg Val Ala Ala Trp Val
                165                 170                 175

Val Ser Asn Phe Gln Glu Arg Gln Leu Arg Ala Arg Leu Tyr Arg Gln
            180                 185                 190

Leu Ala Pro His Leu Arg Val Asp Val Phe Gly Arg Ala Asn Gly Arg
        195                 200                 205

Pro Leu Cys Ala Ser Cys Leu Val Pro Thr Val Ala Gln Tyr Arg Phe
    210                 215                 220

Tyr Leu Ser Phe Glu Asn Ser Gln His Arg Asp Tyr Ile Thr Glu Lys
225                 230                 235                 240

Phe Trp Arg Asn Ala Leu Val Ala Gly Thr Val Pro Val Val Leu Gly
                245                 250                 255

Pro Pro Arg Ala Thr Tyr Glu Ala Phe Val Pro Ala Asp Ala Phe Val
            260                 265                 270

His Val Asp Asp Phe Gly Ser Ala Arg Glu Leu Ala Ala Phe Leu Thr
        275                 280                 285
```

```
Gly Met Asn Glu Ser Arg Tyr Gln Arg Phe Phe Ala Trp Arg Asp Arg
            290                 295                 300

Leu Arg Val Arg Leu Phe Thr Asp Trp Arg Glu Arg Phe Cys Ala Ile
305                 310                 315                 320

Cys Asp Arg Tyr Pro His Leu Pro Arg Ser Gln Val Tyr Glu Asp Leu
                325                 330                 335

Glu Gly Trp Phe Gln Ala
            340

<210> SEQ ID NO 36
<211> LENGTH: 1671
<212> TYPE: DNA
<213> ORGANISM: Homo sapiens

<400> SEQUENCE: 36
cccaactggc agcgacagct gcagacgggc tgaaccagct ttgttcccag ggtggcgcct      60
gctctccatc caggccccat tccggctccc acccgacgct gcttttgttc ccacgtttcg     120
gggggcagct ggcactgtga ttcctgcccc atgagtgcct agaggcacgg agccaccagg     180
gatcacccca cgtgggacac agggcttggg aggatgggg caggaccaga ccaagcagca     240
gatcgagaag gggctccagc tgtaccagtc caaccagaca gagaaggcat gcaggtgtg     300 gacaaaggtg ctggagaaga gctcggacct catggggcgc ttccgcgtgc tgggctgcct     360
ggtcacagcc cactcggaga tgggccgcta caaggagatg ctgaagttcg ctgtggtcca     420
gatcgacacg gcccgggagc tggaggatgc cgacttcctc ctggagagct acctgaacct     480
ggcacgcagc aacgagaagc tgtgcgagtt tcacaagacc atctcctact gcaagacctg     540
ccttgggctg cctggtacca gggcaggtgc ccagctcgga ggccaggtca gcctgagcat     600
gggcaatgcc ttcctgggcc tcagcgtctt ccagaaggc ctggagagct cgagaaggc      660 cctgcgctat gcccacaaca atgatgacgc catgctcgag tgccgcgtgt gctgcagcct     720
gggcagcttc tatgcccagg tcaaggacta cgagaaagcc ctgttcttcc cctgcaaggc     780
ggcagagctt gtcaacaact atggcaaagg ctggagcctg aagtaccggg ccatgagcca     840
gtaccacatg gccgtggcct atcgcctgct gggccgcctg gcagtgcca tggagtgttg     900 tgaggagtct atgaagatcg cgctgcagca cggggaccgg ccactgcagg cgctctgcct     960
gctctgcttc gctgacatcc accggagccg tgggacctg gagacagcct tccccaggta    1020
cgactccgcc atgagcatca tgaccgagat cggaaaccgc ctggggcagg tgcaggcgct    1080
gctgggtgtg gccaagtgct gggtggccag gaaggcgctg acaaggctc tggatgccat    1140 cgagagagcc caggatctgg ccgaggaggt ggggaacaag ctgagccagc tcaagctgca    1200
ctgtctgagc gagagcattt accgcagcaa agggctgcag cgggaactgc gggcgcacgt    1260
tgtgaggttc cacgagtgcg tggaggagac ggagctctac tgcggcctgt gcggcgagtc    1320
cataggcgag aagaacagcc ggctgcaggc cctaccttgc tcccacatct tccacctcag    1380
gtgcctgcag aacaacggga cccggagctg tcccaactgc cgccgctcat ccatgaagcc    1440
tggctttgta tgactcctgg cagcaggcgt gggcttcctc ctcgccactc ctgctctttc    1500
tccactgcac gccagaggcc catttactcc tggggcagct gccaggtcgt cctcaccata    1560
gccaaggcct ggggcctgc ccagggctgc tcccctgggc ccagctcccc tcctgcctc     1620 tttgtacttt gctctttata gaaaaataaa ctgtttgtac ctggtcccag g             1671

<210> SEQ ID NO 37
```

```
<211> LENGTH: 1494
<212> TYPE: DNA
<213> ORGANISM: Homo sapiens

<400> SEQUENCE: 37
cccaactggc agcgacagct gcagacgggc tgaaccagct tgttcccag ggtggcgcct      60 gctctccatc caggccccat tccggctccc acccgacgct gcttttgttc ccacgtttcg    120
gggggcagct ggcactgtga ttcctgcccc atgagtgcct agaggcacgg agccaccagg    180
gatcacccca cgtgggacac agggcttggg gaggatgggg caggaccaga ccaagcagca    240
gatcgagaag gggctccagc tgtaccagtc caaccagaca gagaaggcat tgcaggtgtg    300
gacaaaggtg ctggagaaga gctcggacct catggggcgc ttccgcgtgc tgggctgcct    360
ggtcacagcc cactcggaga tgggccgcta caaggagatg ctgaagttcg ctgtggtcca    420
gatcgacacg gcccgggagc tggaggatgc cgacttcctc ctggagagct acctgaacct    480
ggcacgcagc aacgagaagc tgtgcgagtt cacaagacc atctcctact gcaagacctg    540
ccttgggctg cctggtacca gggcaggtgc ccagctcgga ggccaggtca gcctgagcat    600
gggcaatgcc ttcctgggcc tcagcgtctt ccagaaggcc ctggagagct cgagaaggc    660 cctgcgctat gcccacaaca atgatgacgc catgctcgag tgccgcgtgt gctgcagcct    720
gggcagcttc tatgcccagg tcaaggacta cgagaaagcc ctgttcttcc cctgcaaggc    780
ggcagagctt gtcaacaact atggcaaagg ctggagcctg aagtaccggg ccatgagcca    840
gtaccacatg gccgtggcct atcgcctgct gggccgcctg ggcagtgcca tggagtgttg    900
tgaggagtct atgaagatcg cgctgcagca cggggaccgg ccactgcagg cgctctgcct    960
gctctgcttc gctgacatcc accggagccg tgggggacctg gagctgagcc agctcaagct   1020
gcactgtctg agcgagagca tttaccgcag caaagggctg cagcgggaac tgcgggcgca   1080
cgttgtgagg ttccacgagt gcgtggagga gacggagctc tactgcggcc tgtgcggcga   1140
gtccataggc gagaagaaca gccggctgca ggccctacct tgctcccaca tcttccacct   1200
caggtgcctg cagaacaacg ggacccggag ctgtcccaac tgccgccgct catccatgaa   1260
gcctggcttt gtatgactcc tggcagcagg cgtgggcttc ctcctcgcca ctcctgctct   1320
ttctccactg cacgccagag gcccatttac tcctggggca gctgccaggt cgtcctcacc   1380
atagccaagg ccttggggcc tgcccagggc tgctcccctg ggcccagctc ccctcccctgc  1440 ctctttgtac tttgctcttt atagaaaaat aaactgtttg tacctggtcc cagg          1494

<210> SEQ ID NO 38
<211> LENGTH: 412
<212> TYPE: PRT
<213> ORGANISM: Homo sapiens

<400> SEQUENCE: 38

Met Gly Gln Asp Gln Thr Lys Gln Gln Ile Glu Lys Gly Leu Gln Leu
1               5                   10                  15

Tyr Gln Ser Asn Gln Thr Glu Lys Ala Leu Gln Val Trp Thr Lys Val
                20                  25                  30

Leu Glu Lys Ser Ser Asp Leu Met Gly Arg Phe Arg Val Leu Gly Cys
            35                  40                  45

Leu Val Thr Ala His Ser Glu Met Gly Arg Tyr Lys Glu Met Leu Lys
        50                  55                  60

Phe Ala Val Val Gln Ile Asp Thr Ala Arg Glu Leu Glu Asp Ala Asp
65                  70                  75                  80
```

Phe Leu Leu Glu Ser Tyr Leu Asn Leu Ala Arg Ser Asn Glu Lys Leu
                85                  90                  95

Cys Glu Phe His Lys Thr Ile Ser Tyr Cys Lys Thr Cys Leu Gly Leu
            100                 105                 110

Pro Gly Thr Arg Ala Gly Ala Gln Leu Gly Gly Gln Val Ser Leu Ser
        115                 120                 125

Met Gly Asn Ala Phe Leu Gly Leu Ser Val Phe Gln Lys Ala Leu Glu
    130                 135                 140

Ser Phe Glu Lys Ala Leu Arg Tyr Ala His Asn Asn Asp Asp Ala Met
145                 150                 155                 160

Leu Glu Cys Arg Val Cys Cys Ser Leu Gly Ser Phe Tyr Ala Gln Val
                165                 170                 175

Lys Asp Tyr Glu Lys Ala Leu Phe Phe Pro Cys Lys Ala Ala Glu Leu
            180                 185                 190

Val Asn Asn Tyr Gly Lys Gly Trp Ser Leu Lys Tyr Arg Ala Met Ser
        195                 200                 205

Gln Tyr His Met Ala Val Ala Tyr Arg Leu Leu Gly Arg Leu Gly Ser
    210                 215                 220

Ala Met Glu Cys Cys Glu Glu Ser Met Lys Ile Ala Leu Gln His Gly
225                 230                 235                 240

Asp Arg Pro Leu Gln Ala Leu Cys Leu Leu Cys Phe Ala Asp Ile His
                245                 250                 255

Arg Ser Arg Gly Asp Leu Glu Thr Ala Phe Pro Arg Tyr Asp Ser Ala
            260                 265                 270

Met Ser Ile Met Thr Glu Ile Gly Asn Arg Leu Gly Gln Val Gln Ala
        275                 280                 285

Leu Leu Gly Val Ala Lys Cys Trp Val Ala Arg Lys Ala Leu Asp Lys
    290                 295                 300

Ala Leu Asp Ala Ile Glu Arg Ala Gln Asp Leu Ala Glu Glu Val Gly
305                 310                 315                 320

Asn Lys Leu Ser Gln Leu Lys Leu His Cys Leu Ser Glu Ser Ile Tyr
                325                 330                 335

Arg Ser Lys Gly Leu Gln Arg Glu Leu Arg Ala His Val Val Arg Phe
            340                 345                 350

His Glu Cys Val Glu Glu Thr Glu Leu Tyr Cys Gly Leu Cys Gly Glu
        355                 360                 365

Ser Ile Gly Glu Lys Asn Ser Arg Leu Gln Ala Leu Pro Cys Ser His
    370                 375                 380

Ile Phe His Leu Arg Cys Leu Gln Asn Asn Gly Thr Arg Ser Cys Pro
385                 390                 395                 400

Asn Cys Arg Arg Ser Ser Met Lys Pro Gly Phe Val
                405                 410

<210> SEQ ID NO 39
<211> LENGTH: 353
<212> TYPE: PRT
<213> ORGANISM: Homo sapiens

<400> SEQUENCE: 39

Met Gly Gln Asp Gln Thr Lys Gln Gln Ile Glu Lys Gly Leu Gln Leu
1               5                   10                  15

Tyr Gln Ser Asn Gln Thr Glu Lys Ala Leu Gln Val Trp Thr Lys Val
            20                  25                  30

Leu Glu Lys Ser Ser Asp Leu Met Gly Arg Phe Arg Val Leu Gly Cys
        35                  40                  45

```
Leu Val Thr Ala His Ser Glu Met Gly Arg Tyr Lys Glu Met Leu Lys
     50                  55                  60

Phe Ala Val Val Gln Ile Asp Thr Ala Arg Glu Leu Glu Asp Ala Asp
 65                  70                  75                  80

Phe Leu Leu Glu Ser Tyr Leu Asn Leu Ala Arg Ser Asn Glu Lys Leu
                 85                  90                  95

Cys Glu Phe His Lys Thr Ile Ser Tyr Cys Lys Thr Cys Leu Gly Leu
            100                 105                 110

Pro Gly Thr Arg Ala Gly Ala Gln Leu Gly Gly Gln Val Ser Leu Ser
        115                 120                 125

Met Gly Asn Ala Phe Leu Gly Leu Ser Val Phe Gln Lys Ala Leu Glu
130                 135                 140

Ser Phe Glu Lys Ala Leu Arg Tyr Ala His Asn Asn Asp Asp Ala Met
145                 150                 155                 160

Leu Glu Cys Arg Val Cys Cys Ser Leu Gly Ser Phe Tyr Ala Gln Val
                165                 170                 175

Lys Asp Tyr Glu Lys Ala Leu Phe Phe Pro Cys Lys Ala Ala Glu Leu
            180                 185                 190

Val Asn Asn Tyr Gly Lys Gly Trp Ser Leu Lys Tyr Arg Ala Met Ser
        195                 200                 205

Gln Tyr His Met Ala Val Ala Tyr Arg Leu Leu Gly Arg Leu Gly Ser
210                 215                 220

Ala Met Glu Cys Cys Glu Glu Ser Met Lys Ile Ala Leu Gln His Gly
225                 230                 235                 240

Asp Arg Pro Leu Gln Ala Leu Cys Leu Leu Cys Phe Ala Asp Ile His
                245                 250                 255

Arg Ser Arg Gly Asp Leu Glu Leu Ser Gln Leu Lys Leu His Cys Leu
            260                 265                 270

Ser Glu Ser Ile Tyr Arg Ser Lys Gly Leu Gln Arg Glu Leu Arg Ala
        275                 280                 285

His Val Val Arg Phe His Glu Cys Val Glu Glu Thr Glu Leu Tyr Cys
290                 295                 300

Gly Leu Cys Gly Glu Ser Ile Gly Glu Lys Asn Ser Arg Leu Gln Ala
305                 310                 315                 320

Leu Pro Cys Ser His Ile Phe His Leu Arg Cys Leu Gln Asn Asn Gly
                325                 330                 335

Thr Arg Ser Cys Pro Asn Cys Arg Arg Ser Ser Met Lys Pro Gly Phe
            340                 345                 350

Val

<210> SEQ ID NO 40
<211> LENGTH: 510
<212> TYPE: DNA
<213> ORGANISM: Homo sapiens

<400> SEQUENCE: 40
tgaggctgcc ttataaagca ccaagaggct gccagtggga catttctcg gccctgccag      60 cccccaggag gaaggtgggt ctgaatctag caccatgacg gaactagaga cagccatggg    120
catgatcata gacgtctttt cccgatattc gggcagcgag ggcagcacgc agaccctgac    180
caagggggag ctcaaggtgc tgatggagaa ggagctacca ggcttcctgc agagtggaaa    240
agacaaggat gccgtggata aattgctcaa ggacctggac gccaatggag atgcccaggt    300
ggacttcagt gagttcatcg tgttcgtggc tgcaatcacg tctgcctgtc acaagtactt    360
```

```
tgagaaggca ggactcaaat gatgccctgg agatgtcaca gattcctggc agagccatgg    420
tcccaggctt cccaaaagtg tttgttggca attattcccc taggctgagc ctgctcatgt    480
acctctgatt aataaatgct tatgaaatga                                     510
```

<210> SEQ ID NO 41
<211> LENGTH: 95
<212> TYPE: PRT
<213> ORGANISM: Homo sapiens

<400> SEQUENCE: 41

```
Met Thr Glu Leu Glu Thr Ala Met Gly Met Ile Ile Asp Val Phe Ser
1               5                  10                   15

Arg Tyr Ser Gly Ser Glu Gly Ser Thr Gln Thr Leu Thr Lys Gly Glu
                20                  25                  30

Leu Lys Val Leu Met Glu Lys Glu Leu Pro Gly Phe Leu Gln Ser Gly
            35                  40                  45

Lys Asp Lys Asp Ala Val Asp Lys Leu Leu Lys Asp Leu Asp Ala Asn
        50                  55                  60

Gly Asp Ala Gln Val Asp Phe Ser Glu Phe Ile Val Phe Val Ala Ala
65                  70                  75                  80

Ile Thr Ser Ala Cys His Lys Tyr Phe Glu Lys Ala Gly Leu Lys
                85                  90                  95
```

<210> SEQ ID NO 42
<211> LENGTH: 968
<212> TYPE: DNA
<213> ORGANISM: Homo sapiens

<400> SEQUENCE: 42

```
tggagggtaa gaagtttgtc ccacgaggtt tctcttactt tgcctccgca gtatacacgt     60
acatccaaag ccggttctac cgatccccag aagtgatcct gggccacccc tacgacgtgg    120
ccattgacat gtggagcctg gctgcatca cggcggagtt gtacacgggc taccccctgt    180
tccccgggga gaatgaggtg gagcagctgg cctgcatcat ggaggtgctg ggtctgccgc    240
cagccggctt cattcagaca gcctccagga gacagacatt ctttgattcc aaaggttttc    300
ctaaaaatat aaccaacaac agggggaaaa aaagataccc agattccaag gacctcacga    360
tggtgctgaa aacctatgac accagcttcc tggactttct cagaaggtgt ttggtatggg    420
aaccttctct tcgcatgacc ccggaccagg ccctcaagca tgcttggatt catcagtctc    480
ggaacctcaa gccacagccc aggccccaga ccctgaggaa atccaattcc tttttcccct    540
ctgagacaag gaaggacaag gttcaaggct gtcatcactc gagcagaaaa gcagatgaga    600
tcaccaaaga gactacagag aaaacaaaag atagccccac gaagcatgtt cagcattcag    660
gtgatcagca ggactgtctc cagcacggag ctgacactgt tcagctgcct caactggtag    720
acgctcccaa gaagtcagag gcagctgtcg gggcggaggt gtccatgacc tcccaggac    780 agagcaaaaa cttctccctc aagaacacaa acgttttacc ccctattgta tgacctttgc    840
tgagggtatg tcctgctcct ttccaccagt gatttgtatt aagacagcac ttatattgta    900
caatacttca gactgttttt tttaaataca taaaacttta tgttaaaaaa ctctattaac    960
atggccaa                                                            968
```

<210> SEQ ID NO 43
<211> LENGTH: 965
<212> TYPE: DNA
<213> ORGANISM: Homo sapiens

<400> SEQUENCE: 43

```
tggagggtaa gaagtttgtc ccacgaggtt tctcttactt tgcctccgca gtatacacgt    60
acatccaaag ccggttctac cgatccccag aagtgatcct gggccacccc tacgacgtgg   120
ccattgacat gtggagcctg gctgcatca cggcggagtt gtacacgggc tacccccctgt   180
tccccgggga gaatgaggtg gagcagctgg cctgcatcat ggaggtgctg ggtctgccgc   240
cagccggctt cattcagaca gcctccagga gacagacatt ctttgattcc aaaggttttc   300
ctaaaaatat aaccaacaac aggggggaaaa aaagataccc agattccaag gacctcacga   360
tggtgctgaa aacctatgac accagcttcc tggactttct cagaaggtgt ttggtatggg   420
aaccttctct tcgcatgacc ccggaccagg ccctcaagca tgcttggatt catcagtctc   480
ggaacctcaa gccacagccc aggccccaga ccctgaggaa atccaattcc tttttcccct   540
ctgagacaag gaaggacaag gttcaaggct gtcatcactc gagcagaaaa gatgagatca   600
ccaaagagac tacagagaaa acaaaagata gccccacgaa gcatgttcag cattcaggtg   660
atcagcagga ctgtctccag cacggagctg acactgttca gctgcctcaa ctggtagacg   720
ctcccaagaa gtcagaggca gctgtcgggg cggaggtgtc catgacctcc ccaggacaga   780
gcaaaaactt ctccctcaag aacacaaacg ttttaccccc tattgtatga cctttgctga   840
gggtatgtcc tgctcctttc caccagtgat ttgtattaag acagcactta tattgtacaa   900
tacttcagac tgttttttt aaatacataa aactttatgt taaaaaactc tattaacatg   960
gccaa                                                              965
```

<210> SEQ ID NO 44
<211> LENGTH: 1864
<212> TYPE: DNA
<213> ORGANISM: Homo sapiens

<400> SEQUENCE: 44

```
agagtcagtg tgagctgttg aaagcctgca gctaaacacc agtgttactt cactcccctt    60
tgtggacacc aagggggaaga agaatacggt aagcttccca cacattagca agaaagtcct   120
gctgaagtca tccctgctgt atcaggagaa tcaagctcac aatcagatgc cggcctcaga   180
gctcaaggct tcagaaatac cttttccaccc tagcattaaa acccaggatc ccaaggcaga   240
ggagaagtca ccaaagaagc aaaaggtgac tctgacagcg gcagaggccc taaagctttt   300
taagaaccag ctgtctccat atgaacaaag tgaaatcctg gctacgcgg agctgtggtt   360
cctgggtctt gaagccaaga agctcgacac ggctcctgag aaatttagca agacgagttt   420
tgatgatgag catggcttct atctgaaggt cctgcatgat cacattgcct accgctatga   480
agttctggag acaatcggga aggggtcctt ggacaggtg gccaagtgct ggatcacaa   540
aaacaatgag ctggtggccc tgaaaatcat caggaacaag aagaggtttc accagcaggc   600
cctgatggag ctgaagatcc tggaagctct cagaaagaag gacaaagaca cacctacaa   660
tgtggtgcat atgaaggact ttttctactt tcgcaatcac ttctgcatca cctttgagct   720
cctgggaatc aacttgtatg agttgatgaa gaataacaac tttcaaggct tcagtctgtc   780
catagttcgg cgcttcactc tctctgtttt gaagtgcttg cagatgcttt cggtagagaa   840
aatcattcac tgtgatctca agcccgaaaa tatagtgcta taccaaaagg gccaagcctc   900
tgttaaagtc attgactttg gatcaagctg ttatgaacac cagaaagtat acacgtacat   960
ccaaagccgg ttctaccgat ccccagaagt gatcctgggc caccctacg acgtggccat  1020
```

```
tgacatgtgg agcctgggct gcatcacggc ggagttgtac acgggctacc ccctgttccc    1080
cggggagaat gaggtggagc agctggcctg catcatggag gtgctgggtc tgccgccagc    1140
cggcttcatt cagacagcct ccaggagaca gacattcttt gattccaaag gttttcctaa    1200
aaatataacc aacaacaggg ggaaaaaaag atacccagat tccaaggacc tcacgatggt    1260
gctgaaaacc tatgacacca gcttcctgga ctttctcaga aggtgtttgg tatgggaacc    1320
ttctcttcgc atgaccccgg accaggccct caagcatgct tggattcatc agtctcggaa    1380
cctcaagcca cagcccaggc cccagaccct gaggaaatcc aattccttttt tccctctga    1440 gacaaggaag gacaaggttc aaggctgtca tcactcgagc agaaaagcag atgagatcac    1500
caaagagact acagagaaaa caaagatag ccccacgaag catgttcagc attcaggtga    1560
tcagcaggac tgtctccagc acggagctga cactgttcag ctgcctcaac tggtagacgc    1620
tcccaagaag tcagaggcag ctgtcggggc ggaggtgtcc atgacctccc caggacagag    1680
caaaaacttc tccctcaaga acacaaacgt tttacccccct attgtatgac ctttgctgag    1740
ggtatgtcct gctcctttcc accagtgatt tgtattaaga cagcacttat attgtacaat    1800
acttcagact gttttttta aatacataaa actttatgtt aaaaaactct attaacatgg    1860
ccaa                                                                 1864

<210> SEQ ID NO 45
<211> LENGTH: 234
<212> TYPE: PRT
<213> ORGANISM: Homo sapiens

<400> SEQUENCE: 45

Met Trp Ser Leu Gly Cys Ile Thr Ala Glu Leu Tyr Thr Gly Tyr Pro
1               5                   10                  15

Leu Phe Pro Gly Glu Asn Glu Val Glu Gln Leu Ala Cys Ile Met Glu
            20                  25                  30

Val Leu Gly Leu Pro Pro Ala Gly Phe Ile Gln Thr Ala Ser Arg Arg
        35                  40                  45

Gln Thr Phe Phe Asp Ser Lys Gly Phe Pro Lys Asn Ile Thr Asn Asn
    50                  55                  60

Arg Gly Lys Lys Arg Tyr Pro Asp Ser Lys Asp Leu Thr Met Val Leu
65                  70                  75                  80

Lys Thr Tyr Asp Thr Ser Phe Leu Asp Phe Leu Arg Arg Cys Leu Val
                85                  90                  95

Trp Glu Pro Ser Leu Arg Met Thr Pro Asp Gln Ala Leu Lys His Ala
            100                 105                 110

Trp Ile His Gln Ser Arg Asn Leu Lys Pro Gln Pro Arg Pro Gln Thr
        115                 120                 125

Leu Arg Lys Ser Asn Ser Phe Phe Pro Ser Glu Thr Arg Lys Asp Lys
    130                 135                 140

Val Gln Gly Cys His His Ser Ser Arg Lys Ala Asp Glu Ile Thr Lys
145                 150                 155                 160

Glu Thr Thr Glu Lys Thr Lys Asp Ser Pro Thr Lys His Val Gln His
                165                 170                 175

Ser Gly Asp Gln Gln Asp Cys Leu Gln His Gly Ala Asp Thr Val Gln
            180                 185                 190

Leu Pro Gln Leu Val Asp Ala Pro Lys Lys Ser Glu Ala Ala Val Gly
        195                 200                 205

Ala Glu Val Ser Met Thr Ser Pro Gly Gln Ser Lys Asn Phe Ser Leu
    210                 215                 220
```

```
Lys Asn Thr Asn Val Leu Pro Pro Ile Val
225                 230

<210> SEQ ID NO 46
<211> LENGTH: 233
<212> TYPE: PRT
<213> ORGANISM: Homo sapiens

<400> SEQUENCE: 46

Met Trp Ser Leu Gly Cys Ile Thr Ala Glu Leu Tyr Thr Gly Tyr Pro
1               5                   10                  15

Leu Phe Pro Gly Glu Asn Glu Val Glu Gln Leu Ala Cys Ile Met Glu
            20                  25                  30

Val Leu Gly Leu Pro Pro Ala Gly Phe Ile Gln Thr Ala Ser Arg Arg
        35                  40                  45

Gln Thr Phe Phe Asp Ser Lys Gly Phe Pro Lys Asn Ile Thr Asn Asn
    50                  55                  60

Arg Gly Lys Lys Arg Tyr Pro Asp Ser Lys Asp Leu Thr Met Val Leu
65                  70                  75                  80

Lys Thr Tyr Asp Thr Ser Phe Leu Asp Phe Leu Arg Arg Cys Leu Val
                85                  90                  95

Trp Glu Pro Ser Leu Arg Met Thr Pro Asp Gln Ala Leu Lys His Ala
            100                 105                 110

Trp Ile His Gln Ser Arg Asn Leu Lys Pro Gln Pro Arg Pro Gln Thr
        115                 120                 125

Leu Arg Lys Ser Asn Ser Phe Phe Pro Ser Glu Thr Arg Lys Asp Lys
    130                 135                 140

Val Gln Gly Cys His His Ser Ser Arg Lys Asp Glu Ile Thr Lys Glu
145                 150                 155                 160

Thr Thr Glu Lys Thr Lys Asp Ser Pro Thr Lys His Val Gln His Ser
                165                 170                 175

Gly Asp Gln Gln Asp Cys Leu Gln His Gly Ala Asp Thr Val Gln Leu
            180                 185                 190

Pro Gln Leu Val Asp Ala Pro Lys Lys Ser Glu Ala Ala Val Gly Ala
        195                 200                 205

Glu Val Ser Met Thr Ser Pro Gly Gln Ser Lys Asn Phe Ser Leu Lys
    210                 215                 220

Asn Thr Asn Val Leu Pro Pro Ile Val
225                 230

<210> SEQ ID NO 47
<211> LENGTH: 520
<212> TYPE: PRT
<213> ORGANISM: Homo sapiens

<400> SEQUENCE: 47

Met Pro Ala Ser Glu Leu Lys Ala Ser Glu Ile Pro Phe His Pro Ser
1               5                   10                  15

Ile Lys Thr Gln Asp Pro Lys Ala Glu Glu Lys Ser Pro Lys Lys Gln
            20                  25                  30

Lys Val Thr Leu Thr Ala Ala Glu Ala Leu Lys Leu Phe Lys Asn Gln
        35                  40                  45

Leu Ser Pro Tyr Glu Gln Ser Glu Ile Leu Gly Tyr Ala Glu Leu Trp
    50                  55                  60

Phe Leu Gly Leu Glu Ala Lys Lys Leu Asp Thr Ala Pro Glu Lys Phe
65                  70                  75                  80
```

-continued

Ser Lys Thr Ser Phe Asp Asp Glu His Gly Phe Tyr Leu Lys Val Leu
            85                  90                  95

His Asp His Ile Ala Tyr Arg Tyr Glu Val Leu Glu Thr Ile Gly Lys
            100                 105                 110

Gly Ser Phe Gly Gln Val Ala Lys Cys Leu Asp His Lys Asn Asn Glu
            115                 120                 125

Leu Val Ala Leu Lys Ile Ile Arg Asn Lys Lys Arg Phe His Gln Gln
        130                 135                 140

Ala Leu Met Glu Leu Lys Ile Leu Glu Ala Leu Arg Lys Lys Asp Lys
145                 150                 155                 160

Asp Asn Thr Tyr Asn Val Val His Met Lys Asp Phe Phe Tyr Phe Arg
            165                 170                 175

Asn His Phe Cys Ile Thr Phe Glu Leu Leu Gly Ile Asn Leu Tyr Glu
            180                 185                 190

Leu Met Lys Asn Asn Phe Gln Gly Phe Ser Leu Ser Ile Val Arg
            195                 200                 205

Arg Phe Thr Leu Ser Val Leu Lys Cys Leu Gln Met Leu Ser Val Glu
        210                 215                 220

Lys Ile Ile His Cys Asp Leu Lys Pro Glu Asn Ile Val Leu Tyr Gln
225                 230                 235                 240

Lys Gly Gln Ala Ser Val Lys Val Ile Asp Phe Gly Ser Ser Cys Tyr
            245                 250                 255

Glu His Gln Lys Val Tyr Thr Tyr Ile Gln Ser Arg Phe Tyr Arg Ser
            260                 265                 270

Pro Glu Val Ile Leu Gly His Pro Tyr Asp Val Ala Ile Asp Met Trp
            275                 280                 285

Ser Leu Gly Cys Ile Thr Ala Glu Leu Tyr Thr Gly Tyr Pro Leu Phe
        290                 295                 300

Pro Gly Glu Asn Glu Val Glu Gln Leu Ala Cys Ile Met Glu Val Leu
305                 310                 315                 320

Gly Leu Pro Pro Ala Gly Phe Ile Gln Thr Ala Ser Arg Arg Gln Thr
            325                 330                 335

Phe Phe Asp Ser Lys Gly Phe Pro Lys Asn Ile Thr Asn Asn Arg Gly
            340                 345                 350

Lys Lys Arg Tyr Pro Asp Ser Lys Asp Leu Thr Met Val Leu Lys Thr
        355                 360                 365

Tyr Asp Thr Ser Phe Leu Asp Phe Leu Arg Arg Cys Leu Val Trp Glu
370                 375                 380

Pro Ser Leu Arg Met Thr Pro Asp Gln Ala Leu Lys His Ala Trp Ile
385                 390                 395                 400

His Gln Ser Arg Asn Leu Lys Pro Gln Pro Arg Pro Gln Thr Leu Arg
            405                 410                 415

Lys Ser Asn Ser Phe Phe Pro Ser Glu Thr Arg Lys Asp Lys Val Gln
            420                 425                 430

Gly Cys His His Ser Ser Arg Lys Ala Asp Glu Ile Thr Lys Glu Thr
        435                 440                 445

Thr Glu Lys Thr Lys Asp Ser Pro Thr Lys His Val Gln His Ser Gly
450                 455                 460

Asp Gln Gln Asp Cys Leu Gln His Gly Ala Asp Thr Val Gln Leu Pro
465                 470                 475                 480

Gln Leu Val Asp Ala Pro Lys Lys Ser Glu Ala Ala Val Gly Ala Glu
            485                 490                 495

```
Val Ser Met Thr Ser Pro Gly Gln Ser Lys Asn Phe Ser Leu Lys Asn
            500                 505                 510

Thr Asn Val Leu Pro Pro Ile Val
        515                 520

<210> SEQ ID NO 48
<211> LENGTH: 37
<212> TYPE: DNA
<213> ORGANISM: Artificial Sequence
<220> FEATURE:
<223> OTHER INFORMATION: synthetic-sense sequence of HYAL2 primer

<400> SEQUENCE: 48
aggaagagag ttttaaattt agtagggtgt gagagga                          37

<210> SEQ ID NO 49
<211> LENGTH: 56
<212> TYPE: DNA
<213> ORGANISM: Artificial Sequence
<220> FEATURE:
<223> OTHER INFORMATION: synthetic-antisense sequence HYAL2 primer

<400> SEQUENCE: 49
cagtaatacg actcactata gggagaaggc tctcatccat attataaaaa accccc     56

<210> SEQ ID NO 50
<211> LENGTH: 35
<212> TYPE: DNA
<213> ORGANISM: Artificial Sequence
<220> FEATURE:
<223> OTHER INFORMATION: synthetic-sense sequence of HYAL2-is-310 primer

<400> SEQUENCE: 50
aggaagagag ttttttttggg gtgagttttt ttagt                           35

<210> SEQ ID NO 51
<211> LENGTH: 56
<212> TYPE: DNA
<213> ORGANISM: Artificial Sequence
<220> FEATURE:
<223> OTHER INFORMATION: synthetic-antisense sequence HYAL2-is-310
      primer

<400> SEQUENCE: 51
cagtaatacg actcactata gggagaaggc tcacctaatc ctaaacccat aacctt     56

<210> SEQ ID NO 52
<211> LENGTH: 35
<212> TYPE: DNA
<213> ORGANISM: Artificial Sequence
<220> FEATURE:
<223> OTHER INFORMATION: synthetic-sense sequence of HYAL2-is-325 primer

<400> SEQUENCE: 52
aggaagagag ttgtttagtt tttgaggttt tttgg                            35

<210> SEQ ID NO 53
<211> LENGTH: 55
<212> TYPE: DNA
<213> ORGANISM: Artificial Sequence
<220> FEATURE:
<223> OTHER INFORMATION: synthetic-antisense sequence HYAL2-is-325
      primer

<400> SEQUENCE: 53
cagtaatacg actcactata gggagaaggc tattacactc cctccctctc ctaac      55
```

```
<210> SEQ ID NO 54
<211> LENGTH: 35
<212> TYPE: DNA
<213> ORGANISM: Artificial Sequence
<220> FEATURE:
<223> OTHER INFORMATION: synthetic-sense sequence MGRN1 primer

<400> SEQUENCE: 54
aggaagagag ttttggggta taagggaagt ttaag                          35

<210> SEQ ID NO 55
<211> LENGTH: 56
<212> TYPE: DNA
<213> ORGANISM: Artificial Sequence
<220> FEATURE:
<223> OTHER INFORMATION: synthetic-antisense sequence MGRN1 primer

<400> SEQUENCE: 55
cagtaatacg actcactata gggagaaggc tcctaaccaa caaaaaacct aaaaaa    56

<210> SEQ ID NO 56
<211> LENGTH: 34
<212> TYPE: DNA
<213> ORGANISM: Artificial Sequence
<220> FEATURE:
<223> OTHER INFORMATION: synthetic-sense sequence RPTOR primer

<400> SEQUENCE: 56
aggaagagag gtggggtttt tgtagtagtt gaga                           34

<210> SEQ ID NO 57
<211> LENGTH: 56
<212> TYPE: DNA
<213> ORGANISM: Artificial Sequence
<220> FEATURE:
<223> OTHER INFORMATION: synthetic-antisense sequence RPTOR primer

<400> SEQUENCE: 57
cagtaatacg actcactata gggagaaggc ttaataaccc aaaaccaaac cctaac    56

<210> SEQ ID NO 58
<211> LENGTH: 35
<212> TYPE: DNA
<213> ORGANISM: Artificial Sequence
<220> FEATURE:
<223> OTHER INFORMATION: synthetic-sense sequence of SLC22A18 primer

<400> SEQUENCE: 58
aggaagagag taagtggaat tttggtattt ttgga                          35

<210> SEQ ID NO 59
<211> LENGTH: 56
<212> TYPE: DNA
<213> ORGANISM: Artificial Sequence
<220> FEATURE:
<223> OTHER INFORMATION: synthetic-antisense sequence SLC22A18 primer

<400> SEQUENCE: 59
cagtaatacg actcactata gggagaaggc tcactccaaa cctaaactca cctcta    56

<210> SEQ ID NO 60
<211> LENGTH: 35
<212> TYPE: DNA
<213> ORGANISM: Artificial Sequence
<220> FEATURE:
```

<223> OTHER INFORMATION: synthetic-sense sequence FUT7 primer

<400> SEQUENCE: 60
aggaagagag gaagaggaag ggatttagtt tgaag                          35

<210> SEQ ID NO 61
<211> LENGTH: 56
<212> TYPE: DNA
<213> ORGANISM: Artificial Sequence
<220> FEATURE:
<223> OTHER INFORMATION: synthetic-antisense sequence FUT7 primer

<400> SEQUENCE: 61
cagtaatacg actcactata gggagaaggc tacaaacctt aacctcccaa aatact    56

<210> SEQ ID NO 62
<211> LENGTH: 35
<212> TYPE: DNA
<213> ORGANISM: Artificial Sequence
<220> FEATURE:
<223> OTHER INFORMATION: synthetic-sense sequence RAPSN primer

<400> SEQUENCE: 62
aggaagagag gatttttagt tggtgagagg tttga                          35

<210> SEQ ID NO 63
<211> LENGTH: 56
<212> TYPE: DNA
<213> ORGANISM: Artificial Sequence
<220> FEATURE:
<223> OTHER INFORMATION: synthetic-antisense sequence RAPSN primer

<400> SEQUENCE: 63
cagtaatacg actcactata gggagaaggc taaaaccact aaattaccca accaaa    56

<210> SEQ ID NO 64
<211> LENGTH: 35
<212> TYPE: DNA
<213> ORGANISM: Artificial Sequence
<220> FEATURE:
<223> OTHER INFORMATION: synthetic-sense sequence S100P primer

<400> SEQUENCE: 64
aggaagagag ggaaggtggg tttgaattta gtatt                          35

<210> SEQ ID NO 65
<211> LENGTH: 56
<212> TYPE: DNA
<213> ORGANISM: Artificial Sequence
<220> FEATURE:
<223> OTHER INFORMATION: synthetic-antisense sequence S100P primer

<400> SEQUENCE: 65
cagtaatacg actcactata gggagaaggc tctatccctc ttacctctaa acccct    56

<210> SEQ ID NO 66
<211> LENGTH: 35
<212> TYPE: DNA
<213> ORGANISM: Artificial Sequence
<220> FEATURE:
<223> OTHER INFORMATION: synthetic-sense sequence DYRK4 primer

<400> SEQUENCE: 66
aggaagagag ggttttttta aaattggttt tggat                          35

```
<210> SEQ ID NO 67
<211> LENGTH: 55
<212> TYPE: DNA
<213> ORGANISM: Artificial Sequence
<220> FEATURE:
<223> OTHER INFORMATION: synthetic-antisense sequence DYRK4 primer

<400> SEQUENCE: 67
cagtaatacg actcactata gggagaaggc taaaccccat ttttattccc ataat          55
```

BIOMARKER PANEL FOR THE DETECTION OF CANCER

CROSS-REFERENCE TO RELATED APPLICATION

This application is a national stage application of International Patent Application No. PCT/EP2016/053813 filed Feb. 24, 2016, which claims priority to European Patent Application No. 15156389.7 filed Feb. 24, 2015, both of which are hereby incorporated by reference in their entirety.

The present invention relates to panels of methylation and miRNA marker as well as their use in the prognosing, diagnosing and/or treatment of cancer, means for detecting said marker, kits comprising said means, and devices for analysing the marker panel.

BACKGROUND

Cancer is one of the most important medical and health problems in the world. As the leading cause of death worldwide, there were 12.4 million new cancer cases and 7.6 million cancer related deaths in 2008. It has been predicted that the deaths from cancer worldwide is continuously rising and 12 million deaths would be caused by cancer in the year of 2030. Breast cancer is the most common cancer among women. About one out of nine women will develop breast cancer during her life (Feuer, E. J., et al., The lifetime risk of developing breast cancer. J Natl Cancer Inst 85, 892-897 (1993)). Worldwide approximately 1.3 million women develop breast cancer each year. Mortality rates have continued to decrease over the years due to all the efforts and advances made in early diagnosis and treatment (Jemal A, Bray F, Center M M, Ferlay J, Ward E, Forman D. Global cancer statistics. CA Cancer J Clin 2011; 61:69-90). Nevertheless, thousands of women die from this disease each year. In US women the overall five-year survival is 98% when diagnosed at an early stage as opposed to 23% when the disease has already spread to distant organs. Thus, early breast cancer detection belongs to one of the major challenges in the struggle against this disease. Mammographic screening is currently applied as the diagnostic standard. However, it has limitations due to its use of ionizing radiation and a false positive rate of 8-10%, also depending on the age of the individuals to be screened (Taplin S, Abraham L, Barlow W E, Fenton J J, Berns E A, Carney P A, Cutter G R, Sickles E A, Carl D, Elmore J G. Mammography facility characteristics associated with interpretive accuracy of screening mammography. J Natl Cancer Inst 2008; 100: 876-87).

Most of the breast cancers occur sporadic, whereas familial breast cancer accounts for about 10% of all breast cancer cases (Fackenthal, J. D. & Olopade, O. I. Breast cancer risk associated with BRCA1 and BRCA2 in diverse populations. Nat Rev Cancer 7, 937-948 (2007)). Mutations in the main breast cancer related genes, BRCA1 and BRCA2 account for 25% and other intermediate- and low-penetrance genes for about 5% of all familial cases (Yang, R. & Burwinkel, B. (eds.). Familial risk in breast cancer, 251-256 (Springer, 2010)). Recent genome-wide association studies (GWAS) and single candidate gene approaches have been quite successful in detecting genetic low-risk variants for breast cancer (Thomas, G., et al. A multistage genome-wide association study in breast cancer identifies two new risk alleles at 1 p 11.2 and 14q24.1 (RAD51 L1). Nat Genet 41, 579-584 (2009); Cox, A., et al. A common coding variant in CASP8 is associated with breast cancer risk. Nat Genet 39, 352-358 (2007); Stacey, S. N., et al. Common variants on chromosome 5p12 confer susceptibility to estrogen receptor-positive breast cancer. Nat Genet 40, 703-706 (2008); Ahmed, S., et al. Newly discovered breast cancer susceptibility loci on 3p24 and 17q23.2. Nat Genet 41,585-590 (2009); Easton, D. F., et al. Genome-wide association study identifies novel breast cancer susceptibility loci. Nature 447, 1087-1093 (2007); Milne, R. L., et al. Risk of estrogen receptor-positive and -negative breast cancer and single-nucleotide polymorphism 2q35-rs13387042. J Natl Cancer Inst 101, 1012-1018 (2009); Frank, B., et al. Association of a common AKAP9 variant with breast cancer risk: a collaborative analysis. J Natl Cancer Inst 100,437-442 (2008)). However, a large number of breast cancer risk factors remain to be explored.

Compared to BC, ovarian cancer (OvCa) is comparable rare in occurrence, but is the leading cause of death from gynecologic cancers because of its high malignancy. In 2008, 225,000 women were diagnosed with ovarian cancer worldwide, and 140,000 of these women died from the disease. Typically, women with the OvCa present with few early symptoms, and thus nearly three-quarters of ovarian cancer cases present at an advanced stage, with the disease spread well beyond the ovaries. Pancreatic cancer (PaCa) is the most aggressive of all epithelial malignancies. With 279,000 new diagnoses of PaCa worldwide, the 5-year overall survival rate of PaCa patients is less than 5%. Although recent genome-wide association studies (GWAS) have successfully detected several genetic variants associated with the risk of BC, OvCa and PaCa, no valuable marker for the early detection of BC has been identified.

Metastatic breast cancer (MBC) is a major health issue, worldwide. Current treatment strategies target primarily palliative care with very few cases being cured. An alternate approach of tackling MBC is development of screening methods and applying biomarkers to identify high risk groups and therapy response. This could facilitate decision making for clinicians and help them adopt the appropriate treatment regime for the patients.

Circulating tumor cells (CTC) have been proposed as an FDA approved independent prognostic marker for metastasis, specifically for progression-free survival and overall survival. A cardinal cut off of greater than 5 CTCs per 7.5 ml of blood has been defined as CTC positive (Cristofanilli M, Budd G T, Ellis M J, Stopeck A, et al; Circulating tumor cells, disease progression, and survival in metastatic breast cancer; N Engl J Med. 2004 Aug. 19; 351(8):781-91). However, it is important to note that a significant fraction of patients with overt distant metastases are negative for CTCs. This could be partly contributed to the phenomenon of epithelial-mesenchymal transition in CTCs, in which case they can be missed by enumeration techniques that exploit the expression of epithelial markers such as EpCAM or cytokeratin,-8,-18 and -19.

Beside CTCs, also protein based circulating tumor markers like carcinoembryonic antigen (CEA) and carbohydrate antigen 15-3 (CA 15-3) are widely used as prognostic markers, as well as in monitoring breast cancer treatment success and follow-up (Uehara M, Kinoshita T, Hojo T, Akashi-Tanaka S, Iwamoto E, Fukutomi T. Long-term prognostic study of carcinoembryonic antigen (CEA) and carbohydrate antigen 15-3 (CA 15-3) in breast cancer. Int J Clin Oncol 2008; 13:447-51; Harris L, Fritsche H, Mennel R, Norton L, Ravdin P, Taube S, Somerfield M R, Hayes D F, Bast R C, Jr. American Society of Clinical Oncology 2007 update of recommendations for the use of tumor markers in breast cancer. J Clin Oncol 2007; 25:5287-312) However, the sensitivity of these markers is low. Therefore, new sensitive and specific as well as minimally invasive markers are needed.

Epigenetic changes are defined as changes in gene expression that are not due to any alterations in the genomic DNA sequence. Aberrant epigenetic signatures have been considered as a hallmark of human cancer (Esteller, M. Cancer epigenomics: DNA methylomes and histone-modification maps. Nat Rev Genet 8, 286-298 (2007).). One of the most important epigenetic signatures, DNA methylation, has critical roles in the control of gene activities and in the architecture of the nucleus of the cell Weber, M., et al. Chromosome-wide and promoter-specific analyses identify sites of differential DNA methylation in normal and transformed human cells. Nat Genet 37, 853-862 (2005)). Furthermore, unlike genetic markers or variants, DNA methylation is principally reversible. Therefore, the methylation profile of specific genes are considered as therapeutic targets (Mack, G. S. Epigenetic cancer therapy makes headway. J Natl Cancer Inst 98, 1443-1444 (2006)). Meanwhile, due to the variable character, DNA methylation may serve as a link between environmental factors and the genome. DNA methylation modulated by environmental factors or aging may alter the expression of critical genes of cells and consequently induce malignant transformation of cells or even a cancer (Widschwendter, M., et al. Epigenotyping in peripheral blood cell DNA and breast cancer risk: a proof of principle study. P LoS One 3, e2656 (2008)).

As an early event in the development of cancer, changes of DNA methylation are particularly promising as markers for the early detection of cancer. Recent studies have shown that methylation analysis of blood cell DNA can serve as a reliable and robust marker. Intensive studies have disclosed altered DNA methylation signatures in cancer on the somatic level, whereas only a few studies with candidate-gene-approach have analysed methylation signatures in peripheral blood DNA in cancer.

Previous studies have explored hypermethylation in the promoter regions of tumor suppressor genes and hypomethylation in the promoter regions of oncogenes in breast cancer compared to their normal adjacent tissues (Ito, Y., et al. Somatically acquired hypomethylation of IGF2 in breast and colorectal cancer. Hum Mol Genet 17, 2633-2643 (2008); Potapova, A., Hoffman, A. M., Godwin, A. K., Al-Saleem, T. & Cairns, P. Promoter hypermethylation of the PALB2 susceptibility gene in inherited and sporadic breast and ovarian cancer. Cancer Res 68, 998-1002 (2008); Radpour, R., et al. Methylation profiles of 22 candidate genes in breast cancer using high-throughput MALDI-TOF mass array. Oncogene 28, 2969-2978 (2009); Widschwendter, M. & Jones, P. A. DNA methylation and breast carcinogenesis. Oncogene 21, 5462-5482 (2002)). Very few studies have focused on the methylation signatures in the peripheral blood DNA and-breast cancer risk. In these studies, only specific genes, like BRCA1 (Iwamoto, T., Yamamoto, N., Taguchi, T., Tamaki, Y. & Noguchi, S. BRCA1 promoter methylation in peripheral blood cells is associated with increased risk of breast cancer with BRCA1 promoter methylation. Breast Cancer Res Treat 129, 69-77 (2011)), ATM (Flanagan, J. M., et al. Gene-body hypermethylation of ATM in peripheral blood DNA of bilateral breast cancer patients. Hum Mol Genet 18, 1332-1342 (2009)), and genes in specific pathways (Widschwendter et al. (2008), loc. cit.) have been investigated.

There is thus a need in the art for the identification of further epigenetic markers of breast cancer and other cancers, preferably allowing the identification of afflicted subjects by obtaining a sample by a means of low invasiveness, e.g. by taking a blood sample.

MiRNAs are small, non-coding RNAs (-18-25 nucleotides in length) that regulate gene expression on a post-transcriptional level by degrading mRNA molecules or blocking their translation (Bartel D P.: MicroRNAs: genomics, biogenesis, mechanism, and function. Cell 2004; 116: 281-97). Hence, they play an essential role in the regulation of a large number of biological processes, including cancer (Calin G A, Dumitru C D, Shimizu M, Bichi R, Zupo S, Noch E, Aldler H, Rattan S, Keating M, Rai K, Rassenti L, Kipps T, et al. Frequent deletions and down-regulation of micro-RNA genes miR15 and miR16 at 13q14 in chronic lymphocytic leukemia. Proc Natl Acad Sci USA 2002; 99:15524-9). Under the standard nomenclature system, names are assigned to experimentally confirmed miRNAs. The prefix "mir" is followed by a dash and a number. The uncapitalized "mir-" refers to the pre-miRNA, while a capitalized "miR-" refers to the mature form. MiRNAs with nearly identical sequences bar one or two nucleotides are annotated with an additional lower case letter. Species of origin is designated with a three-letter prefix, e.g. hsa for Homo sapiens (human) Two mature miRNAs originating from opposite arms of the same pre-miRNA are denoted with a -3p or -5p suffix.

Circulating miRNAs are defined as miRNAs present in the cell-free component of body fluids like plasma, serum, and the like. Lawrie et al. (Lawrie C H, Gal S, Dunlop H M, Pushkaran B, Liggins A P, Pulford K, Banham A H, Pezzella F, Boultwood J, Wainscoat J S, Hatton C S, Harris A L. Detection of elevated levels of tumour-associated microRNAs in serum of patients with diffuse large B-cell lymphoma. Br J Haematol 2008; 141:672-5) were among the first to demonstrate the presence of miRNAs in bodily fluids. Since then, circulating miRNAs have been reported as aberrantly expressed in blood plasma or serum in different types of cancer, e.g. prostate, colorectal or esophageal carcinoma (Brase J C, Johannes M, Schlomm T, Falth M, Haese A, Steuber T, Beissbarth T, Kuner R, Sultmann H. Circulating miRNAs are correlated with tumor progression in prostate cancer. Int J Cancer 2011; 128:608-16; Huang Z, Huang D, Ni S, Peng Z, Sheng W, Du X. Plasma microRNAs are promising novel markers for early detection of colorectal cancer. Int J Cancer 2010; 127:118-26; Zhang C, Wang C, Chen X, Yang C, Li K, Wang J, Dai J, Hu Z, Zhou X, Chen L, Zhang Y, Li Y, et al. Expression profile of microRNAs in serum: a fingerprint for esophageal squamous cell carcinoma. Clin Chem 2010; 56:1871-9.). Their most important advantages include the possibility to be measured repeatedly in a minimally invasive manner as well as their remarkable stability in plasma/serum, where they circulate mostly outside of exosomes and are stable due to their binding to Argonaute proteins (Mitchell P S, Parkin R K, Kroh E M, Fritz B R, Wyman S K, Pogosova-Agadjanyan E L, Peterson A, Noteboom J, O'Briant K C, Allen A, Lin D W, Urban N, et al. Circulating microRNAs as stable blood-based markers for cancer detection. Proc Natl Acad Sci USA 2008; 105: 10513-8; Turchinovich A, Weiz L, Langheinz A, Burwinkel B. Characterization of extracellular circulating microRNA. Nucleic Acids Res 2011; 39:7223-33; Arroyo J D, Chevillet J R, Kroh E M, Ruf I K, Pritchard C C, Gibson D F, Mitchell P S, Bennett C F, Pogosova-Agadjanyan E L, Stirewalt D L, Tait J F, Tewari M. Argonaute2 complexes carry a population of circulating microRNAs independent of vesicles in human plasma. Proc Natl Acad Sci USA 2011; 108:5003-8).

There is thus an urgent need in the art for improved methods for the diagnosis and prognosis of breast cancer, in particular primarybreast cancer, and metastasizing breast cancer. These methods would preferably be also used in preventive screening of apparently healthy subjects, a low grade of invasiveness would be preferred.

SUMMARY OF THE INVENTION

In a first aspect, the present invention relates to a method of prognosing and/or diagnosing cancer, in particular BC, OvaCa, and/or PaCA, in a subject, comprising (a) determining the methylation status and/or expression level of at least one methylation marker selected from the group consisting of HYAL2, MGRN1, RPTOR, SLC22A18, FUT7, RAPSN, S100P, DYRK4, and (b) determining the presence, in particular the amount, of at least one miRNA marker selected from the group consisting of miR-652, miR-801, miR-376c, miR-376a, miR-127-3p, miR-409-3p, miR-148b, in a subject, wherein the methylation status and/or expression level of at least one methylation marker and the presence of at least one miRNA is indicative of the prognosis and/or diagnosis of said subject.

In a second aspect, the present invention relates to a method for determining the dosage of a pharmaceutical for the alteration of cancer or the prevention or treatment of cancer in a subject, comprising the steps of (a) determining the methylation status and/or expression level of at least one methylation marker and the amount of at least one miRNA marker in a sample of a subject, and optionally determining the methylation status and/or expression level of at least one methylation marker and the amount of at least one miRNA marker in a reference for comparison with the methylation status and/or expression level of at least one methylation marker and the amount of at least one miRNA marker in the sample of interest, and (b) determining the dosage of a pharmaceutical depending on the methylation status and/or expression level of at least one methylation marker and the amount of at least one miRNA marker in the sample of interest, optionally depending on the comparison of the methylation status and/or expression level of at least one methylation marker and the amount of at least one miRNA marker a in the sample of interest and the reference or reference sample.

In a third aspect, the present invention relates to a method for adapting the dosage of a pharmaceutical for the alteration of cancer or the prevention or treatment of cancer, comprising the steps of (a) determining the methylation status and/or expression level of at least one methylation marker and the amount of at least one miRNA marker in a sample, (b) determining the methylation status and/or expression level of at least one methylation marker and the amount of at least one miRNA marker in one or more references or reference samples, (c) examining the tested sample as to whether the methylation status and/or expression level of at least one methylation marker and the amount of at least one miRNA marker present in said sample of interest is different from the level in the one or more references or reference samples, and (d) adapting the dosage of a pharmaceutical depending on whether the methylation status and/or expression level of at least one methylation marker and the amount of at least one miRNA marker in the sample of interest is different from the level in the one or more references or reference samples.

In a fourth aspect, the present invention relates to a method of determining the beneficial and/or adverse effects of a substance on cancer or the development of cancer, comprising the steps of (a) determining the methylation status and/or expression level of at least one methylation marker and the amount of at least one miRNA marker in a sample of interest, (b) determining the methylation status and/or expression level of at least one methylation marker and the amount of at least one miRNA marker in one or more references or reference samples, and (c) examining the sample of interest as to whether the methylation status and/or expression level of at least one methylation marker and the amount of at least one miRNA marker present in said sample of interest is different from the level in the one or more references or reference samples, wherein the sample of interest was exposed differently to said substance than the one or more references or reference samples.

In a fifth aspect, the present invention relates to a method for identifying a patient as a responder to a cancer treatment, comprising determining the methylation status of at least one methylation marker and/or the expression level of at least one methylation marker, and the amount of at least one miRNA in a first and in one or more further samples taken subsequently to the first sample, wherein an increased methylation status of the at least one methylation marker and/or a lower expression level of the at least one methylation marker, and the absence or decreased amount of the at least one miRNA marker indicates a response to the treatment.

In a sixth aspect, the present invention relates to a method for identifying a patient as a non-responder to a cancer treatment, comprising determining the methylation status of at least one methylation marker and/or the expression level of at least one methylation marker, and the amount of at least one miRNA in a first and in one or more further samples taken subsequently to the first sample, wherein a decreased methylation status of the at least one methylation marker and/or an increased expression level of the at least one methylation marker, and the presence or increased amount of the at least one miRNA marker indicates a lack of response to the treatment.

In a seventh aspect, the present invention relates to a method for treating cancer, comprising the steps: (i) determining the methylation status of at least one methylation marker and/or the expression level of at least one methylation marker, and the amount of at least one miRNA in a first sample of a subject; (ii) starting treatment of said patient with a first treatment regimen comprising one or more anti-cancer agents or therapies, (iii) determining the methylation status of at least one methylation marker and/or the expression level of at least one methylation marker, and the amount of at least one miRNA in one or more subsequently taken further samples of said subject; (iv) optionally repeating steps (ii) and (iii) one or more times; (v) continuing treating the patient with the first treatment regimen if there is a substantial increase of the methylation status of the at least one methylation marker and/or a lower expression level of the at least one methylation marker, and a decreased amount or absence of the at least one miRNA marker, or (vi) amending the treatment or terminating treating the patient with the first treatment regimen and treating the patient instead with a second treatment regimen comprising one or more anti-cancer agents or therapies not comprised in the first treatment regimen if there is a decreased methylation status of the at least one methylation marker and/or an increased expression level of the at least one methylation marker, and an increased amount or presence of the at least one miRNA marker.

In an eighth aspect, the present invention relates to means for prognosing and/or diagnosing i. the risk of developing cancer, in particular BC, OvaCa, and/or PaCA, ii. the presence of cancer, in particular BC, OvaCa, and/or PaCA, and/or iii. the progression of cancer, in particular BC, OvaCa, and/or PaCA, comprising a) one or more means of detecting the methylation status and/or expression level of at least one methylation marker, and b) one or more means of detecting the amount of at least one miRNA marker.

In a ninth aspect, the present invention relates to a kit comprising the means of the eighth aspect.

In a tenth aspect, the present invention relates to the use of the means of the eighth aspect, or the kit of the ninth aspect for prognosing and/or diagnosing i. the risk of developing cancer, in particular BC, OvaCa, and/or PaCA, ii. the presence of cancer, in particular BC, OvaCa, and/or PaCA, and/or iii. the progression of cancer, in particular BC, OvaCa, and/or PaCA.

In a eleventh aspect, the present invention relates to a device for identifying cancer, in particular BC, OvaCa, and/or PaCA, comprising: (a) an analyzing unit comprising (i) a detection agent for determining the methylation status and/or expression level of at least one methylation marker selected from the group consisting of: HYAL2, MGRN1, RPTOR, SLC22A18, FUT7, RAPSN, S100P, DYRK4, and (ii) a detection agent for determining the presence of at least one miRNA selected from the group consisting of: miR-652, miR-801, miR-376c, miR-376a, miR-127-3p, miR-409-3p, miR-148b in a sample of a subject; and (b) an evaluation unit comprising a data processor having tangibly embedded an algorithm for carrying out a comparison of the amount determined by the analyzing unit with a reference and which is capable of generating an output file containing a diagnosis established based on the said comparison.

LIST OF FIGURES

FIG. 1: Sample Description of blood-based biomarker panel for the early detection of breast cancer FIG. 2: Methylation differences of eight genes in three validation rounds FIG. 3: The discriminatory power of DNA methylation marker sets to distinguish BC cases from healthy controls in samples of other centres FIG. 4: The discriminatory power of DNA methylation marker sets and miRNA marker sets to distinguish BC cases from healthy controls in samples from our group FIG. 5: The methylation level of the eight genes in sporadic BC patients with different clinical characteristics (cases from the second validation round)

FIG. 6: The methylation level of the eight genes in sporadic BC patients with different clinical characteristics (cases from our group)

FIG. 7: Sample Description of blood-based biomarker panel for the early detection of pancreatic cancer FIG. 8: Methylation differences in genes comparing PaCa cases and controls FIG. 9: Methylation differences in genes comparing PaCa cases and controls stratified by gender FIG. 10: The discriminatory power of the methylation in genes to distinguish PaCa cases from healthy controls FIG. 11: The methylation of genes in PaCa patients with different clinical characteristics FIG. 12: Sample Description of blood-based biomarker panel for the early detection of ovarian cancer FIG. 13: Methylation differences in genes comparing OvCa cases and controls FIG. 14: The discriminatory power of the methylation in genes to distinguish OvCa cases from healthy controls FIG. 15: The determination of breast cancer related CpG island shore in HYAL2

FIG. 16: The inverse correlation between the methylation and expression of S100P, SLC22A18 and DYRK4 in leucocytes FIG. 17: The methylation levels of HYAL2 CpG sites by Illumina 450K FIG. 18: The methylation levels of S100P CpG sites by Illumina 450K FIG. 19: The methylation levels of SLC22A18 CpG sites by Illumina 450K FIG. 20: The methylation levels of DYRK4 CpG sites by Illumina 450K FIG. 21: The methylation levels of FUT7 CpG sites by Illumina 450K FIG. 22: The methylation levels of RAPSN CpG sites by Illumina 450K FIG. 23: The methylation levels of RPTOR CpG sites by Illumina 450K FIG. 24: The methylation levels of MGRN1 CpG sites by Illumina 450K FIG. 25: The inverse correlation between the methylation and expression of HYAL2 in leucocytes. (a) The box plots show the methylation levels of cg27091787 and adjacent CpG sites in the HYAL2-A amplicon in leucocytes from 36 sporadic BC cases and 40 healthy controls. The box plot of cg27091787 is framed in box for emphasis. (b) The box plot shows the expression level of HYAL2 in leucocytes from sporadic BC cases and healthy controls. The presented p-values were calculated by Mann-Whitney U test. The circles indicate outliers. (c) The inverse correlation between the methylation level of cg27091787 and HYAL2 expression in leucocytes.

Figure 26:
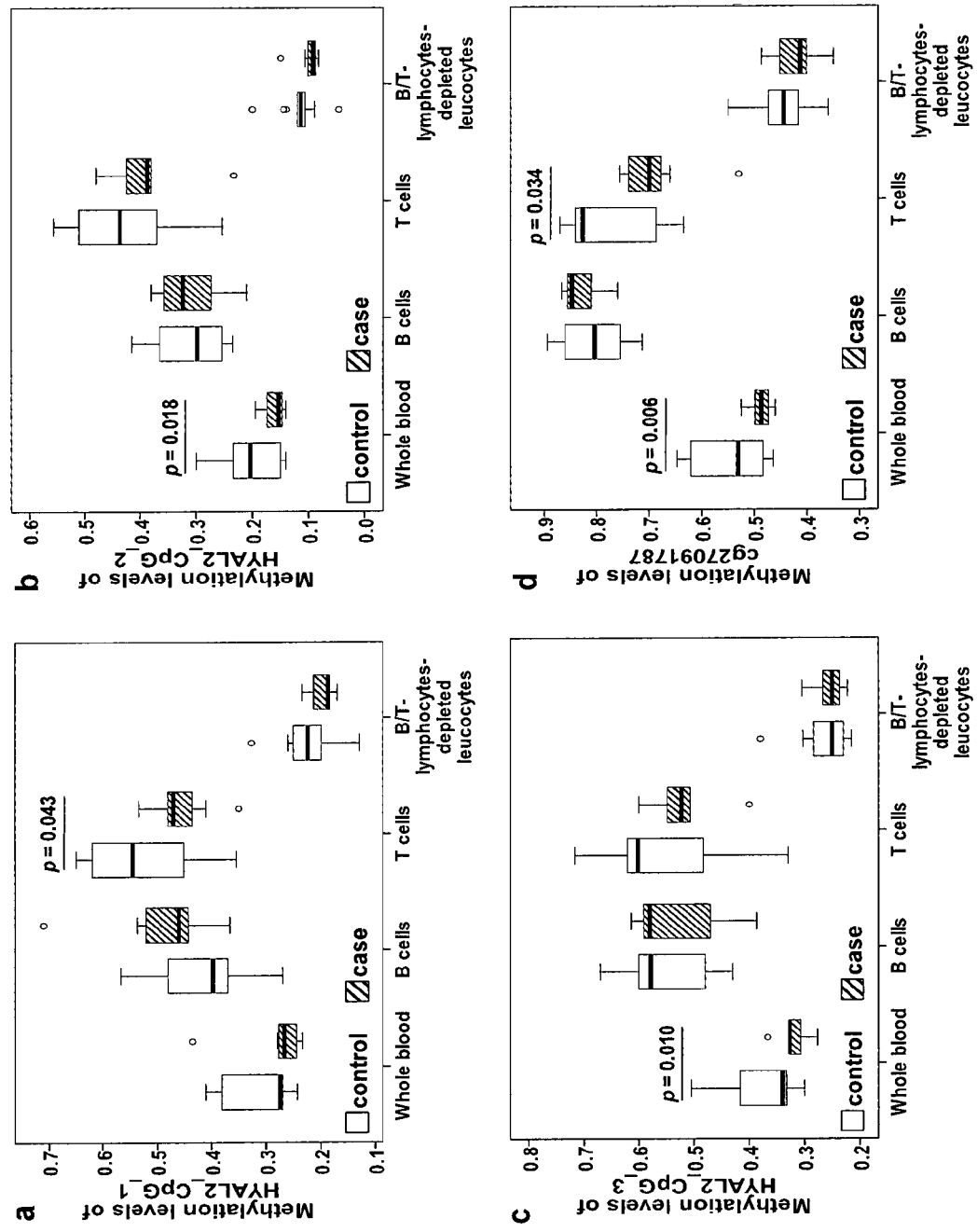

FIG. 26: The methylation levels of four CpG sites in HYAL2-A amplicon in sorted leucocytes fractions. The methylation levels were measured in triplicates in the samples (DNA from whole blood and from sorted leucocytes fractions) from seven sporadic BC cases and 14 healthy controls. The methylation difference between cases and controls was calculated by t-test. The methylation levels of cg27091787 are presented by box and whisker plot. The circle indicates an outlier.

LIST OF SEQUENCES

| | | |
|---|---|---|
| SEQ ID NO: 1 | hsa-miR-652-3p (MIMAT0003322): | aauggcgccacuagggguugug |
| SEQ ID NO: 2 | hsa-miR-652-5p (MIMAT0022709): | caacccuaggagagggugccauuca |
| SEQ ID NO: 3 | miR-801 located on chromosome 1: 28847698-28847793: | gauugcucugcgugcggaaucgac |
| SEQ ID NO: 4 | hsa-miR-376c-3p (MIMAT0000720): | aacauagaggaaauuccacgu |
| SEQ ID NO: 5 | hsa-miR-376c-5p (MIMAT0022861): | gguggauauuccuucuauguu |
| SEQ ID NO: 6 | hsa-miR-376a-3p (MIMAT0000729): | aucauagaggaaaauccacgu |
| SEQ ID NO: 7 | hsa-miR-376a-5p (MIMAT0003386): | guagauucuccuucuaugagua |
| SEQ ID NO: 8 | hsa-miR-127-3p (MIMAT0000446): | ucggauccgucugagcuuggcu |

-continued

| | | |
|---|---|---|
| SEQ ID NO: 9 | hsa-miR-127-5p (MIMAT0004604): cugaagcucagagggcucugau | |
| SEQ ID NO: 10 | hsa-miR-409-3p (MIMAT0001639): gaauguugcucggugaaccccu | |
| SEQ ID NO: 11 | hsa-miR-409-5p (MIMAT0001638): agguuacccgagcaacuuugcau | |
| SEQ ID NO: 12 | hsa-miR-148b-3p (MIMAT0000759): ucagugcaucacagaacuuugu | |
| SEQ ID NO: 13 | hsa-miR-148b-5p (MIMAT0004699): aaguucuguuauacacucaggc | |
| SEQ ID NO: 14 | HYAL2 (NM_003773.4) | |
| SEQ ID NO: 15 | HYAL2 (NM_033158.4) | |
| SEQ ID NO: 16 | HYAL2 (NP_003764.3) | |
| SEQ ID NO: 17 | HYAL2 (NP_149348.2) | |
| SEQ ID NO: 18 | MGRN1 (NM_001142289.2) | |
| SEQ ID NO: 19 | MGRN1 (NM_001142290.2) | |
| SEQ ID NO: 20 | MGRN1 (NM_001142291.2) | |
| SEQ ID NO: 21 | MGRN1 (NM_015246.3) | |
| SEQ ID NO: 22 | MGRN1 (NP_001135761.2) | |
| SEQ ID NO: 23 | MGRN1 (NP_001135762.1) | |
| SEQ ID NO: 24 | MGRN1 (NP_001135763.2) | |
| SEQ ID NO: 25 | MGRN1 (NP_056061.1) | |
| SEQ ID NO: 26 | RPTOR (NM_001163034.1) | |
| SEQ ID NO: 27 | RPTOR (NM_020761.2) | |
| SEQ ID NO: 28 | RPTOR (NP_001156506.1) | |
| SEQ ID NO: 29 | RPTOR (NP_065812.1) | |
| SEQ ID NO: 30 | SLC22A18 (NM_002555.5) | |
| SEQ ID NO: 31 | SLC22A18 (NM_183233.2) | |
| SEQ ID NO: 32 | SLC22A18 (NP_002546.3) | |
| SEQ ID NO: 33 | SLC22A18 (NP_899056.2) | |
| SEQ ID NO: 34 | FUT7 (NM_004479.3) | |
| SEQ ID NO: 35 | FUT7 (NP_004470.1) | |
| SEQ ID NO: 36 | RAPSN (NM_005055.4) | |
| SEQ ID NO: 37 | RAPSN (NM_032645.4) | |
| SEQ ID NO: 38 | RAPSN (NP_005046.2) | |
| SEQ ID NO: 39 | RAPSN (NP_116034.2) | |
| SEQ ID NO: 40 | S100P (NM_005980.2) | |
| SEQ ID NO: 41 | S100P (NP_005971.1) | |
| SEQ ID NO: 42 | DYRK4 (NM_001282285.1) | |
| SEQ ID NO: 43 | DYRK4 (NM_001282286.1) | |
| SEQ ID NO: 44 | DYRK4 (NM_003845.2) | |
| SEQ ID NO: 45 | DYRK4 (NP_001269214.1) | |
| SEQ ID NO: 46 | DYRK4 (NP_001269215.1) | |
| SEQ ID NO: 47 | DYRK4 (NP_003836.1) | |
| SEQ ID NO: 48 | sense sequence of HYAL2 primer | |
| SEQ ID NO: 49 | antisense sequence HYAL2 primer | |
| SEQ ID NO: 50 | sense sequence of HYAL2-is-310 primer | |
| SEQ ID NO: 51 | antisense sequence HYAL2-is-310 primer | |
| SEQ ID NO: 52 | sense sequence of HYAL2-is-325 primer | |
| SEQ ID NO: 53 | antisense sequence HYAL2-is-325 primer | |
| SEQ ID NO: 54 | sense sequence MGRN1 primer | |
| SEQ ID NO: 55 | antisense sequence MGRN1 primer | |
| SEQ ID NO: 56 | sense sequence RPTOR primer | |
| SEQ ID NO: 57 | antisense sequence RPTOR primer | |
| SEQ ID NO: 58 | sense sequence of SLC22A18 primer | |
| SEQ ID NO: 59 | antisense sequence SLC22A18 primer | |
| SEQ ID NO: 60 | sense sequence FUT7 primer | |
| SEQ ID NO: 61 | antisense sequence FUT7 primer | |
| SEQ ID NO: 62 | sense sequence RAPSN primer | |
| SEQ ID NO: 63 | antisense sequence RAPSN primer | |
| SEQ ID NO: 64 | sense sequence S100P primer | |
| SEQ ID NO: 65 | antisense sequence S100P primer | |
| SEQ ID NO: 66 | sense sequence DYRK4 primer | |
| SEQ ID NO: 67 | antisense sequence DYRK4 primer | |

DETAILED DESCRIPTION OF THE INVENTION

Definitions

Before the present invention is described in detail below, it is to be understood that this invention is not limited to the particular methodology, protocols and reagents described herein as these may vary. It is also to be understood that the terminology used herein is for the purpose of describing particular embodiments only, and is not intended to limit the scope of the present invention which will be limited only by the appended claims. Unless defined otherwise, all technical and scientific terms used herein have the same meanings as commonly understood by one of ordinary skill in the art.

Several documents are cited throughout the text of this specification. Each of the documents cited herein (including all patents, patent applications, scientific publications, manufacturer's specifications, instructions etc.), whether supra or infra, is hereby incorporated by reference in its entirety. Nothing herein is to be construed as an admission that the invention is not entitled to antedate such disclosure by virtue of prior invention. Some of the documents cited herein are characterized as being "incorporated by reference". In the event of a conflict between the definitions or teachings of such incorporated references and definitions or teachings recited in the present specification, the text of the present specification takes precedence.

In the following, the elements of the present invention will be described. These elements are listed with specific embodiments, however, it should be understood that they may be combined in any manner and in any number to create additional embodiments. The variously described examples and preferred embodiments should not be construed to limit the present invention to only the explicitly described embodiments. This description should be understood to support and encompass embodiments which combine the explicitly described embodiments with any number of the disclosed and/or preferred elements. Furthermore, any permutations and combinations of all described elements in this application should be considered disclosed by the description of the present application unless the context indicates otherwise.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

As used in this specification and the appended claims, the singular forms "a", "an", and "the" include plural referents, unless the content clearly dictates otherwise.

The term "about" when used in connection with a numerical value is meant to encompass numerical values within a range having a lower limit that is 5% smaller than the indicated numerical value and having an upper limit that is 5% larger than the indicated numerical value.

"Nucleic acid molecules" are understood as a polymeric or oligomeric macromolecule made from nucleotide monomers. Nucleotide monomers are composed of a nucleobase, a five-carbon sugar (such as but not limited to ribose or 2'-deoxyribose), and one to three phosphate groups. Typically, a polynucleotide is formed through phosphodiester bonds between the individual nucleotide monomers. In the context of the present invention referred to nucleic acid molecules include but are not limited to ribonucleic acid (RNA), deoxyribonucleic acid (DNA), and mixtures thereof such as e.g. RNA-DNA hybrids. The terms "polynucleotide", "nucleic acid" and "nucleic acid molecule" are used interchangeably herein. The nucleic acids, can e.g. be synthesized chemically, e.g. in accordance with the phosphotriester method (see, for example, Uhlmann, E. & Peyman, A. (1990) Chemical Reviews, 90, 543-584). Aptamers are nucleic acids which bind with high affinity to a polypeptide, here mir146-a. Aptamers can be isolated by selection methods such as SELEmir146-a (see e.g. Jayasena (1999) Clin. Chem., 45, 1628-50; Klug and Famulok (1994) M. Mol. Biol. Rep., 20, 97-107; U.S. Pat. No. 5,582,981) from a large pool of different single-stranded RNA molecules. Aptamers can also be synthesized and selected in their mirror-image form, for example as the L-ribonucleotide (Nolte et al. (1996) Nat. Biotechnol., 14, 1116-9; Klussmann et al. (1996) Nat. Biotechnol., 14, 1112-5). Forms which have been isolated in this way enjoy the advantage that they are not degraded by naturally occurring ribonucleases and, therefore, possess greater stability. Nucleic acids may be degraded by endonucleases or exonucleases, in particular by DNases and RNases which can be found in the cell. It is, therefore, advantageous to modify the nucleic acids in order to stabilize them against degradation, thereby ensuring that a high concentration of the nucleic acid is maintained in the cell over a long period of time (Beigelman et al. (1995) Nucleic Acids Res. 23:3989-94; WO95/11910; WO98/37240; WO97/29116). Typically, such a stabilization can be obtained by introducing one or more internucleotide phosphorus groups or by introducing one or more non-phosphorus internucleotides. Suitable modified internucleotides are compiled in Uhlmann and Peyman (1990), supra (see also Beigelman et al. (1995) Nucleic Acids Res. 23:3989-94; WO95/11910; WO98/37240; WO 97/29116). Modified internucleotide phosphate radicals and/or non-phosphorus bridges in a nucleic acid which can be employed in one of the uses according to the invention contain, for example, methyl phosphonate, phosphorothioate, phosphoramidate, phosphorodithioate and/or phosphate esters, whereas non-phosphorus internucleotide analogues contain, for example, siloxane bridges, carbonate bridges, carboxymethyl esters, acetamidate bridges and/or thioether bridges. It is also the intention that this modification should improve the durability of a pharmaceutical composition which can be employed in one of the uses according to the invention. Nucleic acids may be selected from the group consisting of, a peptide nucleic acid (PNA), a locked nucleic acid (LNA), a glycol nucleic acid (GNA), a threose nucleic acid (TNA), a microRNA (miRNA), and a small interfering RNA (siRNA), a polynucleotide probe, a primer(s) (e.g. a primer pair), in particular a primer(s) for polymerase chain reaction (PCR), reverse transcription (RT) reaction, or DNA sequencing.

In the context of the different aspects of present invention, the term nucleic acid comprises genomic DNA, cDNA, recombinant DNA, cRNA, mRNA, microRNA (miRNA) and small interfering RNA (siRNA). A nucleic acid may consist of an entire gene, or a portion thereof. The nucleic acid can also be an artificial nucleic acid. Artificial nucleic acids include polyamide or peptide nucleic acid (PNA), morpholino and locked nucleic acid (LNA), as well as glycol nucleic acid (GNA) and threose nucleic acid (TNA). Each of these is distinguished from naturally-occurring DNA or RNA by changes to the backbone of the molecule as well known to the person skilled in the art.

As used herein, the term "microRNA" and variations such as "miRNA" and "miR" is understood by the skilled artisan and relates to a short ribonucleic acid (RNA) molecule found in eukaryotic cells and in body fluids of metazoan organisms. MiRNA include human miRNAs, mature single stranded miRNAs, precursor miRNAs (pre-miR), and variants thereof, which may be naturally occurring. In some instances, the term "miRNA" also includes primary miRNA transcripts (pri-miRNAs) and duplex miRNAs. Unless otherwise noted, when used herein, the name of a specific miRNA refers to the mature miRNA. MiRNA-precursor may consists of 25 to several thousand nucleotides, typically 40 to 130, 50 to 120, or 60 to 110 nucleotides. Typically, a mature miRNA consists of 5 to 100 nucleotides, often 10 to 50, 12 to 40, or 18 to 26 nucleotides. The term miRNA also includes the "guide" strand which eventually enters the RNA-induced silencing complex (RISC) as well as to the "passenger" strand complementary thereto.

The sequence of several miRNAs is known in the art and readily assessable to the skilled person via well-known sequence databases, such as e.g. miRBase (Griffiths-Jones S., NAR 2004 32(Database Issue):D109-D111; Kozomara A, Griffiths-Jones S., NAR 2011 39(Database Issue):D152-D157). It is understood that below indicated database accession numbers of the individual miRNAs are those of miRNAs of human origin. However these database entries also provide the database accession numbers of the respective miRNA of different origin, such as e.g. mirNAs of any mammal, reptile, or bird origin, such as e.g. those selected from the group consisting of laboratory animals (e.g. mouse or rat), domestic animals (including e.g. guinea pig, rabbit, horse, donkey, cow, sheep, goat, pig, chicken, camel, cat, dog, turtle, tortoise, snake, or lizard), or primates including chimpanzees, bonobos, and gorillas miRNA. It is also understood that the reference to a specific miRNA by its number (e.g. miR-652) equally refers to the -3p and -5p sequence (miR-652-3p and miR-652-5p).

The sequence of miR-652 is deposited at miRBase ID MI0003667 which comprises hsa-miR-652-3p (MIMAT0003322) and hsa-miR-652-5p (MIMAT0022709), which corresponds to SEQ ID NO: 1 and 2, respectively, of the present invention.

The sequence of miR-801 was deposited at miRBase ID MI0005202: 5'-GAUUGCUCUGCGUGCGGAAUCGAC-3', however, it is now considered as a fragment of U11 spliceosomal RNA and was thus remove from miRBase. The pre-miRNA-801 is located at chr1: 28847698-28847793. Its sequence corresponds to SEQ ID NO: 3 of the present invention.

miR-376c, also referred to as miR-368, is deposited at miRBase ID MI0000776, which comprises miR-376c-3p (MIMAT0000720) and hsa-miR-376c-5p (MIMAT0022861), which corresponds to SEQ ID NO: 4 and 5, respectively, of the present invention.

The sequence of miR-376a is deposited at miRBase ID MI0000784, which comprises hsa-miR-376a-3p (MIMAT0000729) and hsa-miR-376a-5p (MIMAT0003386), which corresponds to SEQ ID NO: 6 and 7, respectively, of the present invention.

The sequence of miR-127 is deposited at miRBase ID MI0000472, which comprises hsa-miR-127-3p (MIMAT0000446) and hsa-miR-127-5p (MIMAT0004604), which corresponds to SEQ ID NO: 8 and 9, respectively, of the present invention.

The sequence of miR-409 is deposited at miRBase ID MI0001735, which comprises hsa-miR-409-3p (MIMAT0001639) and hsa-miR-409-5p (MIMAT0001638), which corresponds to SEQ ID NO: 10 and 11, respectively, of the present invention.

The sequence of miR-148b is deposited at miRBase ID MI0000811, which comprises hsa-miR-148b-3p (MIMAT0000759) and hsa-miR-148b-5p (MIMAT0004699), which corresponds to SEQ ID NO: 12 and 13, respectively, of the present invention.

The term "combination of miRNAs" relates to combinations of the miRNAs of the present invention. The amount of a miRNA can be determined in a sample of a subject by techniques well known in the art. Depending on the nature of the sample, the amount may be determined by PCR based techniques for quantifying the amount of a polynucleotide or by other methods like mass spectrometry or (next generation) sequencing or one of the methods described in the examples (Cissell K A, Deo S K. Trends in microRNA detection. Anal Bioanal Chem. 2009; 394(4):1109-1116 or de Planell-Saguer M, Rodicio M C. Analytical aspects of microRNA in diagnostics: a review. Anal Chim Acta 2011 Aug. 12; 699(2):134-52). The term "determining the amounts of at least the miRNAs of a combination of miRNAs", as used herein, preferably relates to determining the amount of each of the miRNAs of the combination separately in order to be able to compare the amount of each miRNA of the combination to a reference specific for said miRNA.

The term "probe" as used herein refers to a single-strand oligonucleotide which is typically used for the detection of target RNA and/or DNA sequences that is complementary to the sequence of the probe. A probe hybridizes to single-stranded nucleic acid (DNA or RNA) whose nucleotide sequence allows for nucleotide pairing due to complementarity between the probe and the target sequence. The length of a probe depends on the intended use as well as the required specificity of the probe. Typically, a probe is 20-500 (i.e. 50, 55, 60, 65, 70, 75, 80, 85, 90, 95, 100, 110, 120, 130, 140, 150, 160, 170, 180, 190, 200, 300, 400, 500) nucleotides long, preferably 20-100 nucleotides, more preferably 20-50. For detection of microRNA probes are between 12 and 30 nucleotides. Probes are used in various experimental set ups such as but not limited to Southern and Northern Blots, for real-time PCR and In Situ Hybridization (ISH) as well as for microarray experiments. A probe may be unlabeled, directly labelled, or indirectly labelled, such as with biotin to which a streptavidin complex may later bind. Said label may be a molecule detectable by spectroscopic, photochemical, biochemical, immunochemical, chemical, or other physical means. For example, suitable labels include $32P$, fluorescent dyes, electron-dense reagents, enzymes (e.g., as commonly used in an ELISA), biotin, digoxigenin, or haptens and other entities which are or can be made detectable. A label may be incorporated into nucleic acids at any position, e.g. at the 3' end, at the 5' end or internally. The term "probe" also encompasses nucleic acids differing in the composition of their backbone such as but not limited to peptide nucleic acids (PNAs), locked nucleic acids (LNAs), glycol nucleic acids (GNAs) and threose nucleic acids (TNAs).

The term "primer" as used herein refers to a single-strand oligonucleotide which typically serves as a starting point for DNA-replicating enzymes. A primer binds to or hybridises with a DNA template and typically comprises a sequence being complementary to the DNA sequence to which it is supposed to bind. A primer may also comprise additional sequences e.g. sequences serving as nuclease cleavage sites (e.g. Bam H1, Hind III, etc.). The length of a primer is chosen depending on the intended use. For instance, primers used for the amplification of DNA in Polymerase-Chain Reactions (PCR) typically have a length of at least 10 nucleotides, preferably between 10 to 50 (i.e. 15, 16, 17, 18, 19, 20, 21, 22, 23, 24, 25, 26, 27, 28, 29, 30, 31, 32, 33, 34, 35, 36, 37, 38, 39, 40, 45, 50) nucleotides, more preferably between 15 and 30 nucleotides. Shorter primers of at least 5 nucleotides are used for sequencing of DNA templates. Also encompassed in the term "primer" are "degenerate primers" which are a mixture of similar, but not identical primers. A primer may be tagged or labelled with a marker molecule detectable by spectroscopic, photochemical, biochemical, immunochemical, chemical, or other physical means.

The term "expression level" refers to the amount of gene product present in the body or a sample at a certain point of time. The expression level can e.g. be measured/quantified/detected by means of the protein or mRNA expressed from the gene. The expression level can for example be quantified by normalizing the amount of gene product of interest present in a sample with the total amount of gene product of the same category (total protein or mRNA) in the same sample or a reference sample (e.g. a sample taken at the same time from the same individual or a part of identical size (weight, volume) of the same sample) or by identifying the amount of gene product of interest per defined sample size (weight, volume, etc.). The expression level can be measured or detected by means of any method as known in the art, e.g. methods for the direct detection and quantification of the gene product of interest (such as mass spectrometry) or methods for the indirect detection and measurement of the gene product of interest that usually work via binding of the gene product of interest with one or more different molecules or detection means (e.g. primer(s), probes, antibodies, protein scaffolds) specific for the gene product of interest. The determination of the level of gene copies comprising also the determination of the absence or presence of one or more fragments (e.g. via nucleic acid probes or primers, e.g. quantitative PCR, Multiplex ligation-dependent probe amplification (MLPA) PCR) is also within the knowledge of the skilled artisan.

The terms "protein" and "polypeptide" are used interchangeably herein and refer to any peptide-linked chain of amino acids, regardless of length or post-translational modification. Proteins usable in the present invention (including protein derivatives, protein variants, protein fragments, protein segments, protein epitops and protein domains) can be further modified by chemical modification. This means such a chemically modified polypeptide comprises other chemical groups than the 20 naturally occurring amino acids. Examples of such other chemical groups include without limitation glycosylated amino acids and phosphorylated amino acids. Chemical modifications of a polypeptide may provide advantageous properties as compared to the parent polypeptide, e.g. one or more of enhanced stability, increased biological half-life, or increased water solubility. Chemical modifications applicable to the variants usable in the present invention include without limitation: PEGylation, glycosylation of non-glycosylated parent polypeptides, or the modification of the glycosylation pattern present in the parent polypeptide.

In the context of the different aspects of present invention, the term "peptide" refers to a short polymer of amino acids linked by peptide bonds. It has the same chemical (peptide) bonds as proteins, but is commonly shorter in length. The shortest peptide is a dipeptide, consisting of two amino acids joined by a single peptide bond. There can also be a tripeptide, tetrapeptide, pentapeptide, etc. Preferably, the peptide has a length of up to 8, 10, 12, 15, 18 or 20 amino acids. A peptide has an amino end and a carboxyl end, unless it is a cyclic peptide.

In the context of the different aspects of present invention, the term "polypeptide" refers to a single linear chain of amino acids bonded together by peptide bonds and preferably comprises at least about 21 amino acids. A polypeptide can be one chain of a protein that is composed of more than one chain or it can be the protein itself if the protein is composed of one chain.

In the context of the different aspects of present invention, the term "protein" refers to a molecule comprising one or more polypeptides that resume a secondary and tertiary structure and additionally refers to a protein that is made up of several polypeptides, i.e. several subunits, forming quaternary structures. The protein has sometimes non-peptide groups attached, which can be called prosthetic groups or cofactors. The primary structure of a protein or polypeptide is the sequence of amino acids in the polypeptide chain. The secondary structure in a protein is the general three-dimensional form of local segments of the protein. It does not, however, describe specific atomic positions in three-dimensional space, which are considered to be tertiary structure. In proteins, the secondary structure is defined by patterns of hydrogen bonds between backbone amide and carboxyl groups. The tertiary structure of a protein is the three-dimensional structure of the protein determined by the atomic coordinates. The quaternary structure is the arrangement of multiple folded or coiled protein or polypeptide molecules molecules in a multi-subunit complex. The terms "amino acid chain" and "polypeptide chain" are used synonymously in the context of present invention. The term "post-translational" used herein refers to events that occur after the translation of a nucleotide triplet into an amino acid and the formation of a peptide bond to the proceeding amino acid in the sequence. Such post-translational events may occur after the entire polypeptide was formed or already during the translation process on those parts of the polypeptide that have already been translated. Post-translational events typically alter or modify the chemical or structural properties of the resultant polypeptide. Examples of post-translational events include but are not limited to events such as glycosylation or phosphorylation of amino acids, or cleavage of the peptide chain, e.g. by an endopeptidase. The term "co-translational" used herein refers to events that occur during the translation process of a nucleotide triplet into an amino acid chain. Those events typically alter or modify the chemical or structural properties of the resultant amino acid chain. Examples of co-translational events include but are not limited to events that may stop the translation process entirely or interrupted the peptide bond formation resulting in two discreet translation products.

The term "segment" refers to any part of a macromolecule (e.g. a polypeptide, protein or polyprotein) into which this macromolecule can be divided. A macromolecule may consist of one or more segments. Such segmentation may exist due to functional (e.g. having immunoreactive features or membrane attachment functions) or structural (e.g. nucleotide or amino acid sequence, or secondary or tertiary structure) properties of the macromolecule and/or the individual segment. In the context of the present invention it is preferred that the term "segment" refers to a part of a protein or polyprotein. It is particularly preferred that such segment folds and/or functions independently of the rest of the protein or polyprotein.

An "epitope", also known as antigenic determinant, is the segment of a macromolecule that is recognized by the immune system, specifically by antibodies, B cells, or T cells. Such epitope is that part or segment of a macromolecule capable of binding to an antibody or antigen-binding fragment thereof. In this context, the term "binding" preferably relates to a specific binding. In the context of the present invention it is preferred that the term "epitope" refers to the segment of protein or polyprotein that is recognized by the immune system. Epitopes usually consist of chemically active surface groupings of molecules such as amino acids or sugar side chains and usually have specific three-dimensional structural characteristics, as well as specific charge characteristics. Conformational and non-conformational epitopes are distinguished in that the binding to the former but not the latter is lost in the presence of denaturing solvents.

As used herein, the term "domain" refers to the segment of a protein or polyprotein sequence or structure (or corresponding nucleotide sequence) that can evolve, function, and/or exist independently of the rest of the protein chain. Typically, a protein consists of one or several domains with each of them being three-dimensional structure that are stable and folded independently of the rest of the protein chain. Such domain typically forms an independent functional unit within the protein (e.g. transmembrane-domains, immunoglobulin-like domains, or DNA-binding domains).

The amino acid sequence of several peptides and proteins, as well as the nucleotide sequences encoding the respective peptides and proteins are well known in the art and readily assessable to the skilled person via well-known sequence databases, such as e.g. Genbank. It is understood that below indicated database accession numbers of the individual sequence are those of human origin. However these database entries also provide the database accession numbers of the respective nucleotide sequences of different origin, such as e.g. amino acid or nucleotides sequences of any mammal, reptile, or bird origin, such as e.g. those selected from the group consisting of laboratory animals (e.g. mouse or rat), domestic animals (including e.g. guinea pig, rabbit, horse, donkey, cow, sheep, goat, pig, chicken, camel, cat, dog, turtle, tortoise, snake, or lizard), or primates including chimpanzees, bonobos, and gorillas nucleotide amino acid or nucleotides sequences.

HYAL2:
Genbank Acc No: NM_003773.4 (GI:289802998) for transcript variant 1, which corresponds to SEQ ID NO:14 of the present invention
Genbank Acc No: NM_033158.4 (GI:289802999) for transcript variant 2, which corresponds to SEQ ID NO:15 of the present application;
Genbank Acc No: NP_003764.3 (GI:15022801), for the HYAL2 polypeptide encoded by transcript variant 1, which corresponds to SEQ ID NO:16 of the present invention, and
Genbank Acc No: NP_149348.2 (GI:34304377), for the HYAL2 polypeptide encoded by transcript variant 2, which corresponds to SEQ ID NO:17 of the present invention MGRN1:
Genbank Acc No: NM_001142289.2 for the transcript variant 2, which corresponds to SEQ ID NO:18 of the present invention, and
Genbank Acc No: NM_001142290.2 for the transcript variant 3, which corresponds to SEQ ID NO:19 of the present invention, and
Genbank Acc No: NM_001142291.2 for the transcript variant 4, which corresponds to SEQ ID NO:20 of the present invention, and
Genbank Acc No: NM_015246.3 for the transcript variant 1, which corresponds to SEQ ID NO:21 of the present invention, and
Genbank Acc No: NP_001135761.2 for the MGRN1 polypetide encoded by the transcript variant 2, which corresponds to SEQ ID NO:22 of the present invention;
Genbank Acc No: NP_001135762.1 for the MGRN1 polypetide encoded by the transcript variant 3, which corresponds to SEQ ID NO:23 of the present invention;
Genbank Acc No: NP_001135763.2 for the MGRN1 polypetide encoded by the transcript variant 4, which corresponds to SEQ ID NO:24 of the present invention;
Genbank Acc No: NP_056061.1 for the MGRN1 polypeptide encoded by the transcript variant 1, which corresponds to SEQ ID NO:25 of the present invention;

RPTOR
Genbank Acc No: NM_001163034.1 for the transcript variant 2, which corresponds to SEQ ID NO:26 of the present invention
Genbank Acc No: NM_020761.2 for the transcript variant 1, which corresponds to SEQ ID NO:27 of the present invention
Genbank Acc No: NP_001156506.1 for the RPTOR polypetide encoded by the transcript variant 2, which corresponds to SEQ ID NO:28 of the present invention;
Genbank Acc No: NP_065812.1 for the RPTOR polypetide encoded by the transcript variant 1, which corresponds to SEQ ID NO:29 of the present invention;

SLC22A18
Genbank Acc No: NM_002555.5 for the transcript variant 1, which corresponds to SEQ ID NO:30 of the present invention
Genbank Acc No: NM_183233.2 for the transcript variant 2, which corresponds to SEQ ID NO:31 of the present invention
Genbank Acc No: NP_002546.3 for the SLC22A18 polypeptide encoded by the transcript variant 1, which corresponds to SEQ ID NO:32 of the present invention;
Genbank Acc No: NP_899056.2 for the SLC22A18 polypeptide encoded by the transcript variant 2, which corresponds to SEQ ID NO:33 of the present invention;

FUT7
Genbank Acc No: NM_004479.3 for the transcript, which corresponds to SEQ ID NO:34 of the present invention
Genbank Acc No: NP_004470.1 for the FUT7 polypeptide encoded by the transcript, which corresponds to SEQ ID NO:35 of the present invention;

RAPSN
Genbank Acc No: NM_005055.4 for the transcript variant 1, which corresponds to SEQ ID NO:36 of the present invention
Genbank Acc No: NM_032645.4 for the transcript variant 2, which corresponds to SEQ ID NO:37 of the present invention
Genbank Acc No: NP_005046.2 for the RAPSN polypeptide encoded by the transcript variant 1, which corresponds to SEQ ID NO:38 of the present invention;
Genbank Acc No: NP_116034.2 for the RAPSN polypeptide encoded by the transcript variant 1, which corresponds to SEQ ID NO:39 of the present invention;

S100P
Genbank Acc No: NM_005980.2 for the transcript, which corresponds to SEQ ID NO:40 of the present invention
Genbank Acc No: NP_005971.1 for the S100P polypeptide encoded by the transcript, which corresponds to SEQ ID NO:41 of the present invention;

DYRK4
Genbank Acc No: NM_001282285.1 for the transcript variant 2, which corresponds to SEQ ID NO:42 of the present invention
Genbank Acc No: NM_001282286.1 for the transcript variant 3, which corresponds to SEQ ID NO:43 of the present invention
Genbank Acc No: NM_003845.2 for the transcript variant 1, which corresponds to SEQ ID NO:44 of the present invention
Genbank Acc No: NP_001269214.1 for the DYRK4 polypetide encoded by the transcript variant 2, which corresponds to SEQ ID NO:45 of the present invention;
Genbank Acc No: NP_001269215.1 for the DYRK4 polypetide encoded by the transcript variant 3, which corresponds to SEQ ID NO:46 of the present invention;
Genbank Acc No: NP_003836.1 for the DYRK4 polypeptide encoded by the transcript variant 1, which corresponds to SEQ ID NO:47 of the present invention;

As used herein, the term "variant" is to be understood as a polynucleotide or protein which differs in comparison to the polynucleotide or protein from which it is derived by one or more changes in its length or sequence. The polypeptide or polynucleotide from which a protein or nucleic acid variant is derived is also known as the parent polypeptide or polynucleotide. The term "variant" comprises "fragments" or "derivatives" of the parent molecule. Typically, "fragments" are smaller in length or size than the parent molecule, whilst "derivatives" exhibit one or more differences in their sequence in comparison to the parent molecule. Also encompassed modified molecules such as but not limited to post-translationally modified proteins (e.g. glycosylated, biotinylated, phosphorylated, ubiquitinated, palmitoylated, or proteolytically cleaved proteins) and modified nucleic acids such as methylated DNA. Also mixtures of different molecules such as but not limited to RNA-DNA hybrids, are encompassed by the term "variant". Typically, a variant is constructed artificially, preferably by gene-technological means whilst the parent polypeptide or polynucleotide is a wild-type protein or polynucleotide. However, also naturally occurring variants are to be understood to be encompassed by the term "variant" as used herein. Further, the variants usable in the present invention may also be derived from homologs, orthologs, or paralogs of the parent molecule or from artificially constructed variant, provided that the variant exhibits at least one biological activity of the parent molecule, i.e. is functionally active.

In preferred embodiments, a variant usable in the present invention exhibits a total number of up to 200 (up to 1, 2, 3, 4, 5, 6, 7, 8, 9, 10, 15, 20, 25, 30, 35, 40, 45, 50, 55, 60, 65, 70, 75, 80, 85, 90, 95, 100, 110, 120, 130, 140, 1 50, 160, 170, 180, 190, or 200) changes in the amino acid or nucleotide sequence (i.e. exchanges, insertions, deletions, 5'-, 3'-, N-terminal, and/or C-terminal truncations). Amino acid exchanges may be conservative and/or non-conservative. In preferred embodiments, a variant usable in the present invention differs from the protein or polynucleotide from which it is derived by up to 1, 2, 3, 4, 5, 6, 7, 8, 9, 10, 15, 20, 25, 30, 35, 40, 45, 50, 55, 60, 65, 70, 75, 80, 85, 90, 95, or 100 amino acid or nucleic acid exchanges. Alternatively or additionally, a "variant" as used herein, can be characterized by a certain degree of sequence identity to the parent polypeptide or parent polynucleotide from which it is derived. More precisely, a protein variant in the context of the present invention exhibits at least 80% sequence identity to its parent polypeptide. A polynucleotide variant in the context of the present invention exhibits at least 80% sequence identity to its parent polynucleotide. Preferably, the sequence identity of protein variants is over a continuous stretch of 20, 30, 40, 45, 50, 60, 70, 80, 90, 100 or more amino acids. Preferably, the sequence identity of polynucleotide variants is over a continuous stretch of 60, 90, 120, 135, 1 50, 180, 210, 240, 270, 300 or more nucleotides.

The term "at least 80% sequence identity" is used throughout the specification with regard to polypeptide and polynucleotide sequence comparisons. This expression preferably refers to a sequence identity of at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% to the respective reference polypeptide or to the respective reference polynucleotide. Preferably, the polypeptide in question and the reference polypeptide exhibit the indicated sequence identity over a continuous stretch of 20, 30, 40, 45, 50, 60, 70, 80, 90, 100 or more amino acids or over the entire length of the reference polypeptide. Preferably, the polynucleotide in question and the reference polynucleotide exhibit the indicated sequence identity over a continuous stretch of 60, 90, 120, 135, 1 50, 180, 210, 240, 270, 300 or more nucleotides or over the entire length of the reference polypeptide.

The terms "deletion variant" and "fragment" are used interchangeably herein. A fragment may be naturally occurring (e.g. splice variants) or it may be constructed artificially, preferably by gene-technological means. Preferably, a fragment (or deletion variant) has a deletion of up to 1, 2, 3, 4, 5, 6, 7, 8, 9, 10, 15, 20, 25, 30, 35, 40, 45, 50, 55, 60, 65, 70, 75, 80, 85, 90, 95, or 100 amino acids or nucleic acids as compared to the parent polypeptide. In case where two sequences are compared and the reference sequence is not specified in comparison to which the sequence identity percentage is to be calculated, the sequence identity is to be calculated with reference to the longer of the two sequences to be compared, if not specifically indicated otherwise. If the reference sequence is indicated, the sequence identity is determined on the basis of the full length of the reference sequence indicated by SEQ ID, if not specifically indicated otherwise.

The similarity of nucleotide and amino acid sequences, i.e. the percentage of sequence identity, can be determined via sequence alignments. Such alignments can be carried out with several art-known algorithms, preferably with the mathematical algorithm of Karlin and Altschul (Karlin & Altschul (1993) Proc. Natl. Acad. Sci. USA 90: 5873-5877), with hmmalign (HMMER package; or with the CLUSTAL algorithm (Thompson, J. D., Higgins, D. G. & Gibson, T. J. (1994) Nucleic Acids Res. 22, 4673-80). Preferred parameters used are the default parameters as they are set on the CLUSTAL algorithm. The grade of sequence identity (sequence matching) may be calculated using e.g. BLAST, BLAT or BlastZ (or BlastX). A similar algorithm is incorporated into the BLASTN and BLASTP programs of Altschul et al. (1990) J. Mol. Biol. 215: 403-410. BLAST polynucleotide searches are performed with the BLASTN program, score=100, word length=12, to obtain homologous polynucleotide sequences.

"Hybridization" can also be used as a measure of sequence identity or homology between two nucleic acid sequences. A nucleic acid sequence encoding F, N, or M2-1, or a portion of any of these can be used as a hybridization probe according to standard hybridization techniques. The hybridization of an F, N, or M2-1 probe to DNA or RNA from a test source is an indication of the presence of the F DNA or RNA, N DNA or RNA, or M2-1 DNA or RNA, respectively, in the test source. Hybridization conditions are known to those skilled in the art and can be found, for example, in Current Protocols in Molecular Biology, John Wiley & Sons, N. Y., 6.3.1-6.3.6, 1991. "Moderate hybridization conditions" are defined as equivalent to hybridization in 2× sodium chloride/sodium citrate (SSC) at 30° C., followed by a wash in 1×SSC, 0.1% SDS at 50° C. "Highly stringent conditions" are defined as equivalent to hybridization in 6× sodium chloride/sodium citrate (SSC) at 45° C., followed by a wash in 0.2×SSC, 0.1% SDS at 65° C.

Semi-conservative and especially conservative amino acid substitutions, wherein an amino acid is substituted with a chemically related amino acid are preferred. Typical substitutions are among the aliphatic amino acids, among the amino acids having aliphatic hydroxyl side chain, among the amino acids having acidic residues, among the amide derivatives, among the amino acids with basic residues, or the amino acids having aromatic residues. Typical semi-conservative and conservative substitutions are:

| Amino acid | Conservative substitution | Semi-conservative substitution |
|---|---|---|
| A | G; S; T | N; V; C |
| C | A; V; L | M; I; F; G |
| D | E; N; Q | A; S; T; K; R; H |
| E | D; Q; N | A; S; T; K; R; H |
| F | W; Y; L; M; H | I; V; A |

-continued

| Amino acid | Conservative substitution | Semi-conservative substitution |
|---|---|---|
| G | A | S; N; T; D; E; N; Q |
| H | Y; F; K; R | L; M; A |
| I | V; L; M; A | F; Y; W; G |
| K | R; H | D; E; N; Q; S; T; A |
| L | M; I; V; A | F; Y; W; H; C |
| M | L; I; V; A | F; Y; W; C; |
| N | Q | D; E; S; T; A; G; K; R |
| P | V; I | L; A; M; W; Y; S; T; C; F |
| Q | N | D; E; A; S; T; L; M; K; R |
| R | K; H | N; Q; S; T; D; E; A |
| S | A; T; G; N | D; E; R; K |
| T | A; S; G; N; V | D; E; R; K; I |
| V | A; L; I | M; T; C; N |
| W | F; Y; H | L; M; I; V; C |
| Y | F; W; H | L; M; I; V; C |

Changing from A, F, H, I, L, M, P, V, W or Y to C is semi-conservative if the new cysteine remains as a free thiol. Furthermore, the skilled person will appreciate that glycines at sterically demanding positions should not be substituted and that P should not be introduced into parts of the protein which have an alpha-helical or a beta-sheet structure.

The term "tissue" as used herein, refers to an ensemble of cells of the same origin which fulfil a specific function concertedly. Examples of a tissue include but are not limited to connective tissue, muscle tissue, nervous tissue, and epithelial tissue. Multiple tissues together form an "organ" to carry out a specific function. Examples of an organ include but are not limited to glands, muscle, blood, brain, heart, liver, kidney, stomach, skeleton, joint, and skin.

The term "disease" and "disorder" are used interchangeably herein, referring to an abnormal condition, especially an abnormal medical condition such as an illness or injury, wherein a tissue, an organ or an individual is not able to efficiently fulfil its function anymore. Typically, but not necessarily, a disease is associated with specific symptoms or signs indicating the presence of such disease. The presence of such symptoms or signs may thus, be indicative for a tissue, an organ or an individual suffering from a disease. An alteration of these symptoms or signs may be indicative for the progression of such a disease. A progression of a disease is typically characterised by an increase or decrease of such symptoms or signs which may indicate a "worsening" or "bettering" of the disease. The "worsening" of a disease is characterised by a decreasing ability of a tissue, organ or organism to fulfil its function efficiently, whereas the "bettering" of a disease is typically characterised by an increase in the ability of a tissue, an organ or an individual to fulfil its function efficiently. A tissue, an organ or an individual being at "risk of developing" a disease is in a healthy state but shows potential of a disease emerging. Typically, the risk of developing a disease is associated with early or weak signs or symptoms of such disease. In such case, the onset of the disease may still be prevented by treatment. Examples of a disease include but are not limited to traumatic diseases, inflammatory diseases, infectious diseases, cutaneous conditions, endocrine diseases, intestinal diseases, neurological disorders, joint diseases, genetic disorders, autoimmune diseases, and various types of cancer.

"Cancer" refers to a proliferative disorder involving abnormal cell growth which may invade or spread to other tissues or organs of a subject. Cancers are classified by the type of cell that the tumor cells resemble and is therefore presumed to be the origin of the tumor. These types include but are not limited to carcinoma (cancers derived from epithelial cells) sarcoma (cancers arising from connective tissue such as e.g. bone, cartilage, fat, nerve), lymphoma and leukemia (cancer arising from hematopoietic cells that leave the marrow and tend to mature in the lymph nodes and blood), germ cell tumor (cancers derived from pluripotent cells), and blastoma (cancers derived from immature "precursor" cells or embryonic tissue). In particular, cancer includes but is not limited to acute lymphoblastic leukemia (ALL), acute myeloid leukemia, adrenocortical carcinoma, AIDS-related cancers, AIDS-related lymphoma, anal cancer, appendix cancer, astrocytoma, childhood cerebellar or cerebral cancer, basal-cell carcinoma, bile duct cancer, extrahepatic, bladder cancer, bone tumor, osteosarcoma/malignant fibrous histiocytoma, brainstem glioma, brain cancer, brain tumor (cerebellar astrocytoma, cerebral astrocytoma/malignant glioma, ependymoma, medulloblastoma, supratentorial primitive neuroectodermal tumors, visual pathway and hypothalamic glioma), breast cancer, bronchial adenomas/carcinoids, Burkitt's lymphoma, carcinoid tumor, central nervous system lymphoma, cerebellar astrocytoma, Cervical cancer, Chronic bronchitis, chronic lymphocytic leukemia, chronic myelogenous leukemia, chronic myeloproliferative disorders, colon cancer, cutaneous T-cell lymphoma, desmoplastic small round cell tumor, endometrial cancer, ependymoma, esophageal cancer, Ewing's sarcoma in the Ewing family of tumors, extracranial germ cell tumor, extragonadal germ cell tumor, extrahepatic bile duct cancer, eye cancer (intraocular melanoma, retinoblastoma), gallbladder cancer, gastric (stomach) cancer, gastrointestinal carcinoid tumor, gastrointestinal stromal tumor (GIST), germ cell tumor (extracranial, extragonadal, or ovarian), gestational trophoblastic tumor, glioma of the brain stem, gastric carcinoid, hairy cell leukemia, head and neck cancer, heart cancer, hepatocellular (liver) cancer, Hodgkin lymphoma, hypopharyngeal cancer, hypothalamic and visual pathway glioma, intraocular melanoma, islet cell carcinoma (endocrine pancreas), Kaposi sarcoma, kidney cancer (renal cell cancer), Laryngeal cancer, leukaemia (acute lymphoblastic, acute myeloid, chronic lymphocytic, chronic myelogenous), lip and oral cavity cancer, liposarcoma, liver cancer, lung cancer (non-small cell, small cell), lymphomas (AIDS-related, Burkitt, cutaneous T-Cell, Hodgkin, primary central nervous system), macroglobulinemia (Waldenström), male breast cancer, malignant fibrous histiocytoma of bone/osteosarcoma, medulloblastoma, melanoma, Merkel cell cancer, Mesothelioma, metastatic squamous neck cancer with occult primary, mouth cancer, multiple endocrine neoplasia syndrome, multiple myeloma/plasma cell neoplasm, Mycosis fungoides, myelodysplastic syndromes, myelodysplastic/myeloproliferative diseases, myelogenous leukemia, chronic, myeloid leukemia, myeloma, myeloproliferative disorders, nasal cavity and paranasal sinus cancer, nasopharyngeal carcinoma, neuroblastoma, oligodendroglioma, oral cancer, oropharyngeal cancer, osteosarcoma/malignant fibrous histiocytoma of bone, ovarian cancer, ovarian epithelial cancer, ovarian germ cell tumor, ovarian low malignant potential tumor, pancreatic cancer, paranasal sinus and nasal cavity cancer, parathyroid cancer, penile cancer, pharyngeal cancer, pheochromocytoma, pineal astrocytoma, pineal germinoma, pineoblastoma and supratentorial primitive neuroectodermal tumors, pituitary adenoma, plasma cell neoplasia/Multiple myeloma, pleuropulmonary blastoma, primary central nervous system lymphoma, prostate cancer, rectal cancer, renal cell carcinoma, renal pelvis and ureter, retinoblastoma, rhabdomyosarcoma, salivary gland cancer, sarcoma (Ewing family of tumors, Kaposi, soft tissue, uterine), Sezary syndrome, skin cancer (carcinoma, melanoma, non-melanoma, Merkel cell), small cell lung cancer, small intestine cancer, soft tissue sarcoma, squamous cell carcinoma, supratentorial primitive neuroectodermal tumor, testicular cancer, throat cancer, thymoma, thymoma and thymic carcinoma, thyroid cancer, transitional cell cancer of the renal pelvis and ureter, trophoblastic tumor, urethral cancer, uterine cancer, (endometrial, sarcoma), vaginal cancer, visual pathway and hypothalamic glioma, vulvar cancer, Wilms tumor (kidney cancer), As used herein, the term "breast tumor" relates to an abnormal hyperproliferation of breast tissue cells in a subject, which may be a benign (non-cancerous) tumor or a malign (cancerous) tumor. Benign breast tumors, preferably, include fibroadenomas, granular cell tumors, intraductal papillomas, and phyllodes tumors. A malign tumor, is a breast cancer (BC) as specified herein above.

As used herein, the term "metastatic breast cancer" (MBC) relates to a breast cancer wherein cancer cells grow as a metastasis at least one secondary site, i.e. a non-adjacent organ or part of the body of a subject.

As used herein, the term "ovary tumor" relates to an abnormal hyperproliferation of ovary tissue cells in a subject, which may be a benign (non-cancerous) tumor or a malign (cancerous) tumor. A malign tumor is an ovary cancer (OvaCa) as specified herein above.

As used herein, the term "pancreatic tumor" relates to an abnormal hyperproliferation of ovary tissue cells in a subject, which may be a benign (non-cancerous) tumor or a malign (cancerous) tumor. A malign tumor is a pancreatic cancer (PaCa) as specified herein above.

The term "circulating tumor cell" or "CTC" is understood by the skilled artisan and relates to a tumor cell detached from the primary or metastatic tumor and circulating in the bloodstream. It is to be understood that the number of CTC is a prognostic marker for disease and therapy outcome in breast cancer, e.g. for overall survival. The term "CTC status" relates to the presence or absence of more than a reference amount of CTC in a sample. Preferably, the reference amount of CTC is 2, 2.5, 3, 3.5, 4, 4.5, 5, 5.5, 6, 6.5, 7, or 7.5 CTC/7.5 ml blood, 5 CTC/7.5 ml blood being more preferred. In subjects where a blood sample comprises more than said reference amount of CTC, the CTC status is unfavorable, indicating a low probability of successful treatment and a low progression-free and overall survival probability. Conversely, in subjects where a blood sample comprises less than said reference amount of CTC, the CTC status is favorable, indicating a high probability of successful treatment and a high progression-free and overall survival probability. Advantageously, it has been found in the present invention that the amounts of the miRNAs used for determining the CTC status of a subject as defined herein below are indicative of the CTC status of a subject. Thus, determining the CTC status in a subject as used herein relates to determining the amount or amounts of said miRNA or miRNAs and thus obtaining an indication of the subject's CTC status. Preferably, the status can be diagnosed to be "favorable" or "unfavorable"

"Symptoms" of a disease are implication of the disease noticeable by the tissue, organ or organism having such disease and include but are not limited to pain, weakness, tenderness, strain, stiffness, and spasm of the tissue, an organ or an individual. "Signs" or "signals" of a disease include but are not limited to the change or alteration such as the presence, absence, increase or elevation, decrease or decline, of specific indicators such as biomarkers or molecular markers, or the development, presence, or worsening of symptoms.

The term "indicator" and "marker" are used interchangeably herein, and refer to a sign or signal for a condition or is used to monitor a condition. Such a "condition" refers to the biological status of a cell, tissue or organ or to the health and/or disease status of an individual. An indicator may be the presence or absence of a molecule, including but not limited to peptide, protein, and nucleic acid, or may be a change in the expression level or pattern of such molecule in a cell, or tissue, organ or individual. An indicator may be a sign for the onset, development or presence of a disease in an individual or for the further progression of such disease. An indicator may also be a sign for the risk of developing a disease in an individual.

As used herein, the term "gene product" relates to a, preferably macromolecular, physical entity, the presence of which in a cell depends on the expression of said gene in said cell. The mechanisms of gene expression are well-known to the one skilled in the art to include the basic mechanisms of transcription, i.e. formation of RNA corresponding to the said gene or parts thereof, and translation, i.e. production of polypeptide molecules having an amino acid sequence encoded by said RNA according to the genetic code; it is well-known to the one skilled in the art that other cellular processes may be involved in gene expression as well, e.g. RNA processing, RNA editing, proteolytic processing, protein editing, and the like. The term gene product thus includes RNA, preferably mRNA, as well as polypeptides expressed from said gene. It is clear from the above that the term gene product also includes fragments of said RNA(s), preferably with a length of at least ten, at least twelve, at least 20, at least 50, or at least 100 nucleotides, and fragments (peptides) from said polypeptides, preferably with a length of at least eight, at least ten, at least twelve, at least 15, at least 20 amino acids.

"Determining" the amount of a gene product relates to measuring the amount of said gene product, preferably semi-quantitatively or quantitatively. Measuring can be done directly or indirectly. Preferably, measuring is performed on a processed sample, said processing comprising extraction of polynucleotides or polypeptides from the sample. It is, however, also envisaged by the present invention that the gene product is determined in situ, e.g. by immune-histo-chemistry (IHC)

The amount of the polynucleotides of the present invention can be determined with several methods well-known in the art. Quantification preferably is absolute, i.e. relating to a specific number of polynucleotides or, more preferably, relative, i.e. measured in arbitrary normalized units. Preferably, a normalization is carried out by calculating the ratio of a number of specific polynucleotides and total number of polynucleotides or a reference amplification product. Methods allowing for absolute or relative quantification are well known in the art. E.g., quantitative PCR methods are methods for relative quantification; if a calibration curve is incorporated in such an assay, the relative quantification can be used to obtain an absolute quantification. Other methods known are, e.g. nucleic acid sequence-based amplification (NASBA) or the Branched DNA Signal Amplification Assay method in combination with dot blot or luminex detection of amplified polynucleotides. Preferably, the polynucleotide amounts are normalized polynucleotide amounts, i.e. the polynucleotide amounts obtained are set into relation to at least one reference amplification product, thereby, preferably, setting the polynucleotide amounts into relation to the number of cells in the sample and/or the efficiency of polynucleotide amplification. Thus, preferably, the reference amplification product is a product obtained from a polynucleotide known to have a constant abundancy in each cell, i.e. a polynucleotide comprised in most, preferably all, cells of a sample in approximately the same amount. More preferably, the reference amplification product is amplified from a chromosomal or mitochondrial gene or from the mRNA of a housekeeping gene. The amout of polynucleotides could be determined by Shotgun sequencing, Bridge PCR, Sanger sequencing, pyrosequencing, next-generation sequeing, Single-molecule real-time sequencing, Ion Torrent sequencing, Sequencing by synthesis, Sequencing by ligation, Massively parallel signature sequencing, Polony sequencing, DNA nanoball sequencing, Heliscope single molecule sequencing, Single molecule real time (SMRT) sequencing, Nanopore DNA sequencing, Tunnelling currents DNA sequencing, Sequencing by hybridization, Sequencing with mass spectrometry, Microfluidic Sanger sequencing, Transmission electron microscopy DNA sequencing, RNA polymerase sequencing, In vitro virus high-throughput sequencing, Chromatin Isolation by RNA Purification (ChIRP-Seq), Global Run-on Sequencing (GRO-Seq), Ribosome Profiling Sequencing (Ribo-Seq)/ARTseq, RNA Immunoprecipitation Sequencing (RIP-Seq), High-Throughput Sequencing of CLIP cDNA library (HITS-CLIP), Crosslinking and Immunoprecipitation Sequencing, Photoactivatable Ribonucleoside-Enhanced Crosslinking and Immunoprecipitation (PAR-CLIP), Individual Nucleotide Resolution CLIP (iCLIP), Native Elongating Transcript Sequencing (NET-Seq), Targeted Purification of Polysomal mRNA (TRAP-Seq), Crosslinking, Ligation, and Sequencing of Hybrids (CLASH-Seq), Parallel Analysis of RNA Ends Sequencing (PARE-Seq), Genome-Wide Mapping of Uncapped Transcripts (GMUCT), Transcript Isoform Sequencing (TIF-Seq), Paired-End Analysis of TSSs (PEAT), Selective 2'-Hydroxyl Acylation Analyzed by Primer Extension Sequencing (SHAPE-Seq), Parallel Analysis of RNA Structure (PARS-Seq), Fragmentation Sequencing (FRAG-Seq), CXXC Affinity Purification Sequencing (CAP-Seq), Alkaline Phosphatase Calf Intestine-Tobacco Acid Pyrophosphatase Sequencing (CIP-TAP), Inosine Chemical Erasing Sequencing (ICE), m6A-Specific Methylated RNA Immunoprecipitation Sequencing (MeRIP-Seq), Digital RNA Sequencing, Whole-Transcript Amplification for Single Cells (Quartz-Seq), Designed Primer-Based RNA Sequencing (DP-Seq), Switch Mechanism at the 5' End of RNA Templates (Smart-Seq), Switch Mechanism at the 5' End of RNA Templates Version 2 (Smart-Seq2), Unique Molecular Identifiers (UMI), Cell Expression by Linear Amplification Sequencing (CEL-Seq), Single-Cell Tagged Reverse Transcription Sequencing (STRT-Seq), Single-Molecule Molecular Inversion Probes (smMIP), Multiple Displacement Amplification (MDA), Multiple Annealing and Looping-Based Amplification Cycles (MALBAC), Oligonucleotide-Selective Sequencing (OS-Seq), Duplex Sequencing (Duplex-Seq), Bisulfite Sequencing (BS-Seq), Post-Bisulfite Adapter Tagging (PBAT), Tagmentation-Based Whole Genome Bisulfite Sequencing (T-WGBS), Oxidative Bisulfite Sequencing (oxBS-Seq), Tet-Assisted Bisulfite Sequencing (TAB-Seq), Methylated DNA Immunoprecipitation Sequencing (MeDIP-Seq), Methylation-Capture (MethylCap) Sequencing, Methyl-Binding-Domain-Capture (MBDCap) Sequencing, Reduced-Representation Bisulfite Sequencing (RRBS-Seq), DNase 1 Hypersensitive Sites Sequencing (DNase-Seq), MNase-Assisted Isolation of Nucleosomes Sequencing (MAINE-Seq), Chromatin Immunoprecipitation Sequencing (ChIP-Seq), Formaldehyde-Assisted Isolation of Regulatory Elements (FAIRE-Seq), Assay for Transposase-Accessible Chromatin Sequencing (ATAC-Seq), Chromatin Interaction Analysis by Paired-End Tag Sequencing (ChIA-PET), Chromatin Conformation Capture (Hi-C/3C-Seq), Circular Chromatin Conformation Capture (4-C or 4C-Seq), Chromatin Conformation Capture Carbon Copy (5-C), Retrotransposon Capture Sequencing (RC-Seq), Transposon Sequencing (Tn-Seq) or Insertion Sequencing (INSeq), Translocation-Capture Sequencing (TC-Seq), fluorescence based methods (such as: mircoarray, real-time PCR), mass-based methods (mass spectrometry), restriction enzyme based methods, antibody-immunoprecipitation based methods, and digital PCR.

The amount of peptides or polypeptides of the present invention can be determined in various ways. Direct measuring relates to measuring the amount of the peptide or polypeptide based on a signal which is obtained from the peptide or polypeptide itself and the intensity of which directly correlates with the number of molecules of the peptide present in the sample. Such a signal—sometimes referred to as intensity signal—may be obtained, e.g., by measuring an intensity value of a specific physical or chemical property of the peptide or polypeptide. Indirect measuring includes measuring of a signal obtained from a secondary component (i.e. a component not being the peptide or polypeptide itself) or a biological read out system, e.g., measurable cellular responses, ligands, labels, or enzymatic reaction products.

Determining the amount of a peptide or polypeptide can be achieved by all known means for determining the amount of a peptide in a sample. Said means comprise immunoassay and/or immunohistochemistry devices and methods which may utilize labeled molecules in various sandwich, competition, or other assay formats. Said assays will develop a signal which is indicative for the presence or absence of the peptide or polypeptide. Moreover, the signal strength can, preferably, be correlated directly or indirectly (e.g. reverse—proportional) to the amount of polypeptide present in a sample. Further suitable methods comprise measuring a physical or chemical property specific for the peptide or polypeptide such as its precise molecular mass or NMR spectrum. Said methods comprise, preferably, biosensors, optical devices coupled to immunoassays, biochips, analytical devices such as mass-spectrometers, NMR-analyzers, or chromatography devices. Further, methods include microplate ELISA-based methods, fully-automated or robotic immunoassays, Cobalt Binding Assays, and latex agglutination assays.

Determining the amount of a peptide or polypeptide comprises the step of measuring a specific intensity signal obtainable from the peptide or polypeptide in the sample. As described above, such a signal may be the signal intensity observed at an m/z variable specific for the peptide or polypeptide observed in mass spectra or a NMR spectrum specific for the peptide or polypeptide.

Determining the amount of a peptide or polypeptide may, preferably, comprise the steps of (a) contacting the peptide with a specific ligand, (b) (optionally) removing non-bound ligand, (c) measuring the amount of bound ligand. The bound ligand will generate an intensity signal. Binding according to the present invention includes both covalent and non-covalent binding. A ligand according to the present invention can be any compound, e.g., a peptide, polypeptide, nucleic acid, or small molecule, binding to the peptide or polypeptide described herein. Preferred ligands include antibodies, nucleic acids, peptides or polypeptides such as receptors or binding partners for the peptide or polypeptide and fragments thereof comprising the binding domains for the peptides, and aptamers, e.g. nucleic acid or peptide aptamers. Methods to prepare such ligands are well-known in the art. For example, identification and production of suitable antibodies or aptamers is also offered by commercial suppliers. The person skilled in the art is familiar with methods to develop derivatives of such ligands with higher affinity or specificity. For example, random mutations can be introduced into the nucleic acids, peptides or polypeptides. The term "antibody" as used herein refers to secreted immunoglobulins which lack the transmembrane region and can thus, be released into the bloodstream and body cavities. Antibodies are typically made of four polypeptide chains comprising two identical heavy chains and identical two light chains which are connected via disulfide bonds and resemble a "Y"-shaped macro-molecule. Papain digestion of antibodies produces two identical antigen binding fragments, called "Fab fragments" (also referred to as "Fab portion" or "Fab region") each with a single antigen binding site, and a residual "Fc fragment" (also referred to as "Fc portion" or "Fc region") whose name reflects its ability to crystallize readily. The crystal structure of the human IgG Fc region has been determined (Deisenhofer (1981) Biochemistry 20:2361-2370). In IgG, IgA and IgD isotypes, the Fc region is composed of two identical protein fragments, derived from the CH2 and CH3 domains of the antibody's two heavy chains; in IgM and IgE isotypes, the Fc regions contain three heavy chain constant domains (CH2-4) in each polypeptide chain. In addition, smaller immunoglobulin molecules exist naturally or have been constructed artificially. The term "Fab' fragment" refers to a Fab fragment additionally comprising the hinge region of an Ig molecule whilst "F(a')2 fragments" are understood to comprise two Fab' fragments being either chemically linked or connected via a disulfide bond. Whilst "single domain antibodies (sdAb)" (Desmyter et al. (1996) Nat. Structure Biol. 3:803-811) and "Nanobodies" only comprise a single VH domain, "single chain Fv (scFv)" fragments comprise the heavy chain variable domain joined via a short linker peptide to the light chain variable domain (Huston et al. (1988) Proc. Natl. Acad. Sci. USA 85, 5879-5883). Divalent single-chain variable fragments (di-scFvs) can be engineered by linking two scFvs (scFvA-scFvB). This can be done by producing a single peptide chain with two VH and two VL regions, yielding "tandem scFvs" (VHA-VLA-VHB-VLB). Another possibility is the creation of scFvs with linkers that are too short for the two variable regions to fold together, forcing scFvs to dimerize. Usually linkers with a length of 5 residues are used to generate these dimers. This type is known as "diabodies". Still shorter linkers (one or two amino acids) between a VH and VL domain lead to the formation of monospecific trimers, so-called "triabodies" or "tribodies". Bispecific diabodies are formed by expressing to chains with the arrangement VHA-VLB and VHB-VLA or VLA-VHB and VLB-VHA, respectively. Single-chain diabodies (scDb) comprise a VHA-VLB and a VHB-VLA fragment which are linked by a linker peptide (P) of 12-20 amino acids, preferably 14 amino acids, (VHA-VLB-P-VHB-VLA). "Bispecific T-cell engagers (BiTEs)" are fusion proteins consisting of two scFvs of different antibodies wherein one of the scFvs binds to T cells via the CD3 receptor, and the other to a tumor cell via a tumor specific molecule (Kufer et al. (2004) Trends Biotechnol. 22:238-244). Dual affinity retargeting molecules ("DART") molecules) are diabodies additionally stabilized through a C-terminal disulfide bridge. The present invention also includes single chain antibodies and humanized hybrid antibodies wherein amino acid sequences of a non-human donor antibody exhibiting a desired antigen-specificity are combined with sequences of a human acceptor antibody.

The donor sequences will usually include at least the antigen-binding amino acid residues of the donor but may comprise other structurally and/or functionally relevant amino acid residues of the donor antibody as well. Such hybrids can be prepared by several methods well known in the art. Preferably, the ligand or agent binds specifically to the peptide or polypeptide. Specific binding according to the present invention means that the ligand or agent should not bind substantially to ("cross-react" with) another peptide, polypeptide or substance present in the sample to be analyzed. Preferably, the specifically bound peptide or polypeptide should be bound with at least 3 times higher, more preferably at least 10 times higher and even more preferably at least 50 times higher affinity than any other relevant peptide or polypeptide. Nonspecific binding may be tolerable, if it can still be distinguished and measured unequivocally, e.g. according to its size on a Western Blot, or by its relatively higher abundance in the sample. Binding of the ligand can be measured by any method known in the art. Preferably, said method is semi-quantitative or quantitative. Suitable methods are described in the following.

First, binding of a ligand may be measured directly, e.g. by NMR or surface plasmon resonance. Second, if the ligand also serves as a substrate of an enzymatic activity of the peptide or polypeptide of interest, an enzymatic reaction product may be measured (e.g. the amount of a protease can be measured by measuring the amount of cleaved substrate, e.g. on a Western Blot). Alternatively, the ligand may exhibit enzymatic properties itself and the "ligand/peptide or polypeptide" complex or the ligand which was bound by the peptide or polypeptide, respectively, may be contacted with a suitable substrate allowing detection by the generation of an intensity signal. For measurement of enzymatic reaction products, preferably the amount of substrate is saturating. The substrate may also be labeled with a detectable label prior to the reaction. Preferably, the sample is contacted with the substrate for an adequate period of time. An adequate period of time refers to the time necessary for a detectable, preferably measurable, amount of product to be produced. Instead of measuring the amount of product, the time necessary for appearance of a given (e.g. detectable) amount of product can be measured. Third, the ligand may be coupled covalently or non-covalently to a label allowing detection and measurement of the ligand. Labelling may be done by direct or indirect methods. Direct labelling involves coupling of the label directly (covalently or non-covalently) to the ligand. Indirect labelling involves binding (covalently or non-covalently) of a secondary ligand to the first ligand. The secondary ligand should specifically bind to the first ligand. Said secondary ligand may be coupled with a suitable label and/or be the target (receptor) of tertiary ligand binding to the secondary ligand. The use of secondary, tertiary or even higher order ligands is often used to increase the signal intensity. Suitable secondary and higher order ligands may include antibodies, secondary antibodies, and the well-known streptavidin-biotin system (Vector Laboratories, Inc.). The ligand or substrate may also be "tagged" with one or more tags as known in the art. Such tags may then be targets for higher order ligands. Suitable tags include biotin, digoxygenin, His-Tag, Glutathion-S-Transferase, FLAG, GFP, myc-tag, influenza A virus haemagglutinin (HA), maltose binding protein, and the like. In the case of a peptide or polypeptide, the tag is preferably at the N-terminus and/or C-terminus. Suitable labels are any labels detectable by an appropriate detection method. Typical labels include gold particles, latex beads, acridan ester, luminol, ruthenium, enzymatically active labels, radioactive labels, magnetic labels ("e.g. magnetic beads", including paramagnetic and superparamagnetic labels), and fluorescent labels. Enzymatically active labels include e.g. horseradish peroxidase, alkaline phosphatase, beta-Galactosidase, Luciferase, and derivatives thereof. Suitable substrates for detection include di-amino-benzidine (DAB), 3,3'-5,5'-tetramethylbenzidine, NBT-BCIP (4-nitro blue tetrazolium chloride and 5-bromo-4-chloro-3-indolyl-phosphate), CDP-Star™ (Amersham Biosciences), ECF™ (Amersham Biosciences). A suitable enzyme-substrate combination may result in a colored reaction product, fluorescence or chemo luminescence, which can be measured according to methods known in the art (e.g. using a light-sensitive film or a suitable camera system). As for measuring the enzymatic reaction, the criteria given above apply analogously. Typical fluorescent labels include fluorescent proteins (such as GFP and its derivatives), Cy3, Cy5, Texas Red, Fluorescein, and the Alexa dyes (e.g. Alexa 568). Further fluorescent labels are available e.g. from Molecular Probes (Oregon). Also the use of quantum dots as fluorescent labels is contemplated. Typical radioactive labels include 35S, 125I, 32P, 33P and the like. A radioactive label can be detected by any method known and appropriate, e.g. a light-sensitive film or a phosphor imager. Suitable measurement methods according the present invention also include precipitation (particularly immunoprecipitation), electrochemiluminescence (electrogenerated chemiluminescence), RIA (radioimmunoassay), ELISA (enzyme-linked immunosorbent assay), sandwich enzyme immune tests, electrochemiluminescence sandwich immunoassays (ECLIA), dissociation-enhanced lanthanide fluoro immuno assay (DELFIA), scintillation proximity assay (SPA), turbidimetry, nephelometry, latex-enhanced turbidimetry or nephelometry, or solid phase immune tests, like e.g. reverse phase protein arrays or antibody arrays. Further methods known in the art (such as gel electrophoresis, 2D gel electrophoresis, SDS polyacrylamid gel electrophoresis (SDS-PAGE), Western Blotting, and mass spectrometry), can be used alone or in combination with labelling or other detection methods as described above.

The amount of a peptide or polypeptide may also be determined as follows: (a) contacting a solid support comprising a ligand for the peptide or polypeptide as specified above with a sample comprising the peptide or polypeptide and (b) measuring the amount peptide or polypeptide which is bound to the support. The ligand, preferably chosen from the group consisting of nucleic acids, peptides, polypeptides, antibodies and aptamers, is preferably present on a solid support in immobilized form. Materials for manufacturing solid supports are well known in the art and include, inter alia, commercially available column materials, polystyrene beads, latex beads, magnetic beads, colloid metal particles, glass and/or silicon chips and surfaces, nitrocellulose strips, membranes, sheets, duracytes, wells and walls of reaction trays, plastic tubes etc. The ligand or agent may be bound to many different carriers. Examples of well-known carriers include glass, polystyrene, polyvinyl chloride, polypropylene, polyethylene, polycarbonate, dextran, nylon, amyloses, natural and modified celluloses, polyacrylamides, agaroses, and magnetite. The nature of the carrier can be either soluble or insoluble for the purposes of the invention. Suitable methods for fixing/immobilizing said ligand are well known and include, but are not limited to ionic, hydrophobic, covalent interactions and the like. It is also contemplated to use "suspension arrays" as arrays according to the present invention (Nolan 2002, Trends Biotechnol. 20(1):9-12). In such suspension arrays, the carrier, e.g. a microbead or microsphere, is present in suspension. The array consists of different microbeads or microspheres, possibly labeled, carrying different ligands. Methods of producing such arrays, for example based on solid-phase chemistry and photo-labile protective groups, are generally known (U.S. Pat. No. 5,744, 305).

As used herein, the term "CpG site" relates to a dinucleotide sequence 5'-CG-3' comprised in a polynucleotide, preferably comprised in DNA, more preferably comprised in genomic DNA of a subject. The CpG sites to be analyzed according to the present invention are the CpG sites located in the intron, exon or promoter region of a gene of interest. In case the CpG sites are located in the promoter region, said region is preferably 3000 nucleotides, 2500 nucleotides, 2100 nucleotides, or 1750 nucleotides upstream of the translation start site of the respective gene of interest. More preferably, the CpG sites to be analyzed according to the present invention are the CpG sites located in the region 1750-3000 nucleotides, 2100-3000 nucleotides, or 2500-3000 nucleotides upstream of the translation start site of the gene of interest gene.

Thus, analysis of a CpG site corresponding to a CpG site of the present invention is also encompassed by the present invention. The skilled person knows how to determine the CpG sites in a sample corresponding to the CpG sites detailed herein above, e.g. by determining the translation start site of the gene of interest and/or by aligning said sequence from a sample to the sequence of the gene of interest. Further, it is also envisaged by the present invention that the methylation status of other CpG sites is determined in addition to determining the methylation status of a CpG site of the present invention.

The term "determining the methylation status" relates to determining if a methyl group is present at the 5 position of the pyrimidine ring of a cytosine in a polynucleotide. Preferably, the cytosine residue is followed in 3' direction by a guanosine residue, the two residues forming a CpG site. The presence of said methyl group can be determined by various methods well known to the skilled person, including, e.g., methylation-specific PCR (MSP), whole genome bisulfite sequencing or other sequencing based methods (Bisulfite Sequencing (BS-Seq), Post-Bisulfite Adapter Tagging (PBAT), Tagmentation-Based Whole Genome Bisulfite Sequencing (T-WGBS), Oxidative Bisulfite Sequencing (oxBS-Seq), Tet-Assisted Bisulfite Sequencing (TAB-Seq), Methylated DNA Immunoprecipitation Sequencing (MeDIP-Seq), Methylation-Capture (MethylCap) Sequencing, Methyl-Binding-Domain-Capture (MBDCap) Sequencing, Reduced-Representation Bisulfite Sequencing (RRBS-Seq)), real-time PCR based methods of bisulfite treated DNA, e.g. Methylight, restriction with a methylation-sensitive restriction enzyme, e.g. in the HpaII tiny fragment enrichment by ligation-mediated PCR (HELP)-Assay, pyrosequencing of bisulfite treated DNA, or the like AIMS, amplification of inter-methylated sites; BC-seq, bisulphite conversion followed by capture and sequencing; BiMP, bisulphite methylation profiling; BS, bisulphite sequencing; BSPP, bisulphite padlock probes; CHARM, comprehensive high-throughput arrays for relative methylation; COBRA, combined bisulphite restriction analysis; DMH, differential methylation hybridization; HELP, HpaII tiny fragment enrichment by ligation-mediated PCR; MCA, methylated CpG island amplification; MCAM, MCA with microarray hybridization; MeDIP, mDIP and mCIP, methylated DNA immunoprecipitation; MIRA, methylated CpG island recovery assay; MMASS, microarray-based methylation assessment of single samples; MS-AP-PCR, methylation-sensitive arbitrarily primed PCR; MSCC, methylation-sensitive cut counting; MSP, methylation-specific PCR; MS-SNuPE, methylation-sensitive single nucleotide primer extension; NGS, next-generation sequencing; RLGS, restriction landmark genome scanning; RRBS, reduced representation bisulphite sequencing; -seq, followed by sequencing; WGSBS, whole-genome shotgun bisulphite sequencing. (Manel Esteller, Cancer epigenomics: DNA methylomes and histone-modification maps, Nature, 2007, 8:286-298; Peter W. Laird, Principles and challenges of genome-wide DNA methylation analysis. Nature Review Genetics, 2010, 11: 191-203). Preferably, the methylation status is determined by the methods described in the examples herein below, e.g. the sequencing-based Infinium 27K methylation assay or the mass spectrometry based method of MALDI-TOF mass spectrometry. As such, the methylation status of a specific cytosine residue in a specific polynucleotide molecule can only be "unmethylated" (meaning 0% methylation) or "methylated" (meaning 100% methylation). In the case of a CpG site in a double-stranded DNA molecule, which comprises two cytosine residues, the methylation status can be "unmethylated" (meaning 0% methylation, i.e. none of the two cytosine residues methylated), "hemimethylated" (meaning 50% methylation, i.e. one of the two cystosine residues methylated), or "methylated" or "fully methylated" (meaning 100% methylation, i.e. both cytosine residues methylated) It is, however, understood by the person skilled in the art that if polynucleotides from a multitude of cells are obtained and the methylation status of a specific cytosine residue within said multitude of polynucleotides is determined, an average methylation status is determined, which can e.g, preferably, be expressed as a percentage (% methylation), and which can assume any value between 0% and 100%. It is also understood by the skilled person, that the methylation status can be expressed as a percentage in case the average methylation of different cell populations is determined. E.g. the blood cells according to the present invention are a mixture of variant cell types. It is possible that certain cell types have high methylation levels whereas other cell types have lower methylation levels, and finally reach an average methylation of e.g. 50%.

As used herein, the term "detection agent" relates to an agent specifically interacting with, and thus recognizing, the expression level of a gene of interest, the methylation status of a gene of interest, or the presence or amount of a miRNA of the present invention. Preferably, said detection agent is a protein, polypeptide, peptide, polynucleotide or an oligonucleotide. Preferably, the detection agent is labeled in a way allowing detection of said detection agent by appropriate measures. Labeling can be done by various techniques well known in the art and depending of the label to be used. Preferred labels to be used are fluorescent labels comprising, inter alia, fluorochromes such as fluorescein, rhodamin, or Texas Red. However, the label may also be an enzyme or an antibody. It is envisaged that an enzyme to be used as a label will generate a detectable signal by reacting with a substrate. Suitable enzymes, substrates and techniques are well known in the art. An detection agent to be used as label may specifically recognize a target molecule which can be detected directly (e.g., a target molecule which is itself fluorescent) or indirectly (e.g., a target molecule which generates a detectable signal, such as an enzyme). The labeled detection agents of the sample will be contacted to the sample to allow specific interaction. Washing may be required to remove non-specifically bound detection agent which otherwise would yield false values. After this interaction step is complete, a researcher will place the detection device into a reader device or scanner. A device for detecting fluorescent labels, preferably, consists of some lasers, preferably a special microscope, and a camera. The fluorescent labels will be excited by the laser, and the microscope and camera work together to create a digital image of the sample. These data may be then stored in a computer, and a special program will be used, e.g., to subtract out background data. The resulting data are, preferably, normalized, and may be converted into a numeric and common unit format. The data will be analyzed to compare samples to references and to identify significant changes.

"Comparing" as used herein encompasses comparing the presence, absence or amount of an indicator referred to herein which is comprised by the sample to be analyzed with the presence, absence or amount of said indicator in a suitable reference sample. It is to be understood that comparing as used herein refers to a comparison of corresponding parameters or values, e.g., an absolute amount of the indicator as referred to herein is compared to an absolute reference amount of said indicator; a concentration of the indicator is compared to a reference concentration of said indicator; an intensity signal obtained from the indicator as referred to herein in a sample is compared to the same type of intensity signal of said indicator in a reference sample. The comparison referred to may be carried out manually or computer assisted. For a computer assisted comparison, the value of the determined amount may be compared to values corresponding to suitable references which are stored in a database by a computer program. The computer program may further evaluate the result of the comparison by means of an expert system. Accordingly, the result of the identification referred to herein may be automatically provided in a suitable output format.

The term "sample" or "sample of interest" are used interchangeably herein, referring to a part or piece of a tissue, organ or individual, typically being smaller than such tissue, organ or individual, intended to represent the whole of the tissue, organ or individual. Upon analysis, a sample provides information about the tissue status or the health or diseased status of an organ or individual. Examples of samples include but are not limited to fluid samples such as blood, serum, plasma, synovial fluid, urine, saliva, lymphatic fluid, lacrimal fluid, and fluid obtainable from the glands such as e.g. breast or prostate, or tissue samples such as e.g. tissue extracts obtained from tumour tissue or tissue adjacent to a tumour. Further examples of samples are cell cultures or tissue cultures such as but not limited to cultures of various cancer cells.

Samples can be obtained by well known techniques and include, preferably, scrapes, swabs or biopsies from the digestive tract, liver, pancreas, anal canal, the oral cavity, the upper aerodigestive tract and the epidermis. Such samples can be obtained by use of brushes, (cotton) swabs, spatula, rinse/wash fluids, punch biopsy devices, puncture of cavities with needles or surgical instrumentation. Tissue or organ samples may be obtained from any tissue or organ by, e.g., biopsy or other surgical procedures. More preferably, samples are samples of body fluids, e.g., preferably, blood, plasma, serum, urine, saliva, lacrimal fluid, and fluids obtainable from the breast glands, e.g. milk. Most preferably, the sample of a body fluid comprises cells of the subject. Separated cells may be obtained from the body fluids or the tissues or organs by separating techniques such as filtration, centrifugation or cell sorting. Preferably, samples are obtained from those body fluids described herein below. More preferably, cells are isolated from said body fluids as described herein below.

Analysis of a sample may be accomplished on a visual or chemical basis. Visual analysis includes but is not limited to microscopic imaging or radiographic scanning of a tissue, organ or individual allowing for morphological evaluation of a sample. Chemical analysis includes but is not limited to the detection of the presence or absence of specific indicators or alterations in their amount or level.

The term "reference sample" as used herein, refers to a sample which is analysed in a substantially identical manner as the sample of interest and whose information is compared to that of the sample of interest. A reference sample thereby provides a standard allowing for the evaluation of the information obtained from the sample of interest. A reference sample may be derived from a healthy or normal tissue, organ or individual, thereby providing a standard of a healthy status of a tissue, organ or individual. Differences between the status of the normal reference sample and the status of the sample of interest may be indicative of the risk of disease development or the presence or further progression of such disease or disorder. A reference sample may be derived from an abnormal or diseased tissue, organ or individual thereby providing a standard of a diseased status of a tissue, organ or individual. Differences between the status of the abnormal reference sample and the status of the sample of interest may be indicative of a lowered risk of disease development or the absence or bettering of such disease or disorder. A reference sample may also be derived from the same tissue, organ, or individual as the sample of interest but has been taken at an earlier time point. Differences between the status of the earlier taken reference sample and the status of the sample of interest may be indicative of the progression of the disease, i.e. a bettering or worsening of the disease over time. A reference sample was taken at an earlier or later time point in case a period of time has lapsed between taking of the reference sample and taking of the sample of interest. Such period of time may represent years (e.g. 1, 2, 3, 4, 5, 10, 15, 20, 25, 30, 35, 40, 45, 50, 60, 70, 80, 90, 100 years), months (1, 2, 3, 4, 5, 6, 7, 8, 9, 10, 11, 12 months), weeks (e.g. 1, 2, 3, 4, 5, 6, 7, 8 weeks), days (e.g. 1, 2, 3, 4, 5, 10, 15, 20, 25, 30, 35, 40, 45, 50, 60, 70, 80, 90, 100, 200, 300, 400, 500 days), hours (1, 2, 3, 4, 5, 6, 7, 8, 9, 10, 11, 12 hours), minutes (e.g. 1, 2, 3, 4, 5, 10, 15, 20, 25, 30, 35, 40, 45, 50, 60 minutes), or seconds (e.g. 1, 2, 3, 4, 5, 10, 15, 20, 25, 30, 35, 40, 45, 50, 60 seconds).

A reference sample may be "treated differently" or "exposed differently" than a sample of interest in case both samples are treated in a substantially identical way except from a single factor. Such single factors include but are not limited to the time of exposure, the concentration of exposure, or the temperature of exposure to a certain substance. Accordingly, a sample of interest may be exposed to a different dosage of a certain substance than the reference sample or may be exposed for a different time interval than the reference sample or may be exposed at a different temperature than the reference sample. Different dosages to which a sample of interest may be exposed to include but are not limited to the 2-fold, 5-fold, 10-fold, 20-fold, 30-fold, 40-fold, 50-fold, 100-fold and/or 1000-fold increased or decreased dosage of the dosage the reference sample is exposed to. Different exposure times to which a sample of interest may be exposed to include but are not limited to the 2-fold, 5-fold, 10-fold, 20-fold, 30-fold, 40-fold, 50-fold, 100-fold and/or 1000-fold longer or shorter time period than the exposure of the reference. Different temperatures of exposure to which a sample of interest may be exposed to include but are not limited to the 2-fold, 5-fold, 10-fold, 20-fold, 30-fold, 40-fold, 50-fold, 100-fold and/or 1000-fold increased or decreased temperature than the exposure of the reference. In a non-limiting example a sample of interest may be exposed to a 10-fold increased concentration of a substance than the reference sample. The analysis of both samples is then conducted in a substantially identical manner allowing determining the effects, i.e. a beneficial or an adverse effect, of the increased concentration of such substance on the sample of interest. The skilled person will appreciate that this example applies mutatis mutandis to different ranges of concentrations, different exposure times, and/or different temperatures at exposure.

The terms "lowered" or "decreased" level of an indicator refer to the level of such indicator in the sample being reduced in comparison to the reference or reference sample. The terms "elevated" or "increased" level of an indicator refer to the level of such indicator in the sample being higher in comparison to the reference or reference sample.

Reference amounts can, in principle, be calculated for a group or cohort of subjects as specified herein based on the average or median values for a given miRNA by applying standard methods of statistics. In particular, accuracy of a test such as a method aiming to diagnose an event, or not, is best described by its receiver-operating characteristics (ROC) (see especially Zweig 1993, Clin. Chem. 39:561-577). The ROC graph is a plot of all of the sensitivity versus specificity pairs resulting from continuously varying the decision threshold over the entire range of data observed. The clinical performance of a diagnostic method depends on its accuracy, i.e. its ability to correctly allocate subjects to a certain prognosis or diagnosis. The ROC plot indicates the overlap between the two distributions by plotting the sensitivity versus 1-specificity for the complete range of thresholds suitable for making a distinction. On the y-axis is sensitivity, or the true-positive fraction, which is defined as the ratio of number of true-positive test results to the sum of number of true-positive and number of false-negative test results. This has also been referred to as positivity in the presence of a disease or condition. It is calculated solely from the affected subgroup. On the x-axis is the false-positive fraction, or 1-specificity, which is defined as the ratio of number of false-positive results to the sum of number of true-negative and number of false-positive results. It is an index of specificity and is calculated entirely from the unaffected subgroup. Because the true- and false-positive fractions are calculated entirely separately, by using the test results from two different subgroups, the ROC plot is independent of the prevalence of the event in the cohort. Each point on the ROC plot represents a sensitivity/-specificity pair corresponding to a particular decision threshold. A test with perfect discrimination (no overlap in the two distributions of results) has an ROC plot that passes through the upper left corner, where the true-positive fraction is 1.0, or 100% (perfect sensitivity), and the false-positive fraction is 0 (perfect specificity). The theoretical plot for a test with no discrimination (identical distributions of results for the two groups) is a 45° diagonal line from the lower left corner to the upper right corner. Most plots fall in between these two extremes. If the ROC plot falls completely below the 45° diagonal, this is easily remedied by reversing the criterion for "positivity" from "greater than" to "less than" or vice versa. Qualitatively, the closer the plot is to the upper left corner, the higher the overall accuracy of the test. Dependent on a desired confidence interval, a threshold can be derived from the ROC curve allowing for the diagnosis or prediction for a given event with a proper balance of sensitivity and specificity, respectively. Accordingly, the reference to be used for the methods of the present invention can be generated, preferably, by establishing a ROC for said cohort as described above and deriving a threshold amount there from. Dependent on a desired sensitivity and specificity for a diagnostic method, the ROC plot allows deriving suitable thresholds. Preferably, the reference amounts lie within the range of values that represent a sensitivity of at least 75% and a specificity of at least 45%, or a sensitivity of at least 80% and a specificity of at least 40%, or a sensitivity of at least 85% and a specificity of at least 33%, or a sensitivity of at least 90% and a specificity of at least 25%.

Preferably, the reference amount as used herein is derived from samples of subjects obtained before treatment, but for which it is known if their donors were being afflicted with BC or MBC or not. This reference amount level may be a discrete figure or may be a range of figures. Evidently, the reference level or amount may vary between individual species of miRNA. The measuring system therefore, preferably, is calibrated with a sample or with a series of samples comprising known amounts of each specific miRNA. It is understood by the skilled person that in such case the amount of miRNA can preferably be expressed as arbitrary units (AU). Thus, preferably, the amounts of miRNA are determined by comparing the signal obtained from the sample to signals comprised in a calibration curve. The reference amount applicable for an individual subject may vary depending on various physiological parameters such as age or subpopulation. Thus, a suitable reference amount may be determined by the methods of the present invention from a reference sample to be analyzed together, i.e. simultaneously or subsequently, with the test sample. Moreover, a threshold amount can be preferably used as a reference amount. A reference amount may, preferably, be derived from a sample of a subject or group of subjects being afflicted with BC or MBC which is/are known to be afflicted with BC or MBC. A reference amount may, preferably, also be derived from a sample of a subject or group of subjects known to be not afflicted with BC or MBC. It is to be understood that the aforementioned amounts may vary due to statistics and errors of measurement. A deviation, i.e. a decrease or an increase of the miRNA amounts referred to herein is, preferably, a statistically significant deviation, i.e. a statistically significant decrease or a statistically significant increase.

As used herein, "treat", "treating" or "treatment" of a disease or disorder means accomplishing one or more of the following: (a) reducing the severity of the disorder; (b) limiting or preventing development of symptoms characteristic of the disorder(s) being treated; (c) inhibiting worsening of symptoms characteristic of the disorder(s) being treated; (d) limiting or preventing recurrence of the disorder(s) in an individual that have previously had the disorder(s); and (e) limiting or preventing recurrence of symptoms in individuals that were previously symptomatic for the disorder(s).

As used herein, "prevent", "preventing", "prevention", or "prophylaxis" of a disease or disorder means preventing that such disease or disorder occurs in patient.

As used herein, the term "therapy" refers to all measures applied to a subject to ameliorate the diseases or disorders referred to herein or the symptoms accompanied therewith to a significant extent. Said therapy as used herein also includes measures leading to an entire restoration of the health with respect to the diseases or disorders referred to herein. It is to be understood that therapy as used in accordance with the present invention may not be effective in all subjects to be treated. However, the term shall require that a statistically significant portion of subjects being afflicted with a disease or disorder referred to herein can be successfully treated. Whether a portion is statistically significant can be determined without further ado by the person skilled in the art using various well known statistic evaluation tools discussed herein above.

The term "breast cancer therapy", as used herein, relates to applying to a subject afflicted with breast cancer, including metastasizing breast cancer, measures to remove cancer cells from the subject, to inhibit growth of cancer cells, to kill cancer cells, or to cause the body of a patient to inhibit the growth of or to kill cancer cells. Preferably, breast cancer therapy is chemotherapy, anti-hormone therapy, targeted therapy, immunotherapy, or any combination thereof. It is, however, also envisaged that the cancer therapy is radiation therapy or surgery, alone or combination with other therapy regimens. It is understood by the skilled person that the selection of the breast cancer therapy depends on several factors, like age of the subject, tumor staging, and receptor status of tumor cells. It is, however, also understood by the person skilled in the art, that the selection of the breast cancer therapy can be assisted by the methods of the present invention: if, e.g. BC is diagnosed by the method for diagnosing BC, but no MBC is diagnosed by the method for diagnosing MBC, surgical removal of tumor may be sufficient. If, e.g. BC is diagnosed by the method for diagnosing BC and MBC is diagnosed by the method for diagnosing MBC, therapy measures in addition to surgery, e.g. chemotherapy and/or targeted therapy, may be appropriate. Likewise, if, e.g. BC is diagnosed by the method for diagnosing BC, and an unfavorable CTC status is determined by the method for determining the CTC status, e.g. a further addition of immunotherapy to the therapy regimen may be required.

As used herein, the term "chemotherapy" relates to treatment of a subject with an antineoplastic drug. Preferably, chemotherapy is a treatment including alkylating agents (e.g. cyclophosphamide), platinum (e.g. carboplatin), anthracyclines (e.g. doxorubicin, epirubicin, idarubicin, or daunorubicin) and topoisomerase II inhibitors (e.g. etoposide, irinotecan, topotecan, camptothecin, or VP16), anaplastic lymphoma kinase (ALK)-inhibitors (e.g. Crizotinib or AP26130), aurora kinase inhibitors (e.g. N-[4-[4-(4-Methylpiperazin-1-yl)-6-[(5-methyl-1H-pyrazol-3-yl)amino]pyrimidin-2-yl]sulfanylphenyl]cyclopropanecarboxamide (VX-680)), antiangiogenic agents (e.g. Bevacizumab), or Iodine131-1-(3-iodobenzyl)guanidine (therapeutic metaiodobenzylguanidine), histone deacetylase (HDAC) inhibitors, alone or any suitable combination thereof. It is to be understood that chemotherapy, preferably, relates to a complete cycle of treatment, i.e. a series of several (e.g. four, six, or eight) doses of antineoplastic drug or drugs applied to a subject separated by several days or weeks without such application.

The term "anti-hormone therapy" relates to breast cancer therapy by blocking hormone receptors, e.g. estrogen receptor or progesterone receptor, expressed on tumor cells, or by blocking the biosynthesis of estrogen. Blocking of hormone receptors can preferably be achieved by administering compounds, e.g. tamoxifen, binding specifically and thereby blocking the activity of said hormone receptors. Blocking of estrogen biosynthesis is preferably achieved by administration of aromatase inhibitors like, e.g. anastrozole or letrozole. It is known to the skilled artisan that anti-hormone therapy is only advisable in cases where tumor cells are expressing hormone receptors.

The term "targeted therapy", as used herein, relates to application to a patient a chemical substance known to block growth of cancer cells by interfering with specific molecules known to be necessary for tumorigenesis or cancer or cancer cell growth. Examples known to the skilled artisan are small molecules like, e.g. PARD-inhibitors (e.g. Iniparib), or monoclonal antibodies like, e.g., Trastuzumab.

The term "immunotherapy" as used herein relates to the treatment of cancer by modulation of the immune response of a subject. Said modulation may be inducing, enhancing, or suppressing said immune response. The term "cell based immunotherapy" relates to a breast cancer therapy comprising application of immune cells, e.g. T-cells, preferably tumor-specific NK cells, to a subject.

The terms "radiation therapy" or "radiotherapy" is known to the skilled artisan. The term relates to the use of ionizing radiation to treat or control cancer. The skilled person also knows the term "surgery", relating to operative measures for treating breast cancer, e.g. excision of tumor tissue.

As used herein, the term "therapy monitoring" relates to obtaining an indication on the effect of a treatment against cancer on the cancer status of a subject afflicted with said cancer. Preferably, therapy monitoring comprises application of a method of the present invention on two samples from the same subject, wherein a first sample is obtained at a time point before the second sample. Preferably, the time point of obtaining the first sample is separated from the time point of obtaining the second sample by about one week, about two weeks, about three weeks, about for weeks, about five weeks, about, six weeks, about seven weeks, about two months, about three months, about five months, about six month, or more than about six months. It is, however, also envisaged by the present invention that the method of therapy monitoring is used for long-term monitoring of subjects, e.g. monitoring the time of relapse-free survival or the like. In such case, the time point of obtaining the first sample is separated from the time point of obtaining the second sample, preferably, by at least six months, at least one year, at least two years, at least three years, at least four years, at least five years, or at least six years. It is known to the person skilled in the art that the first sample is preferably obtained before cancer therapy is started, while the second sample is preferably obtained after therapy is started. It is, however, also envisaged by the present invention that both samples are obtained after therapy is started. The skilled artisan also understands that more than two successive samples may be obtained according to the method for therapy monitoring of the present invention and that in such case the sample obtained at the first point in time may be used as the first sample relative to the second sample as well as for a third sample. Mutatis mutandis, the sample obtained at the second point in time may nonetheless be used as a first sample relative to a third sample, and the like.

The term "treatment success", as used herein, preferably relates to an amelioration of the diseases or disorders referred to herein or the symptoms accompanied therewith to a significant extent. More preferably, the term relates to a complete cure of said subject, i.e. to the prevention of progression and/or relapse of metastasizing breast cancer for at least five years. Accordingly, "determining treatment success" relates to assessing the probability according to which a subject was successfully treated. Preferably, the term relates to predicting progression free survival and/or overall survival of the subject, more preferably for a specific period of time. The term "predicting progression free survival" relates to determining the probability of a subject surviving without relapse and/or progression of metastatic breast cancer for a specific period of time. Accordingly, the term "predicting overall survival" relates to determining the probability according to which a subject will survive for a specific period of time. Preferably, said period of time is at least 12 months, more preferably at least 24 months. The terms "pharmaceutical", "medicament" and "drug" are used interchangeably herein referring to a substance and/or a combination of substances being used for the identification, prevention or treatment of a tissue status or disease.

The term "kit" as used herein refers to a collection of the aforementioned components, preferably, provided separately or within a single container. The container, also preferably, comprises instructions for carrying out the method of the present invention. Examples for such the components of the kit as well as methods for their use have been given in this specification. The kit, preferably, contains the aforementioned components in a ready-to-use formulation. Preferably, the kit may additionally comprise instructions, e.g., a user's manual for adjusting the components, e.g. concentrations of the detection agents, and for interpreting the results of any determination(s) with respect to the diagnoses provided by the methods of the present invention. Particularly, such manual may include information for allocating the amounts of the determined a gene product to the kind of diagnosis. Details are to be found elsewhere in this specification. Additionally, such user's manual may provide instructions about correctly using the components of the kit for determining the amount(s) of the respective biomarker. A user's manual may be provided in paper or electronic form, e.g., stored on CD or CD ROM. The present invention also relates to the use of said kit in any of the methods according to the present invention.

The term "device" as used herein relates to a system of means comprising at least the aforementioned means operatively linked to each other as to allow the diagnosis. Preferred means for determining the methylation status or the amount of gene product and means for carrying out the comparison are disclosed above in connection with the methods of the invention. How to link the means in an operating manner will depend on the type of means included into the device. For example, where means for automatically determining the methylation status or the amount of a gene product are applied, the data obtained by said automatically operating means can be processed by, e.g., a computer program in order to establish a diagnosis. Preferably, the means are comprised by a single device in such a case. Said device may accordingly include an analyzing unit for determining the methylation status or the amount of a gene product in a sample and an evaluation unit for processing the resulting data for the diagnosis. Preferred means for detection are disclosed in connection with embodiments relating to the methods of the invention above. In such a case, the means are operatively linked in that the user of the system brings together the result of the determination of the amount and the diagnostic value thereof due to the instructions and interpretations given in a manual. The means may appear as separate devices in such an embodiment and are, preferably, packaged together as a kit. The person skilled in the art will realize how to link the means without further inventive skills. Preferred devices are those which can be applied without the particular knowledge of a specialized clinician, e.g., test stripes or electronic devices which merely require loading with a sample. The results may be given as output of parametric diagnostic raw data, preferably, as absolute or relative amounts. It is to be understood that these data will need interpretation by the clinician. However, also envisaged are expert system devices wherein the output comprises processed diagnostic raw data the interpretation of which does not require a specialized clinician. Further preferred devices comprise the analyzing units/devices (e.g., biosensors, arrays, solid supports coupled to ligands specifically recognizing the polypeptides, Plasmon surface resonance devices, NMR spectrometers, mass-spectrometers etc.) or evaluation units/devices referred to above in accordance with the methods of the invention.

Embodiments

In a first aspect the present invention relates to a method of prognosing and/or diagnosing a disease in a subject, comprising
  a) determining the methylation status and/or expression level of at least one methylation marker selected from the group consisting of HYAL2, MGRN1, RPTOR, SLC22A18, FUT7, RAPSN, S100P, DYRK4, and
  b) determining the presence, of at least one miRNA marker selected from the group consisting of miR-652, miR-801, miR-376c, miR-376a, miR-127, miR-409, miR-148b, in a subject.

In particular embodiments, the disease is a proliferative cell disease. In particular embodiments the disease is cancer. In particular, the cancer is selected from the group consisting of breast cancer, pancreatic cancer and ovarian cancer.

In particular embodiments, the term miR-652 refers to the sequence of the -3p or -5p strand (in particular miR-652-3p), the term miR-801 refers to the sequence of the -3p or -5p strand, the term miR-376c refers to the sequence of the -3p or -5p strand (in particular miR-376c-3p), the term miR-376a refers to the sequence of the -3p or -5p strand (in particular miR-376a-3p), the term miR-127 refers to the sequence of the -3p or -5p strand (in particular miR-127-3p), the term miR-409 refers to the sequence of the -3p or -5p strand (in particular miR-409-3p), the term miR-148b refers to the sequence of the -3p or -5p strand (in particular miR-148-3p).

In further embodiments, an alteration in the methylation status and/or expression level of HYAL2, MGRN1, RPTOR, SLC22A18, FUT7, RAPSN, S100P, and/or DYRK4, indicates a change in tissue status or disease such as the worsening or bettering of a tissue status or disease, in particular cancer. In particular, a decreased methylation status of HYAL2, MGRN1, RPTOR, SLC22A18, FUT7, RAPSN, S100P, and/or DYRK4, is indicative of a worsening of a tissue status or disease. An increased methylation status of HYAL2, MGRN1, RPTOR, SLC22A18, FUT7, RAPSN, S100P, and/or DYRK4, is indicative of a bettering of a tissue status or disease. An alteration in the methylation status of HYAL2, MGRN1, RPTOR, SLC22A18, FUT7, RAPSN, S100P, and/or DYRK4, is also indicative of the risk of developing an altered tissue status or a disease, in particular cancer. More specifically, a decreased methylation status of HYAL2, MGRN1, RPTOR, SLC22A18, FUT7, RAPSN, S100P, and/or DYRK4, is indicative of the risk of developing a degenerative tissue status or disease, in particular cancer. An altered methylation status of HYAL2, MGRN1, RPTOR, SLC22A18, FUT7, RAPSN, S100P, and/or DYRK4, in particular decreased methylation status of HYAL2, MGRN1, RPTOR, SLC22A18, FUT7, RAPSN, S100P, and/or DYRK4, is also indicative of an individual suffering from an altered tissue status or a disease, in particular cancer. Furthermore, an altered methylation status of HYAL2, MGRN1, RPTOR, SLC22A18, FUT7, RAPSN, S100P, and/or DYRK4, e.g. an elevated or lowered level of methylation status of HYAL2, MGRN1, RPTOR, SLC22A18, FUT7, RAPSN, S100P, and/or DYRK4, indicates the progression or a stage of a tissue status or a disease, in particular cancer, in a subject. In particular a decreased methylation status of HYAL2, MGRN1, RPTOR, SLC22A18, FUT7, RAPSN, S100P, and/or DYRK4, is indicative of a worsening of a tissue status or disease, in particular cancer.

In particular, an increased expression level of HYAL2, MGRN1, RPTOR, SLC22A18, FUT7, RAPSN, S100P, and/or DYRK4, is indicative of a worsening of a tissue status or disease. A decreased expression level of HYAL2, MGRN1, RPTOR, SLC22A18, FUT7, RAPSN, S100P, and/or DYRK4, is indicative of a bettering of a tissue status or disease. An alteration in the expression level of HYAL2, MGRN1, RPTOR, SLC22A18, FUT7, RAPSN, S100P, and/or DYRK4, is also indicative of the risk of developing an altered tissue status or a disease, in particular cancer. More specifically, an increased expression level of HYAL2, MGRN1, RPTOR, SLC22A18, FUT7, RAPSN, S100P, and/or DYRK4, is indicative of the risk of developing a degenerative tissue status or disease, in particular cancer. An altered expression level of HYAL2, MGRN1, RPTOR, SLC22A18, FUT7, RAPSN, S1 00P, and/or DYRK4, in particular increased expression level of HYAL2, MGRN1, RPTOR, SLC22A18, FUT7, RAPSN, S100P, and/or DYRK4, is also indicative of an individual suffering from an altered tissue status or a disease, in particular cancer. Furthermore, an altered expression level of HYAL2, MGRN1, RPTOR, SLC22A18, FUT7, RAPSN, S100P, and/or DYRK4, e.g. an elevated or lowered expression level of HYAL2, MGRN1, RPTOR, SLC22A18, FUT7, RAPSN, S100P, and/or DYRK4, indicates the progression or a stage of a tissue status or a disease, in particular cancer, in a subject. In particular, an increased expression level of HYAL2, MGRN1, RPTOR, SLC22A18, FUT7, RAPSN, S100P, and/or DYRK4, is indicative of a worsening of a tissue status or disease, in particular cancer.

In further embodiments an alteration in the miR-652, miR-801, miR-376c, miR-376a, miR-127, miR-409, and/or miR-148b level indicates a change in tissue status or disease such as the worsening or bettering of a tissue status or disease, in particular cancer.

In particular, an elevated level of miR-652, miR-801, miR-376c, miR-376a, miR-127, miR-409, and/or miR-148b is indicative of a worsening of a tissue status or disease. A lowered level of miR-652, miR-801, miR-376c, miR-376a, miR-127, miR-409, and/or miR-148b is indicative of a bettering of a tissue status or disease. An alteration in the miR-652, miR-801, miR-376c, miR-376a, miR-127, miR-409, and/or miR-148b level is also indicative of the risk of developing an altered tissue status or a disease, in particular cancer. More specifically an elevated level of miR-652, miR-801, miR-376c, miR-376a, miR-127, miR-409, and/or miR-148b is indicative of the risk of developing a degenerative tissue status or disease, in particular cancer. An altered miR-652, miR-801, miR-376c, miR-376a, miR-127, miR-409, and/or miR-148b level, in particular an elevated miR-652, miR-801, miR-376c, miR-376a, miR-127, miR-409, and/or miR-148b level, is also indicative of an individual suffering from an altered tissue status or a disease, in particular cancer. Furthermore, an altered miR-652, miR-801, miR-376c, miR-376a, miR-127, miR-409, and/or miR-148b level, e.g. an elevated or lowered level of miR-652, miR-801, miR-376c, miR-376a, miR-127, miR-409, and/or miR-148b, indicates the progression or a stage of a tissue status or a disease, in a subject. In particular an elevated miR-652, miR-801, miR-376c, miR-376a, miR-127, miR-409, and/or miR-148b level is indicative of a worsening of a tissue status or disease, in particular cancer.

The methylation status and/or expression level of the at least one methylation marker and the presence, in particular the amount, of at least one miRNA is indicative of the prognosis and/or diagnosis of said subject. The prognosis and/or diagnosis of cancer includes i. the risk of developing cancer,
ii. the presence of cancer, and/or
iii. the progression, in particular the worsening or bettering, of cancer.

In particular embodiments, the presence, in particular the amount, of one miRNA marker selected from the group consisting of miR-652, miR-801, miR-376c, miR-376a, miR-127p, miR-409, and miR-148b, is determined.

In particular embodiments, the methylation status and/or expression level of one methylation marker selected from the group consisting of HYAL2, MGRN1, RPTOR, SLC22A18, FUT7, RAPSN, S100P, and DYRK4 is determined.

In particular embodiments, the methylation status and/or the expression level of at least 2, 3, 4, 5, 6, 7 or 8 different methylation markers is determined, and/or the presence, in particular the amount, of at least 2, 3, 4, 5, 6, or 7 different miRNA marker is determined. In particular, all 7 miRNA marker are determined. In case all seven miRNA marker are determined, this combination is reffered to as miR-7, i.e. miR-7 encompasses all seven miRNA marker miR-652, miR-801, miR-376c, miR-376a, miR-127p, miR-409, and miR-148b.

It is to be understood that various specific combination of methylation marker and miRNAs may be used for prognosing and/or diagnosing cancer.

In particular embodiments, the methylation status and/or expression level of one or more of the following combinations of methylation markers is determined:

HYAL2+RAPSN; S100P+RAPSN; RPTOR+HYAL2; MGRN1+HYAL2; SLC22A18+S100P; HYAL2+SLC22A18; RPTOR+S100P; miR-7+DYRK4; RPTOR+RAPSN; FUT7+RAPSN; MGRN1+SLC22A18; RPTOR+FUT7; FUT7+MGRN1; miR-7+MGRN1; MGRN1+S100P; DYRK4+RAPSN; FUT7+S100P; RPTOR+DYRK4; RPTOR+miR-7; DYRK4+MGRN1; FUT7+HYAL2; miR-7+RAPSN; MGRN1+RAPSN; HYAL2+S100P; miR-7+SLC22A18; RPTOR+MGRN1; DYRK4+SLC22A18; SLC22A18+RAPSN; DYRK4+HYAL2; DYRK4+S100P; FUT7+SLC22A18; miR-7+HYAL2; RPTOR+SLC22A18; miR-7+S100P; miR-7+FUT7; DYRK4+FUT7; miR-7+DYRK4+FUT7; miR-7+MGRN1+HYAL2; RPTOR+MGRN1+RAPSN; MGRN1+SLC22A18+RAPSN; RPTOR+miR-7+S100P; miR-7+MGRN1+S100P; RPTOR+MGRN1+SLC22A18; RPTOR+FUT7+HYAL2; FUT7+HYAL2+SLC22A18; FUT7+HYAL2+RAPSN; miR-7+SLC22A18+S100P; miR-7+S100P+RAPSN; RPTOR+DYRK4+S100P; DYRK4+SLC22A18+S100P; DYRK4+MGRN1+HYAL2; DYRK4+MGRN1+SLC22A18; RPTOR+DYRK4+MGRN1; miR-7+DYRK4+S100P; DYRK4+S100P+RAPSN; DYRK4+MGRN1+RAPSN; RPTOR+miR-7+MGRN1; DYRK4+FUT7+MGRN1; miR-7+FUT7+RAPSN; miR-7+MGRN1+RAPSN; RPTOR+HYAL2+S100P; HYAL2+S100P+RAPSN; DYRK4+FUT7+RAPSN; MGRN1+HYAL2+SLC22A18; FUT7+MGRN1+S100P; RPTOR+DYRK4+RAPSN; FUT7+S100P+RAPSN; RPTOR+FUT7+S100P; DYRK4+HYAL2+RAPSN; FUT7+HYAL2+S100P; RPTOR+SLC22A18+RAPSN; RPTOR+miR-7+HYAL2; HYAL2+SLC22A18+RAPSN; DYRK4+MGRN1+S100P; miR-7+HYAL2+RAPSN; RPTOR+miR-7+RAPSN; miR-7+FUT7+MGRN1; RPTOR+DYRK4+HYAL2; FUT7+MGRN1+RAPSN; miR-7+DYRK4+MGRN1; FUT7+MGRN1+SLC22A18; RPTOR+miR-7+DYRK4; miR-7+DYRK4+SLC22A18; RPTOR+S100P+RAPSN; miR-7+DYRK4+RAPSN; RPTOR+HYAL2+SLC22A18; SLC22A18+S100P+RAPSN; RPTOR+HYAL2+RAPSN; RPTOR+FUT7+MGRN1; RPTOR+SLC22A18+S100P; MGRN1+SLC22A18+S100P; MGRN1+HYAL2+S100P; miR-7+HYAL2+S100P; RPTOR+MGRN1+S100P; RPTOR+FUT7+SLC22A18; MGRN1+S100P+RAPSN; RPTOR+DYRK4+FUT7; DYRK4+FUT7+HYAL2; RPTOR+FUT7+RAPSN; DYRK4+HYAL2+S100P; FUT7+SLC22A18+RAPSN; RPTOR+miR-7+FUT7; miR-7+FUT7+HYAL2; miR-7+MGRN1+SLC22A18; miR-7+FUT7+SLC22A18; miR-7+DYRK4+HYAL2; MGRN1+HYAL2+RAPSN; FUT7+MGRN1+HYAL2; DYRK4+FUT7+SLC22A18; HYAL2+SLC22A18+S100P; DYRK4+FUT7+S100P; RPTOR+DYRK4+SLC22A18; DYRK4+HYAL2+SLC22A18; RPTOR+MGRN1+HYAL2; DYRK4+SLC22A18+RAPSN; FUT7+SLC22A18+S100P; miR-7+SLC22A18+RAPSN; RPTOR+miR-7+SLC22A18; miR-7+FUT7+S100P; miR-7+HYAL2+SLC22A18;

RPTOR+MGRN1+HYAL2+S100P; RPTOR+FUT7+SLC22A18+RAPSN; DYRK4+FUT7+S100P+RAPSN; RPTOR+DYRK4+FUT7+HYAL2; DYRK4+FUT7+HYAL2+SLC22A18; RPTOR+DYRK4+FUT7+S100P; miR-7+DYRK4+SLC22A18+RAPSN; RPTOR+HYAL2+S100P+RAPSN; RPTOR+miR-7+DYRK4+SLC22A18; miR-7+FUT7+HYAL2+SLC22A18; DYRK4+FUT7+HYAL2+RAPSN; MGRN1+HYAL2+SLC22A18+S100P; DYRK4+FUT7+SLC22A18+S100P; MGRN1+HYAL2+S100P+RAPSN; RPTOR+miR-7+DYRK4+RAPSN; miR-7+DYRK4+MGRN1+SLC22A18; miR-7+DYRK4+MGRN1+S100P; FUT7+MGRN1+HYAL2+RAPSN; RPTOR+FUT7+MGRN1+RAPSN; DYRK4+FUT7+MGRN1+HYAL2; RPTOR+FUT7+MGRN1+HYAL2; miR-7+FUT7+HYAL2+S100P; miR-7+FUT7+SLC22A18+S100P; FUT7+MGRN1+HYAL2+SLC22A18; RPTOR+FUT7+MGRN1+SLC22A18; RPTOR+miR-7+SLC22A18+RAPSN; RPTOR+HYAL2+SLC22A18+RAPSN; miR-7+FUT7+S100P+RAPSN; FUT7+MGRN1+SLC22A18+RAPSN; miR-7+FUT7+MGRN1+HYAL2; RPTOR+miR-7+FUT7+S100P; RPTOR+miR-7+HYAL2+S100P; DYRK4+MGRN1+HYAL2+S100P; FUT7+HYAL2+SLC22A18+RAPSN; FUT7+SLC22A18+S100P+RAPSN; RPTOR+FUT7+S100P+RAPSN; RPTOR+FUT7+HYAL2+SLC22A18; MGRN1+SLC22A18+S100P+RAPSN; miR-7+HYAL2+S100P+RAPSN; RPTOR+DYRK4+MGRN1+SLC22A18; DYRK4+FUT7+HYAL2+S100P; miR-7+DYRK4+HYAL2+RAPSN; miR-7+DYRK4+FUT7+MGRN1; DYRK4+MGRN1+SLC22A18+RAPSN; RPTOR+miR-7+DYRK4+HYAL2; miR-7+MGRN1+HYAL2+S100P; RPTOR+DYRK4+SLC22A18+RAPSN; miR-7+DYRK4+MGRN1+RAPSN; RPTOR+MGRN1+HYAL2+RAPSN; RPTOR+DYRK4+FUT7+RAPSN; RPTOR+MGRN1+SLC22A18+S100P; DYRK4+FUT7+MGRN1+SLC22A18; miR-7+DYRK4+SLC22A18+S100P; miR-7+DYRK4+MGRN1+HYAL2; miR-7+MGRN1+SLC22A18+RAPSN; RPTOR+miR-7+MGRN1+SLC22A18; RPTOR+HYAL2+SLC22A18+S100P; miR-7+FUT7+HYAL2+RAPSN; HYAL2+SLC22A18+S100P+RAPSN; RPTOR+SLC22A18+S100P+RAPSN; RPTOR+miR-7+DYRK4+MGRN1; RPTOR+miR-7+FUT7+RAPSN; FUT7+MGRN1+SLC22A18+S100P; RPTOR+

DYRK4+S100P+RAPSN; DYRK4+FUT7+MGRN1+S100P; DYRK4+HYAL2+S100P+RAPSN; RPTOR+miR-7+FUT7+HYAL2; miR-7+FUT7+MGRN1+S100P; miR-7+MGRN1+HYAL2+SLC22A18; RPTOR+DYRK4+HYAL2+S100P; RPTOR+miR-7+SLC22A18+S100P; DYRK4+MGRN1+SLC22A18+S100P; RPTOR+DYRK4+MGRN1+S100P; FUT7+HYAL2+S100P+RAPSN; RPTOR+FUT7+HYAL2+S100P; RPTOR+miR-7+S100P+RAPSN; RPTOR+DYRK4+HYAL2+RAPSN; miR-7+HYAL2+SLC22A18+RAPSN; miR-7+DYRK4+HYAL2+S100P; DYRK4+MGRN1+HYAL2+SLC22A18; RPTOR+MGRN1+SLC22A18+RAPSN; DYRK4+SLC22A18+S100P+RAPSN; RPTOR+DYRK4+HYAL2+SLC22A18; FUT7+MGRN1+HYAL2+S100P; DYRK4+HYAL2+SLC22A18+RAPSN; RPTOR+miR-7+MGRN1+S100P; DYRK4+FUT7+MGRN1+RAPSN; miR-7+DYRK4+FUT7+RAPSN; RPTOR+miR-7+DYRK4+FUT7; miR-7+DYRK4+FUT7+SLC22A18; miR-7+MGRN1+SLC22A18+S100P; miR-7+FUT7+MGRN1+SLC22A18; miR-7+MGRN1+S100P+RAPSN; miR-7+DYRK4+FUT7+HYAL2; RPTOR+DYRK4+FUT7+MGRN1; miR-7+FUT7+MGRN1+RAPSN; RPTOR+FUT7+SLC22A18+S100P; FUT7+HYAL2+SLC22A18+S100P; RPTOR+miR-7+HYAL2+SLC22A18; RPTOR+miR-7+HYAL2+RAPSN; DYRK4+MGRN1+S100P+RAPSN; RPTOR+miR-7+FUT7+MGRN1; miR-7+HYAL2+SLC22A18+S100P; RPTOR+MGRN1+HYAL2+SLC22A18; RPTOR+MGRN1+S100P+RAPSN; RPTOR+DYRK4+FUT7+SLC22A18; DYRK4+FUT7+SLC22A18+RAPSN; MGRN1+HYAL2+SLC22A18+RAPSN; RPTOR+miR-7+DYRK4+S100P; RPTOR+FUT7+MGRN1+S100P; miR-7+DYRK4+S100P+RAPSN; miR-7+DYRK4+HYAL2+SLC22A18; miR-7+DYRK4+FUT7+S100P; miR-7+FUT7+SLC22A18+RAPSN; RPTOR+miR-7+MGRN1+RAPSN; miR-7+MGRN1+HYAL2+RAPSN; RPTOR+miR-7+FUT7+SLC22A18; FUT7+MGRN1+S100P+RAPSN; RPTOR+miR-7+MGRN1+HYAL2; DYRK4+HYAL2+SLC22A18+S100P; RPTOR+DYRK4+MGRN1+RAPSN; RPTOR+DYRK4+SLC22A18+S100P; DYRK4+MGRN1+HYAL2+RAPSN; miR-7+SLC22A18+S100P+RAPSN; RPTOR+FUT7+HYAL2+RAPSN; RPTOR+DYRK4+MGRN1+HYAL2; miR-7+DYRK4+FUT7+S100P+RAPSN; RPTOR+miR-7+DYRK4+FUT7+HYAL2; RPTOR+miR-7+FUT7+MGRN1+SLC22A18; miR-7+DYRK4+FUT7+MGRN1+HYAL2; RPTOR+miR-7+MGRN1+HYAL2+S100P; RPTOR+miR-7+FUT7+MGRN1+RAPSN; DYRK4+FUT7+MGRN1+SLC22A18+RAPSN; RPTOR+miR-7+DYRK4+FUT7+S100P; RPTOR+DYRK4+SLC22A18+S100P+RAPSN; RPTOR+DYRK4+FUT7+MGRN1+SLC22A18; RPTOR+DYRK4+HYAL2+SLC22A18+RAPSN; RPTOR+miR-7+FUT7+SLC22A18+RAPSN; miR-7+DYRK4+FUT7+MGRN1+S100P; RPTOR+DYRK4+FUT7+MGRN1+RAPSN; miR-7+FUT7+MGRN1+SLC22A18+RAPSN; miR-7+HYAL2+SLC22A18+S100P+RAPSN; RPTOR+miR-7+SLC22A18+S100P+RAPSN; RPTOR+miR-7+DYRK4+HYAL2+S100P; RPTOR+miR-7+HYAL2+SLC22A18+S100P; RPTOR+MGRN1+HYAL2+SLC22A18+RAPSN; RPTOR+DYRK4+MGRN1+HYAL2+SLC22A18; RPTOR+DYRK4+MGRN1+HYAL2+RAPSN; RPTOR+FUT7+MGRN1+HYAL2+S100P; miR-7+DYRK4+FUT7+SLC22A18+S100P; FUT7+MGRN1+HYAL2+S100P+RAPSN; FUT7+MGRN1+HYAL2+SLC22A18+S100P; RPTOR+miR-7+MGRN1+SLC22A18; RPTOR+miR-7+HYAL2+S100P+RAPSN; RPTOR+miR-7+FUT7+MGRN1+S100P; RPTOR+miR-7+MGRN1+HYAL2+RAPSN; RPTOR+DYRK4+FUT7+RAPSN; RPTOR+miR-7+DYRK4+MGRN1+SLC22A18; miR-7+FUT7+MGRN1+HYAL2+SLC22A18; RPTOR+DYRK4+HYAL2+SLC22A18+S100P; miR-7+DYRK4+MGRN1+SLC22A18+S100P; miR-7+DYRK4+MGRN1+SLC22A18+RAPSN; miR-7+FUT7+MGRN1+SLC22A18+S100P; RPTOR+miR-7+FUT7+S100P+RAPSN; DYRK4+FUT7+MGRN1+HYAL2+SLC22A18; RPTOR+miR-7+DYRK4+FUT7+MGRN1; miR-7+FUT7+HYAL2+SLC22A18+RAPSN; RPTOR+DYRK4+FUT7+HYAL2+S100P; miR-7+DYRK4+HYAL2+S100P+RAPSN; DYRK4+HYAL2+SLC22A18+S100P+RAPSN; DYRK4+FUT7+MGRN1+SLC22A18+S100P; RPTOR+miR-7+FUT7+HYAL2+SLC22A18; RPTOR+DYRK4+MGRN1+SLC22A18+S100P; RPTOR+MGRN1+HYAL2+S100P+RAPSN; DYRK4+MGRN1+SLC22A18+S100P+RAPSN; RPTOR+DYRK4+FUT7+SLC22A18+RAPSN; DYRK4+FUT7+HYAL2+SLC22A18+RAPSN; FUT7+HYAL2+SLC22A18+S100P+RAPSN; RPTOR+FUT7+SLC22A18+S100P+RAPSN; RPTOR+miR-7+HYAL2+SLC22A18+RAPSN; DYRK4+MGRN1+HYAL2+SLC22A18+S100P; RPTOR+DYRK4+FUT7+HYAL2+SLC22A18; miR-7+MGRN1+HYAL2+SLC22A18+S100P; RPTOR+FUT7+HYAL2+SLC22A18+S100P; RPTOR+miR-7+MGRN1+SLC22A18+S100P; RPTOR+miR-7+FUT7+HYAL2+S100P; miR-7+MGRN1+SLC22A18+S100P+RAPSN; RPTOR+FUT7+MGRN1+HYAL2+RAPSN; miR-7+DYRK4+FUT7+HYAL2+RAPSN; miR-7+DYRK4+MGRN1+HYAL2+RAPSN; miR-7+FUT7+MGRN1+HYAL2+S100P; miR-7+DYRK4+MGRN1+S100P+RAPSN; RPTOR+miR-7+MGRN1+SLC22A18+RAPSN; RPTOR+miR-7+DYRK4+MGRN1+HYAL2; RPTOR+miR-7+DYRK4+MGRN1+S100P; miR-7+DYRK4+MGRN1+HYAL2+SLC22A18; FUT7+MGRN1+HYAL2+SLC22A18+RAPSN; miR-7+FUT7+HYAL2+S100P+RAPSN; DYRK4+FUT7+MGRN1+HYAL2+S100P; RPTOR+miR-7+DYRK4+HYAL2+RAPSN; miR-7+FUT7+HYAL2+SLC22A18+S100P; RPTOR+miR-7+DYRK4+S100P+RAPSN; RPTOR+DYRK4+FUT7+SLC22A18+S100P; RPTOR+DYRK4+MGRN1+SLC22A18+RAPSN; miR-7+DYRK4+MGRN1+SLC22A18+S100P; RPTOR+DYRK4+FUT7+S100P+RAPSN; DYRK4+FUT7+HYAL2+S100P+RAPSN; RPTOR+FUT7+HYAL2+SLC22A18+RAPSN; DYRK4+FUT7+HYAL2+SLC22A18+S100P; DYRK4+FUT7+SLC22A18+S100P+RAPSN; RPTOR+miR-7+DYRK4+HYAL2+SLC22A18; RPTOR+FUT7+MGRN1+S100P+RAPSN; FUT7+MGRN1+SLC22A18+S100P+RAPSN; miR-7+DYRK4+FUT7+MGRN1+SLC22A18; RPTOR+miR-7+DYRK4+SLC22A18+RAPSN; miR-7+DYRK4+HYAL2+SLC22A18+RAPSN; miR-7+DYRK4+FUT7+MGRN1+RAPSN; RPTOR+HYAL2+SLC22A18+S100P+RAPSN; RPTOR+FUT7+MGRN1+SLC22A18+S100P; miR-7+DYRK4+FUT7+SLC22A18+RAPSN; miR-7+FUT7+MGRN1+S100P+RAPSN; RPTOR+miR-7+MGRN1+S100P+RAPSN; RPTOR+miR-7+FUT7+MGRN1+HYAL2; miR-7+MGRN1+HYAL2+SLC22A18+RAPSN; RPTOR+DYRK4+HYAL2+S100P+RAPSN; miR-7+DYRK4+FUT7+HYAL2+S100P; RPTOR+DYRK4+FUT7+MGRN1+S100P; miR-7+FUT7+MGRN1+HYAL2+RAPSN; RPTOR+miR-7+FUT7+SLC22A18+S100P; RPTOR+DYRK4+FUT7+MGRN1+HYAL2; DYRK4+FUT7+MGRN1+S100P+RAPSN; RPTOR+miR-7+FUT7+HYAL2+RAPSN; DYRK4+MGRN1+HYAL2+SLC22A18+RAPSN; DYRK4+FUT7+MGRN1+HYAL2+RAPSN; RPTOR+miR-7+DYRK4+MGRN1+RAPSN; miR-7+FUT7+SLC22A18+S100P+RAPSN; miR-7+DYRK4+HYAL2+SLC22A18+S100P; MGRN1+HYAL2+

SLC22A18+S100P+RAPSN; RPTOR+DYRK4+MGRN1+ S100P+RAPSN; DYRK4+MGRN1+HYAL2+S100P+ RAPSN; RPTOR+DYRK4+FUT7+HYAL2+RAPSN; RPTOR+miR-7+DYRK4+SLC22A18+S100P; RPTOR+ MGRN1+HYAL2+SLC22A18+S100P; miR-7+DYRK4+ SLC22A18+S100P+RAPSN; RPTOR+MGRN1+ SLC22A18+S100P+RAPSN; RPTOR+FUT7+MGRN1+ HYAL2+SLC22A18; RPTOR+FUT7+MGRN1+ SLC22A18+RAPSN; RPTOR+miR-7+DYRK4+FUT7+ SLC22A18; miR-7+MGRN1+HYAL2+S100P+RAPSN; miR-7+DYRK4+FUT7+HYAL2+SLC22A18; RPTOR+ FUT7+HYAL2+S100P+RAPSN; RPTOR+DYRK4+ MGRN1+HYAL2+S100P;

RPTOR+miR-7+DYRK4+SLC22A18+S100P+RAPSN; DYRK4+FUT7+MGRN1+HYAL2+SLC22A18+S100P; RPTOR+DYRK4+FUT7+HYAL2+S100P+RAPSN; RPTOR+FUT7+MGRN1+SLC22A18+S100P+RAPSN; RPTOR+DYRK4+FUT7+HYAL2+SLC22A18+S100P; RPTOR+FUT7+MGRN1+HYAL2+SLC22A18+RAPSN; DYRK4+FUT7+MGRN1+HYAL2+S100P+RAPSN; RPTOR+miR-7+FUT7+HYAL2+S100P+RAPSN; miR-7+ FUT7+HYAL2+SLC22A18+S100P+RAPSN; RPTOR+ miR-7+DYRK4+MGRN1+SLC22A18+S100P; RPTOR+ miR-7+DYRK4+MGRN1+S100P+RAPSN; RPTOR+ DYRK4+FUT7+MGRN1+HYAL2+S100P; RPTOR+miR-7+FUT7+HYAL2+SLC22A18+S100P; RPTOR+miR-7+ DYRK4+MGRN1+HYAL2+RAPSN; miR-7+DYRK4+ MGRN1+HYAL2+SLC22A18+RAPSN; RPTOR+miR-7+ DYRK4+MGRN1+HYAL2+SLC22A18; RPTOR+miR-7+ DYRK4+FUT7+SLC22A18+RAPSN; RPTOR+miR-7+ MGRN1+SLC22A18+S100P+RAPSN; RPTOR+MGRN1+ HYAL2+SLC22A18+S100P+RAPSN; RPTOR+DYRK4+ FUT7+HYAL2+SLC22A18+RAPSN; RPTOR+miR-7+ DYRK4+HYAL2+S100P+RAPSN; RPTOR+DYRK4+ FUT7+SLC22A18+S100P+RAPSN; miR-7+DYRK4+ MGRN1+HYAL2+S100P; RPTOR+miR-7+ FUT7+SLC22A18+S100P+RAPSN; RPTOR+DYRK4+ FUT7+MGRN1+SLC22A18+S100P; miR-7+FUT7+ MGRN1+HYAL2+SLC22A18+S100P; RPTOR+miR-7+ FUT7+MGRN1+SLC22A18+S100P; miR-7+DYRK4+ MGRN1+SLC22A18+S100P+RAPSN; RPTOR+DYRK4+ FUT7+MGRN1+HYAL2+RAPSN; miR-7+DYRK4+ FUT7+MGRN1+SLC22A18+RAPSN; RPTOR+miR-7+ DYRK4+FUT7+HYAL2+S100P; RPTOR+miR-7+ DYRK4+FUT7+MGRN1+SLC22A18; RPTOR+miR-7+ DYRK4+HYAL2+SLC22A18+RAPSN; DYRK4+FUT7+ HYAL2+SLC22A18+S100P+RAPSN; miR-7+DYRK4+ FUT7+MGRN1+HYAL2+SLC22A18; RPTOR+miR-7+ DYRK4+FUT7+S100P+RAPSN; miR-7+DYRK4+FUT7+ HYAL2+S100P+RAPSN; RPTOR+FUT7+MGRN1+ HYAL2+S100P+RAPSN; RPTOR+DYRK4+MGRN1+ HYAL2+S100P+RAPSN; RPTOR+miR-7+HYAL2+ SLC22A18+S100P+RAPSN; RPTOR+DYRK4+MGRN1+ HYAL2+SLC22A18+S100P; RPTOR+miR-7+FUT7+ MGRN1+HYAL2+RAPSN; RPTOR+DYRK4+HYAL2+ SLC22A18+S100P+RAPSN; RPTOR+miR-7+FUT7+ MGRN1+HYAL2+SLC22A18; DYRK4+MGRN1+ HYAL2+SLC22A18+S100P+RAPSN; miR-7+FUT7+ MGRN1+SLC22A18+S100P+RAPSN; miR-7+DYRK4+ FUT7+MGRN1+SLC22A18+S100P; RPTOR+miR-7+ DYRK4+MGRN1+SLC22A18+RAPSN; miR-7+DYRK4+ FUT7+MGRN1+S100P+RAPSN; miR-7+DYRK4+FUT7+ HYAL2+SLC22A18+RAPSN; RPTOR+miR-7+DYRK4+ FUT7+MGRN1+S100P; miR-7+DYRK4+FUT7+ MGRN1+HYAL2+S100P; RPTOR+miR-7+FUT7+ HYAL2+SLC22A18+RAPSN; miR-7+MGRN1+HYAL2+ SLC22A18+S100P+RAPSN; DYRK4+MGRN1+

SLC22A18+S100P+RAPSN; RPTOR+miR-7+DYRK4+ FUT7+HYAL2+SLC22A18; RPTOR+miR-7+MGRN1+ HYAL2+SLC22A18+S100P; RPTOR+miR-7+DYRK4+ FUT7+HYAL2+RAPSN; RPTOR+miR-7+MGRN1+ HYAL2+S100P+RAPSN; miR-7+DYRK4+HYAL2+ SLC22A18+S100P+RAPSN; RPTOR+DYRK4+MGRN1+ SLC22A18+S100P+RAPSN; RPTOR+DYRK4+MGRN1+ HYAL2+SLC22A18+RAPSN; RPTOR+FUT7+MGRN1+ HYAL2+SLC22A18+S100P; RPTOR+miR-7+DYRK4+ HYAL2+SLC22A18+S100P; RPTOR+DYRK4+FUT7+ MGRN1+HYAL2+SLC22A18; FUT7+MGRN1+HYAL2+ SLC22A18+S100P+RAPSN; RPTOR+DYRK4+FUT7+ MGRN1+S100P+RAPSN; RPTOR+miR-7+DYRK4+ MGRN1+HYAL2+S100P; RPTOR+FUT7+HYAL2+ SLC22A18+S100P+RAPSN; RPTOR+miR-7+FUT7+ MGRN1+SLC22A18+RAPSN; miR-7+DYRK4+MGRN1+ HYAL2+S100P+RAPSN; miR-7+FUT7+MGRN1+ HYAL2+S100P+RAPSN; RPTOR+miR-7+FUT7+ MGRN1+HYAL2+S100P; RPTOR+miR-7+DYRK4+ FUT7+MGRN1+HYAL2; miR-7+FUT7+MGRN1+ HYAL2+SLC22A18+RAPSN; RPTOR+miR-7+MGRN1+ HYAL2+SLC22A18+RAPSN; RPTOR+miR-7+FUT7+ MGRN1+S100P+RAPSN; miR-7+DYRK4+FUT7+ SLC22A18+S100P+RAPSN; RPTOR+miR-7+DYRK4+ FUT7+MGRN1+RAPSN; DYRK4+FUT7+MGRN1+ HYAL2+SLC22A18+RAPSN; miR-7+DYRK4+FUT7+ HYAL2+SLC22A18+S100P; RPTOR+DYRK4+FUT7+ MGRN1+SLC22A18+RAPSN; RPTOR+miR-7+DYRK4+ FUT7+SLC22A18+S100P; miR-7+DYRK4+FUT7+ MGRN1+HYAL2+RAPSN;

miR-7+DYRK4+FUT7+MGRN1+HYAL2+SLC22A18+ S100P; RPTOR+miR-7+FUT7+MGRN1+SLC22A18+ S100P+RAPSN; RPTOR+miR-7+DYRK4+FUT7+ MGRN1+HYAL2+S100P; RPTOR+miR-7+FUT7+ MGRN1+HYAL2+SLC22A18+RAPSN; miR-7+DYRK4+ FUT7+HYAL2+SLC22A18+S100P+RAPSN; RPTOR+ DYRK4+MGRN1+HYAL2+SLC22A18+S100P+RAPSN; RPTOR+miR-7+DYRK4+FUT7+HYAL2+SLC22A18+ S100P; RPTOR+DYRK4+FUT7+MGRN1+HYAL2+ SLC22A18+RAPSN; RPTOR+miR-7+DYRK4+FUT7+ HYAL2+S100P+RAPSN; RPTOR+miR-7+DYRK4+ FUT7+MGRN1+SLC22A18+S100P; RPTOR+miR-7+ FUT7+MGRN1+HYAL2+S100P+RAPSN; miR-7+ DYRK4+FUT7+MGRN1+SLC22A18+S100P+RAPSN; RPTOR+miR-7+DYRK4+FUT7+SLC22A18+S100P+ RAPSN; RPTOR+miR-7+DYRK4+FUT7+HYAL2+ SLC22A18+RAPSN; RPTOR+DYRK4+FUT7+MGRN1+ HYAL2+S100P+RAPSN; RPTOR+miR-7+DYRK4+ HYAL2+SLC22A18+S100P+RAPSN; RPTOR+miR-7+ DYRK4+FUT7+MGRN1+SLC22A18+RAPSN; RPTOR+ miR-7+DYRK4+MGRN1+HYAL2+S100P+RAPSN; RPTOR+FUT7+MGRN1+HYAL2+SLC22A18+S100P+ RAPSN; RPTOR+miR-7+FUT7+HYAL2+SLC22A18+ S100P+RAPSN; RPTOR+miR-7+DYRK4+MGRN1+ HYAL2+SLC22A18+S100P; miR-7+DYRK4+MGRN1+ HYAL2+SLC22A18+S100P+RAPSN; RPTOR+miR-7+ DYRK4+MGRN1+SLC22A18+S100P+RAPSN; RPTOR+ miR-7+DYRK4+FUT7+MGRN1+HYAL2+RAPSN; RPTOR+DYRK4+FUT7+HYAL2+SLC22A18+S100P+ RAPSN; RPTOR+miR-7+DYRK4+FUT7+MGRN1+ HYAL2+SLC22A18; miR-7+FUT7+MGRN1+HYAL2+ SLC22A18+S100P+RAPSN; miR-7+DYRK4+FUT7+ MGRN1+HYAL2+SLC22A18+RAPSN; RPTOR+miR-7+ MGRN1+HYAL2+SLC22A18+S100P+RAPSN; RPTOR+ miR-7+FUT7+MGRN1+HYAL2+SLC22A18+S100P; RPTOR+DYRK4+FUT7+MGRN1+HYAL2+SLC22A18+ S100P; RPTOR+DYRK4+FUT7+MGRN1+SLC22A18+

S100P+RAPSN; RPTOR+miR-7+DYRK4+MGRN1+HYAL2+SLC22A18+RAPSN; DYRK4+FUT7+MGRN1+HYAL2+SLC22A18+S100P+RAPSN; miR-7+DYRK4+FUT7+MGRN1+HYAL2+S100P+RAPSN; RPTOR+miR-7+DYRK4+FUT7+MGRN1+S100P+RAPSN;

RPTOR+miR-7+DYRK4+FUT7+MGRN1+HYAL2+SLC22A18+RAPSN; RPTOR+miR-7+DYRK4+FUT7+MGRN1+SLC22A18+S100P+RAPSN; RPTOR+miR-7+DYRK4+FUT7+HYAL2+SLC22A18+S100P+RAPSN; RPTOR+miR-7+DYRK4+FUT7+MGRN1+HYAL2+S100P+RAPSN; miR-7+DYRK4+FUT7+MGRN1+HYAL2+SLC22A18+S100P+RAPSN; RPTOR+miR-7+DYRK4+FUT7+MGRN1+HYAL2+SLC22A18+S100P; RPTOR+miR-7+FUT7+MGRN1+HYAL2+SLC22A18+S100P+RAPSN; RPTOR+DYRK4+FUT7+MGRN1+HYAL2+SLC22A18+S100P+RAPSN; RPTOR+miR-7+DYRK4+MGRN1+HYAL2+SLC22A18+S100P+RAPSN; and RPTOR+miR-7+DYRK4+FUT7+MGRN1+HYAL2+SLC22A18+S100P+RAPSN.

In particular embodiments, the methylation status and/or expression level of the methylation marker RPTOR, MGRN1, and RAPSN, is determined, and the presence, in particular the amount, of the miRNA marker miR-652, miR-801, miR-376c, miR-376a, miR-127-3p, miR-409-3p, and miR-148b is determined. Optionally, the methylation status and/or expression level of HYAL2 is also determined.

In particular embodiments, the methylation status and/or expression level of the methylation marker DYRK4, S100P, FUT7, and SLC22A18 is determined, and the presence, in particular the amount, of the miRNA marker miR-652, miR-801, miR-376c, miR-376a, miR-127-3p, miR-409-3p, and miR-148b is determined. Optionally, the methylation status and/or expression level of HYAL2 is also determined.

In further embodiments, the methylation status and/or expression level of the methylation marker MGRN1, RPTOR, SLC22A18, FUT7, RAPSN, S100P, and DYRK4 is determined, and the presence of the miRNA marker miR-652, miR-801, miR-376c, miR-376a, miR-127-3p, miR-409-3p, and miR-148b is determined. Optionally, the methylation status and/or expression level of HYAL2 is also determined.

In particular embodiments, the determination of the methylation status comprises determining methylation of at least one CpG site within the HYAL2, MGRN1, RPTOR, SLC22A18, FUT7, RAPSN, S100P, and/or DYRK4 gene. In particular, the methylation status of the promoter, intron and/or exon region of said genes is determined.

In particular, the HYAL2 gene is the human HYAL2 gene located on human chromosome 3 (Genbank Acc No: NC_000003.11 GI: 224589815). In particular, the methylation status of at least one of the CpG sites located between position 50334760 and position 50335700 on human chromosome 3 is determined. More specifically, in particular referring to build 36.1/hg18 of the human genome, the methylation status of at least one of the CpG sites located at position 50335694 (cg27091787), 50335584 (HYAL_CpG_1), 50335646 (HYAL_CpG_2), or 50335671 (HYAL_CpG_3), 50335166 (HYAL-is-310 CpG_1), 50335180 (HYAL-is-310 CpG_2), 50335192 (HYAL-is-310 CpG_3), 50335195 (HYAL-is-310 CpG_4), 50335227 (HYAL-is-310 CpG_5), 50335233 (HYAL-is-310 CpG_6), 50335300 (HYAL-is-310 CpG_7), 50335315 (HYAL-is-310 CpG_8), 50335375 (HYAL-is-310 CpG_9), 50335392 (HYAL-is-310 CpG_10), 50335401 (HYAL-is-310 CpG_11), 50334744 (HYAL2-is-325_CpG_1), 50334761 (HYAL2-is-325_CpG_2), 50334804 (HYAL2-is-325_CpG_3), 50334844 (HYAL2-is-325_CpG_4), 50334853 (HYAL2-is-325_CpG_5), 50334862 (HYAL2-is-325_CpG_6), 50334880 (HYAL2-is-325_CpG_7), 50334906 (HYAL2-is-325_CpG_8), 50334913 (HYAL2-is-325_CpG_9), 50334917 (HYAL2-is-325_CpG_10), 0334928 (HYAL2-is-325_CpG_11), 50334944 (HYAL2-is-325_CpG_12), 50334956 (HYAL2-is-325_CpG_13), 50334980 (HYAL2-is-325_CpG_14), 50334982 (HYAL2-is-325_CpG_15), 50335010 (HYAL2-is-325_CpG_16) 50335014 (HYAL2-is-325_CpG_17), 50331237 (cg08776109) and 50330420 (cg06721473) is determined.

Most specifically, at least one CpG site is selected from the list consisting of cg27091787 at position 50335694, HYAL_CpG_1 at position 50335584, HYAL_CpG_2 at position 50335646, and HYAL_CpG_3 at position 50335671. In particular, the methylation status of at least two, at least three, at least four, at least five, at least six, at least seven, at least eight, at least nine, at least ten, at least eleven, at least twelve, or at least fifteen CpG sites of the present invention is determined. It is understood by the skilled person that the exact numbering of said CpG sites may depend on the specific genomic sequence and on the specific sequence of the HYAL2 promoter region comprised in the sample to be analyzed. E.g the HYAL2 gene is located on Chromosome 3: positions 50355221-50360337 in build37/hg19, but on Chromosome 3: positions 50330244-50335146 in build36/hg18.

In particular, the MGRN1 gene is the human MGRN1 gene located at human chromosome 16 (Genbank Acc No: NC_000016.10, range: 4624824-4690974, Reference GRCh38 Primary Assembly; Genbank Acc No: NC_018927.2, range: 4674882-4741756, alternate assembly CHM1_1.1; Genbank Acc No: AC_000148.1, range: 4641815-4707494, alternate assembly HuRef). In particular, the methylation status of at least one of the CpG sites located between position 4654000 and position 4681000 on human chromosome 16 is determined. In particular, the CpG site(s) is/are located in one or more of the following regions of chromosome 16: 4670069-4670542, 4654000-4655000, 4669000-4674000, and 4678000-4681000. More specifically, in particular referring to build 36.1/hg18 of the human genome, the methylation status of at least one of the CpG sites located at position: 4670487 (MGRN1_CpG_1), 4670481 (MGRN1_CpG_2), 4670466 (MGRN1_CpG_3), 4670459 (MGRN1_CpG_4), 4670442 (MGRN1_CpG_5), 4670440 (MGRN1_CpG_6), 4670435 (MGRN1_CpG_7), 4670433 (MGRN1_CpG_8), 4670422 (MGRN1_CpG_9), 4670414 (MGRN1_CpG_10), 4670411 (MGRN1_CpG_11), 4670402 (MGRN1_CpG_12), 4670393 (MGRN1_CpG_13), 4670357 (MGRN1_CpG_14), 4670352 (MGRN1_CpG_15), 4670343 (MGRN1_CpG_16), 4670341 (MGRN1_CpG_17), 4670336 (MGRN1_CpG_18), 4670313 (MGRN1_CpG_19), 4670310 (MGRN1_CpG_20), 4670301 (MGRN1_CpG_21), 4670292 (MGRN1_CpG_22), 4670287 (MGRN1_CpG_23), 4670281 (MGRN1_CpG_24), 4670276 (MGRN1_CpG_25), 4670264 (MGRN1_CpG_26), 4670234 (MGRN1_CpG_27), 4670211 (MGRN1_CpG_28), 4670180 (MGRN1_CpG_29), 4670174 (MGRN1_CpG_30), 4670157 (MGRN1_CpG_31), 4670137 (MGRN1_CpG_32), 4670123 (MGRN1_CpG_33), 4670117 (MGRN1_CpG_34). In particular, the methylation status of at least two, at least three, at least four, at least five, at least six, at least seven, at least eight, at least nine, at least ten, at least eleven, at least twelve, or at least fifteen CpG sites of the present invention is determined. It is understood by the skilled person that the exact numbering of said CpG sites may depend on the specific genomic sequence and on the specific sequence of the MGRN1 promoter region comprised in the sample to be analyzed.

In particular, the RPTOR gene is the human RPTOR gene located at human chromosome 17 (Genbank Acc No: NC_000017.11, range: 80544825-80966373, GRCh38 Primary Assembly; Genbank Acc No: NG_013034.1, range: 5001-426549, RefSeqGene; Genbank Acc No: NC_018928.2, range: 78604958-79026514, Alternate assembly CHM1_1.1; Genbank Acc No: NG_013034.1; Genbank Acc No: AC_000149.1, range: 73954508-74378467, alternate assembly HuRef). In particular, the methylation status of at least one of the CpG sites located between position 76.297.000 and position 76.416.000 on human chromosome 17 is determined. In particular, the CpG site(s) is/are located in one or more of the following regions of chromosome 17: 76.369.937-76.370.536. 76.297.000-76.310.000, 76.333.000-76.341.000, 76.360.000-76.380.000, and 76.411.000-76.416.000. More specifically, in particular referring to build 36.1/hg18 of the human genome, the methylation status of at least one of the CpG sites located at position: 76370001 (RPTOR_CpG_1), 76370037 (RPTOR_CpG_2), 76370073 (RPTOR_CpG_3), 76370092 (RPTOR_CpG_4), 76370172 (RPTOR_CpG_5), 76370199 (RPTOR_CpG_6), 76370220 (RPTOR_CpG_7), 76370253 (RPTORCpG_8). In particular, the methylation status of at least two, at least three, at least four, at least five, at least six, at least seven, at least eight, at least nine, at least ten, at least eleven, at least twelve, or at least fifteen CpG sites of the present invention is determined. It is understood by the skilled person that the exact numbering of said CpG sites may depend on the specific genomic sequence and on the specific sequence of the RPTOR promoter region comprised in the sample to be analyzed.

In particular, the SLC22A18 gene is the human SLC22A18 gene located at human chromosome 11 (Genbank Acc No: NC_000011.10, range: 2899721-2925246, Reference GRCh38 primary assembly; Genbank Acc No: NG_011512.1, range: 5001-30526, RefSeqGene; Genbank Acc No: NT_187585.1, range: 131932-157362, Reference GRCh38 ALT_REF_LOCI_1; Genbank Acc No: AC_000143.1, range: 2709509-2734907, alternate assembly HuRef; Genbank Acc No: NC_018922.2, range:2919878-2945340, alternate assembly CHM1_1.1). In particular, the methylation status of at least one of the CpG sites located between position 2876000 and position 2883000 on human chromosome 11 is determined. In particular the CpG sites are located at 2.877.113-2.877.442. More specifically, chr11: 2.876.000-chr11: 2.883.000, a 7000 bp cancer-associated, in particular BC, OvaCa, and/or PaCA-associated, differential methylation region covering, the promoter region, a CpG island and part of the gene body region of SLC22A18 (transcript variants). More specifically, in particular referring to build 36.1/hg18 of the human genome, the methylation status of at least one of the CpG sites located at position: 2877395 (SLC22A18_CpG_1), 2877375 (SLC22A18_CpG_2), 2877365 (SLC22A18_CpG_3), 2877341 (SLC22A18_CpG_4), 2877323 (SLC22A18_CpG_5), 2877311 (SLC22A18_CpG_6), 2877193 (SLC22A18_CpG_7), 2877140 (SLC22A18_CpG_8). In particular, the methylation status of at least two, at least three, at least four, at least five, at least six, at least seven, at least eight, at least nine, at least ten, at least eleven, at least twelve, or at least fifteen CpG sites of the present invention is determined. It is understood by the skilled person that the exact numbering of said CpG sites may depend on the specific genomic sequence and on the specific sequence of the SLC22A18 promoter region comprised in the sample to be analyzed.

In particular, the FUT7 gene is the human FUT7 gene located at human chromosome 9 (Genbank Acc No: NC_000009.12, range: 137030174-137032840, Reference GRCh38 primary assembly; Genbank Acc No: NG_007527.1, range: 5001-7667, RefSeqGene; Genbank Acc No: AC_000141.1, range: 109383478-109386144, Alternate assembly HuRef; Genbank Acc No: NC_018920.2, range: 140073389-140076055, Alternate assembly CHM1_1.1). In particular, the methylation status of at least one of the CpG sites located between position 139046000 and position 139048000 on human chromosome 9 is determined. More specifically, a 2000 bp BC, OvaCa, and/or PaCA-associated differential methylation region located at the promoter region of FUT7. In particular the CpG sites are located at 139.047.218-139.047.610, 139.046.000-139.048.000, and 139.045.065-139.045.817. More specifically, in particular referring to build 36.1/hg18 of the human genome, the methylation status of at least one of the CpG sites located at position: 139047253 (FUT_CpG_1), 139047314 (FUT_CpG_2), 139047346 (FUT_CpG_3), 139047427 (FUT_CpG_4), 139047445 (FUT_CpG_5), 139047467 (FUT_CpG_6), 139047483 (FUT_CpG_7), 139047566 (FUT_CpG_8). In particular, the methylation status of at least two, at least three, at least four, at least five, at least six, at least seven, at least eight, at least nine, at least ten, at least eleven, at least twelve, or at least fifteen CpG sites of the present invention is determined. It is understood by the skilled person that the exact numbering of said CpG sites may depend on the specific genomic sequence and on the specific sequence of the FUT7 promoter region comprised in the sample to be analyzed.

In particular, the RAPSN gene is the human RAPSN gene located at human chromosome 11 (Genbank Acc No: NC_000011.10, range: 47437757-.47449178, Reference GRCh38 primary assembly; Genbank Acc No: NG_008312.1, range: 5001-16423, RefSeqGene; Genbank Acc No: NC_018922.2, range: 47458570-47469991, alternate assembly CHM1_1.1; Genbank Acc No: AC_000143.1, range: 47159075-47170494, alternate assembly HuRef). In particular, the methylation status of at least one of the CpG sites located between position 47427500 and position 47428500 on human chromosome 11 is determined. Preferably the CpG sites are located at 47427500-47428300. More specificly, a 1000 bp cancer-associated, preferably BC, OvaCa, and/or PaCA-associated, differential methylation region located at the promoter region of RAPSN. More specifically, in particular referring to build 36.1/hg18 of the human genome, the methylation status of at least one of the CpG sites located at position: 47427787 (RAPSN_CpG_1), 47427825 (RAPSN_CpG_2), 47427883 (RAPSN_CpG_3), 47427915 (RAPSN_CpG_4), 47427930 (RAPSN_CpG_5), 47427976 (RAPSN_CpG_6), 47428029 (RAPSN_CpG_7), 47428110 (RAPSN_CpG_8). In particular, the methylation status of at least two, at least three, at least four, at least five, at least six, at least seven, at least eight, at least nine, at least ten, at least eleven, at least twelve, or at least fifteen CpG sites of the present invention is determined. It is understood by the skilled person that the exact numbering of said CpG sites may depend on the specific genomic sequence and on the specific sequence of the RAPSN promoter region comprised in the sample to be analyzed.

In particular, the S100P gene is the human S100P gene located at human chromosome 4 (Genbank Acc No:

NC_000004.12, range: 6693839-6697170, Reference GRCh38 primary assembly; Genbank Acc No: AC_000136.1, range: 6627254-6630595, alternate assembly HuRef; Genbank Acc No: NC_018915.2, range: 6693944-6697285, alternate assembly CHM1_1.1). In particular, the methylation status of at least one of the CpG sites located between position 6746000 and position 6747000 on human chromosome 4 is determined. More specifically, a 1000 bp cancer-associated (preferably BC, OvaCa, and/or PaCA-associated) differential methylation region located from the promoter region till the first exon of S100P. In particular the CpG sites are located at 6.746.537-6.746.823. More specifically, in particular referring to build 36.1/hg18 of the human genome, the methylation status of at least one of the CpG sites located at position: 6746565 (S100P_CpG_1), 6746599 (S100P_CpG_2), 6746609 (S100P_CpG_3), 6746616 (S100P_CpG_4), 6746623 (S100P_CpG_5), 6746634 (S100P_CpG_6), 6746710 (S100P_CpG_7), 6746728 (S100P_CpG_8), 6746753 (S100P_CpG_9), 6746779 (S100P_CpG_10), 6746788 (S100P_CpG_11), 6746791 (S100P_CpG_12). In particular, the methylation status of at least two, at least three, at least four, at least five, at least six, at least seven, at least eight, at least nine, at least ten, at least eleven, at least twelve, or at least fifteen CpG sites of the present invention is determined. It is understood by the skilled person that the exact numbering of said CpG sites may depend on the specific genomic sequence and on the specific sequence of the S100P promoter region comprised in the sample to be analyzed.

In particular, the DYRK4 gene is the human DYRK4 gene located at human chromosome 12 (Genbank Acc No: NC_000012.12, range: 4590072-4613888, Reference GRCh38 primary assembly; Genbank Acc No: AC_000144.1, range: 4555932-4579747, Alternate assembly HuRef; Genbank Acc No: NC_018923.2, range: 4698860-4722666, alternate assembly CHM1_1.1). In particular, the methylation status of at least one of the CpG sites located between position 4569000 and position 4571000 on human chromosome 12 is determined. More specifically, a 2000 bp cancer-associated, preferably BC, OvaCa, and/or PaCA associated, differential methylation region located at the promoter region of DYRK4. In particular the CpG sites are located at 4569448-4569945. More specifically, in particular referring to build 36.1/hg18 of the human genome, the methylation status of at least one of the CpG sites located at position: 4569879 (DYRK4_CpG_1), 4569809 (DYRK4_CpG_2), 4569707 (DYRK4_CpG_3), 4569493 (DYRK4_CpG_4). In particular, the methylation status of at least two, at least three, at least four, at least five, at least six, at least seven, at least eight, at least nine, at least ten, at least eleven, at least twelve, or at least fifteen CpG sites of the present invention is determined. It is understood by the skilled person that the exact numbering of said CpG sites may depend on the specific genomic sequence and on the specific sequence of the DYRK4 promoter region comprised in the sample to be analyzed.

In further embodiments, the method of prognosing and/or diagnosing cancer further comprises the step of comparing the methylation status of the at least one methylation marker and the presence, in particular the amount, of the at least one miRNA marker, in said subject, to the methylation status of the at least one methylation marker and the presence, in particular the amount, of the at least one miRNA marker in one or more reference(s). In particular, the reference is a threshold value, a reference value or a reference sample.

In embodiments, wherein the reference is a threshold value, a methylation status of the at least on methylation marker selected from the group consisting of HYAL2, MGRN1, RPTOR, SLC22A18, FUT7, RAPSN, S100P, and DYRK4, which is below a threshold value is indicative of a subject being afflicted with cancer, an increased risk of developing cancer, or a worsening of the disease; whereas a methylation status which is equal to or above the threshold value is indicative of a subject not afflicted with cancer, of a decreased risk of developing cancer, or of a bettering of the disease. It is to be understood that the aforementioned level may vary due to statistics and errors of measurement.

In embodiments, wherein the reference is a threshold value, an expression level of the at least on methylation marker selected from the group consisting of HYAL2, MGRN1, RPTOR, SLC22A18, FUT7, RAPSN, S100P, and DYRK4, which is equal to or above the threshold value is indicative of a subject being afflicted with cancer, an increased risk of developing cancer, or a worsening of the disease; whereas an expression level which is below the threshold value is indicative of a subject not being afflicted with cancer, of a decreased risk of developing cancer, or of a bettering of the disease. It is to be understood that the aforementioned level may vary due to statistics and errors of measurement.

In embodiments, wherein the reference is a threshold value, an amount of the at least on miRNA marker selected from the group consisting of miR-652, miR-801, miR-376c, miR-376a, miR-127, miR-409, and miR-148b, which is equal to or above the threshold value is indicative of a subject being afflicted with cancer, an increased risk of developing cancer, or a worsening of the disease; whereas an amount which is below the threshold value is indicative of a subject not being afflicted with cancer, of a decreased risk of developing cancer, or of a bettering of the disease. It is to be understood that the aforementioned amounts may vary due to statistics and errors of measurement.

In particular embodiments, the threshold value for a subject being afflicted with cancer, an increased risk of developing cancer, or a worsening of the disease; for HYAL2 is a methylation status of less than 90% of the controls and an expression level of more than 1.2 folds higher than the controls. In particular embodiments the threshold value for MGRN1 is a methylation status of less than 90% of the controls. In particular embodiments the threshold value for RPTOR is a methylation status of less than 95% of the controls. In particular embodiments the threshold value for SLC22A18 is a methylation status of less than 95% of the controls and an expression level of more than 1.1 folds higher than the controls. In particular embodiments the threshold value for FUT7 is a methylation status of less than 92% of the controls. In particular embodiments the threshold value for RAPSN is a methylation status of less than 98% of the controls. In particular embodiments the threshold value for S100P is a methylation status of less than 90% of the controls and an expression level of more than 2 folds higher than the controls. In particular embodiments the threshold value for DYRK4 is a methylation status of less than 85% of the controls.

In particular embodiments the threshold level for miR-652 is an amount of at least 0.5 Ct value less than the controls (or more than 1.4 folds higher than the controls). In particular embodiments the threshold level for miR-801 is an amount of at least 0.6 Ct value less than the controls (or more than 1.5 folds higher than the controls). In particular embodiments the threshold level for miR-376c is an amount of at least 0.5 Ct value less than the controls (or more than 1.4 folds higher than the controls). In particular embodiments the threshold level for miR-376a is an amount of at least 0.6 Ct value less than the controls (or more than 1.5 folds higher than the controls). In particular embodiments the threshold level for miR-127 is an amount of at least 0.5 Ct value less than the controls (or more than 1.4 folds higher than the controls). In particular embodiments the threshold level for miR-409 is an amount of at least 0.4 Ct value less than the controls (or more than 1.3 folds higher than the controls). In particular embodiments the threshold level for miR-148b is an amount of at least 0.3 Ct value less than the controls (or more than 1.2 folds higher than the controls).

In embodiments, wherein the reference is a reference value, said reference value is a representative value of the absence of cancer, of the presence of cancer, or of an increased or decreased risk of developing cancer.

In further embodiments, the reference sample is selected from the group consisting of a reference sample derived from a healthy individual, a reference sample derived from a diseased individual, a reference sample derived from the same individual as the sample of interest taken at an earlier or later time point, and a reference sample representative for a healthy individual or representative for the presence or absence of cancer or representative for an increased or decreased risk of developing cancer.

In embodiments, wherein the reference is a healthy subject or an subject with a decreased risk of developing cancer or a methylation status of a methylation marker or an amount of miRNA representative of the absence of cancer, a decreased methylation level and/or an increased expression of the at least one methylation marker and the presence or an increased amount of the at least one miRNA marker compared to the reference indicates
    i. the risk of developing cancer, in particular BC, OvaCa, and/or PaCA,
    ii. the presence of cancer, in particular BC, OvaCa, and/or PaCA, and/or
    iii. the progression of cancer, in particular BC, OvaCa, and/or PaCA
    in the subject.

In embodiments, wherein the reference is a diseased subject or a subject with an increased risk of developing cancer or a methylation status of a methylation marker or an amount of miRNA representative of the presence of cancer, a similar methylation status or expression level of the at least one methylation marker and a similar amount of the at least one miRNA marker indicates
    i. the risk of developing cancer, in particular BC, OvaCa, and/or PaCA,
    ii. the presence of cancer, in particular BC, OvaCa, and/or PaCA, and/or
    iii. the progression of cancer, in particular BC, OvaCa, and/or PaCA
    in the subject.

In embodiments, wherein the reference sample is derived from the same subject as the sample of interest and was taken at an earlier time point,
    (i) a decreased methylation and/or an increased expression of the at least one methylation marker and the presence or an increased amount of the at least one miRNA marker compared to the reference indicates
        i. the risk of developing cancer, in particular BC, OvaCa, and/or PaCA,
        ii. the presence of cancer, in particular BC, OvaCa, and/or PaCA, and/or
        iii. the progression of cancer, in particular BC, OvaCa, and/or PaCA,
    (ii) an increased methylation and/or lower expression of the at least one methylation marker and the absence or a decreased amount of the at least one miRNA marker compared to the reference indicates
        i. a decreased risk to develop cancer, in particular BC, OvaCa, and/or PaCA,
        ii. the absence of cancer, in particular BC, OvaCa, and/or PaCA, and/or
        iii. a declined progression of cancer, in particular BC, OvaCa, and/or PaCA, and/or
    (iii) a similar level of methylation and/or expression of the at least one methylation marker and a similar amount of the at least one miRNA marker compared to the reference indicates
        i. a similar risk to develop cancer, in particular BC, OvaCa, and/or PaCA,
        ii. a stagnation in the progression of cancer, in particular BC, OvaCa, and/or PaCA, and/or
        iii. a persistence of cancer, in particular BC, OvaCa, and/or PaCA, in the subject.

In particular embodiments, the amount of at least one miRNA marker selected from the group consisting of miR-652, miR-801, miR-376c, miR-376a, miR-127, miR-409, miR-148b is determined. In particular, an amount of at least 0.5 Ct value less than the controls (or more than 1.4 folds higher than the controls) miR-652 is indicative of cancer. In particular embodiments, an amount of at least 0.6 Ct value less than the controls (or more than 1.5 folds higher than the controls) miR-801 is indicative of cancer. In particular embodiments, an amount of at least 0.5 Ct value less than the controls (or more than 1.4 folds higher than the controls) miR-376c is indicative of cancer. In particular embodiments, an amount of at least 0.6 Ct value less than the controls (or more than 1.5 folds higher than the controls) miR-376a is indicative of cancer. In particular embodiments, an amount of at least 0.5 Ct value less than the controls (or more than 1.4 folds higher than the controls) miR-127 is indicative of cancer. In particular embodiments, an amount of at least 0.4 Ct value less than the controls (or more than 1.3 folds higher than the controls) miR-409 is indicative of cancer. In particular embodiments, an amount of at least 0.3 Ct value less than the controls (or more than 1.2 folds higher than the controls) miR-148b is indicative of cancer.

In particular embodiments, the sample of interest and/or the reference sample is a body fluid samples or a tissue samples. In further embodiments, the body fluid sample is selected from the group consisting of blood, serum, plasma, synovial fluid, urine, saliva, lymphatic fluid, lacrimal fluid, and fluid obtainable from the glands such as e.g. breast or prostate. In particular embodiments, the body fluid is blood.

In further embodiments, the tissue sample is a tissue extracts obtained from tumour tissue or tissue adjacent to a tumour. In further embodiments, the sample of interest and/or the reference sample is a cell cultures or tissue cultures such as but not limited to cultures of various cancer cells. In further embodiments, the sample of interest and/or the reference sample is medium obtained from said cell cultures or tissue cultures.

In particular embodiments, the subject is a mammal, reptile, or bird. In particular, the subject is selected from the group consisting of laboratory animals (e.g. mouse or rat), domestic animals (including e.g. guinea pig, rabbit, horse, donkey, cow, sheep, goat, pig, chicken, camel, cat, dog, turtle, tortoise, snake, or lizard), or primates including chimpanzees, bonobos, gorillas, and human being. Human beings are particularly preferred.

In a second aspect, the present invention relates to a method for determining the dosage of a pharmaceutical for the alteration of cancer or the prevention of cancer or the treatment of cancer in a subject, comprising the steps of (a) determining the methylation status and/or expression level of at least one methylation marker and the amount of at least one miRNA marker in a sample of a subject, and (b) determining the dosage of a pharmaceutical depending on the methylation status and/or expression level of at least one methylation marker and the amount of at least one miRNA marker in the sample of interest.

In particular embodiments, the methylation status and/or expression level of at least one methylation marker selected from the group consisting of HYAL2, MGRN1, RPTOR, SLC22A18, FUT7, RAPSN, S100P, and DYRK4, as specified in detail above, and the amount of at least one miRNA marker selected from the group consisting of miR-652, miR-801, miR-376c, miR-376a, miR-127, miR-409, miR-148b, as specified in detail above, is determined in a reference for comparison with the methylation status and/or expression level of at least one methylation marker and the amount of at least one miRNA marker in the sample of interest, In particular embodiments, the dosage of a pharmaceutical is determined depending on the comparison of the methylation status and/or expression level of at least one methylation marker and the amount of at least one miRNA marker a in the sample of interest and the reference or reference sample.

In particular embodiments, the sample of interest and/or the reference sample is a body fluid samples or a tissue samples. In particular embodiments, the body fluid sample is selected from the group consisting of blood, serum, plasma, synovial fluid, urine, saliva, lymphatic fluid, lacrimal fluid, and fluid obtainable from the glands such as e.g. breast or prostate. In particular embodiments, the body fluid is blood.

In further embodiments, the tissue sample is a tissue extracts obtained from tumour tissue or tissue adjacent to a tumour. In further embodiments, the sample of interest and/or the reference sample is a cell cultures or tissue cultures such as but not limited to cultures of various cancer cells. In further embodiments, the sample of interest and/or the reference sample is medium obtained from said cell cultures or tissue cultures.

In particular embodiments, the subject is a mammal, reptile, or bird. Preferably, the subject is selected from the group consisting of laboratory animals (e.g. mouse or rat), domestic animals (including e.g. guinea pig, rabbit, horse, donkey, cow, sheep, goat, pig, chicken, camel, cat, dog, turtle, tortoise, snake, or lizard), or primates including chimpanzees, bonobos, gorillas, and human being. Human beings are particularly preferred.

In a third aspect, the present invention relates to a method for adapting the dosage of a pharmaceutical for the alteration of cancer or the prevention or treatment of cancer, comprising the steps of (a) determining the methylation status and/or expression level of at least one methylation marker selected from the group consisting of HYAL2, MGRN1, RPTOR, SLC22A18, FUT7, RAPSN, S100P, and DYRK4, as specified in detail above, and the amount of at least one miRNA marker selected from the group consisting of miR-652, miR-801, miR-376c, miR-376a, miR-127, miR-409, miR-148b, as specified in detail above, in a sample, (b) determining the methylation status and/or expression level of the at least one methylation marker and the amount of the at least one miRNA marker in one or more references or reference samples, (c) examining the tested sample as to whether the methylation status and/or expression level of the at least one methylation marker and the amount of the at least one miRNA marker present in said sample of interest is different from the level in the one or more references or reference samples, and (d) adapting the dosage of a pharmaceutical depending on whether the methylation status and/or expression level of the at least one methylation marker and the amount of the at least one miRNA marker in the sample of interest is different from the level in the one or more references or reference samples.

In particular embodiment, the dosage of a pharmaceutical is increased if a) the methylation status of the at least one methylation marker is decreased in comparison to a reference indicative of the absence of the disease or the decreased risk of developing a disease, or reference sample of a healthy subject or representative of the absence of the disease.

b) the methylation status of the at least one methylation marker is equal to or decreased in comparison to a reference indicative of the presence of the disease or the increased risk of developing a disease, or reference sample of a diseased subject or representative of the presence of the disease.

c) the methylation status of the at least one methylation marker is equal to decreased in comparison to a reference sample obtained from said subject at an earlier time point.

d) the expression level of the at least one methylation marker is increased in comparison to a reference indicative of the absence of the disease or the decreased risk of developing a disease, or reference sample of a healthy subject or representative of the absence of the disease.

e) the expression level of the at least one methylation marker is equal to or increased in comparison to a reference indicative of the presence of the disease or the increased risk of developing a disease, or reference sample of a diseased subject or representative of the presence of the disease.

f) the expression level of the at least one methylation marker is equal to increased in comparison to a reference sample obtained from said subject at an earlier time point.

g) the amount of the at least one miRNA is increased in comparison to a reference indicative of the absence of the disease or the decreased risk of developing a disease, or reference sample of a healthy subject or representative of the absence of the disease.

h) the amount of the at least one miRNA marker is equal to or increased in comparison to a reference indicative of the presence of the disease or the increased risk of developing a disease, or reference sample of a diseased subject or representative of the presence of the disease.

i) the amount of the at least one miRNA marker is equal to or increased in comparison to a reference sample obtained from said subject at an earlier time point.

In particular embodiment, the dosage of a pharmaceutical is decreased if a) the methylation status of the at least one methylation marker is equal to or increased in comparison to a reference indicative of the absence of the disease or the decreased risk of developing a disease, or reference sample of a healthy subject or representative of the absence of the disease.

b) the methylation status of the at least one methylation marker is decreased in comparison to a reference indicative of the presence of the disease or the increased risk of developing a disease, or reference sample of a diseased subject or representative of the presence of the disease.

c) the methylation status of the at least one methylation marker is equal to decreased in comparison to a reference sample obtained from said subject at an earlier time point.

d) the expression level of the at least one methylation marker is equal to or decreased in comparison to a reference indicative of the absence of the disease or the decreased risk of developing a disease, or reference sample of a healthy subject or representative of the absence of the disease.

e) the expression level of the at least one methylation marker is decreased in comparison to a reference indicative of the presence of the disease or the increased risk of developing a disease, or reference sample of a diseased subject or representative of the presence of the disease.

f) the expression level of the at least one methylation marker is decreased in comparison to a reference sample obtained from said subject at an earlier time point.

g) the amount of the at least one miRNA is equal to or decreased in comparison to a reference indicative of the absence of the disease or the decreased risk of developing a disease, or reference sample of a healthy subject or representative of the absence of the disease.

h) the amount of the at least one miRNA marker is decreased in comparison to a reference indicative of the presence of the disease or the increased risk of developing a disease, or reference sample of a diseased subject or representative of the presence of the disease.

i) the amount of the at least one miRNA marker is decreased in comparison to a reference sample obtained from said subject at an earlier time point.

In particular embodiments, the sample of interest and/or the reference sample is a body fluid sample or a tissue sample. In particular embodiments, the body fluid sample is selected from the group consisting of blood, serum, plasma, synovial fluid, urine, saliva, lymphatic fluid, lacrimal fluid, and fluid obtainable from the glands such as e.g. breast or prostate. In particular embodiments, the body fluid sample is a blood sample.

In further embodiments, the tissue sample is a tissue extracts obtained from tumour tissue or tissue adjacent to a tumour. In further embodiments, the sample of interest and/or the reference sample is a cell cultures or tissue cultures such as but not limited to cultures of various cancer cells. In further embodiments, the sample of interest and/or the reference sample is medium obtained from said cell cultures or tissue cultures.

In particular embodiments, the subject is a mammal, reptile, or bird. In particular, the subject is selected from the group consisting of laboratory animals (e.g. mouse or rat), domestic animals (including e.g. guinea pig, rabbit, horse, donkey, cow, sheep, goat, pig, chicken, camel, cat, dog, turtle, tortoise, snake, or lizard), or primates including chimpanzees, bonobos, gorillas, and human being. Human beings are particularly preferred.

In a fourth aspect, the present invention relates to a method of determining the beneficial and/or adverse effects of a substance on cancer or the development of cancer, comprising the steps of (a) determining the methylation status and/or expression level of at least one methylation marker selected from the group consisting of HYAL2, MGRN1, RPTOR, SLC22A18, FUT7, RAPSN, S100P, and DYRK4, as specified in detail above, and the amount of at least one miRNA marker selected from the group consisting of miR-652, miR-801, miR-376c, miR-376a, miR-127, miR-409, miR-148b, as specified in detail above, in a sample, (b) determining the methylation status and/or expression level of the at least one methylation marker and the amount of the at least one miRNA marker in one or more references or reference samples, and (c) examining the sample of interest as to whether the methylation status and/or expression level of at least one methylation marker and the amount of at least one miRNA marker present in said sample of interest is different from the level in the one or more references or reference samples, wherein the sample of interest was exposed differently to said substance than the one or more references or reference samples.

In particular embodiments, the sample of interest is exposed differently to said substance with regard to time and/or concentration. Thus, the sample of interest may be exposed to said substance for a longer or shorter time interval, and/or at a higher or lower concentration of said substance.

In embodiment, wherein the sample of interest is exposed to a higher concentration and/or for a longer time interval, an adverse effect of a substance is determined if a) the methylation status of the at least one methylation marker is decreased in comparison to a reference indicative of the absence of the disease or the decreased risk of developing a disease, or reference sample of a healthy subject or representative of the absence of the disease.

b) the methylation status of the at least one methylation marker is equal to or decreased in comparison to a reference indicative of the presence of the disease or the increased risk of developing a disease, or reference sample of a diseased subject or representative of the presence of the disease.

c) the methylation status of the at least one methylation marker is equal to decreased in comparison to a reference sample obtained from said subject at an earlier time point.

d) the expression level of the at least one methylation marker is increased in comparison to a reference indicative of the absence of the disease or the decreased risk of developing a disease, or reference sample of a healthy subject or representative of the absence of the disease.

e) the expression level of the at least one methylation marker is equal to or increased in comparison to a reference indicative of the presence of the disease or the increased risk of developing a disease, or reference sample of a diseased subject or representative of the presence of the disease.

f) the expression level of the at least one methylation marker is equal to increased in comparison to a reference sample obtained from said subject at an earlier time point.

g) the amount of the at least one miRNA is increased in comparison to a reference indicative of the absence of the disease or the decreased risk of developing a disease, or reference sample of a healthy subject or representative of the absence of the disease.

h) the amount of the at least one miRNA marker is equal to or increased in comparison to a reference indicative of the presence of the disease or the increased risk of developing a disease, or reference sample of a diseased subject or representative of the presence of the disease.

i) the amount of the at least one miRNA marker is equal to or increased in comparison to a reference sample obtained from said subject at an earlier time point.

In embodiment, wherein the sample of interest is exposed to a higher concentration and/or for a longer time interval, a beneficial effect of a substance is determined if a) the methylation status of the at least one methylation marker is equal to or increased in comparison to a reference indicative of the absence of the disease or the decreased risk of developing a disease, or reference sample of a healthy subject or representative of the absence of the disease.

b) the methylation status of the at least one methylation marker is decreased in comparison to a reference indicative of the presence of the disease or the increased risk of developing a disease, or reference sample of a diseased subject or representative of the presence of the disease.

c) the methylation status of the at least one methylation marker is equal to decreased in comparison to a reference sample obtained from said subject at an earlier time point.

d) the expression level of the at least one methylation marker is equal to or decreased in comparison to a reference indicative of the absence of the disease or the decreased risk of developing a disease, or reference sample of a healthy subject or representative of the absence of the disease.

e) the expression level of the at least one methylation marker is decreased in comparison to a reference indicative of the presence of the disease or the increased risk of developing a disease, or reference sample of a diseased subject or representative of the presence of the disease.

f) the expression level of the at least one methylation marker is decreased in comparison to a reference sample obtained from said subject at an earlier time point.

g) the amount of the at least one miRNA is equal to or decreased in comparison to a reference indicative of the absence of the disease or the decreased risk of developing a disease, or reference sample of a healthy subject or representative of the absence of the disease.

h) the amount of the at least one miRNA marker is decreased in comparison to a reference indicative of the presence of the disease or the increased risk of developing a disease, or reference sample of a diseased subject or representative of the presence of the disease.

i) the amount of the at least one miRNA marker is decreased in comparison to a reference sample obtained from said subject at an earlier time point.

In embodiment, wherein the sample of interest is exposed to a lower concentration and/or for a shorter time interval, no effect or an adverse effect of a substance is determined if a) the methylation status of the at least one methylation marker is decreased in comparison to a reference indicative of the absence of the disease or the decreased risk of developing a disease, or reference sample of a healthy subject or representative of the absence of the disease.

b) the methylation status of the at least one methylation marker is equal to or decreased in comparison to a reference indicative of the presence of the disease or the increased risk of developing a disease, or reference sample of a diseased subject or representative of the presence of the disease.

c) the methylation status of the at least one methylation marker is equal to decreased in comparison to a reference sample obtained from said subject at an earlier time point.

d) the expression level of the at least one methylation marker is increased in comparison to a reference indicative of the absence of the disease or the decreased risk of developing a disease, or reference sample of a healthy subject or representative of the absence of the disease.

e) the expression level of the at least one methylation marker is equal to or increased in comparison to a reference indicative of the presence of the disease or the increased risk of developing a disease, or reference sample of a diseased subject or representative of the presence of the disease.

f) the expression level of the at least one methylation marker is equal to increased in comparison to a reference sample obtained from said subject at an earlier time point.

g) the amount of the at least one miRNA is increased in comparison to a reference indicative of the absence of the disease or the decreased risk of developing a disease, or reference sample of a healthy subject or representative of the absence of the disease.

h) the amount of the at least one miRNA marker is equal to or increased in comparison to a reference indicative of the presence of the disease or the increased risk of developing a disease, or reference sample of a diseased subject or representative of the presence of the disease.

i) the amount of the at least one miRNA marker is equal to or increased in comparison to a reference sample obtained from said subject at an earlier time point.

In embodiment, wherein the sample of interest is exposed to a lower concentration and/or for a shorter time interval, a beneficial effect of a substance is determined if a) the methylation status of the at least one methylation marker is equal to or increased in comparison to a reference indicative of the absence of the disease or the decreased risk of developing a disease, or reference sample of a healthy subject or representative of the absence of the disease.

b) the methylation status of the at least one methylation marker is decreased in comparison to a reference indicative of the presence of the disease or the increased risk of developing a disease, or reference sample of a diseased subject or representative of the presence of the disease.

c) the methylation status of the at least one methylation marker is equal to decreased in comparison to a reference sample obtained from said subject at an earlier time point.

d) the expression level of the at least one methylation marker is equal to or decreased in comparison to a reference indicative of the absence of the disease or the decreased risk of developing a disease, or reference sample of a healthy subject or representative of the absence of the disease.

e) the expression level of the at least one methylation marker is decreased in comparison to a reference indicative of the presence of the disease or the increased risk of developing a disease, or reference sample of a diseased subject or representative of the presence of the disease.

f) the expression level of the at least one methylation marker is decreased in comparison to a reference sample obtained from said subject at an earlier time point.

g) the amount of the at least one miRNA is equal to or decreased in comparison to a reference indicative of the absence of the disease or the decreased risk of developing a disease, or reference sample of a healthy subject or representative of the absence of the disease.

h) the amount of the at least one miRNA marker is decreased in comparison to a reference indicative of the presence of the disease or the increased risk of developing a disease, or reference sample of a diseased subject or representative of the presence of the disease.

i) the amount of the at least one miRNA marker is decreased in comparison to a reference sample obtained from said subject at an earlier time point.

In particular embodiments, the sample of interest and/or the reference sample is a body fluid samples or a tissue samples. In particular embodiments, the body fluid sample is selected from the group consisting of blood, serum, plasma, synovial fluid, urine, saliva, lymphatic fluid, lacrimal fluid, and fluid obtainable from the glands such as e.g. breast or prostate. In particular embodiments, the body fluid sample is a blood sample.

In further embodiments, the tissue sample is a tissue extracts obtained from tumour tissue or tissue adjacent to a tumour. In further embodiments, the sample of interest and/or the reference sample is a cell cultures or tissue cultures such as but not limited to cultures of various cancer cells. In further embodiments, the sample of interest and/or the reference sample is medium obtained from said cell cultures or tissue cultures.

In particular embodiments, the subject is a mammal, reptile, or bird. In particular, the subject is selected from the group consisting of laboratory animals (e.g. mouse or rat), domestic animals (including e.g. guinea pig, rabbit, horse, donkey, cow, sheep, goat, pig, chicken, camel, cat, dog, turtle, tortoise, snake, or lizard), or primates including chimpanzees, bonobos, gorillas, and human being. Human beings are particularly preferred.

In a fifth aspect, the present invention relates to a method for identifying a patient as a responder to a cancer treatment, comprising determining the methylation status and/or expression level of at least one methylation marker selected from the group consisting of HYAL2, MGRN1, RPTOR, SLC22A18, FUT7, RAPSN, S100P, and DYRK4, as specified in detail above, and the amount of at least one miRNA marker selected from the group consisting of miR-652, miR-801, miR-376c, miR-376a, miR-127, miR-409, miR-148b, as specified in detail above, in a first sample and in one or more further samples taken from the subject subsequently to the first sample, wherein an increased methylation status of the at least one methylation marker and/or a lower expression level of the at least one methylation marker, and the absence or decreased amount of the at least one miRNA marker indicates a response to the treatment.

In particular embodiments, the sample of interest and/or the reference sample is a body fluid samples or a tissue samples. In particular embodiments, the body fluid sample is selected from the group consisting of blood, serum, plasma, synovial fluid, urine, saliva, lymphatic fluid, lacrimal fluid, and fluid obtainable from the glands such as e.g. breast or prostate. In particular embodiments, the body fluid sample is a blood sample.

In further embodiments, the tissue sample is a tissue extracts obtained from tumour tissue or tissue adjacent to a tumour. In further embodiments, the sample of interest and/or the reference sample is a cell cultures or tissue cultures such as but not limited to cultures of various cancer cells. In further embodiments, the sample of interest and/or the reference sample is medium obtained from said cell cultures or tissue cultures.

In particular embodiments, the subject is a mammal, reptile, or bird. In particular, the subject is selected from the group consisting of laboratory animals (e.g. mouse or rat), domestic animals (including e.g. guinea pig, rabbit, horse, donkey, cow, sheep, goat, pig, chicken, camel, cat, dog, turtle, tortoise, snake, or lizard), or primates including chimpanzees, bonobos, gorillas, and human being. Human beings are particularly preferred.

In a sixth aspect, the present invention relates to a method for identifying a patient as a non-responder to a cancer treatment, comprising determining the methylation status and/or expression level of at least one methylation marker selected from the group consisting of HYAL2, MGRN1, RPTOR, SLC22A18, FUT7, RAPSN, S100P, and DYRK4, as specified in detail above, and the amount of at least one miRNA marker selected from the group consisting of miR-652, miR-801, miR-376c, miR-376a, miR-127, miR-409, miR-148b, as specified in detail above, in a first sample and in one or more further samples taken subsequently to the first sample, wherein a decreased methylation status of the at least one methylation marker and/or an increased expression level of the at least one methylation marker, and the presence or increased amount of the at least one miRNA marker indicates a lack of response to the treatment.

In particular embodiments, the sample of interest and/or the reference sample is a body fluid samples or a tissue samples. In particular embodiments, the body fluid sample is selected from the group consisting of blood, serum, plasma, synovial fluid, urine, saliva, lymphatic fluid, lacrimal fluid, and fluid obtainable from the glands such as e.g. breast or prostate. In further embodiments, the tissue sample is a tissue extracts obtained from tumour tissue or tissue adjacent to a tumour. In further embodiments, the sample of interest and/or the reference sample is a cell cultures or tissue cultures such as but not limited to cultures of various cancer cells. In further embodiments, the sample of interest and/or the reference sample is medium obtained from said cell cultures or tissue cultures.

In particular embodiments, the subject is a mammal, reptile, or bird. In particular, the subject is selected from the group consisting of laboratory animals (e.g. mouse or rat), domestic animals (including e.g. guinea pig, rabbit, horse, donkey, cow, sheep, goat, pig, chicken, camel, cat, dog, turtle, tortoise, snake, or lizard), or primates including chimpanzees, bonobos, gorillas, and human being. Human beings are particularly preferred.

In a seventh aspect, the present invention relates to a method for treating cancer, comprising the steps:
(i) determining the methylation status and/or expression level of at least one methylation marker selected from the group consisting of HYAL2, MGRN1, RPTOR, SLC22A18, FUT7, RAPSN, S100P, and DYRK4, as specified in detail above, and the amount of at least one miRNA marker selected from the group consisting of miR-652, miR-801, miR-376c, miR-376a, miR-127, miR-409, miR-148b, as specified in detail above, in a first sample of a subject;
(ii) starting treatment of said subject with a first treatment regimen comprising one or more anti-cancer agents or therapies,
(iii) determining the methylation status of the at least one methylation marker and/or the expression level of the at least one methylation marker, and the amount of the at least one miRNA in one or more subsequently taken second samples of said subject;
(iv) optionally repeating steps (ii) and (iii) one or more times;
(v) continuing treating the subject with the first treatment regimen if there is a substantial increase of the methylation status of the at least one methylation marker and/or a lower expression level of the at least one methylation marker, and a decreased amount or absence of the at least one miRNA marker, or
(vi) amending the treatment or terminating treating the subject with the first treatment regimen and treating the subject instead with a second treatment regimen comprising one or more anti-cancer agents or therapies not comprised in the first treatment regimen if there is a decreased methylation status of the at least one methylation marker and/or an increased expression level of the at least one methylation marker, and an increased amount or presence of the at least one miRNA marker.

In particular embodiments, the sample of interest and/or the reference sample is a body fluid samples or a tissue samples. In particular embodiments, the body fluid sample is selected from the group consisting of blood, serum, plasma, synovial fluid, urine, saliva, lymphatic fluid, lacrimal fluid, and fluid obtainable from the glands such as e.g. breast or prostate. In particular embodiments, the body fluid sample is a blood sample.

In further embodiments, the tissue sample is a tissue extracts obtained from tumour tissue or tissue adjacent to a tumour. In further embodiments, the sample of interest and/or the reference sample is a cell cultures or tissue cultures such as but not limited to cultures of various cancer cells. In further embodiments, the sample of interest and/or the reference sample is medium obtained from said cell cultures or tissue cultures.

In particular embodiments, the subject is a mammal, reptile, or bird. In particular, the subject is selected from the group consisting of laboratory animals (e.g. mouse or rat), domestic animals (including e.g. guinea pig, rabbit, horse, donkey, cow, sheep, goat, pig, chicken, camel, cat, dog, turtle, tortoise, snake, or lizard), or primates including chimpanzees, bonobos, gorillas, and human being. Human beings are particularly preferred.

In particular embodiments, the treatment regime is selected from the list consisting of chemotherapy, anti-hormone therapy, immunotherapy, and radiation therapy.

In an eighth aspect, the present invention relates to means for prognosing and/or diagnosing
  i. the risk of developing cancer, in particular BC, OvaCa, and/or PaCA,
  ii. the presence of cancer, in particular BC, OvaCa, and/or PaCA, and/or
  iii. the progression of cancer, in particular BC, OvaCa, and/or PaCA, comprising
  c) one or more means of detecting the methylation status and/or expression level of at least one methylation marker, and
  d) one or more means of detecting the amount of at least one miRNA marker.

In particular embodiments, said means detect the methylation status and/or expression level of at least one methylation marker selected from the group consisting of HYAL2, MGRN1, RPTOR, SLC22A18, FUT7, RAPSN, S100P, DYRK4, as specified in detail above.

In further embodiments, the one or more means for detecting the methylation status of at least one methylation marker comprise at least one methylation-specific polynucleotide. In particular embodiments, the methylation-specific polynucleotide is a methylation-specific primer and/or a methylation-specific probe.

In further embodiments, the one or more means for detecting the expression level of at least one methylation marker comprise a binding moiety. Said binding moiety is in particular a polynucleotide, peptide, protein, or aptamer. In further embodiments, the binding moiety is selected from the group consisting of monoclonal antibodies, polyclonal antibodies, Fab fragments, Fc fragments, Fab' fragments, F(ab')2 fragments, single domain antibodies (sdAb), nanobodies, single chain Fv (scFv), divalent single-chain variable fragments (di-scFvs), tandem scFvs, diabodies, triabodies, bispecific diabodies, single-chain diabodies (scDb), bi-specific T-cell engagers (BiTEs), and DART" molecules.

In particular embodiments, the binding moiety binds to a part of the gene product of the methylation marker. Accordingly, in embodiments wherein the binding moiety is a polynucleotide, said polynucleotide binds to the mRNA transcribed from the gene of the respective methylation marker, i.e. the gene of HYAL2, MGRN1, RPTOR, SLC22A18, FUT7, RAPSN, S100P, or DYRK4.

In embodiments, wherein the binding moiety is a peptide, protein or aptamer, said peptide, protein, or aptamer, binds to a part, in particular an epitope, of the protein translated from the gene of the respective methylation marker, i.e. the gene of HYAL2, MGRN1, RPTOR, SLC22A18, FUT7, RAPSN, S100P, or DYRK4.

In particular embodiments, said means detect at least one miRNA marker selected from the group consisting of miR-652, miR-801, miR-376c, miR-376a, miR-127, miR-409, miR-148b, as specified in detail above.

In further embodiments the one or more means for detecting the amount of at least one miRNA marker comprise at least one miRNA specific polynucleotide.

In particular embodiments said at least one miRNA specific polynucleotide has a sequence according to SEQ ID NO: 1-13

In particular embodiments, the said means are for use in the method of specified in detail above. In particular, said means are for use in a method selected from the group consisting of:
  (i) a method of prognosing and/or diagnosing cancer, in particular BC, OvaCa, and/or PaCA, in a subject, comprising (a) determining the methylation status and/or expression level of at least one methylation marker selected from the group consisting of HYAL2, MGRN1, RPTOR, SLC22A18, FUT7, RAPSN, S100P, DYRK4, and (b) determining the presence, in particular the amount, of at least one miRNA marker selected from the group consisting of miR-652, miR-801, miR-376c, miR-376a, miR-127, miR-409, miR-148b, in a subject, wherein the methylation status and/or expression level of at least one methylation marker and the presence of at least one miRNA is indicative of the prognosis and/or diagnosis of said subject,
  (ii) a method for determining the dosage of a pharmaceutical for the alteration of cancer or the prevention or treatment of cancer in a subject, comprising the steps of (a) determining the methylation status and/or expression level of at least one methylation marker selected from the group consisting of HYAL2, MGRN1, RPTOR, SLC22A18, FUT7, RAPSN, S100P, DYRK4, as specified in detail above, and the amount of at least one miRNA marker selected from the group consisting of miR-652, miR-801, miR-376c, miR-376a, miR-127, miR-409, miR-148b, as specified in detail above, in a sample of a subject, and optionally determining the methylation status and/or expression level of at least one methylation marker and the amount of at least one miRNA marker in a reference for comparison with the methylation status and/or expression level of at least one methylation marker and the amount of at least one miRNA marker in the sample of interest, and (b) determining the dosage of a pharmaceutical depending on the methylation status and/or expression level of at least one methylation marker and the amount of at least one miRNA marker in the sample of interest, optionally depending on the comparison of the methylation status and/or expression level of at least one methylation marker and the amount of at least one miRNA marker a in the sample of interest and the reference or reference sample,
  (iii) a method for adapting the dosage of a pharmaceutical for the alteration of cancer or the prevention or treatment of cancer, comprising the steps of (a) determining the methylation status and/or expression level of at least one methylation marker selected from the group consisting of HYAL2, MGRN1, RPTOR, SLC22A18, FUT7, RAPSN, S100P, DYRK4, as specified in detail above, and the amount of at least one miRNA marker selected from the group consisting of miR-652, miR-801, miR-376c, miR-376a, miR-127, miR-409, miR-148b, as specified in detail above, in a sample, (b) determining the methylation status and/or expression level of at least one methylation marker and the amount of at least one miRNA marker in one or more references or reference samples, (c) examining the tested sample as to whether the methylation status and/or expression level of at least one methylation marker and the amount of at least one miRNA marker present in said sample of interest is different from the level in the one or more references or reference samples, and (d) adapting the dosage of a pharmaceutical depending on whether the methylation status and/or expression level of at least one methylation marker and the amount of at least one miRNA marker in the sample of interest is different from the level in the one or more references or reference samples, (iv) a method of determining the beneficial and/or adverse effects of a substance on cancer or the development of cancer, comprising the steps of (a) determining the methylation status and/or expression level of at least one methylation marker selected from the group consisting of HYAL2, MGRN1, RPTOR, SLC22A18, FUT7, RAPSN, S100P, DYRK4, as specified in detail above, and the amount of at least one miRNA marker selected from the group consisting of miR-652, miR-801, miR-376c, miR-376a, miR-127, miR-409, miR-148b, as specified in detail above, in a sample of interest, (b) determining the methylation status and/or expression level of at least one methylation marker and the amount of at least one miRNA marker in one or more references or reference samples, and (c) examining the sample of interest as to whether the methylation status and/or expression level of at least one methylation marker and the amount of at least one miRNA marker present in said sample of interest is different from the level in the one or more references or reference samples, wherein the sample of interest was exposed differently to said substance than the one or more references or reference samples, (v) a method for identifying a patient as a responder to a cancer treatment, comprising determining the methylation status and/or expression level of at least one methylation marker selected from the group consisting of HYAL2, MGRN1, RPTOR, SLC22A18, FUT7, RAPSN, S100P, DYRK4, as specified in detail above, and the amount of at least one miRNA marker selected from the group consisting of miR-652, miR-801, miR-376c, miR-376a, miR-127, miR-409, miR-148b, as specified in detail above, in a first sample and in one or more further samples taken subsequently to the first sample, wherein an increased methylation status of the at least one methylation marker and/or a lower expression level of the at least one methylation marker, and the absence or decreased amount of the at least one miRNA marker indicates a response to the treatment, (vi) a method for identifying a patient as a non-responder to a cancer treatment, comprising determining the methylation status and/or expression level of at least one methylation marker selected from the group consisting of HYAL2, MGRN1, RPTOR, SLC22A18, FUT7, RAPSN, S100P, DYRK4, as specified in detail above, and the amount of at least one miRNA marker selected from the group consisting of miR-652, miR-801, miR-376c, miR-376a, miR-127, miR-409, miR-148b, as specified in detail above, in a first sample and in one or more further samples taken subsequently to the first sample, wherein a decreased methylation status of the at least one methylation marker and/or an increased expression level of the at least one methylation marker, and the presence or increased amount of the at least one miRNA marker indicates a lack of response to the treatment, and (vii) a method for treating cancer, comprising the steps: (i) determining the methylation status and/or expression level of at least one methylation marker selected from the group consisting of HYAL2, MGRN1, RPTOR, SLC22A18, FUT7, RAPSN, S100P, DYRK4, as specified in detail above, and the amount of at least one miRNA marker selected from the group consisting of miR-652, miR-801, miR-376c, miR-376a, miR-127, miR-409, miR-148b, as specified in detail above, in a first sample of a subject; (ii) starting treatment of said patient with a first treatment regimen comprising one or more anti-cancer agents or therapies, (iii) determining the methylation status of at least one methylation marker and/or the expression level of at least one methylation marker, and the amount of at least one miRNA in one or more subsequently taken further samples of said subject; (iv) optionally repeating steps (ii) and (iii) one or more times; (v) continuing treating the patient with the first treatment regimen if there is a substantial increase of the methylation status of the at least one methylation marker and/or a lower expression level of the at least one methylation marker, and a decreased amount or absence of the at least one miRNA marker, or (vi) amending the treatment or terminating treating the patient with the first treatment regimen and treating the patient instead with a second treatment regimen comprising one or more anti-cancer agents or therapies not comprised in the first treatment regimen if there is a decreased methylation status of the at least one methylation marker and/or an increased expression level of the at least one methylation marker, and an increased amount or presence of the at least one miRNA marker.

In a ninth aspect, the present invention relates to a kit comprising above specified means for detecting the methylation status and/or expression level of at least one methylation marker selected from the group consisting of HYAL2, MGRN1, RPTOR, SLC22A18, FUT7, RAPSN, S100P, DYRK4, as specified in detail above, and the presence, in particular the amount, of at least one miRNA marker selected from the group consisting of miR-652, miR-801, miR-376c, miR-376a, miR-127, miR-409, miR-148b, as specified in detail above.

In particular embodiments, the kit further comprises
(a) a container, and/or
(b) a data carrier, wherein the data carrier comprises information such as
(i) instructions concerning methods for identifying the risk for developing and/or identifying the presence and/or monitoring progression of cancer
(ii) instructions for use of the means for detecting the methylation status and/or expression level of at least one methylation marker and the amount of at least one miRNA marker, in particular in a sample, more specifically in a sample from an individual and/or of the kit,
(iii) quality information such as information about the lot/batch number of the means for detecting the methylation status and/or expression level of at least one methylation marker and the amount of at least one miRNA marker and/or of the kit, the manufacturing or assembly site or the expiry or sell-by date, information concerning the correct storage or handling of the kit,
(iv) information concerning the composition of the buffer(s), diluent(s), reagent(s) for detecting the methylation status and/or expression level of at least one methylation marker and the amount of at least one miRNA marker and/or of the means for detecting the methylation status and/or expression level of at least one methylation marker and the amount of at least one miRNA marker, (v) information concerning the interpretation of information obtained when performing the above-mentioned methods identifying and/or monitoring progression of cancer, (vi) a warning concerning possible misinterpretations or wrong results when applying unsuitable methods and/or unsuitable means, and/or (vii) a warning concerning possible misinterpretations or wrong results when using unsuitable reagent(s) and/or buffer(s).

In particular embodiments, the kid is for use in the method of specified in detail above. In particular, the kid is for use in a method selected from the group consisting of:

(i) a method of prognosing and/or diagnosing cancer, in particular BC, OvaCa, and/or PaCA, in a subject, comprising (a) determining the methylation status and/or expression level of at least one methylation marker selected from the group consisting of HYAL2, MGRN1, RPTOR, SLC22A18, FUT7, RAPSN, S100P, DYRK4, and (b) determining the presence, in particular the amount, of at least one miRNA marker selected from the group consisting of miR-652, miR-801, miR-376c, miR-376a, miR-127, miR-409, miR-148b, in a subject, wherein the methylation status and/or expression level of at least one methylation marker and the presence of at least one miRNA is indicative of the prognosis and/or diagnosis of said subject, (ii) a method for determining the dosage of a pharmaceutical for the alteration of cancer or the prevention or treatment of cancer in a subject, comprising the steps of (a) determining the methylation status and/or expression level of at least one methylation marker selected from the group consisting of HYAL2, MGRN1, RPTOR, SLC22A18, FUT7, RAPSN, S100P, DYRK4, as specified in detail above, and the amount of at least one miRNA marker selected from the group consisting of miR-652, miR-801, miR-376c, miR-376a, miR-127, miR-409, miR-148b, as specified in detail above, in a sample of a subject, and optionally determining the methylation status and/or expression level of at least one methylation marker and the amount of at least one miRNA marker in a reference for comparison with the methylation status and/or expression level of at least one methylation marker and the amount of at least one miRNA marker in the sample of interest, and (b) determining the dosage of a pharmaceutical depending on the methylation status and/or expression level of at least one methylation marker and the amount of at least one miRNA marker in the sample of interest, optionally depending on the comparison of the methylation status and/or expression level of at least one methylation marker and the amount of at least one miRNA marker a in the sample of interest and the reference or reference sample, (iii) a method for adapting the dosage of a pharmaceutical for the alteration of cancer or the prevention or treatment of cancer, comprising the steps of (a) determining the methylation status and/or expression level of at least one methylation marker selected from the group consisting of HYAL2, MGRN1, RPTOR, SLC22A18, FUT7, RAPSN, S100P, DYRK4, as specified in detail above, and the amount of at least one miRNA marker selected from the group consisting of miR-652, miR-801, miR-376c, miR-376a, miR-127, miR-409, miR-148b, as specified in detail above, in a sample, (b) determining the methylation status and/or expression level of at least one methylation marker and the amount of at least one miRNA marker in one or more references or reference samples, (c) examining the tested sample as to whether the methylation status and/or expression level of at least one methylation marker and the amount of at least one miRNA marker present in said sample of interest is different from the level in the one or more references or reference samples, and (d) adapting the dosage of a pharmaceutical depending on whether the methylation status and/or expression level of at least one methylation marker and the amount of at least one miRNA marker in the sample of interest is different from the level in the one or more references or reference samples, (iv) a method of determining the beneficial and/or adverse effects of a substance on cancer or the development of cancer, comprising the steps of (a) determining the methylation status and/or expression level of at least one methylation marker selected from the group consisting of HYAL2, MGRN1, RPTOR, SLC22A18, FUT7, RAPSN, S100P, DYRK4, as specified in detail above, and the amount of at least one miRNA marker selected from the group consisting of miR-652, miR-801, miR-376c, miR-376a, miR-127, miR-409, miR-148b, as specified in detail above, in a sample of interest, (b) determining the methylation status and/or expression level of at least one methylation marker and the amount of at least one miRNA marker in one or more references or reference samples, and (c) examining the sample of interest as to whether the methylation status and/or expression level of at least one methylation marker and the amount of at least one miRNA marker present in said sample of interest is different from the level in the one or more references or reference samples, wherein the sample of interest was exposed differently to said substance than the one or more references or reference samples, (v) a method for identifying a patient as a responder to a cancer treatment, comprising determining the methylation status and/or expression level of at least one methylation marker selected from the group consisting of HYAL2, MGRN1, RPTOR, SLC22A18, FUT7, RAPSN, S100P, DYRK4, as specified in detail above, and the amount of at least one miRNA marker selected from the group consisting of miR-652, miR-801, miR-376c, miR-376a, miR-127, miR-409, miR-148b, as specified in detail above, in a first sample and in one or more further samples taken subsequently to the first sample, wherein an increased methylation status of the at least one methylation marker and/or a lower expression level of the at least one methylation marker, and the absence or decreased amount of the at least one miRNA marker indicates a response to the treatment, (vi) a method for identifying a patient as a non-responder to a cancer treatment, comprising determining the methylation status and/or expression level of at least one methylation marker selected from the group consisting of HYAL2, MGRN1, RPTOR, SLC22A18, FUT7, RAPSN, S100P, DYRK4, as specified in detail above, and the amount of at least one miRNA marker selected from the group consisting of miR-652, miR-801, miR-376c, miR-376a, miR-127, miR-409, miR-148b, as specified in detail above, in a first sample and in one or more further samples taken subsequently to the first sample, wherein a decreased methylation status of the at least one methylation marker and/or an increased expression level of the at least one methylation marker, and the presence or increased amount of the at least one miRNA marker indicates a lack of response to the treatment, and (vii) a method for treating cancer, comprising the steps: (i) determining the methylation status and/or expression level of at least one methylation marker selected from the group consisting of HYAL2, MGRN1, RPTOR, SLC22A18, FUT7, RAPSN, S100P, DYRK4, as specified in detail above, and the amount of at least one miRNA marker selected from the group consisting of miR-652, miR-801, miR-376c, miR-376a, miR-127, miR-409, miR-148b, as specified in detail above, in a first sample of a subject; (ii)

starting treatment of said patient with a first treatment regimen comprising one or more anti-cancer agents or therapies, (iii) determining the methylation status of at least one methylation marker and/or the expression level of at least one methylation marker, and the amount of at least one miRNA in one or more subsequently taken further samples of said subject; (iv) optionally repeating steps (ii) and (iii) one or more times; (v) continuing treating the patient with the first treatment regimen if there is a substantial increase of the methylation status of the at least one methylation marker and/or a lower expression level of the at least one methylation marker, and a decreased amount or absence of the at least one miRNA marker, or (vi) amending the treatment or terminating treating the patient with the first treatment regimen and treating the patient instead with a second treatment regimen comprising one or more anti-cancer agents or therapies not comprised in the first treatment regimen if there is a decreased methylation status of the at least one methylation marker and/or an increased expression level of the at least one methylation marker, and an increased amount or presence of the at least one miRNA marker.

In a tenth aspect, the present invention relates to the use of the means for detecting the methylation status and/or expression level of at least one methylation marker selected from the group consisting of HYAL2, MGRN1, RPTOR, SLC22A18, FUT7, RAPSN, S100P, DYRK4, as specified in detail above, and the presence, in particular the amount, of at least one miRNA marker selected from the group consisting of miR-652, miR-801, miR-376c, miR-376a, miR-127, miR-409, miR-148b, as specified in detail above, or the kit comprising said means, as specified in detail above, for prognosing and/or diagnosing i. the risk of developing cancer, in particular BC, OvaCa, and/or PaCA, ii. the presence of cancer, in particular BC, OvaCa, and/or PaCA, and/or iii. the progression of cancer, in particular BC, OvaCa, and/or PaCA.

In particular embodiments the use of said means and/or said kit is a use in one of the methods specified in detail above. In particular a use in a method selected from the group consisting of:

(i) a method of prognosing and/or diagnosing cancer, preferably BC, OvaCa, and/or PaCA, in a subject, comprising (a) determining the methylation status and/or expression level of at least one methylation marker selected from the group consisting of HYAL2, MGRN1, RPTOR, SLC22A18, FUT7, RAPSN, S100P, DYRK4, and (b) determining the presence, in particular the amount, of at least one miRNA marker selected from the group consisting of miR-652, miR-801, miR-376c, miR-376a, miR-127, miR-409, miR-148b, in a subject, wherein the methylation status and/or expression level of at least one methylation marker and the presence of at least one miRNA is indicative of the prognosis and/or diagnosis of said subject, (ii) a method for determining the dosage of a pharmaceutical for the alteration of cancer or the prevention or treatment of cancer in a subject, comprising the steps of (a) determining the methylation status and/or expression level of at least one methylation marker selected from the group consisting of HYAL2, MGRN1, RPTOR, SLC22A18, FUT7, RAPSN, S100P, DYRK4, as specified in detail above, and the amount of at least one miRNA marker selected from the group consisting of miR-652, miR-801, miR-376c, miR-376a, miR-127, miR-409, miR-148b, as specified in detail above, in a sample of a subject, and optionally determining the methylation status and/or expression level of at least one methylation marker and the amount of at least one miRNA marker in a reference for comparison with the methylation status and/or expression level of at least one methylation marker and the amount of at least one miRNA marker in the sample of interest, and (b) determining the dosage of a pharmaceutical depending on the methylation status and/or expression level of at least one methylation marker and the amount of at least one miRNA marker in the sample of interest, optionally depending on the comparison of the methylation status and/or expression level of at least one methylation marker and the amount of at least one miRNA marker a in the sample of interest and the reference or reference sample, (iii) a method for adapting the dosage of a pharmaceutical for the alteration of cancer or the prevention or treatment of cancer, comprising the steps of (a) determining the methylation status and/or expression level of at least one methylation marker selected from the group consisting of HYAL2, MGRN1, RPTOR, SLC22A18, FUT7, RAPSN, S100P, DYRK4, as specified in detail above, and the amount of at least one miRNA marker selected from the group consisting of miR-652, miR-801, miR-376c, miR-376a, miR-127, miR-409, miR-148b, as specified in detail above, in a sample, (b) determining the methylation status and/or expression level of at least one methylation marker and the amount of at least one miRNA marker in one or more references or reference samples, (c) examining the tested sample as to whether the methylation status and/or expression level of at least one methylation marker and the amount of at least one miRNA marker present in said sample of interest is different from the level in the one or more references or reference samples, and (d) adapting the dosage of a pharmaceutical depending on whether the methylation status and/or expression level of at least one methylation marker and the amount of at least one miRNA marker in the sample of interest is different from the level in the one or more references or reference samples, (iv) a method of determining the beneficial and/or adverse effects of a substance on cancer or the development of cancer, comprising the steps of (a) determining the methylation status and/or expression level of at least one methylation marker selected from the group consisting of HYAL2, MGRN1, RPTOR, SLC22A18, FUT7, RAPSN, S100P, DYRK4, as specified in detail above, and the amount of at least one miRNA marker selected from the group consisting of miR-652, miR-801, miR-376c, miR-376a, miR-127, miR-409, miR-148b, as specified in detail above, in a sample of interest, (b) determining the methylation status and/or expression level of at least one methylation marker and the amount of at least one miRNA marker in one or more references or reference samples, and (c) examining the sample of interest as to whether the methylation status and/or expression level of at least one methylation marker and the amount of at least one miRNA marker present in said sample of interest is different from the level in the one or more references or reference samples, wherein the sample of interest was exposed differently to said substance than the one or more references or reference samples.

(v) a method for identifying a patient as a responder to a cancer treatment, comprising determining the methylation status and/or expression level of at least one methylation marker selected from the group consisting of HYAL2, MGRN1, RPTOR, SLC22A18, FUT7, RAPSN, S100P, DYRK4, as specified in detail above, and the amount of at least one miRNA marker selected from the group consisting of miR-652, miR-801, miR-376c, miR-376a, miR-127, miR-409, miR-148b, as specified in detail above, in a first sample and in one or more further samples taken subsequently to the first sample, wherein an increased methylation status of the at least one methylation marker and/or a lower expression level of the at least one methylation marker, and the absence or decreased amount of the at least one miRNA marker indicates a response to the treatment, (vi) a method for identifying a patient as a non-responder to a cancer treatment, comprising determining the methylation status and/or expression level of at least one methylation marker selected from the group consisting of HYAL2, MGRN1, RPTOR, SLC22A18, FUT7, RAPSN, S100P, DYRK4, as specified in detail above, and the amount of at least one miRNA marker selected from the group consisting of miR-652, miR-801, miR-376c, miR-376a, miR-127, miR-409, miR-148b, as specified in detail above, in a first sample and in one or more further samples taken subsequently to the first sample, wherein a decreased methylation status of the at least one methylation marker and/or an increased expression level of the at least one methylation marker, and the presence or increased amount of the at least one miRNA marker indicates a lack of response to the treatment, and (vii) a method for treating cancer, comprising the steps: (i) determining the methylation status and/or expression level of at least one methylation marker selected from the group consisting of HYAL2, MGRN1, RPTOR, SLC22A18, FUT7, RAPSN, S100P, DYRK4, as specified in detail above, and the amount of at least one miRNA marker selected from the group consisting of miR-652, miR-801, miR-376c, miR-376a, miR-127, miR-409, miR-148b, as specified in detail above, in a first sample of a subject; (ii) starting treatment of said patient with a first treatment regimen comprising one or more anti-cancer agents or therapies, (iii) determining the methylation status of at least one methylation marker and/or the expression level of at least one methylation marker, and the amount of at least one miRNA in one or more subsequently taken further samples of said subject; (iv) optionally repeating steps (ii) and (iii) one or more times; (v) continuing treating the patient with the first treatment regimen if there is a substantial increase of the methylation status of the at least one methylation marker and/or a lower expression level of the at least one methylation marker, and a decreased amount or absence of the at least one miRNA marker, or (vi) amending the treatment or terminating treating the patient with the first treatment regimen and treating the patient instead with a second treatment regimen comprising one or more anti-cancer agents or therapies not comprised in the first treatment regimen if there is a decreased methylation status of the at least one methylation marker and/or an increased expression level of the at least one methylation marker, and an increased amount or presence of the at least one miRNA marker.

In an eleventh aspect, the present invention relates to the device for identifying cancer, in particular BC, OvaCa, and/or PaCA, comprising:
(a) an analyzing unit comprising
    (i) a detection agent for determining the methylation status and/or expression level of at least one methylation marker selected from the group consisting of HYAL2, MGRN1, RPTOR, SLC22A18, FUT7, RAPSN, S100P, DYRK4, and
    (ii) a detection agent for determining the presence of at least one miRNA selected from the group consisting of: miR-652, miR-801, miR-376c, miR-376a, miR-127-3p, miR-409-3p, miR-148b in a sample of a subject; and (b) an evaluation unit comprising a data processor having tangibly embedded an algorithm for carrying out a comparison of the amount determined by the analyzing unit with a reference and which is capable of generating an output file containing a diagnosis established based on the said comparison.

In particular embodiments, said detection agent is a means as specified in detail above.

Particular devices are those which can be applied without the particular knowledge of a specialized clinician, e.g., test stripes or electronic devices which merely require loading with a sample. The results may be given as output of parametric diagnostic raw data, in particular, as absolute or relative amounts. It is to be understood that these data will need interpretation by the clinician. However, also envisaged are expert system devices wherein the output comprises processed diagnostic raw data the interpretation of which does not require a specialized clinician. Further preferred devices comprise the analyzing units/devices (e.g., biosensors, arrays, solid supports coupled to ligands specifically recognizing the miRNAs of the present invention, Plasmon surface resonance devices, NMR spectro-meters, mass-spectrometers etc.) or evaluation units/devices.

Further aspects of the present invention are the following:
1. A method of prognosing and/or diagnosing cancer, in particular BC, OvaCa, and/or PaCA, in a subject, comprising
    Are other cancers also included in the aspect? Just would like to make sure.
    a) determining the methylation status and/or expression level of at least one methylation marker selected from the group consisting of HYAL2, MGRN1, RPTOR, SLC22A18, FUT7, RAPSN, S100P, DYRK4, and
    b) determining the presence, preferably the amount, of at least one miRNA marker selected from the group consisting of miR-652, miR-801, miR-376c, miR-376a, miR-127, miR-409, miR-148b, in a subject
    wherein the methylation status and/or expression level of at least one methylation marker and the presence of at least one miRNA is indicative of the prognosis and/or diagnosis of said subject.
2. The method of aspect 1, wherein the prognosis and/or diagnosis of cancer includes
    i. the risk of developing cancer, in particular BC, OvaCa, and/or PaCA,
    ii. the presence of cancer, in particular BC, OvaCa, and/or PaCA, and/or
    iii. the progression, preferably the worsening or bettering, of cancer, in particular BC, OvaCa, and/or PaCA.
3. The method of any of aspect 1 or 2, wherein
    a) the methylation status and/or expression level of at least 2, 3, 4, 5, 6, or 7 different methylation markers is determined, and/or
    b) the presence of at least 2, 3, 4, 5, 6, or 7 different miRNA marker is determined.
4. The method of any of aspects 1 to 3, wherein
    a) the methylation status and/or expression level of the methylation marker MGRN1, RPTOR, and RAPSN, and optionally HYAL2 is determined, and/or
    b) the presence of the miRNA marker miR-652, miR-801, miR-376c, miR-376a, miR-127, miR-409, and miR-148b is determined.
5. The method of any of aspects 1 to 3, wherein
    a) the methylation status and/or expression level of the methylation marker SLC22A18, FUT7, S100P, and DYRK4, and optionally HYAL2 is determined, and/or b) the presence of the miRNA marker miR-652, miR-801, miR-376c, miR-376a, miR-127, miR-409, and miR-148b is determined.
6. The method of any of aspects 1 to 4, wherein
   a) the methylation status and/or expression level of the methylation marker MGRN1, RPTOR, SLC22A18, FUT7, RAPSN, S100P, and DYRK4, and optionally HYAL2, is determined, and/or
   b) the presence of the miRNA marker miR-652, miR-801, miR-376c, miR-376a, miR-127, miR-409, and miR-148b is determined.
7. The method of any of aspects 1 to 7, wherein the determination of the methylation status comprises determining methylation of at least one CpG site within the HYAL2, MGRN1, RPTOR, SLC22A18, FUT7, RAPSN, S100P, DYRK4, gene, in particular the promoter, intron or exon region of said genes.
8. The method of aspect 7, wherein the at least one CpG site is selected from the group consisting of cg22266967 in S100P, cg21019522 in SLC22A18, cg09418321 in DYRK4, and cg0279745 in FUT7, cg06418238 in RPTOR, cg00736299 in MGRN1, cg01662869 in MGRN1, cg27466532 in RAPSN, cg27091787 in HYAL2
9. The method of any of aspects 1 to 8, further comprising step
   c) comparing the methylation status of the at least one methylation marker and the presence of the at least one miRNA marker, in said subject, to the methylation status of the at least one methylation marker and the amount of the at least one miRNA marker in one or more reference(s).
10. The method of aspect 9, wherein the reference is a threshold value, a reference value or a reference sample.
11. The method of aspect 10, wherein the reference sample is selected from the group consisting of a healthy individual, a diseased individual or the same individual as the tested individual at an earlier or later time point or a representative value in absence of cancer, in presence of cancer, or for an increased or decreased risk of developing cancer.
12. The method of aspect 10 or 11, wherein the reference sample is selected from the group consisting of a reference sample derived from a healthy individual, a reference sample derived from a diseased individual, a reference sample derived from the same individual as the sample of interest taken at an earlier or later time point, and a reference sample representative for a healthy individual or representative for the presence or absence of cancer or representative for an increased or decreased risk of developing cancer.
13. The method of any of aspects 10 to 12, wherein the reference is a healthy subject or an subject with a decreased risk of developing cancer or a methylation status or an amount of miRNA representative of the absence of cancer, wherein the decreased methylation and/or overexpression of the at least one methylation marker and the presence or an increased amount of the at least one miRNA marker compared to the reference indicates
   iv. the risk of developing cancer, in particular BC, OvaCa, and/or PaCA,
   v. the presence of cancer, in particular BC, OvaCa, and/or PaCA, and/or
   vi. the progression of cancer, in particular BC, OvaCa, and/or PaCA in the subject.
14. The method of any of aspects 10 to 12, wherein the reference is a diseased individual or an individual with an increased risk of developing cancer or a value representative of the presence of cancer, wherein a similar methylation status or expression of the at least one methylation marker and a similar amount of the at least one miRNA marker indicates
   iv. the risk of developing cancer, in particular BC, OvaCa, and/or PaCA,
   v. the presence of cancer, in particular BC, OvaCa, and/or PaCA, and/or
   vi. the progression of cancer, in particular BC, OvaCa, and/or PaCA in the subject.
15. The method of any of aspects 10 to 12, wherein the reference sample is derived from the same individual as the sample of interest and was taken at an earlier time point, wherein
   (ii) a decreased methylation and/or overexpression of the at least one methylation marker and the presence or an increased amount of the at least one miRNA marker compared to the reference indicates
      iv. the risk of developing cancer, in particular BC, OvaCa, and/or PaCA,
      v. the presence of cancer, in particular BC, OvaCa, and/or PaCA, and/or
      vi. the progression of cancer, in particular BC, OvaCa, and/or PaCA,
   (ii) an increased methylation and/or lower expression of the at least one methylation marker and the absence or a decreased amount of the at least one miRNA marker compared to the reference indicates
      iv. a decreased risk to develop cancer, in particular BC, OvaCa, and/or PaCA,
      v. the absence of cancer, in particular BC, OvaCa, and/or PaCA, and/or
      vi. a declined progression of cancer, in particular BC, OvaCa, and/or PaCA, and/or
   (iii) a similar level of methylation and/or expression of the at least one methylation marker and a similar amount of the at least one miRNA marker compared to the reference indicates
      iv. a similar risk to develop cancer, in particular BC, OvaCa, and/or PaCA,
      v. a stagnation in the progression of cancer, in particular BC, OvaCa, and/or PaCA, and/or
      vi. a persistence of cancer, in particular BC, OvaCa, and/or PaCA, in the subject.
16. A method for determining the dosage of a pharmaceutical for the alteration of cancer or the prevention or treatment of cancer in a subject, comprising the steps of
   (a) determining the methylation status and/or expression level of at least one methylation marker selected from the group consisting of HYAL2, MGRN1, RPTOR, SLC22A18, FUT7, RAPSN, S100P, DYRK4, and the amount of at least one miRNA marker selected from the group consisting of miR-652, miR-801, miR-376c, miR-376a, miR-127, miR-409, miR-148b, in a sample of a subject, and optionally determining the methylation status and/or expression level of at least one methylation marker and the amount of at least one miRNA marker in a reference for comparison with the methylation status and/or expression level of at least one methylation marker and the amount of at least one miRNA marker in the sample of interest, and
   (b) determining the dosage of a pharmaceutical depending on the methylation status and/or expression level of at least one methylation marker and the amount of at least one miRNA marker in the sample of interest, optionally depending on the comparison of the methylation status and/or expression level of at least one methylation marker and the amount of at least one miRNA marker a in the sample of interest and the reference or reference sample.

17. A method for adapting the dosage of a pharmaceutical for the alteration of cancer or the prevention or treatment of cancer, comprising the steps of
   (a) determining the methylation status and/or expression level of at least one methylation marker selected from the group consisting of HYAL2, MGRN1, RPTOR, SLC22A18, FUT7, RAPSN, S100P, DYRK4, and the amount of at least one miRNA marker selected from the group consisting of miR-652, miR-801, miR-376c, miR-376a, miR-127, miR-409, miR-148b, in a sample,
   (b) determining the methylation status and/or expression level of at least one methylation marker and the amount of at least one miRNA marker in one or more references or reference samples,
   (c) examining the tested sample as to whether the methylation status and/or expression level of at least one methylation marker and the amount of at least one miRNA marker present in said sample of interest is different from the level in the one or more references or reference samples, and
   (d) adapting the dosage of a pharmaceutical depending on whether the methylation status and/or expression level of at least one methylation marker and the amount of at least one miRNA marker in the sample of interest is different from the level in the one or more references or reference samples.

18. A method of determining the beneficial and/or adverse effects of a substance on cancer or the development of cancer, comprising the steps of
   (a) determining the methylation status and/or expression level of at least one methylation marker selected from the group consisting of HYAL2, MGRN1, RPTOR, SLC22A18, FUT7, RAPSN, S100P, DYRK4, and the amount of at least one miRNA marker selected from the group consisting of miR-652, miR-801, miR-376c, miR-376a, miR-127, miR-409, miR-148b, in a sample of interest,
   (b) determining the methylation status and/or expression level of at least one methylation marker and the amount of at least one miRNA marker in one or more references or reference samples, and
   (c) examining the sample of interest as to whether the methylation status and/or expression level of at least one methylation marker and the amount of at least one miRNA marker present in said sample of interest is different from the level in the one or more references or reference samples,
   wherein the sample of interest was exposed differently to said substance than the one or more references or reference samples.

19. A method for identifying a patient as a responder to a cancer treatment, comprising determining the methylation status and/or expression level of at least one methylation marker selected from the group consisting of HYAL2, MGRN1, RPTOR, SLC22A18, FUT7, RAPSN, S100P, DYRK4, and the amount of at least one miRNA marker selected from the group consisting of miR-652, miR-801, miR-376c, miR-376a, miR-127, miR-409, miR-148b, in a first sample and in one or more further samples taken subsequently to the first sample, wherein an increased methylation status of the at least one methylation marker and/or a lower expression level of the at least one methylation marker, and the absence or decreased amount of the at least one miRNA marker indicates a response to the treatment.

20. A method for identifying a patient as a non-responder to a cancer treatment, comprising determining the methylation status and/or expression level of at least one methylation marker selected from the group consisting of HYAL2, MGRN1, RPTOR, SLC22A18, FUT7, RAPSN, S100P, DYRK4, and the amount of at least one miRNA marker selected from the group consisting of miR-652, miR-801, miR-376c, miR-376a, miR-127, miR-409, miR-148b, in a first sample and in one or more further samples taken subsequently to the first sample, wherein a decreased methylation status of the at least one methylation marker and/or an increased expression level of the at least one methylation marker, and the presence or increased amount of the at least one miRNA marker indicates a lack of response to the treatment.

21. A method for treating cancer, comprising the steps:
   (i) determining the methylation status and/or expression level of at least one methylation marker selected from the group consisting of HYAL2, MGRN1, RPTOR, SLC22A18, FUT7, RAPSN, S100P, DYRK4, and the amount of at least one miRNA marker selected from the group consisting of miR-652, miR-801, miR-376c, miR-376a, miR-127, miR-409, miR-148b, in a first sample of a subject;
   (ii) starting treatment of said patient with a first treatment regimen comprising one or more anti-cancer agents or therapies,
   (iii) determining the methylation status of at least one methylation marker and/or the expression level of at least one methylation marker, and the amount of at least one miRNA in one or more subsequently taken further samples of said subject;
   (iv) optionally repeating steps (ii) and (iii) one or more times;
   (v) continuing treating the patient with the first treatment regimen if there is a substantial increase of the methylation status of the at least one methylation marker and/or a lower expression level of the at least one methylation marker, and a decreased amount or absence of the at least one miRNA marker, or
   (vi) amending the treatment or terminating treating the patient with the first treatment regimen and treating the patient instead with a second treatment regimen comprising one or more anti-cancer agents or therapies not comprised in the first treatment regimen if there is a decreased methylation status of the at least one methylation marker and/or an increased expression level of the at least one methylation marker, and an increased amount or presence of the at least one miRNA marker.

22. The method according to any of aspects 1 to 21, wherein the sample of interest is a tissue sample and/or body fluid sample.

23. The method according to aspect 22, wherein the tissue sample is a tumor sample and/or the body fluid sample is selected from the group consisting of blood, plasma, serum, urine, saliva, lacrimal fluid and fluids obtainable from breast glands.

24. Means for prognosing and/or diagnosing
   iv. the risk of developing cancer, in particular BC, OvaCa, and/or PaCA,
   v. the presence of cancer, in particular BC, OvaCa, and/or PaCA, and/or vi. the progression of cancer, in particular BC, OvaCa, and/or PaCA, comprising
  a) one or more means of detecting the methylation status and/or expression level of at least one methylation marker, and
  b) one or more means of detecting the amount of at least one miRNA marker.
25. The means according to aspect 24, wherein
  a) the one or more means for detecting the methylation status of at least one methylation marker comprise at least one methylation-specific polynucleotide, and/or
  b) the one or more means for detecting the expression level of at least one methylation marker comprise mRNA specific polynucleotide, a binding moiety, in particular selected from the group consisting of a protein or peptide, more specifically a monoclonal or polyclonal antibody, and
  c) the one or more means for detecting the amount of at least one miRNA marker comprise at least one miRNA specific polynucleotide.
26. A kit comprising the means of aspect 24 or 25.
27. The kit according to aspect 26, wherein the kit further comprises
  (a) a container, and/or
  (b) a data carrier, wherein the data carrier comprises information such as
    (i) instructions concerning methods for identifying the risk for developing and/or identifying the presence and/or monitoring progression of cancer
    (ii) instructions for use of the means for detecting the methylation status and/or expression level of at least one methylation marker and the amount of at least one miRNA marker, in particular in a sample, more specifically in a sample from an individual and/or of the kit,
    (iii) quality information such as information about the lot/batch number of the means for detecting the methylation status and/or expression level of at least one methylation marker and the amount of at least one miRNA marker and/or of the kit, the manufacturing or assembly site or the expiry or sell-by date, information concerning the correct storage or handling of the kit,
    (iv) information concerning the composition of the buffer(s), diluent(s), reagent(s) for detecting the methylation status and/or expression level of at least one methylation marker and the amount of at least one miRNA marker and/or of the means for detecting the methylation status and/or expression level of at least one methylation marker and the amount of at least one miRNA marker,
    (v) information concerning the interpretation of information obtained when performing the above-mentioned methods identifying and/or monitoring progression of cancer,
    (vi) a warning concerning possible misinterpretations or wrong results when applying unsuitable methods and/or unsuitable means, and/or
    (vii) a warning concerning possible misinterpretations or wrong results when using unsuitable reagent(s) and/or buffer(s).
28. Use of the means of aspects 24 or 25, or the kit of aspects 26 or 27 for prognosing and/or diagnosing
  iv. the risk of developing cancer, in particular BC, OvaCa, and/or PaCA,
  v. the presence of cancer, in particular BC, OvaCa, and/or PaCA, and/or
  vi. the progression of cancer, in particular BC, OvaCa, and/or PaCA.
29. Use of the means of aspects 24 or 25, or the kit of aspects 26 or 27 in a method according to any of aspects 1 to 23.
30. A device for identifying cancer, in particular BC, OvaCa, and/or PaCA, comprising:
  (a) an analyzing unit comprising
    (i) a detection agent for determining the methylation status and/or expression level of at least one methylation marker selected from the group consisting of HYAL2, MGRN1, RPTOR, SLC22A18, FUT7, RAPSN, S100P, DYRK4, and
    (ii) a detection agent for determining the presence of at least one miRNA selected from the group consisting of: miR-652, miR-801, miR-376c, miR-376a, miR-127-3p, miR-409-3p, miR-148b in a sample of a subject; and
  (b) an evaluation unit comprising a data processor having tangibly embedded an algorithm for carrying out a comparison of the amount determined by the analyzing unit with a reference and which is capable of generating an output file containing a diagnosis established based on the said comparison.

The following Examples shall merely illustrate the invention. They shall not be construed, whatsoever, to limit the scope of the invention.

EXAMPLES

Study Population

The present study was approved by the Ethics Committee of the University of Heidelberg (Germany). All the cancer patients and healthy controls were Caucasian. All the recruited cases and controls gave written informed consent for the study. Genomic DNA was isolated from peripheral whole blood using DNA isolation kits from Qiagen. The leucocytes were immediately frozen in liquid nitrogen after isolation and stored at −80° C. until use. DNA and RNA were isolated from leucocytes using AllPrep DNA/RNA/Protein Mini Kit from Qiagen. Detailed information for the samples was shown in Table 1. Please see the clinical data of the sporadic BC patients in Table 5 and Table 6.

BC Cases and Matched Controls

Peripheral blood samples from 270 BRCA1/2 mutation-negative index familial BC patients (first validation round) were collected by the centers of the German Consortium for Hereditary Breast and Ovarian Cancer in Heidelberg and Cologne. All the familial BC cases were recruited according to the criteria of family history. Peripheral blood samples from 350 sporadic BC patients (189 in the second validation round and 161 in the third validation round) were collected at the time point of first BC diagnosis before any BC treatment and surgery at the University Hospital of Heidelberg. The clinical characteristics of sporadic BC patients were defined according to the American Joint Committee on Cancer (AJCC) cancer staging manual. Peripheral blood samples from 459 healthy female controls (251 in the first validation round and 189 in the second validation round) were collected from blood donors by the German Red Cross Blood Service of Baden-Wurttemberg-Hessen. Peripheral blood samples from 151 healthy female controls (third validation round) were collected at the University Hospital of Heidelberg. All the cases and controls in the third validation round were processed with the same manner in parallel. Leucocytes were isolated from peripheral blood using red blood cell lysis buffer within four hours after blood collection at the University Hospital of Heidelberg. All the leucocytes from cases and controls were processed in parallel.

PaCa Cases and Matched Controls

Peripheral blood samples from 147 sporadic PaCa patients (80 male cases and 67 female cases) were collected from multiple centers in Germany. The PaCa cases were specially selected with higher percentage of early stage cases. Peripheral blood samples from 191 healthy controls (115 male cases and 76 female cases) were collected from blood donors by the German Red Cross Blood Service of Baden-Württemberg-Hessen.

OvCa Cases and Matched Controls

Peripheral blood samples from 84 sporadic OvCa patients were collected at the University Hospital of Heidelberg. The OvCa cases were specially selected with higher percentage of early stage cases. Peripheral blood samples from 148 healthy controls were collected at the University Hospital of Heidelberg.

Example 1: Analysis of Methylation Marker

Infinium 27 k Methylation Assay and Infinium 450 k Methylation Assay

In the discovery round, 500 ng genomic DNA from each sample was treated by EZ-96 DNA Methylation Kit (Zymo Research) for bisulfite conversion and subjected to genome-wide methylation screening by Human Methylation27 Bead-Chip (Illumina) and Infinium HumanMethylation450 Bead-Chip Kit (Illumina) according to the manufacturer recommendations (Steemers F J, Chang W, Lee G, Barker D L, Shen R, Gunderson K L. Whole-genome genotyping with the single-base extension assay. Nat Methods 2006; 3:31-3. Bork S, Pfister S, Witt H, et al. DNA methylation pattern changes upon long-term culture and aging of human mesenchymal stromal cells. Aging Cell 2009; 9:54-63). All samples passed the quality control according to manufacturer instructions.

Methylation Analysis Via Maldi-TOF Mass Spectrometry

MALDI-TOF mass spectrometry (Sequenom) described by Breitling et al. (Breitling L P, Yang R, Korn B, Burwinkel B, Brenner H. Tobacco-smoking-related differential DNA methylation: 27K discovery and replication. Am J Hum Genet 2011; 88:450-7.) was used in various verification rounds. DNA was bisulfite converted by EZ-96 DNA Methylation Gold Kit (Zymo Research) and amplified by bisulfite-specific primers (FIG. 1). The PCR products were treated according to the standard protocol of Sequenom EpiTyper Assay and dispensed to a 384 SpectroCHIP by a Nanodispenser. The chips were read by a Sequenom Mass Spectrometer system. Data were collected by SpectroACQUIRE v3.3.1.3 software and visualized with MassArray EpiTyper v1.0 software. 5% samples were randomly chosen for the duplication analysis.

Quantitative Real-Time PCR for RNA Expression 100 ng of total RNA from each sample was transcribed to cDNA by TaqMan® Reverse Transcription Reagents (Applied Biosystems). Quantitative real-time PCR was performed using a LightCycler480 (Roche) in combination with TaqMan gene expression assays (Applied Biosystems) for HYAL2, MGRN1, RPTOR, SLC22A18, FUT7, RAPSN, S100P, and DYRK4 gene and housekeeping gene HPRT1 as endogenous control. Crossing point values were calculated using the second-derivative maximum method by the LightCycler 480 basic software (Roche). Relative expression of genes for each sample was calculated according to the AACt method by normalization to HPRT1. All the cases and controls were processed in parallel.

| Bisulfite-specific primers for different amplicons | | |
|---|---|---|
| Amplicons | Primers | Sequences |
| S100P | sense | aggaagagagGGAAGGTGGGTTTG AATTTAGTATT (SEQ ID NO: 64) |
|  | antisense | cagtaatacgactcactataggga gaaggctCTATCCCTCTTACCTCT AAACCCCT (SEQ ID NO: 65) |
| SLC22A18 | sense | aggaagagagTAAGTGGAATTTTG GTATTTTGGA (SEQ ID NO: 58) |
|  | antisense | cagtaatacgactcactataggga gaaggctCACTCCAAACCTAAACT CACCTCTA (SEQ ID NO: 59) |
| DYRK4 | sense | aggaagagagGGTTTTTTTAAAAT TGGTTTTGGAT (SEQ ID NO: 66) |
|  | antisense | cagtaatacgactcactataggga gaaggctAAACCCCATTTTTATTC CCATAAT (SEQ ID NO: 67) |
| FUT7 | sense | aggaagagagGAAGAGGAAGGGAT TTAGTTTGAAG (SEQ ID NO: 60) |
|  | antisense | cagtaatacgactcactataggga gaaggctACAAACCTTAACCTCCC AAAATACT (SEQ ID NO: 61) |
| RPTOR | sense | aggaagagagGTGGGGTTTTTGTA GTAGTTGAGA (SEQ ID NO: 56) |
|  | antisense | cagtaatacgactcactataggga gaaggctTAATAACCCAAAACCAA ACCCTAAC (SEQ ID NO: 57) |
| MGRN1 | sense | aggaagagagTTTTGGGGTATAAG GGAAGTTTAAG (SEQ ID NO: 54) |
|  | antisense | cagtaatacgactcactataggga gaaggctCCTAACCAACAAAAAAC CTAAAAAA (SEQ ID NO: 55) |
| RAPSN | sense | aggaagagagGATTTTTAGTTGGT GAGAGGTTTGA (SEQ ID NO: 62) |
|  | antisense | cagtaatacgactcactataggga gaaggctAAAACCACTAAATTACC CAACCAAA (SEQ ID NO: 63) |
| HYAL2 | sense | aggaagagagTTTTAAATTTAGTA GGGTGTGAGAGGA (SEQ ID NO: 48) |
|  | antisense | cagtaatacgactcactataggga gaaggctCTCATCCATATTATAAA AAACCCCC (SEQ ID NO: 49) |
| HYAL2-310 | sense | aggaagagagTTTTTTTGGGGTGA GTTTTTTAGT (SEQ ID NO: 50) |
|  | antisense | cagtaatacgactcactataggga gaaggctCACCTAATCCTAAACCC ATAACCTT (SEQ ID NO: 51) |
| HYAL2-325 | sense | aggaagagagTTGTTTAGTTTTTG AGGTTTTTGG (SEQ ID NO: 52) |
|  | antisense | cagtaatacgactcactataggga gaaggctATTACACTCCCTCCCTC TCCTAAC (SEQ ID NO: 53) |

Statistical Analysis

The Illumina 27K Array data were processed by the Illumina BeadStudio software with default settings. Probes with detection P-value>0.01 were removed and samples were quantile-normalized. Association of probes with case/control status was assessed by beta-regression models with a logistic link and associated Wald tests using the R package betareg v2.2-3 30. Likelihood ratio tests were used to compare the case/control model with the nested model for chip differences in order to identify possible false hits due to confounding by chip effects. Multiple testing adjustments were done with the Benjamini-Hochberg method controlling the false discovery rate at the level of 0.05. All analysis was performed with the statistical software R v2.11.1.

All the statistical analyses of the gene expression data were conducted by SPSS Statistics 17.0 software. The correlations were assessed by Spearman's rank correlation coefficients. Logistic regression models and non-parametric tests were used for comparisons between two and multiple groups. The results of logistic regression were adjusted for possible confounding effects of age and different measurement batches by including additional co-variables in the logistic regression models. Receiver operating characteristic (ROC) curve analysis was performed to assess the discriminatory power of methylation levels.

Example 2: Analysis of miRNA Marker

Blood Processing and miRNA Isolation from Plasma

EDTA blood samples were collected from cases and control individuals and processed for plasma within 2 hours of collection. To avoid contamination with epithelial cells from the initial skin puncture the first blood tube collected during phlebotomy was not processed for plasma. Blood was centrifuged at 1300 g for 20 minutes at 10° C. The supernatant (plasma) was transferred into microcentrifuge tubes followed by a second high-speed centrifugation step at 15500 g for 10 minutes at 10° C. to remove cell debris and fragments. The plasma was aliquoted into cryo vials, snap-frozen in liquid nitrogen and stored at −80° C. until use. Total RNA (including miRNAs) was extracted from 400 μL of plasma. Denaturation and phase separation were conducted using TRIzol LS (Invitrogen, Germany) according to manufacturer's protocol, with a minor modification: 10 fmol of a C. elegans miR-39/miR-238 mixture was spiked-in. The aqueous phase was transferred into another tube, 1.5 volumes of absolute ethanol were added and the mixture was applied to miRNeasy Mini kit columns (Qiagen, Germany). After washing miRNAs were eluted in 30 μL of RNase-free water.

Validation of Selected Marker Candidates

Reverse transcription (RT) reactions were performed using TaqMan miRNA Reverse Transcription Kit (Applied Biosystems, Germany) and miRNA-specific RT primers for miR-652, miR-801, miR-376c, miR-376a, miR-127, miR-409, and miR-148b (Applied Biosystems, Germany). Singleplex (primary breast cancer) or multiplex (metastatic breast cancer) reactions were carried out in a volume of 7.5 μl or 15 μl, respectively. Each reaction comprised 1×RT buffer, 1 mM dNTPs, 0.3×miRNA-specific RT primers, 0.25 U RNase inhibitor, 3.3 U Multiscribe Reverse Transcriptase and a fixed volume of miRNA template (2 or 1 μl, respectively). For benign and malignant breast cancer tissue samples the reactions were carried out in 15 μl and comprised the following: 1×RT buffer, 1 mM dNTPs, 0.6× miRNA-specific and RNU6B RT primers, 0.25 U RNase inhibitor, 3.3 U Multiscribe Reverse Transcriptase and 5 ng RNA. Blinding of samples and a randomized, simultaneous investigation of cases and controls on reaction plates was intended to minimize bias and batch effects during validation. RT was carried out in a G-STORM GS2 PCR cycler (Alphametrix, Germany) under the following conditions: 16° C. for 30 min, 42° C. for 30 min and 85° C. for 5 min, followed by a hold at 4° C. TaqMan real-time PCR reactions were performed in triplicates in scaled-down reactions comprising 2.5 μLTaqMan 2× Universal PCR Master Mix with No AmpErase UNG (Applied Biosystems, Germany), 0.25 μL 20×miRNA-specific primer/probe mix (Applied Biosystems, Germany) and 2.25 μL of the reverse transcription product (diluted 1:4). Real-time PCR was carried out in a LightCycler 480 thermocycler (Roche, Germany) under the following conditions: 95° C. for 10 min, then 50 cycles of 95° C. for 15 s, 60° C. for 30 s and 72° C. for 30 s, followed by a hold at 4° C. Raw data from validation studies in blood plasma was normalized to spiked-in cel-miR-39 as described in Kroh et al. (Kroh E M, Parkin R K, Mitchell P S, Tewari M. Analysis of circulating microRNA biomarkers in plasma and serum using quantitative reverse transcription-PCR (qRT-PCR). Methods 2010; 50:298-301). Raw Ct values from breast tissue samples were normalized to RNU6B as described in User Bulletin #2: ABI PRISM 7700 Sequence Detection System (Applied Biosystems).

Comparison of Cancer Cases with Controls

To evaluate the breast cancer and prostate cancer detection potential, receiver operating characteristic (ROC) curves were constructed and the areas under the curves (AUC) calculated. Based on ROC curves with 95% confidence intervals, lowest specificities at pre-defined sensitivities (75% to 90%) were computed for miR-652, miR-801, miR-376c, miR-376a, miR-127, miR-409, and miR-148b. Based on ROC curves, lowest specificities at pre-defined sensitivities (75% to 90%) were computed for the most informative and least redundant model of miRNAs as the lower bounds of the 95% confidence intervals (Tom Fawcett (2006) "An introduction to ROC analysis". Pattern Recognition Letters 27, 861-874. DOI: 10.1016/j.patrec.2005.10.010; using R package pROC v1.3.2).

Diagnostic Potential of miR-652, miR-801, miR-376c, miR-376a, miR-127, miR-409, and miR-148b in Plasma ROC curve analysis was performed to evaluate the diagnostic potential of miR-652, miR-801, miR-376c, miR-376a, miR-127, miR-409, and miR-148b for breast cancer and prostate cancer detection in blood plasma. The discriminatory power between tumor and control samples is depicted by the areas under the curves (AUC).

By investigating different combinations of miR-148b, miR-376c, miR-409-3p and miR-801 we found that a combined ROC curve with all seven miR-652, miR-801, miR-376c, miR-376a, miR-127, miR-409, and miR-148b gave the most informative and least redundant miRNA panel with an AUC of 0.89.

Example 3: Combination of Methylation and miRNA Marker

Sample Perparation

Peripheral blood samples from 161 sporadic BC patients (the third validation round) were collected at the time point of first BC diagnosis before any BC treatment and surgery at the University Hospital of Heidelberg. The clinical characteristics of sporadic BC patients were defined according to the American Joint Committee on Cancer (AJCC) cancer staging manual. Peripheral blood samples from 151 healthy female controls (third validation round) were collected at the University Hospital of Heidelberg. All the cases and controls in the third validation round were processed with the same manner in parallel. The DNA from the whole blood and the miRNA from plasma were extracted from each sample.

Determination of DNA methylation level and miRNA level. The DNA methylation levels were determined by MALDI-TOF mass spectrometry (Sequenom) as described in Example 1. The miRNA levels from plasam were determined by real-time PCR as described in Exapmle 2.

Statistical Analysis

All the statistical analyses of the gene expression data were conducted by SPSS Statistics 17.0 software. Results of the marker set (combination of DNA methylation and miRNA markers) were generated with the use of a logistic-regression algorithm. Logistic regression models was used to and non-parametric tests were used for comparisons between two and multiple groups. The results of logistic regression were adjusted for possible confounding effects of age and different measurement batches by including additional co-variables in the logistic regression models. Receiver operating characteristic (ROC) curve analysis was performed to assess the discriminatory power of methylation levels.

The invention claimed is:

1. A method of treating breast cancer comprising administering a treatment to effectively treat breast cancer in a patient who has been diagnosed as having breast cancer based on the presence in a biological sample from the patient of a biomarker panel having
a decrease in the methylation status of HYAL2 relative to a control, and having an elevated expression level relative to a control of miRNA markers miR-652, miR-801, miR-376c, miR-376a, miR-127, miR-409, and miR-148b.

2. The method of claim 1, wherein the treatment is selected from the group consisting of chemotherapy, anti-hormone therapy, targeted therapy, immunotherapy, surgery, and radiation therapy.

3. The method of claim 1, wherein the biomarker panel further comprises:
(a) a decrease in the methylation status of MGRN1, RPTOR, and RAPSN relative to a control;
(b) a decrease in the methylation status of S100P, SLC22A18, DYRK4, and FUT7 relative to a control; or
(c) a decrease in the methylation status of S100P, SLC22A18, DYRK4, FUT7, MGRN1, RPTOR, and RAPSN relative to a control.

4. The method of claim 3, wherein the patient has been diagnosed as having breast cancer based a decrease in the methylation status of HYAL2, S100P, SLC22A18, DYRK4, and FUT7 relative to a control, and having an elevated expression level relative to a control of miRNA markers miR-652, miR-801, miR-376c, miR-376a, miR-127, miR-409, and miR-148b.

5. The method of claim 3, wherein the patient has been diagnosed as having breast cancer based a decrease in the methylation status of HYAL2, MGRN1, RPTOR, and RAPSN, relative to a control, and having an elevated expression level relative to a control of miRNA markers miR-652, miR-801, miR-376c, miR-376a, miR-127, miR-409, and miR-148.

6. The method of claim 3, wherein the patient has been diagnosed as having breast cancer based a decrease in the methylation status of HYAL2, S100P, SLC22A18, DYRK4, FUT7, MGRN1, RPTOR, and RAPSN relative to a control, and having an elevated expression level relative to a control of miRNA markers miR-652, miR-801, miR-376c, miR-376a, miR-127, miR-409, and miR-148.

7. The method of claim 1, wherein:
(a) the elevated expression level of the miRNA marker miR-652 is at least 1.4-fold higher than a control;
(b) the elevated expression level of the miRNA marker miR-801 is at least 1.5-fold higher than a control;
(c) the elevated expression level of the miRNA marker miR-376c is at least 1.4-fold higher than a control;
(d) the elevated expression level of the miRNA marker miR-376a is at least 1.5-fold higher than a control;
(e) the elevated expression level of the miRNA marker miR-127 is at least 1.4-fold higher than a control;
(f) the elevated expression level of the miRNA marker miR-409 is at least 1.3-fold higher than a control; and
(g) the elevated expression level of the miRNA marker miR-148b is at least 1.2-fold higher than a control.

8. The method of claim 1, wherein the decrease in methylation status of HYAL2 is at least 10% compared to a control.

9. A method of treating breast cancer in a subject, the method comprising:
(a) diagnosing breast cancer in the subject by a method comprising diagnosing the subject as having:
(i) an elevated expression level in a biological sample from the subject of miRNA markers miR-652, miR-801, miR-376c, miR-376a, miR-127, miR-409, and miR-148b relative to a control; and
(ii) a decrease in the methylation status in a biological sample from the subject of HYAL2 relative to a control;
and
(b) administering a treatment to effectively treat breast cancer in the subject.

10. The method of claim 9, wherein the treatment is selected from the group consisting of chemotherapy, anti-hormone therapy, targeted therapy, immunotherapy, surgery, and radiation therapy.

11. The method of claim 9, wherein the method further comprises diagnosing the subject as having a decrease in the methylation status of:
(a) MGRN1, RPTOR, and RAPSN relative to a control;
(b) S100P, SLC22A18, DYRK4, and FUT7 relative to a control; or
(c) S100P, SLC22A18, DYRK4, FUT7, MGRN1, RPTOR, or RAPSN relative to a control.

12. The method of claim 11, wherein the method comprises diagnosing the subject as having a decrease in the methylation status of HYAL2, S100P, SLC22A18, DYRK4, and FUT7 relative to a control.

13. The method of claim 11, wherein the method comprises diagnosing the subject as having a decrease in the methylation status of HYAL2, MGRN1, RPTOR, and RAPSN relative to a control.

14. The method of claim 11, wherein the method comprises diagnosing the subject as having a decrease in the methylation status of HYAL2, S100P, SLC22A18, DYRK4, FUT7, MGRN1, RPTOR, and RAPSN relative to a control.

15. The method of claim 9, wherein:
(a) the elevated expression level of the miRNA marker miR-652 is at least 1.4-fold higher than a control;
(b) the elevated expression level of the miRNA marker miR-801 is at least 1.5-fold higher than a control;
(c) the elevated expression level of the miRNA marker miR-376c is at least 1.4-fold higher than a control;

(d) the elevated expression level of the miRNA marker miR-376a is at least 1.5-fold higher than a control;
(e) the elevated expression level of the miRNA marker miR-127 is at least 1.4-fold higher than a control;
(f) the elevated expression level of the miRNA marker miR-409 is at least 1.3-fold higher than a control; and
(g) the elevated expression level of the miRNA marker miR-148b is at least 1.2-fold higher than a control.

16. The method of claim 9, wherein the decrease in methylation status of HYAL2 is at least 10% compared to a control.

17. The method of claim 9, wherein the methylation status is determined by Maldi-TOF mass spectrometry.

18. The method of claim 9, wherein the miRNA expression levels are measured by real-time PCR.

19. The method of claim 9, wherein the biological sample comprises a blood sample.

* * * * *